(12) United States Patent
Wong et al.

(10) Patent No.: US 7,351,547 B2
(45) Date of Patent: Apr. 1, 2008

(54) DIAGNOSTIC TEST FOR WEST NILE VIRUS

(75) Inventors: Susan J. Wong, Albany, NY (US); Pei-Yong Shi, Albany, NY (US)

(73) Assignee: Health Research, Inc., Reusselaer, NY (US)

( * ) Notice: Subject to any disclaimer, the term of this patent is extended or adjusted under 35 U.S.C. 154(b) by 174 days.

(21) Appl. No.: 10/699,550

(22) Filed: Oct. 31, 2003

(65) Prior Publication Data

US 2004/0197769 A1 Oct. 7, 2004

Related U.S. Application Data

(60) Provisional application No. 60/422,755, filed on Oct. 31, 2002, provisional application No. 60/476,513, filed on Jun. 6, 2003.

(51) Int. Cl.
G01N 33/00 (2006.01)
G01N 33/53 (2006.01)
C12Q 1/70 (2006.01)
A61K 39/193 (2006.01)

(52) U.S. Cl. .......................... 435/7.92; 435/7.1; 435/5; 424/218.1

(58) Field of Classification Search ............. 424/218.1, 424/186.1, 192.1; 435/5, 69.7; 530/350
See application file for complete search history.

(56) References Cited

U.S. PATENT DOCUMENTS 6,416,763 B1 * 7/2002 McDonell et al. ....... 424/218.1
6,766,817 B2 7/2004 da Silva
2006/0115896 A1 6/2006 Wong et al.

OTHER PUBLICATIONS

Monath, TP et al., Flavivruses. In: Fields Virology, 3rd Edition. (1996) p. 961.*
Wang, T. et al. A recombinant envelope protein-based enzyme-linked immunosorbent assay for West Nile virus serodiagnosis. (2002) Vector Borne and Zoonotic Diseases 2(2) pp. 105-109.*
Valdes, K, et al., Human dengue antibodies against structural and nonstructural proteins. (2000) Clinical and Diagnostic Laboratory Immunology 7(5) pp. 856-857.*
Chien, DY et al. Diagnosis of hepatitis C virus infection using an immunodominant cimeric polyprotein . . . (1992) PNAS, vol. 89, pp. 10011-10015.*
Tardei, et al., Evaluation of immunoglobulin M (IgM) and IgG enzyme immunoassays in serologic diagnosis of West Nile virus infection. (2000) J. Clin. Microbiol. vol. 38, No. 6, pp. 2232-2239.*
Davis, B.S. et al. West Nile virus recombinant DNA vaccine protect mouse and horse from virus challenge and expresses in vitro a noninfectious recombinant antigen that can be used in enzyme linked immunosorbent (2001) Journal of Virology, 75(9) 4040-4047.*
Chien, DY et al Use of a novel hepatitis C virus major-epitope chimeric polypeptide for diagnosis of HCV infection. (1999) J. Clin. Microbiol. vol. 37(5) pp. 1393-1397.*

Mandy, FF, et al. Overview and application of suspension array technology (2001) Clinics in Laboratory Medicine. vol. 21(4) pp. 713-729.*
Scaramozzino et al. May 2001, Journal of Clinical Microbiology. p. 1922-1927.*
Tian Wang et al., "A Recombinant Envelope Protein-Based Enzyme-Linked Immunosorbent Assay for West Nile Virus Serodiagnosis", Vector Borne and Zoonotic Diseases, 2000, vol. 2, No. 2, pp. 105-109.
Katia Valdes, et al., "Human Dengue Antibodies against Structural and Nonstructural Proteins", Clinical and Diagnostic Laboratory Immunology, Sep. 2000, vol. 7, No. 5, pp. 856-857.
Robert S. Lanciotti et al., "Rapid Detection of West Nile Virus from Human Clinical Specimens, Field-Collected Mosquitoes, and Avian Samples by a TaqMan Reverse Transcriptase-PCR Assay", Journal of Clinical Microbiology, Nov. 2000, vol. 38, No. 11, pp. 4066-4071.
Anderson, J. F., T. G. Andreadis, C. R. Vossbrinck, S. Tirrell, E. M. Waken, R.A., Science, 1999, vol. 286, pp. 2221-2416.

(Continued)

*Primary Examiner*—Bruce R. Campell
*Assistant Examiner*—Sharon Hurt
(74) *Attorney, Agent, or Firm*—Thomas J. Kowalski; Ljiljana Minwalla; Frommer Lawrence and Haug

(57) ABSTRACT

The present invention provides a rapid and sensitive method for the detection of a West Nile virus (WNV), Japanese encephalitis virus (JEV), St. Louis encephalitis virus (SLEV) and Dengue virus (DENV) and antibodies directed against thereof involving contacting a biological specimen suspected of being infected with WNV, JE, SLE or DEN with a substantially purified and isolated WNV E glycoprotein or subfragment thereof having a native conformation wherein the E glycoprotein or subfragment thereof has a reactivity with antibodies against WNV and a cross-reactivity with antibodies against JEV, SLEV and DENV. The instant invention further provides a rapid, sensitive, and consistent method for the specific detection of WNV by employing diagnostic assays having the antigen NS5 which is specifically reactive with anti-WNV antibodies but not cross-reactive with antibodies against other flaviviruses such as JEV, SLEV, or DENV. The present invention also provides a rapid, sensitive, and consistent method for the specific detection of DENV by employing diagnostic assays having the antigen NS5 which is specifically reactive with anti-DENV antibodies but do not cross-react with antibodies against other flaviviruses such as JEV, SLEV, or WNV. Further, the DENV NS5 antigens are serospecific and do not cross react with antibodies to other DENV strains. Thus, the method of the present invention provides a manner by which to discriminate infections by each DENV strain. Further, diagnostic kits for carrying out the methods are provided. The methods and kits for carrying out the methods of the invention are rapid and require as little as 10 minutes to detect a result.

38 Claims, 61 Drawing Sheets

OTHER PUBLICATIONS

Bellisario, R., R. J. Colinas, and K. A. Pass. 2002. Simultaneous measurement of thyroxine(T4) and thyrotropin (TSH) from newborn dried blood-spot specimens using a multiplexed fluorescent microsphere immunoassay. Clin. Chem. 46:1422-24.

Burke, D. S., A. Nisalak, and M. A. Ussery. 1982. Antibody Capture Immunoassay Detection of Japanese Encephalitis Virus Immunoglobulin M and G Antibodies in Cerebrospinal Fluid. J. Clin. Microbiol. 16:1034-1042.

Burke, D. S. and A. Nisalak. 1982. Detection of Japanese Encephalitis Virus Irrimunoglobulin M Antibodies in Serum by Antibody Capture Radioimmunoassay. J. Clin. Microbiol. 16:353-361.

Crowther, John R. 2001. Validation of Diagnostic Tests for Infectious Diseases, p. 301-345 In Methods in Molecular Biology vol. 149. The ELISA Guidebook. Humana Press, Totowa, NJ.

Davis, B. S., G.-J. J. Chang, B. Cropp, J. T. Roehrig, d. A. Martin, C. J. Mitchell, R. Bowen, and M. L. Bunning. 2001. WNV Recombinant DNA Vaccine Protects Mouse and Horse from Virus Challenge and Expresses in vitro A Noninfectious Recombinant Antigen That Can Be Used in Enzyme-Linked Inununosorbent Assays. J. Virology 75:4040-4047.

Johnson, A. J., D. A. Martin, N. Karabatsos and J. T. Roehrig. 2000. Detection of Anit-Arboviral Immunoblobulin G by Using a Monoclonal Antibody-Based Capture Enzyme-Linked Immunosorbent Assay. J. Clin. Microbiol. 38:1827-1831.

Kellar, K. L., R. R. Kalwar, K. A. Dubous, D. Crouse, W. D. Chafin and B.-E. Kane. 2001. Multiplexed Fluorescent Bead-Based Immunoassays for Quantitation of Human Cytokines in Serum and Culture Supernatants. Cytometry 45:27-36, 2001.

Kittigul, L. and K. Suankeow. Eur. J. Clin. Microbiol. Infect. Dis. 21:224-226 (2002).

Lanciotti, R. S., J. T. Roehrig, V. Deubel, J. Smith, M. Parker, K. Steele, B. Cnse, K.. E. Volpe, M. B. Crabtree. K. H. Scherret, et. al. 1999. Origin of the WNV responsible for an outbreak of encephalitis in the northeastern United States 236:2333.

Mandy, F. F., T. Nakamura, M. Bergeron, and K. Sekiguchi. 2001. Overview and Application of Suspension Array Technology. Clinics in Laboratory Medicine 21:713-729.

Mariella, R. Jr., 2002. MEMS for Bioassays. Biomedical Microdevices 4:77-87.

Martin, D. A., D. A. Muth, T. Brown, A. J. Johnson, N. Karabatsos and J. T. Roehrig. 2000. Standardization of Immunoglobulin M Capture Enzyme-Linked Immunosorbent Assays for routine Diagnosis of Arboviral Infections. J. Clin. I Vficrobiol. 38:1823-1826.

Pickering, J. W., T. B. Martins, R. W. Greer, M. C. Schroeder, M. E. Astill, C. M. Litwin, S. W. Hildreth, and H. R. Hill. 2002. A Multiplexed Fluorescent Microsphere Immunoassay for Antibodies to Pneumococcal Capsular Polysaccharides. Am. J. Clin. Pahtol. 117:589-596.

Schmitt, J. and W. Papisch. 2002. Recombinant autoantigens. Autoimmunity Reviews 1:79-88.

Wong, S.J., R. H. Boyle, V. L. Demarest, A. N. Woodmansee, L.D. Kramer, H. Li, M. Drebot, R.A . Koski, E. fikring, D. A. Martin, P.-Y. Shi. 2003. Immunoassay targeting Nonstructural Protein 5 to Differentiate West Nile Virus Infection from Dengue and St. Louis Encephalitis Virus Infections and from Flavivivirus Vaccination. 41:4217-4223.

Shi, P.-Y., M. Tilgner, M.K. Lo, K.A. Kent, and K.A. Bernard. 2002. Infectious cDNA Clone of the Epidemic West Nile Virus from New York City. J. Virology, 76: 5847-5856.

\* cited by examiner

Peptide 1
"WNE 288-301"
N terminus – C-R-V-K-M-E-K-L-Q-L-K-G-T-T – C terminus
14 amino acid residues

FIG. 1

Peptide 2
"Random 288-301"
N terminus –  C-Q-L-L-M-R-E-V-K-T-G-T-K-K – C terminus
14 amino acid residues

FIG. 2

Peptide 3
"WNE 121-139"
N terminus – C-S-T-K-A-I-G-R-T-I-L-K-E-N-I-K-Y-E-V – C terminus
19 amino acid residues

A.
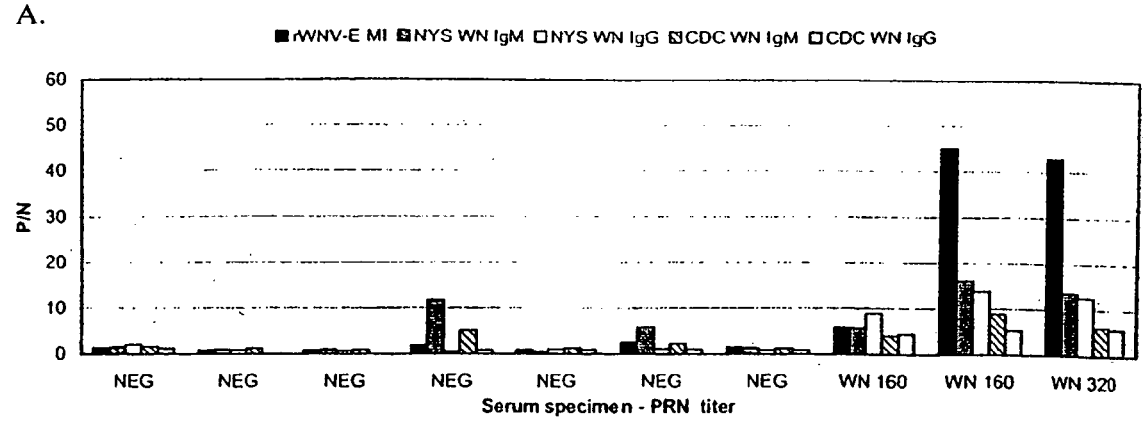
B.
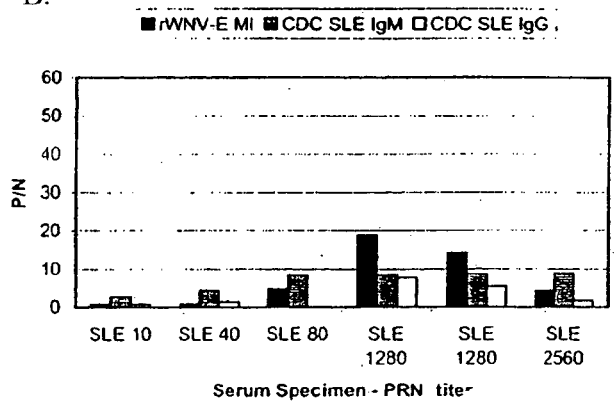
C.
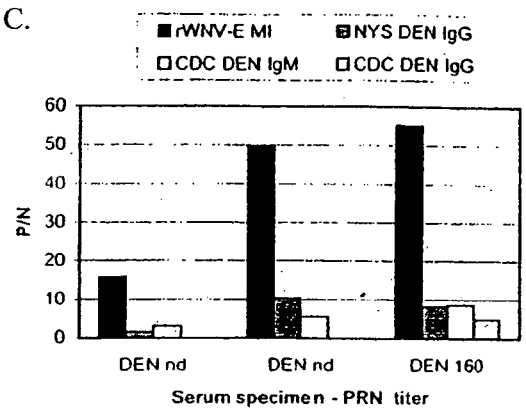
FIG. 10

A.
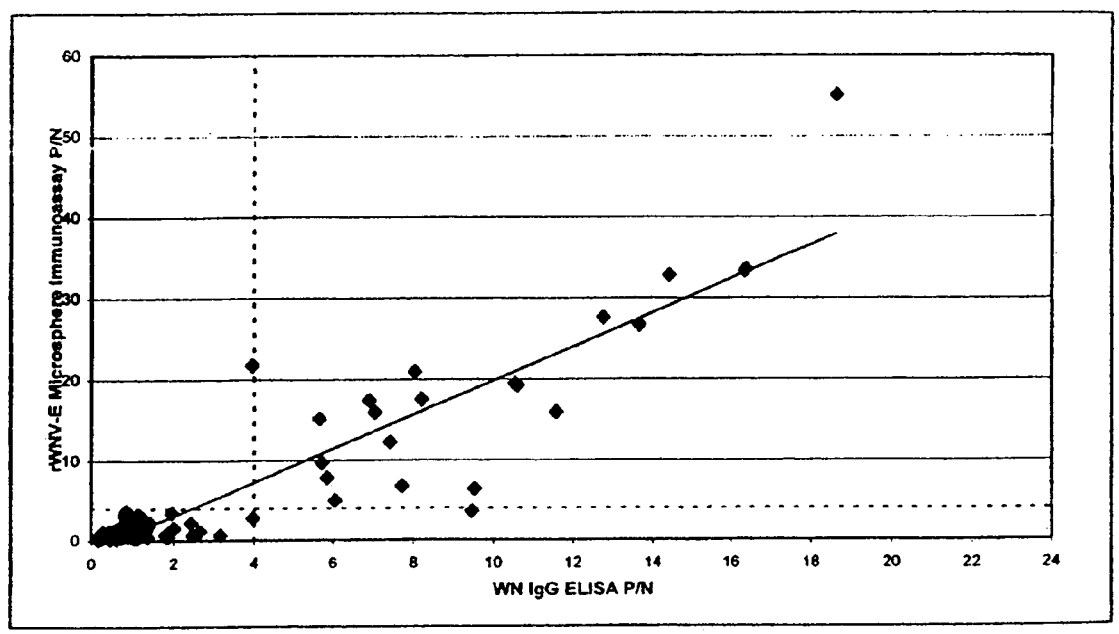
B.
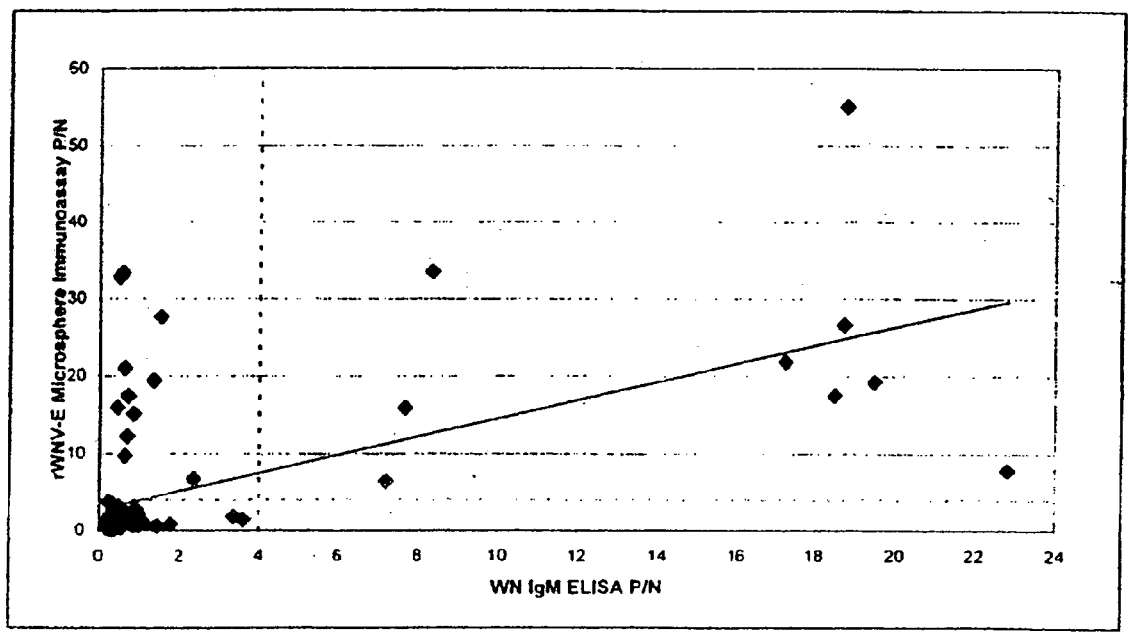
FIG. 11

A.
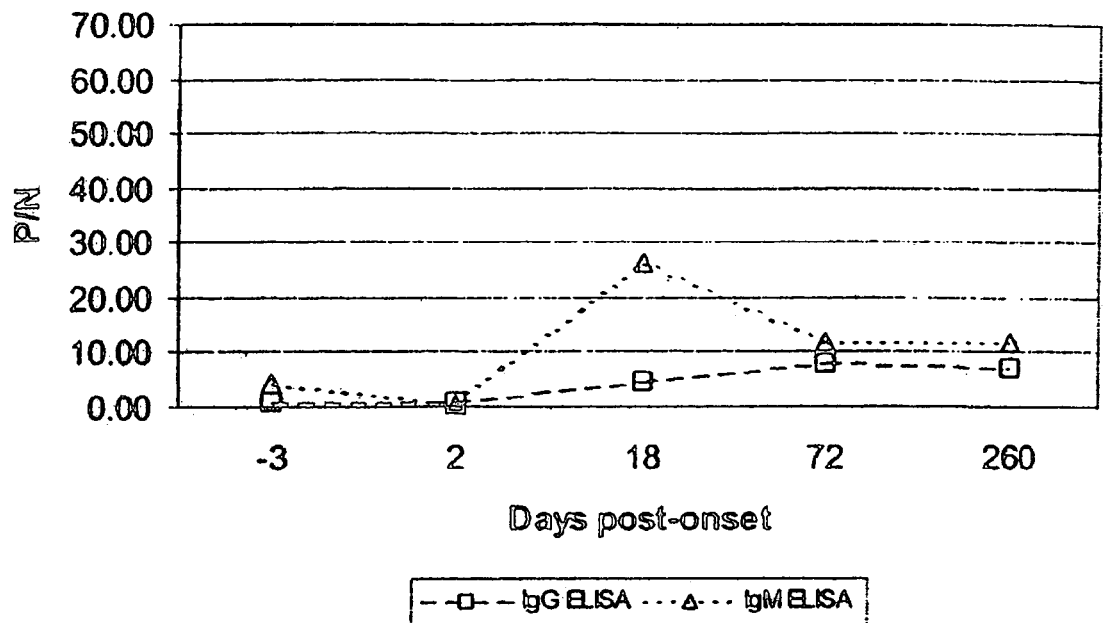
B.
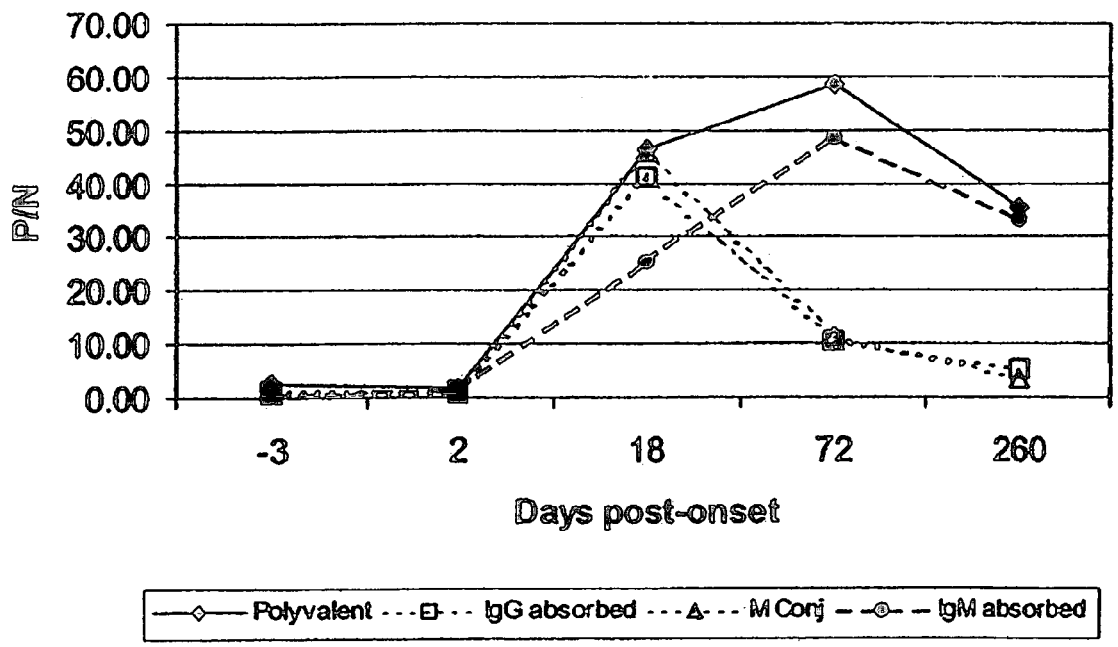
FIG. 12

A
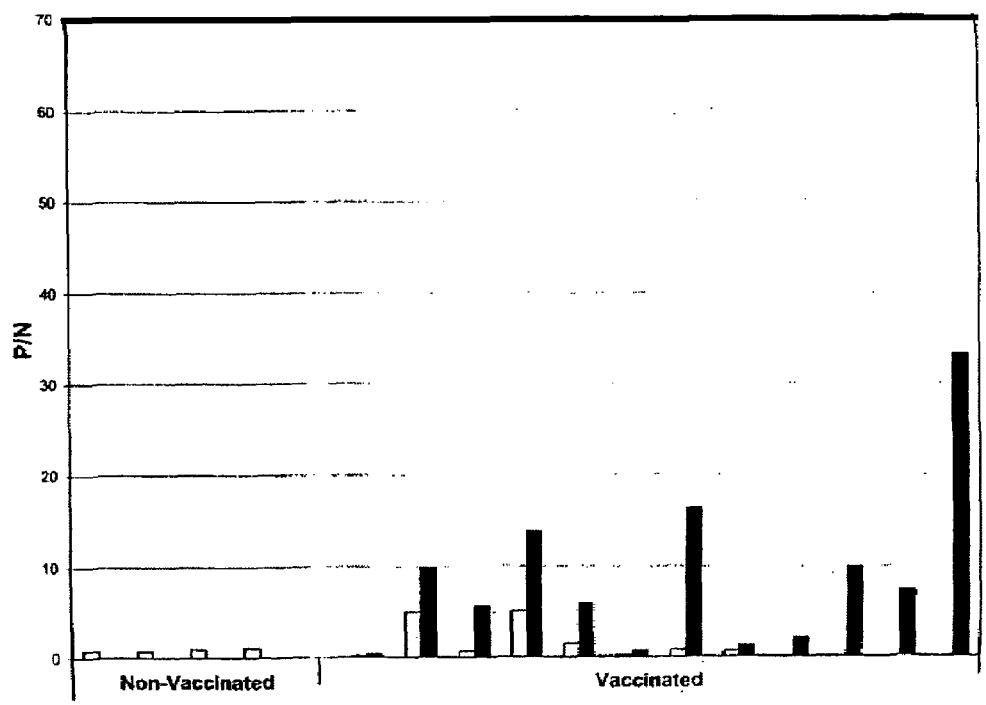
B
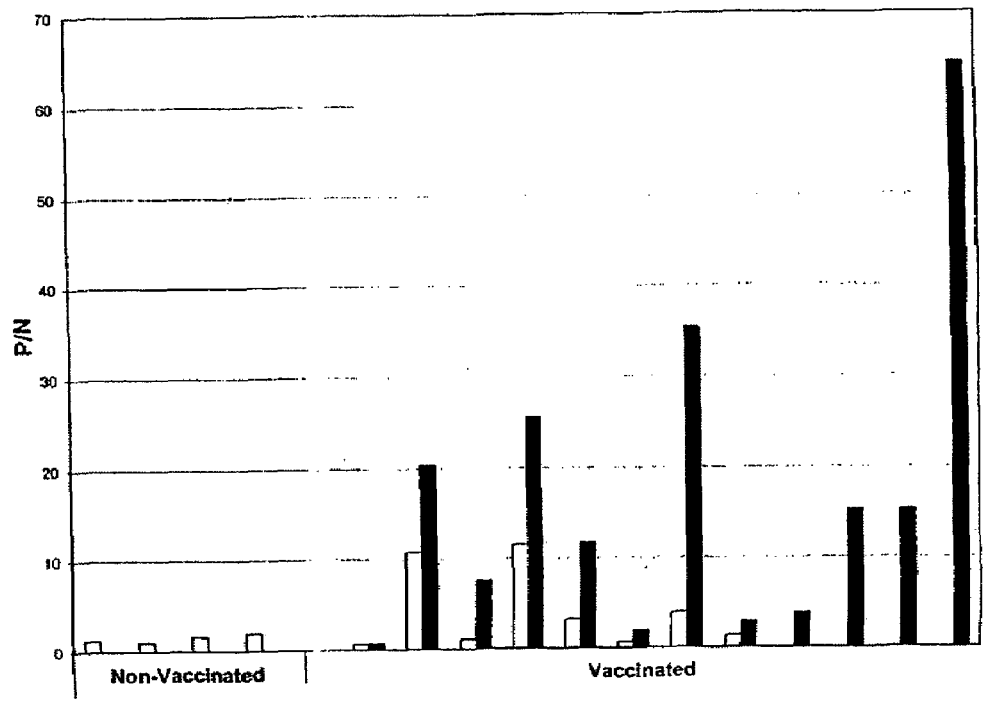
FIG. 13

A.

Specificity control groups tested by polyvalent rE-MI assay

| Specimen Type | Poly Mean P/N | SD | P/N X + 350 | No Tested | No P/N > 4 |
|---|---|---|---|---|---|
| Herpes Simplex | 1.77 | 1.00 | 4.78 | 5 | 0 |
| Epstein Barr | 1.44 | 0.52 | 3.01 | 5 | 0 |
| Syphilis | 21.22 | 15.92 | 68.97 | 10 | 8 |
| Cytonegative | 3.58 | 2.80 | 11.99 | 5 | 2 |
| Human Immuno Deficiency | 3.36 | 5.83 | 20.84 | 10 | 1 |
| Lyme disease | 1.77 | 0.56 | 3.44 | 10 | 0 |
| Ehrlichios Granulocytic | 1.72 | 1.05 | 4.86 | 10 | 2 |
| Antinuclear Antibody | 0.86 | 0.41 | 2.08 | 10 | 0 |
| Rheumatoid Factor - | 0.62 | 0.34 | 1.65 | 5 | 0 |
| Purchased Normal sera | 2.53 | | | 20 | 3 |
| Syph (TP + RPR -) | 5.62 | 10.69 | 37.69 | 10 | 2 |

B.

Polyvalent and IgM rE-MI Results from Spinal Fluids of Patients with Encephalitis due to Flavivirus Infection.

| Diagnosis | Polyvalent MFI | IgM MFI | Polyvalent P/N | IgM P/N | MACELISA P/N |
|---|---|---|---|---|---|
| 1 DEN UT[1] | 1142 | 913 | 16.6 | 13.2 | NA |
| 2 DEN UT | 4066 | 3150 | 58.9 | 45.7 | NA |
| 3 FLAVI UT | 4421 | 3287 | 64.1 | 47.7 | NA |
| 4 FLAVI UT | 589 | 217 | 8.57 | 3.1 | 31.9 |
| 5 FLAVI UT | 9244 | 9040 | 134.0 | 131 | 7.5 |
| 6 WN UT | 1502 | QNS[3] | 21.8 | NA[4] | NA |
| 7 WN C or R[2] | 604 | QNS | 8.8 | NA | NA |
| 8 WN C of R | 4496 | 4879 | 65.2 | 70.1 | NA |
| 9 WN UT | 390 | 39 | 5.6 | .6 | 9.4 |
| 10 WN C of R | 1240 | 1488 | 18.0 | 21.6 | 36.3 |
| 11 WN UT | 196 | 217 | 2.8 | 3.1 | NA |

[1] UT Undetermined time
[2] C or R Current or Recent
[3] QNS Quantity not sufficient for testing
[4] NA Not Available

FIG. 15

Polyvalent and IgM rE-MI on Paired Sera and Spinal Fluids Collected on the Same Day

| | IgG ELISA P/N | MAC ELISA P/N | Sera MFI | G+A+M Sera P/N | CSF MFI 1:2 in PBS | G+A+M CSF P/N | CSF MFI 1:2 in GullSORB[1] | CSF IgM P/N |
|---|---|---|---|---|---|---|---|---|
| Px 1 serum | 3.797 R[2] | 0.448 NR[3] | 8652 | 70.92 | | | | |
| Px 1 csf | | 0.171 NR | | | 908.5 | 41.30 | 931.5 | 39.64 |
| Px 2 serum | 2.476 I[4] | 13.241 R | 4662.5 | 38.22 | | | | |
| Px 2 csf | | 9.391 R | | | 405.5 | 18.43 | QNS | QNS |
| Px 3 serum | 5.446 R | 0.774 NR | 7193 | 58.96 | | | | |
| Px 3 csf | | 1.480 NR | | | 15746 | 715.73 | 7308 | 310.98 |
| Px 4 serum | 1.810 NR | 26.439 R | 2257.5 | 18.50 | | | | |
| Px 4 csf | | 28.697 R | | | 1632.5 | 74.20 | 1050 | 44.68 |
| Px 5 serum | 4.682 R | 1.173 NR | 9012 | 73.87 | | | | |
| Px 5 csf | | 0.316 NR | | | 3838.5 | 174.48 | 3782.5 | 160.96 |
| Px 6 serum | 7.331 R | 0.642 NR | 9979 | 81.80 | | | | |
| Px 6 csf | | 0.409 NR | | | 1629 | 74.05 | 633.5 | 26.96 |
| Px 7 serum | 5.668 R | 0.8484 NR | 6337 | 51.94 | | | | |
| Px 7 csf | | 0.213 NR | | | 2777.5 | 126.25 | 2113.5 | 89.94 |
| Pos. serum Control | | | 7037 | 57.68 | | | | |
| Neg. Serum Control | | | 122 | | | | | |
| Pos. CSF Control | | | | | 1191 | 54.13 | 1889 | 80.38 |
| Neg. CSF Control | | | | | 22 | | 23.5 | |

[1] GullSORB (goat anti-human IgG)
[2] R Reactive
[3] NR Non Reactive
[4] I Indeterminate

FIG. 16

Mouse sera study by MIA using E antigen, NS3 antigen, NS5 antigen with goat anti-mouse polyvalent conjugate

| ID # | E antigen MFI | NS-3 antigen MFI | NS-5 antigen MFI | ID # | E antigen MFI | NS-3 antigen MFI | NS-5 antigen MFI |
|---|---|---|---|---|---|---|---|
| 1 | 56.0 | 78.0 | 469.0 | 50 | 7356.5 | 246.0 | 21734.0 |
| 2 | 92.0 | 135.0 | 532.0 | 51 | 13548.0 | 1400.0 | 23084.0 |
| 3 | 133.0 | 165.5 | 429.0 | 53 | 9808.5 | 206.0 | 10484.0 |
| 4 | 93.0 | 47.0 | 539.0 | 54 | 7226.0 | 271.0 | 15077.0 |
| 5 | 96.0 | 211.0 | 522.0 | 55 | 81.5 | 140.0 | 552.0 |
| 6 | 58.0 | 70.5 | 247.5 | 56 | 88.5 | 168.5 | 746.0 |
| 7 | 74.0 | 43.5 | 295.0 | 57 | 65.0 | 135.0 | 874.0 |
| 8 | 79.0 | 100.0 | 448.0 | 58 | 6642.5 | 239.5 | 1652.0 |
| 9 | 57.5 | 112.5 | 465.0 | 59 | 77.5 | 156.0 | 960.0 |
| 10 | 74.0 | 88.0 | 518.0 | 60 | 81.0 | 117.0 | 590.5 |
| 11 | 160.5 | 182.0 | 536.5 | 61 | 88.5 | 125.0 | 600.5 |
| 12 | 124.0 | 172.0 | 329.0 | 62 | 80.5 | 122.0 | 765.5 |
| 13 | 96.5 | 338.0 | 555.0 | 63 | 7127.5 | 93.5 | 4236.0 |
| 14 | 85.0 | 52.0 | 396.0 | 64 | 79.0 | 137.0 | 807.5 |
| 15 | 104.5 | 120.0 | 686.0 | | | | |
| 16 | 70.5 | 93.5 | 376.0 | | | | |
| 17 | 120.0 | 160.0 | 607.0 | | | | |
| 18 | 234.5 | 150.5 | 682.5 | | | | |
| 19 | 152.5 | 208.0 | 738.5 | | | | |
| 20 | 400.5 | 212.0 | 751.5 | | | | |
| 21 | 328.0 | 338.0 | 976.0 | | | | |
| 22 | 409.0 | 297.0 | 966.0 | | | | |
| 23 | 493.5 | 115.0 | 836.0 | | | | |
| 24 | 553.0 | 158.0 | 913.0 | | | | |
| 25 | 920.5 | 110.0 | 699.0 | | | | |
| 26 | 574.0 | 202.0 | 830.5 | | | | |
| 27 | 296.0 | 171.0 | 871.0 | | | | |
| 28 | 1332.5 | 209.5 | 952.0 | | | | |
| 29 | 2131.0 | 110.0 | 767.0 | | | | |
| 30 | 1348.5 | 54.0 | 1179.0 | | | | |
| 31 | 1288.0 | 83.0 | 1694.0 | | | | |
| 32 | 1739.0 | 96.5 | 1696.0 | | | | |
| 33 | 72.5 | 120.0 | 572.0 | | | | |
| 34 | 91.5 | 189.5 | 536.0 | | | | |
| 35 | 74.0 | 128.5 | 832.0 | | | | |
| 36 | 9541.0 | 241.5 | 22004.0 | | | | |
| 37 | 9368.0 | 855.0 | 8992.0 | | | | |
| 38 | 7283.0 | 240.5 | 23180.0 | | | | |
| 39 | 9929.5 | 364.5 | 23805.0 | | | | |
| 40 | 4615.5 | 217.0 | 12511.0 | | | | |
| 41 | 5827.0 | 285.0 | 15773.0 | | | | |
| 43 | 2501.5 | 711.0 | 17486.0 | | | | |
| 44 | 2177.5 | 579.0 | 8985.0 | | | | |
| 45 | 13731.5 | 305.0 | 22491.0 | | | | |
| 46 | 5674.0 | 232.5 | 22123.0 | | | | |
| 47 | 13299.5 | 668.5 | 23032.5 | | | | |
| 48 | 9109.5 | 289.5 | 20644.5 | | | | |
| 49 | 5647.0 | 190.0 | 11376.0 | | | | |

FIG. 18

NS-5 bead 52 vs 23 Positive West Nile Virus Patient Sera

| Assay ID | MIA Poly MFI NS-5 bead 32 | MIA Poly MFI NS-3 bead 32 | MIA Poly MFI E prot bead 73 | P/N | MIA IgM MFI E prot bead 73 | P/N | ELISA WN IgG | P/N | ELISA WN IgM | P/N | IFA Other |
|---|---|---|---|---|---|---|---|---|---|---|---|
| 1 | 19152.5 | 1114.5 | 5526 | 23.82 | 46.0 | 1.70 | P | 22.088 | P | 16.547 | ND |
| 2 | 11141.5 | 2075.5 | 7334 | 31.61 | 58.5 | 2.17 | P | 22.901 | P | 9.736 | P (SLE) |
| 3 | 3559.5 | 595.5 | 7906 | 34.08 | 79.5 | 2.94 | P | 19.376 | P | 16.112 | P (SLE) |
| 4 | 18598.5 | 785.50 | 3383.5 | 14.58 | 28.0 | 1.04 | P | 17.039 | P | 19.524 | ND |
| 5 | 11156.5 | 1373.00 | 1438 | 6.09 | 1301.5 | 9.36 | P | 5.189 | P | 14.859 | ND |
| 6 | 16613.5 | 1472 | 4015.5 | 17.01 | 323.0 | 2.32 | P | 12.94 | P | 10.581 | P (SLE/LAC) |
| 7 | 13215 | 1528.5 | 3528 | 14.95 | 171.0 | 0.74 | P | 10.096 | P | 15.42 | ND |
| 8 | 18378.5 | 4638.5 | 9605.5 | 32.56 | 629.5 | 2.73 | P | 6.824 | P | 11.027 | P (SLE) |
| 9 | 13870 | 1129 | 20304 | 68.83 | 218.0 | 0.94 | P | 22.835 | P | 13.459 | ND |
| 10 | 18454.5 | 4936 | 10829.5 | 36.71 | 25.0 | 0.18 | P | 18.756 | P | 14.485 | P (SLE) |
| 11 | 18690 | 4162.5 | 10311 | 34.95 | 1055.0 | 7.59 | P | 19.535 | P | 10.537 | |
| 12 | 16793 | 4737 | 10877.5 | 36.87 | 2795.0 | 20.11 | P | 19.871 | P | 9.841 | |
| 13 | 13798.5 | 1396.5 | 10396 | 35.24 | 3964.5 | 28.52 | P | 22.472 | P | 10.331 | |
| 14 | 9524 | 768 | 10845 | 36.76 | QNS | QNS | P | 21.619 | P | 10.594 | |
| 15 | 4131.5 | 1100.5 | 7892.5 | 26.75 | 2943.5 | 21.18 | P | 8.462 | P | 15.004 | |
| 16 | 17687 | 4855 | 8475.5 | 28.73 | 1445.5 | 10.40 | P | 17.764 | P | 14.308 | |
| 17 | 3417 | 887 | 4901.5 | 16.93 | 313.5 | 2.26 | P | 9.694 | P | 8.676 | |
| 18 | 5561.5 | 884 | 3685 | 25.15 | pending | | P | 4.81 | P | 8.587 | |
| 19 | 16529 | 3372.5 | 9713 | 66.30 | pending | | P | 14.904 | P | 8.521 | |
| 20 | 15778 | 586.5 | 3741 | 25.54 | pending | | P | 5.418 | P | 20.56 | |
| 21 | 10346.5 | 698.5 | 5217 | 4.3 | pending | | P | 5.379 | P | 22.062 | |
| 22 | 11725.5 | 1015.5 | 13920 | 11.4 | pending | | P | 9.565 | P | 25.863 | |
| 23 | 17745 | 1873 | 6897 | 5.7 | pending | | P | 6.307 | P | 16.397 | |

Interassay control
rWNV-E

| | | |
|---|---|---|
| bead 52 | WN Pos | 20046 |
| | WN Neg | 2139.5 |

FIG. 19

Paired Dengue Sera Survey

| NY Id # | NS-5 MIA MFI | NS-3 MIA P/N | E-Prot 73 MIA MFI | E-Prot MIA P/N |
|---|---|---|---|---|
| 1 | 1224.5 | 566.5 | 279.5 | 1.03 |
| 2 | 1368 | 552 | 2015.5 | 7.44 |
| 3 | 2324.5 | 542 | 1439.5 | 5.31 |
| 4 | 2613.5 | 482.5 | 2950.5 | 10.89 |
| 5 | 5677 | 308.5 | 6586.5 | 24.30 |
| 6 | 2471.5 | 324.5 | 4893.5 | 18.06 |
| 7 | 1347.5 | 400 | 179.5 | 0.66 |
| 8 | 5749.5 | 366 | 1553.5 | 5.73 |
| 9 | 673.5 | 490.5 | 234.5 | 0.87 |
| 10 | 714.5 | 452 | 1496.5 | 5.52 |
| 11 | 809.5 | 273.5 | 112.5 | 0.42 |
| 12 | 952.5 | 341.5 | 1081 | 3.99 |
| 13 | 2432 | 323 | 298 | 1.10 |
| 14 | 4935 | 147 | 2860 | 10.55 |
| 15 | 720 | 249 | 874.5 | 3.23 |
| 16 | 829 | 290.5 | 558 | 2.06 |
| 17 | 863.5 | 373 | 3459 | 12.76 |
| 18 | 1863.5 | 462.5 | 4825.5 | 17.81 |
| 19 | 1831.5 | 370.5 | 1365.5 | 5.04 |
| 20 | 1754.5 | 301 | 6685.5 | 24.67 |
| 21 | 4657.5 | 505.5 | 7473.5 | 27.58 |
| 22 | 1722.5 | 323.5 | 5013 | 18.50 |
| 23 | 841 | 599.5 | 5343.5 | 19.72 |
| 24 | 794 | 629.5 | 6104.5 | 22.53 |
| 25 | 3833 | 429.5 | 824.5 | 3.04 |
| 26 | 2760.5 | 360.5 | 1549 | 5.72 |
| 27 | 677.5 | 370.5 | 5577.5 | 20.58 |
| 28 | 756.5 | 532 | 4720 | 17.42 |
| 29 | 1548 | 341.5 | 4806.5 | 17.74 |
| 30 | 1586.5 | 208 | 8625.5 | 31.83 |
| 31 | 945 | 500.5 | 6159 | 22.73 |
| 32 | 1127.5 | 665.5 | 6416.5 | 23.68 |
| 33 | 1426.5 | 452.5 | 255 | 0.94 |
| 34 | 1554 | 504 | 3107.5 | 11.47 |

Controls

E-Prot 1/23/2003
WN (+) 7013.5
P/N = 25.88

NS5 Specificity Study 2/12/03 RHB

| Assay Id | NS-5: 52 MFI | E prot MFI | (7/10/02) P/N |
|---|---|---|---|
| Syp 1 | 1736 | 49.5 | 0.18 |
| Syp 2 | 3374.5 | 70 | 0.26 |
| Syp 3 | 2111.5 | 10259.5 | 37.38 |
| Syp 4 | 2357 | 6839 | 24.91 |
| Syp 5 | 1031.5 | 233.5 | 0.85 |
| Syp 6 | 3079 | 7541 | 27.47 |
| Syp 7 | 6.5 | 1052.5 | 3.83 |
| Syp 8 | 1584 | 186 | 0.68 |
| Syp 9 | 17 | 172.5 | 0.63 |
| Syp 10 | 3328.5 | 345 | 1.26 |
| (7/10/02) | | | |
| Ly 1 | 2768 | 342.5 | 1.44 |
| Ly 2 | 1932.5 | 500.5 | 2.11 |
| Ly 3 | 3515 | 321.5 | 1.35 |
| Ly 4 | 1997 | 298.5 | 1.26 |
| Ly 5 | 2288 | 294.5 | 1.24 |
| Ly 6 | 1814.5 | 188 | 0.79 |
| Ly 7 | 2615.5 | 636 | 2.68 |
| Ly 8 | 1587 | 426.5 | 1.8 |
| Ly 9 | 2152.5 | 408 | 1.72 |
| Ly 10 | 2492 | 300.5 | 1.27 |
| (7/12/02) | | | |
| HIV 1 | 1291.5 | 3256.5 | 19.68 |
| HIV 2 | 761 | 41 | 0.25 |
| HIV 3 | 1264 | 100 | 0.60 |
| HIV 4 | 3805 | 276.5 | 1.67 |
| HIV 5 | 1047 | 69 | 0.42 |
| HIV 6 | 1105.5 | 505.5 | 3.05 |
| HIV 7 | 299 | 316 | 1.91 |
| HIV 8 | 1911.5 | 505.5 | 3.05 |
| HIV 9 | 1284.5 | 113 | 0.68 |
| FP → HIV10 | 7517 | 375 | 2.27 |
| (7/10/02) | | | |
| HGE1 | 1935 | 606.5 | 2.55 |
| HGE2 | 2585 | 297 | 1.25 |
| HGE3 | 1244.5 | 262 | 1.1 |
| HGE4 | 1045.5 | 158 | 0.67 |
| HGE5 | 3426.5 | 302 | 1.27 |
| HGE6 | 1883.5 | 73.5 | 0.31 |
| HGE7 | 2274 | 187.5 | 0.79 |
| HGE8 | 1370.5 | 334 | 1.41 |
| HGE9 | 1369.5 | 311.5 | 1.31 |
| HGE10 | 3188 | 696 | 2.93 |

| | Assay Id | NS-5: 52 MFI | E prot MFI | (7/10/02) P/N |
|---|---|---|---|---|
| | ANA 1 | 1905.5 | 165.5 | 0.7 |
| | ANA 2 | 2824.5 | 341.5 | 1.44 |
| | ANA 3 | 942.5 | 252.5 | 1.06 |
| | ANA 4 | 736 | 157 | 0.66 |
| | ANA 5 | 2256.5 | 279 | 1.17 |
| | ANA 6 | 1384.5 | 109 | 0.46 |
| | ANA 7 | 1201 | 147 | 0.62 |
| | ANA 8 | 477 | 139.5 | 0.59 |
| | ANA 9 | 1351 | 66 | 0.28 |
| | ANA 10 | 3723 | 97.5 | 0.41 |
| | (7/10/02) | | | |
| | RF 1 | 85 | 27 | 0.11 |
| | RF 2 | 404 | 60 | 0.25 |
| | RF 3 | 1235.5 | 165 | 0.69 |
| | RF 4 | 667.5 | 109 | 0.46 |
| | RF 5 | 1377 | 197 | 0.83 |
| | RF 6 | 603 | 196.5 | 0.83 |
| | (7/17/02) | | | |
| | HSV 1 | 1031 | 238 | 0.97 |
| | HSV 2 | 1843 | 156.5 | 0.64 |
| | HSV 3 | 2792.5 | 329 | 1.33 |
| | HSV 4 | 2796.5 | 584 | 2.37 |
| | HSV 5 | 1045.5 | 611.5 | 2.48 |
| | (7/17/02) | | | |
| | CMV 1 | 873 | 384.5 | 1.56 |
| | CMV 2 | 3479.5 | 523 | 2.12 |
| | CMV 3 | 809 | 193.5 | 0.78 |
| | CMV 4 | 7 | 2222.5 | 9.02 |
| | CMV 5 | 2898 | 857.5 | 3.48 |
| | (7/17/02) | | | |
| | EBV 1 | 1737.5 | 529.5 | 2.15 |
| | EBV 2 | 1984 | 357 | 1.45 |
| | EBV 3 | 1110.5 | 383 | 1.55 |
| | EBV 4 | 2451 | 194 | 0.79 |
| | EBV 5 | 2727 | 226 | 0.92 |
| | (7/12/02) | | | |
| Vaccine Recipients | JE 10 | 2313.5 | 3383 | 20.44 |
| | JE 11 | 1306 | 1264 | 7.64 |
| | JE 12 | 3260 | 4250 | 25.68 |
| | JE 13 | 638 | 1941 | 11.73 |
| | JE 14 | 1271 | 335 | 2.02 |
| | JE 15 | 3316 | 5862.5 | 35.42 |
| | JE 17 | 1145 | 645 | 3.9 |
| | JE 18 | 1247 | 2540.5 | 15.35 |
| | JE 19 | 1179 | 2527 | 15.27 |
| | JE 20 | 656.5 | 10869 | 64.59 |

FIG. 21

West Nile Virus Case Study-MIA vs. Current Diagnostic Testing Methods

| | | | NYS Current Methods | | | Microsphere Immunoassay (8/27/02) | | | | (2/23/03) |
|---|---|---|---|---|---|---|---|---|---|---|
| ID | Coll. Date | Days from Onset | IgG ELISA P/N | MAC ELISA P/N | SLE IFA G | WN PRNT | MIA Poly Ig's MFI P/N | | MIA IgM MFI P/N | | NS-5 52 MFI |
| 1 | 9-7-01 | -4 d | 1.033 NR | 4.413 IND | <16 | N | 457.5 | 2.56 | 47.5 | 3.65 | 2302 |
| 2 | 9-12-01 | +1 d | 0.934 NR | 0.443 NR | >=16 |  | 338.5 | 1.89 | 27 | 2.08 | 2179 |
| 3 | 9-28-01 | +17 d | 4.848 R | 26.307 R | >=256 | P | 8310 | 46.29 | 751 | 57.77 | 12097.5 |
| 4 | 11-21-01 | +71 d | 8.072 R | 12.021 R | >=16 | P | 10558 | 58.82 | 204 | 15.65 | 13749 |
| 5 | 5-28-02 | +259 d | (****Not done-Employee Screen) | | | | 6371 | 35.49 | 67 | 5.15 | 4055 |
| 6 | 11-15-02 | +431 d | 9.69 R | 8.676 R | >=16 | nd | 4902 | 16.93 | 313.5 | 2.26 | 3510 |

Neg.

Patient Onset = 9/11/01   Pos.

|  | Positive Sera Control | 6532 | | 95 | | 17832 |
|---|---|---|---|---|---|---|
|  | Negative Sera Control | 179.5 | 36.39 | 13 | 7.30769 | 1400 |

Multiplex Data 2/24/03 RHB

| ID | MFI NS-5 52 | MFI E Prot 17 | E-Prot P/N |
|---|---|---|---|
| 1 | 2364.5 | 505 | 1.59 |
| 2 | 2052 | 497 | 1.57 |
| 3 | 10880 | 1482.5 | 4.68 |
| 4 | 10508.5 | 2463 | 7.77 |
| 5 | 3136 | 1546 | 4.88 |
| 6 | 1331.5 | 538.5 | 1.70 |
| 7 | 1331.5 | 1358.5 | 4.29 |
| WN Pos | 15341 | 2524 | 7.96 |
| WN Neg | 1208 | 317 | |

Singlet Data Bead 17-E prot 022603 RHB

| | MFI E Prot 17 |
|---|---|
| 1 | 391 |
| 2 | 343.5 |
| 3 | 1142.5 |
| 4 | 2110.5 |
| 5 | 1038.5 |
| 6 | 440 |
| 7 | 914 |

FIG. 22

Specificity of the NS5-based MIA tested against various human sera

| Specimen type | No. of sera | Mean MFI (range) | SD | No. positive[a] |
|---|---|---|---|---|
| Syphilis (*T. pallidum* positive) | 10 | 1,862 (7–3,375) | 1,241 | 0 |
| *B. burgdorferi* infection | 10 | 2,312 (1,567–2,768) | 563 | 0 |
| HIV infection | 10 | 2,009 (299–7,517) | 2,127 | 1 |
| *A. phagocytophilum* infection | 10 | 2,030 (1,046–3,427) | 825 | 0 |
| Antinuclear antibody positive | 10 | 1,680 (477–3,723) | 1,680 | 0 |
| Rheumatoid factor positive | 6 | 730 (85–1,377) | 730 | 0 |
| Herpes simplex virus positive | 5 | 1,902 (1,031–2,797) | 1,902 | 0 |
| Cytomegalovirus infection | 5 | 1,613 (7–3,480) | 1,492 | 0 |
| Epstein-Barr virus infection | 5 | 2,002 (1,111–2,727) | 631 | 0 |
| JE virus vaccine recipients | 10 | 1,633 (638–3,316) | 984 | 0 |
| YF virus vaccine recipients | 19 | 2,563 (966–5,056) | 1,179 | 1 |
| Normal | 20 | 1,811 (970–3,878) | 853 | 0 |
| Total | 120 | | | 2 |

[a] The cutoff for positivity for NS5 is 4,366.

FIG. 25

Cross-reactivity of WNV NS5 and E protein with DENV patient sera

| Sample[a] | MFI | | Titer | |
|---|---|---|---|---|
| | NS5[b] | E protein[c] | E protein MIA[d] | HI |
| 1A | 1,225 | 280 | <100 | 10 |
| 1B | 1,368 | 2,016 | 200 | 160 |
| 2A | 2,325 | 1,440 | 100 | 20 |
| 2B | 2,614 | 2,951 | 400 | 80 |
| 3A | 5,677 | 6,587 | 25,600 | 10,240 |
| 3B | 2,472 | 4,894 | 3,200 | 320 |
| 4A | 1,348 | 180 | <100 | — |
| 4B | 5,750 | 1,554 | 200 | 640 |
| 5A | 674 | 235 | <100 | — |
| 5B | 715 | 1,497 | 200 | 40 |
| 6A | 810 | 113 | <100 | — |
| 6B | 953 | 1,081 | 100 | 160 |
| 7A | 2,432 | 289 | <100 | — |
| 7B | 4,935 | 2,860 | 100 | 80 |
| 8A | 720 | 875 | <100 | 20 |
| 8B | 829 | 558 | <100 | 80 |
| 9A | 864 | 3,459 | 400 | 160 |
| 9B | 1,864 | 4,826 | 1600 | 160 |
| 10A | 1,832 | 1,366 | 100 | 20 |
| 10B | 1,755 | 6,686 | 6,400 | 10,240 |
| 11A | 4,658 | 7,474 | 51,200 | 10,240 |
| 11B | 1,723 | 5,013 | 6,400 | 1,280 |
| 12A | 841 | 5,344 | 3200 | 640 |
| 12B | 794 | 6,105 | 12,800 | 2,560 |
| 13A | 3,833 | 825 | 100 | 80 |
| 13B | 2,761 | 1,549 | 800 | 80 |
| 14A | 678 | 5,578 | 6400 | 2,560 |
| 14B | 757 | 4,720 | 1600 | 80 |
| 15A | 1,548 | 4,807 | 1600 | 160 |
| 15B | 1,587 | 8,626 | 51,200 | 10,240 |
| 16A | 945 | 6,159 | 3,200 | 640 |
| 16B | 1,128 | 6,417 | 6,400 | 80 |
| 17A | 1,427 | 225 | <100 | |
| 17B | 1,554 | 3,108 | 800 | 800 |

[a] Seventeen pairs of acute-phase (A) and convalescent-phase (B) sera from DEN-infected individuals were tested.

[b] The cutoff for positivity for NS5 is 4,366. There were 3 positive samples out of 34 (8.8%).

[c] The cutoff for positivity for E protein is 1,084 (Wong et al., submitted). There were 24 positive samples out of 34 (71%).

[d] E protein MIA titers represent the maximal dilutions of patient sera that were reactive in the E-protein-based MIA above the MFI cutoff of 1,084.

FIG. 26

Cross-reactivity of WNV NS5 and E protein with SLEV patient sera

| Sample[a] | MFI | | PRNT titer | |
|---|---|---|---|---|
| | NS5[b] | E protein[c] | SLE virus | WNV |
| 1A | 550 | 953 | 640 | 40 |
| 1B | 892 | 1,347 | 1,280 | 40 |
| 2A | 1,081 | 437 | 320 | <10 |
| 2B | 606 | 272 | 320 | <10 |
| 3A | 7,314 | 492 | 320 | 20 |
| 3B | 5,894 | 982 | 640 | 40 |
| 4A | 1,157 | 522 | 640 | 10 |
| 4B | 2,315 | 828 | 1,280 | 40 |
| 5A | 643 | 1,582 | 640 | <10 |
| 5B | 576 | 1,185 | 1,280 | <10 |
| 6A | 924 | 329 | 10 | <10 |
| 6B | 2,093 | 1,020 | 1,280 | 10 |
| 7A | 858 | 456 | 20 | <10 |
| 7B | 738 | 214 | 320 | 10 |
| 8A | 215 | 59 | 40 | <10 |
| 8B | 324 | 323 | 640 | 20 |
| 9A | 834 | 378 | 80 | <10 |
| 9B | 631 | 550 | 160 | 10 |
| 10A | 751 | 196 | 10 | <10 |
| 10B | 1,272 | 284 | 40 | <10 |
| 11A | 778 | 688 | 160 | 10 |
| 11B | 691 | 715 | 320 | 20 |
| 12A | 733 | 864 | 640 | 40 |
| 12B | 1,148 | 1,388 | 640 | <10 |
| 13A | 734 | 966 | 320 | <10 |
| 13B | 1,731 | 1,645 | 320 | 10 |
| 14A | 931 | 409 | 160 | 10 |
| 14B | 802 | 415 | 160 | <10 |
| 15A | 1,241 | 522 | 40 | <10 |
| 15B | 586 | 678 | 320 | 10 |
| 16A | 980 | 3,057 | 5,120 | 640 |
| 16B | 1,420 | 2,740 | 2,560 | 640 |
| 17A | 1,328 | 1,490 | 5,120 | 1,280 |
| 17B | 1,912 | 2,845 | 1,280 | 2,560 |
| 18A | 175 | 1,679 | 40 | <10 |
| 18B | 188 | 1,476 | 80 | <10 |
| 19A | 398 | 489 | 40 | <10 |
| 19B | 628 | 687 | 160 | <10 |
| 20A | 1,281 | 591 | 640 | 10 |
| 20B | 2,296 | 637 | 1,280 | <10 |

[a] Twenty pairs of acute-phase (A) and convalescent-phase (B) sera from SLE-infected individuals were tested.

[b] The cutoff for positivity for NS5 is 4,366. There were 2 positive samples out of 40 (5%).

[c] The cutoff for positivity for E protein is 1,084 (Wong et al., submitted). There were 11 positive samples out of 40 (28%).

FIG. 27

Wild Bird MIA- Sera samples

|  | Poly conjugate | | Prot A treated | |
|---|---|---|---|---|
| Assay ID | NS 5 MFI | E MFI | NS 5 MFI | E MFI |
| 1 | 491 | 594.5 | 192 | 367.5 |
| 2 | 237.5 | 149.5 | 131 | 100 |
| 7 | 159 | 148 | 65.5 | 88.5 |
| 8 | 174.5 | 279 | 122.5 | 261.5 |
| 10 | 92 | 538 | 48 | 298 |
| 14 | 98 | 120.5 | 64.5 | 73 |
| 18 | 441.5 | 699 | 321.5 | 498 |
| 19 | 1294 | 234.5 | 634.5 | 89.5 |
| 22 | 74.5 | 55 | 43 | 40 |
| 25 | 122 | 83.5 | 44 | 44 |
| 30 | 38.5 | 35 | 26 | 35.5 |
| 36 | 57.5 | 31 | 34 | 28 |
| 50 | 290 | 234 | 131 | 167 |
| 80 | 98.5 | 135 | 69 | 80 |
| 115 | 65 | 88 | 41 | 53.5 |
| Crow 1 | 2119.5 | 3558.5 | 1160.5 | 2338.5 |
| Crow 2 | 1925.5 | 1070 | 1259 | 1228.5 |
| Ibis | 196 | 216 | 169.5 | 763.5 |
| Heron | 421.5 | 789.5 | 659 | 790.5 |
| Argus | 169 | 2169 | 91 | 2367.5 |
| Cormorant | 6320.5 | 1280 | 4642.5 | 1078.5 |
| Pelican | 547 | 609 | 362.5 | 255.5 |
| Goose | 754 | 7246 | 374.5 | 5129 |
| Swan | 1643 | 1238.5 | 6000 | 2074 |
| Owl | 2884 | 1513 | 1903 | 853 |
| Ostrich | 482.5 | 472 | 425.5 | 801 |
| Crane | 1506.5 | 1050.5 | 450 | 560.5 |

FIG. 28

Yellow Fever sera from CDC tested against E and NS5 antigens
(polyvalent and IgM)

| ID # | E poly MFI | E IgM MFI | NS-5 poly MFI | NS-5 IgM MFI |
| --- | --- | --- | --- | --- |
| 1 | *695.5 | 326.0 | 2254.0 | 1215.0 |
| 2 | *1852.0 | 910.0 | 2766.5 | 1427.0 |
| 3 | *1101.0 | 455.0 | 2147.5 | 893.0 |
| 4 | 204.0 | 111.0 | 965.5 | 519.0 |
| 5 | *745.5 | 292.5 | 1124.0 | 561.0 |
| 6 | 334.5 | 203.0 | 1501.0 | 733.0 |
| 7 | *886.0 | 388.5 | 4313.5 | 1958.0 |
| 8 | 237.0 | 155.0 | 1793.0 | 1031.5 |
| 9 | *3157.0 | 2001.5 | 4147.0 | 4971.5 |
| 10 | 388.5 | 351.5 | 1369.5 | 914.0 |
| 11 | 256.5 | 279.5 | 2528.5 | 1685.5 |
| 12 | 194.0 | 238.5 | 1906.5 | 1288.5 |
| 13 | *3927.0 | 2061.0 | 2726.5 | 1893.0 |
| 14 | *1350.0 | 866.5 | 1355.5 | 701.5 |
| 15 | 347.5 | 380.0 | 4075.0 | 2464.5 |
| 16 | 568.0 | 510.5 | 2279.0 | 1206.0 |
| 17 | 628.0 | 407.0 | 3410.5 | 1573.5 |
| 18 | *713.5 | 538.5 | *5055.5 | 3437.5 |
| 19 | *891.0 | 401.0 | 2968.5 | 1450.5 |
| WN + | 2602.0 | 1537.0 | 15419.5 | 9033.5 |
| WN - | 339.0 | 177.5 | 1780.5 | 474.5 |
| Cutoff | 676.25 | x | 4368.85 | x |

*MFI values are above the established cutoffs.
Cutoff values for IgM have yet to be established.

FIG. 29

West Nile Virus MIA of Horse Sera (Blinded)
(Poly Ig's)

| Sample # | E (117)MFI | NS 5 (52)MFI | NS 3 MFI | Category | IgM O.D. | P/N | MAC | PRNT | |
|---|---|---|---|---|---|---|---|---|---|
| 1 | 932 | 4567 | 1522 | IgM Positive Non-vac | 0.503 | 4.191 | Positive | Positive | Clinically ill |
| 2 | 895 | 169 | 81 | IgM Positive Non-vac | 1.1685 | 6.023 | Positive | Positive | Clinically ill |
| 3 | 1945.5 | 3681.5 | 573 | IgM Positive Non-vac | 0.476 | 3.39 | Positive | Positive | Clinically ill |
| 4 | 274 | 147 | 85 | IgM Positive Non-vac | 1.4545 | 16.347 | Positive | Positive | Clinically ill |
| 5 | 1806 | 259 | 290 | IgM Positive Non-vac | 0.8475 | 10.463 | Positive | Positive | Clinically ill |
| 6 | 296 | 543.5 | 55 | IgM Positive Non-vac | 0.7231 | 7.546875 | Positive | Positive | Clinically ill |
| Mean | 1024.8 | 1564.5 | 434.3 | | | | | | |
| SD | 718.1 | 2016.0 | 569.1 | | | | | | |
| Mean +SD | 1742.8 | 3580.5 | 1002.5 | | | | | | |
| 7 | 70 | 82.5 | 29 | Pre-bleeds from WNV Neg county | 0.234 | 2.445 | Negative | | Healthy Non-exposed |
| 8 | 63 | 78 | 36.5 | Pre-bleeds from WNV Neg county | 0.020 | 0.975 | Negative | | Healthy Non-exposed |
| 9 | 72 | 71 | 31.5 | Pre-bleeds from WNV Neg county | 0.002 | 0.114 | Negative | | Healthy Non-exposed |
| 10 | 64 | 247.5 | 43 | Pre-bleeds from WNV Neg county | 0.092 | 1.219 | Negative | | Healthy Non-exposed |
| 11 | 128 | 203 | 201 | Pre-bleeds from WNV Neg county | 0.008 | 2.286 | Negative | | Healthy Non-exposed |
| 12 | 64 | 63.5 | 43 | Pre-bleeds from WNV Neg county | 0.123 | 2.526 | Negative | | Healthy Non-exposed |
| 13 | 92 | 112.5 | 256 | Pre-bleeds from WNV Neg county | 0.094 | 1.438 | Negative | | Healthy Non-exposed |
| 14 | 67 | 109.5 | 37 | Pre-bleeds from WNV Neg county | 0.085 | 1.142 | Negative | | Healthy Non-exposed |
| 15 | 63.5 | 63 | 49.5 | Pre-bleeds from WNV Neg county | 0.055 | 1.982 | Negative | | Healthy Non-exposed |
| 16 | 63.5 | 125 | 81 | Pre-bleeds from WNV Neg county | 0.093 | 0.939 | Negative | | Healthy Non-exposed |
| 17 | 92.5 | 115 | 37 | Pre-bleeds from WNV Neg county | 0.039 | 0.886 | Negative | | Healthy Non-exposed |
| Mean | 76.3 | 115.5 | 76.8 | | | | | | |
| SD | 20.3 | 59.3 | 77.3 | | | | | | |
| Mean +SD | 96.6 | 174.8 | 154.0 | | | | | | |
| 18 | 269.5 | 244 | 37.3 | WN IgM Negative/Prevaccination | 0.240 | 1.023 | Negative | | Healthy Non-exposed ath the time of vaccination |
| 19 | 63 | 69 | 89.5 | WN IgM Negative/Prevaccination | -0.003 | 0.455 | Negative | | Healthy Non-exposed ath the time of vaccination |
| 20 | 3513 | 483 | 152 | WN IgM Positive/Prevaccination | 1.498 | 22.358 | Positive | | Healthy Exposed at the time of vaccination |
| 21 | 66 | 239 | 43 | WN IgM Negative/Prevaccination | 0.036 | 1.108 | Negative | | Healthy Non-exposed ath the time of vaccination |
| 22 | 7195 | 883.5 | 31.5 | WN IgM Positive/Prevaccination | 1.474 | 13.965 | Positive | | Healthy Exposed at the time of vaccination |
| Mean | 253.9 | 283.5 | 60.6 | | | | | | |
| SD | 268.1 | 234.0 | 30 | | | | | | |
| Mean +SD | 522.0 | 518 | 73.6 | | | | | | |
| 23 | 4303 | 2123 | 1079 | WN IgM Positive Postvaccination | 1.071 | 2.333 | Positive | | Healthy Exposed at the time of vaccination |
| 24 | 2683 | 1744 | 2008 | WN IgM Positive Postvaccination | 1.552 | 33.373 | Positive | | Healthy Exposed at the time of vaccination |
| 25 | 7231.5 | 2376.5 | 1297.6 | WN IgM Positive Postvaccination | 0.721 | 9.945 | Positive | | Healthy Exposed at the time of vaccination |
| 26 | 2509.5 | 875 | 2374.5 | WN IgM Positive Postvaccination | 0.449 | 3.606 | Positive | | Healthy Exposed at the time of vaccination |
| 27 | 5177.5 | 11146.5 | 11112 | WN IgM Positive Postvaccination | 0.449 | 5.470 | Positive | | Healthy Exposed at the time of vaccination |
| Mean | 3428.9 | 1653.0 | 1574.2 | | | | | | |
| SD | 1273.4 | 635.3 | 584.0 | | | | | | |
| Mean +SD | 4702.3 | 2288.3 | 2158.2 | | | | | | |
| 28 | 296 | 100 | 41.5 | IgM Negative Postvaccination | 0.040 | 0.414 | Negative | | Healthy Non-exposed |
| 29 | 104.5 | 94.5 | 95 | IgM Negative Postvaccination | 0.004 | 0.138 | Negative | | Healthy Non-exposed |
| 30 | 1094 | 41 | 26.5 | IgM Negative Postvaccination | 0.116 | 0.840 | Negative | | Healthy Non-exposed |
| 31 | 61 | 59 | 28.5 | IgM Negative Postvaccination | 0.067 | 0.522 | Negative | | Healthy Non-exposed |
| 32 | 120 | 364.5 | 79.5 | IgM Negative Postvaccination | 0.190 | 0.785 | Negative | | Healthy Non-exposed |
| 33 | 60.5 | 108.5 | 45.5 | IgM Negative Postvaccination | 0.007 | 0.245 | Negative | | Healthy Non-exposed |
| 34 | 836.5 | 84.5 | 63 | IgM Negative Postvaccination | 0.050 | 0.717 | Negative | | Healthy Non-exposed |
| 35 | 127 | 198.5 | 65 | IgM Negative Postvaccination | 0.158 | 0.952 | Negative | | Healthy Non-exposed |
| 36 | 127 | 3504 | 140 | IgM Negative Postvaccination | 0.123 | 0.988 | Negative | | Healthy Non-exposed |
| 37 | 83 | 166 | 11 | IgM Negative Postvaccination | 0.075 | 0.993 | Negative | | Healthy Non-exposed |
| Mean | 291.2 | 472.1 | 58.6 | | | | | | |
| SD | 356.9 | 1069.4 | 38.2 | | | | | | |
| Mean +SD | 558.1 | 1541.4 | 96.7 | | | | | | |

FIG. 30A

Horse West Nile Virus Multiplex

| Horse Id | MFI NS3(21) | MFI NS 5(52) | MFI E(75) | | Previous assay results MFI NS3 | MFI NS 5 | MFI E |
|---|---|---|---|---|---|---|---|
| d0 | 38 | 64 | 49.5 | | 98.5 | 430 | 281 |
| d20 | 51 | 77 | 430 | | 169.5 | 500 | 303.5 |
| d41 | 53 | 66 | 13827 | | 1217 | 424.5 | 273 |
| d49 | 53 | 67 | 17427 | | 1566.5 | 250.5 | 296.5 |
| d78 | 49 | 70 | 13347 | | 1040 | 342 | 312.5 |
| d0 | 38 | 43.5 | 65 | | 264.5 | 2082 | 501.5 |
| d20 | 45.5 | 47 | 168 | 4-9-03 | 242 | 1980.5 | 520 |
| d41 | 39 | 52 | 14347 | E-19,NS5-52 | 1921 | 2144.5 | 597 |
| d49 | 48 | 47 | 18004.5 | NS3-32 | 2721 | 2278 | 629.5 |
| d78 | 35 | 44 | 14353 | | 1897 | 2265.5 | 583.5 |
| d0 | 53 | 112 | 58 | | 45.5 | 832 | 297.5 |
| d20 | 69.5 | 133.5 | 678.5 | | 114.5 | 937 | 343 |
| d41 | 43.5 | 96 | 9680 | | 1232.5 | 863 | 335.5 |
| d49 | 51.5 | 95 | 13811 | | 1372 | 866.5 | 301.5 |
| d78 | 48 | 92 | 8931.5 | | 692.5 | 528 | 190 |
| 02-36646 | 45.5 | 46.5 | 408 | | | | |
| 02-37562 | 381 | 1889.5 | 3831.5 | | | | |
| 02-36729 | 15 | 48.5 | 1978 | | | | |
| 1976 | 38.5 | 233 | 47 | | 59 | 320 | 62 |
| 2761 | 71 | 72 | 70 | | 90 | 122 | 95.5 |
| 2765 | 56 | 67 | 201 | 4- | 231 | 122 | 54 |
| 2874 | 36 | 71.5 | 48 | | 62 | 109 | 5 |
| 2384 | 223 | 126 | 147 | | 171.5 | 176 | 290 |
| 2900 | 34 | 54 | 52 | | 66.5 | 89.5 | 55 |
| 2920 | 41 | 62 | 51.5 | | 72 | 109 | 70 |
| 1 | 182.5 | 3043 | 2071 | | | | |
| 2 | 33.5 | 68 | 1201 | | | | |
| 3 | 94 | 2735 | 2003.5 | | | | |
| 4 | 28.5 | 47.5 | 168 | | | | |
| 5 | 77 | 125.5 | 2087 | | | | |
| 6 | 27 | 368 | 288 | | | | |
| 7 | 28 | 34.5 | 34.5 | | | | |
| 8 | 39 | 41 | 55 | | | | |
| 9 | 20 | 32 | 43 | | | | |
| 10 | 27.5 | 39 | 38.5 | | | | |
| 11 | 51 | 51.5 | 106 | | | | |
| 12 | 34 | 41.5 | 40.5 | | | | |
| 13 | 66 | 45 | 48.5 | | | | |
| 14 | 28.5 | 43.5 | 42 | | | | |
| 15 | 19.5 | 26 | 35 | | | | |
| 16 | 30.5 | 31 | 34 | | | | |
| 17 | 20.5 | 53 | 40 | | | | |
| 18 | 17 | 97 | 36 | | | | |
| 19 | 51 | 29 | 47 | | | | |
| 20 | 34 | 66 | 306 | | | | |
| 21 | 39 | 62.5 | 41 | | | | |
| 22 | 23 | 289.5 | 1003 | | | | |
| 23 | 347.5 | 2598 | 4507 | | | | |
| 24 | 173.5 | 1133 | 3219 | | | | |
| 25 | 165 | 2093 | 2877.5 | | | | |
| 26 | 370 | 463 | 2554 | | | | |
| 27 | 275 | 625 | 6426 | | | | |
| 28 | 36.5 | 74 | 386 | | | | |
| 29 | 45 | 55.5 | 115.5 | | | | |
| 30 | 28.5 | 57 | 1439 | | | | |
| 31 | 31.5 | 43 | 43 | | | | |
| 32 | 73 | 139 | 80 | | | | |
| 33 | 40.5 | 50 | 44 | | | | |
| 34 | 25 | 29.5 | 737 | | | | |
| 35 | 36 | 52 | 136 | | | | |
| 36 | 99.5 | 1688.5 | 94 | | | | |
| 37 | 31 | 60.5 | 70 | | | | |
| | 20 | 34 | 50 | | | | |
| | 23 | 492.5 | 437.5 | | | | |
| | 91.5 | 73 | 1230 | | | | |
| | 30 | 60 | 164.5 | | | | |

FIG. 30B

Detection of flavivirus antibodies by the WNV-E MIA and by ELISA in a blinded serum panel

| Serum no. | Etiologic virus PRN titer | rWNV-E MIA P/N Polyvalent | WN ELISA IgG NYS[3] P/N | WN ELISA IgG CDC P/N | WN ELISA IgM NYS P/N | WN ELISA IgM CDC P/N | DEN ELISA IgG NYS P/N | SLE ELISA IgG CDC P/N | SLE ELISA IgM CDC P/N |
|---|---|---|---|---|---|---|---|---|---|
| 1 | NEG[1] | 1.31 | 2.01 | 1.20 | 1.51 | 1.59 | 0.12 | nd | nd |
| 2 | NEG | 0.79 | 0.78 | nd | 0.93 | 1.17 | 0.08 | nd | nd |
| 3 | NEG | 0.81 | 0.62 | nd | 0.96 | 0.95 | 0.10 | nd | nd |
| 4 | NEG | 1.90 | 0.48 | 0.82 | 11.79 | 5.04 | 0.16 | nd | nd |
| 5 | NEG | 0.86 | 0.96 | 0.89 | 0.46 | 1.26 | 0.14 | nd | nd |
| 6 | NEG | 2.62 | 1.06 | 0.97 | 5.89 | 2.23 | 0.31 | nd | nd |
| 7 | NEG | 1.48 | 0.88 | 0.90 | 1.34 | 1.25 | 0.30 | nd | nd |
| 8 | WN 160 | 5.89 | 8.96 | 4.40 | 5.76 | 4.02 | 0.49 | nd | nd |
| 9 | WN 160 | 45.15 | 13.96 | 5.28 | 16.25 | 8.90 | 2.58 | nd | nd |
| 10 | WN 320 | 42.99 | 12.77 | 5.80 | 13.73 | 6.16 | 3.04 | nd | nd |
| 11 | SLE 2560 | 4.28 | 2.56 | nd | 7.57 | 3.26 | 0.57 | 1.68 | 8.89 |
| 12 | SLE 40 | 0.90 | 1.44 | 1.05 | 1.98 | 1.52 | 0.10 | 1.39 | 4.48 |
| 13 | SLE 1280 | 18.88 | 7.26 | 7.05 | 10.06 | 3.67 | 1.34 | 7.69 | 8.53 |
| 14 | SLE 1280 | 14.34 | 3.17 | 3.63 | 14.33 | 7.00 | 0.86 | 5.45 | 8.69 |
| 15 | SLE 80 | 4.80 | 1.43 | 1.45 | 8.44 | 3.65 | 0.19 | nd | 8.43 |
| 16 | SLE 10 | 0.80 | 0.98 | 0.77 | 3.52 | 1.74 | 0.20 | 0.80 | 2.76 |
| 17 | DEN nd[2] | 49.90 | 20.06 | nd | 12.90 | 1.62 | 10.39 | nd | nd |
| 18 | DEN nd | 15.99 | 3.22 | nd | 13.59 | 1.72 | 1.59 | nd | nd |
| 19 | DEN 160 | 55.23 | 15.85 | nd | 3.85 | nd | 8.28 | nd | nd |

[1] Specimen was negative to neutralizing flavivirus antibodies
[2] Test was not performed on specimen
[3] Tests were performed at the New York State Department of Health, Wadsworth Center, Albany, New York

FIG. 34

Human specificity control sera tested by p lyvalent rWNV-E MIA.

| Specimen Type | n | Mean P/N (range) | P/N > 4.0 | P/N > 5.0 |
|---|---|---|---|---|
| Herpes simplex virus infection | 5 | 1.77 ± 1.00 (0.64-2.83) | 0 | 0 |
| Epstein Barr virus infection | 5 | 1.44 ± 0.52 (0.92-2.31) | 0 | 0 |
| Syphilis panel 1[a] | 10 | 21.22 ± 15.9 (1.15-41.1) | 8 (80%) | 7 (70%) |
| Syphilis panel 2 (TPPA+, RPR-)[b] | 10 | 5.62 ± 10.7 (0.35-32.3) | 2 (20%) | 2 (20%) |
| Cytomegalovirus infection | 5 | 3.58 ± 2.80 (0.89-7.64) | 2 (40%) | 2 (40%) |
| Human immunodeficiency virus infection | 10 | 3.36 ± 5.83 (0.25-19.7) | 1 (10%) | 1 (10%) |
| *B. burgdorferi* infection | 10 | 1.77 ± 0.56 (1.09-3.08) | 0 | 0 |
| *A. phagocytophila* infection | 10 | 1.72 ± 1.05 (0.45-3.78) | 0 | 0 |
| Antinuclear Antibody positive | 10 | 0.86 ± 0.41 (0.37-1.63) | 0 | 0 |
| Rheumatoid Factor positive | 6 | 0.62 ± 0.34 (0.17-1.11) | 0 | 0 |
| Normal sera | 24 | 2.34 ± 1.26 (0.96-4.82) | 4 (17%) | 0 |
| Total: | 105 | | 17 (16%) | 12 (11%) |

[a] Rapid plasma reagin (RPR) positive

[b] *Treponema pallidum* particle agglutination (TPPA) positive, RPR negative

FIG. 35

Detection of anti-flavivirus antibodies in spinal fluid

| Specimen no. | MFI of CSF 1:2 in PBS [a] (IgG+IgA+IgM) | MFI of CSF 1:2 in GullSORB [b] (IgM) | Viral etiology by PRN assays | |
|---|---|---|---|---|
| 1 | 909 | 932 | WN | UT [c] |
| 2 | 1632 | 1050 | WN | C or R [d] |
| 3 | 3838 | 3783 | WN | UT |
| 4 | 1629 | 634 | WN | UT |
| 5 | 2778 | 2114 | WN | UT |
| 6 | 15,746 | 7308 | WN | UT |
| 7 | 4496 | 4879 | WN | C or R |
| 8 | 1240 | 1488 | WN | C or R |
| 9 | 390 | 39 | WN | UT |
| 10 | 196 | 217 | WN | UT |
| 11 | 1142 | 913 | DEN | UT |
| 12 | 4066 | 3150 | DEN | UT |
| 13 | 4421 | 3287 | FLAVI[e] | UT |
| 14 | 589 | 217 | FLAVI | UT |
| 15 | 9244 | 9040 | FLAVI | UT |

[a] Median fluorescent intensity, 100 beads, with polyvalent conjugate
[b] Median fluorescence intensity, 100 beads, following IgG depletion
[c] UT = undetermined time of infection
[d] C or R = current or recent infection
[e] FLAVI = indeterminate flavivirus

```
   1 gctgacaaac ttagtagtgt ttgtgaggat taacaacaat taacacagtg cgagctgttt
  61 cttagcacga agatctcgat gtctaagaaa ccaggagggc ccggcaagag ccgggctgtc
 121 aatatgctaa aacgcggaat gccccgcgtg ttgtccttga ttggactgaa gagggctatg
 181 ttgagcctga tcgacggcaa ggggccaata cgatttgtgt tggctctctt ggcgttcttc
 241 aggttcacag caattgctcc gacccgagca gtgctggatc gatggagagg tgtgaacaaa
 301 caaacagcga tgaaacacct tctgagtttt aagaaggaac tagggacctt gaccagtgct
 361 atcaatcggc ggagctcaaa acaaaagaaa agaggaggaa agaccggaat tgcagtcatg
 421 attggcctga tcgccagcgt aggagcagtt accctctcta acttccaagg gaaggtgatg
 481 atgacggtaa atgctactga cgtcacagat gtcatcacga ttccaacagc tgctggaaag
 541 aacctatgca ttgtcagagc aatggatgtg ggatacatgt gcgatgatac tatcacttat
 601 gaatgcccag tgctgtcggc tggtaatgat ccagaagaca tcgactgttg gtgcacaaag
 661 tcagcagttt acgtcaggta tggaagatgc accaagacac gccactcaag acgcagtcgg
 721 aggtcactga cagtgcagac acacggagaa agcactctag cgaacaagaa gggggcttgg
 781 atggacagca ccaaggccac aaggtacttg gtaaaaacag aatcatggat cttgaggaac
 841 cctggatatg ccctggtggc agccgtcatt ggttggatgc tgggagcaa caccatgcag
 901 agagttgtgt tgtcgtgct attgcttttg gtggcccag cttacagctt caactgcctt
 961 ggaatgagca acagagactt cttggaagga gtgtctggag caacatgggt ggatttggtt
1021 ctcgaaggcg acagctgcgt gactatcatg tctaaggaca agcctaccat cgatgtgaag
1081 atgatgaata tggaggcggc caacctggca gaggtccgca gttattgcta tttggctacc
1141 gtcagcgatc tctccaccaa agctgcgtgc ccgaccatgg agaagctca caatgacaaa
1201 cgtgctgacc cagcttttgt gtgcagacaa ggagtggtgg acaggggctg gggcaacggc
1261 tgcggactat ttggcaaagg aagcattgac acatgcgcca aatttgcctg ctctaccaag
1321 gcaataggaa gaaccatctt gaaagagaat atcaagtacg aagtggccat ttttgtccat
1381 ggaccaacta ctgtggagtc gcacggaaac tactccacac aggttggagc cactcaggca
1441 gggagattca gcatcactcc tgcagcgcct tcatacacac taaagcttgg agaatatgga
1501 gaggtgacag tggactgtga accacggtca gggattgaca ccaatgcata ctacgtgatg
1561 actgttggaa caaagacgtt cttggtccat cgtgagtggt tcatggacct caacctccct
1621 tggagcagtg ctggaagtac tgtgtggagg aacagagaga cgttaatgga gtttgaggaa
1681 ccacacgcca cgaagcagtc tgtgatagca ttgggctcac aagagggagc tctgcatcaa
1741 gctttggctg agccattcc tgtggaattt tcaagcaaca ctgtcaagtt gacgtcgggt
1801 catttgaagt gtagagtgaa gatggaaaaa ttgcagttga agggaacaac ctatgcgtc
1861 tgttcaaagg cttcaagtt tcttggact cccgcagaca caggtcacgg cactgtggtg
1921 ttgaattgc agtacactgg cacggatgga ccttgcaaag ttcctatctc gtcagtggct
1981 tcattgaacg acctaacgcc agtgggcaga ttggtcactg tcaaccctt tgtttcaatg
2041 gccacggcca acgctaaggt cctgattgaa ttggaaccac cctttggaga ctcatacata
2101 gtggtgggca gaggaaacaca acagatcaat caccattggc acaagtctgg aagcagcatt
2161 ggcaaagcct tacaaccac cctcaaagga gcgcagagac tagccgctct aggagacaca
2221 gcttgggact tggatcagt tggagggtg ttcacctcag ttgggaaggc tgtccatcaa
2281 gtgttcggag gagcattccg ctcactgttc ggaggcatgt cctggataac gcaaggattg
2341 ctgggggctc tcctgttgtg gatgggcatc aatgctcgtg ataggtccat agctctcacg
2401 tttctcgcag ttggaggagt tctgctcttc ctctccgtga acgtgcacgc tgacactggg
2461 tgtgccatag acatcagccg gcaagagctg agatgtggaa gtggagtgtt catacacaat
2521 gatgtggagg cttggatgga ccggtacaag tattaccctg aaacgccaca aggcctagcc
2581 aagatcattc agaaagctca taaggaagga gtgtgcggtc tacgatcagt ttccagactg
2641 gagcatcaaa tgtgggaagc agtgaaggac gagctgaaca ctcttttgaa ggagaatggt
2701 gtggacctta gtgtcgtggt tgagaaacag gagggaatgt acaagtcagc acctaaacgc
2761 ctcaccgcca ccacggaaaa attggaaatt ggctggaagg cctggggaaa gagtatttta
2821 tttgcaccag aactcgccaa caacaccttt gtggttgatg gtccggagac caaggaatgt
2881 ccgactcaga tcgcgcttg aatagctta aagtggagg atttggatt tggtctcacc
2941 agcactcgga tgttcctgaa ggtcagagag agcaacacaa ctgaatgtga ctcgaagatc
3001 attggaacgg ctgtcaagaa caacttggcg atccacagtg acctgtccta ttggattgaa
3061 agcaggctca atgatacgtg gaagcttgaa agggcagttc tgggtgaagt caaatcatgt
```

FIG. 37b

```
3121 acgtggcctg agacgcatac cttgtggggc gatggaatcc ttgagagtga cttgataata
3181 ccagtcacac tggcgggacc acgaagcaat cacaatcgga gacctgggta caagacacaa
3241 aaccagggcc catgggacga aggccgggta gagattgact tcgattactg cccaggaact
3301 acggtcaccc tgagtgagag ctgcggacac cgtggacctg ccactcgcac caccacagag
3361 agcggaaagt tgataacaga ttggtgctgc aggagctgca ccttaccacc actgcgctac
3421 caaactgaca gcggctgttg gtatggtatg gagatcagac cacagagaca tgatgaaaag
3481 accctcgtgc agtcacaagt gaatgcttat aatgctgata tgattgaccc ttttcagttg
3541 ggccttctgg tcgtgttctt ggccacccag gaggtccttc gcaagaggtg gacagccaag
3601 atcagcatgc cagctatact gattgctctg ctagtcctgg tgtttggggg cattacttac
3661 actgatgtgt tacgctatgt catcttggtg ggggcagctt cgcagaatc taattcggga
3721 ggagacgtgg tacacttggc gctcatggcg accttcaaga tacaaccagt gtttatggtg
3781 gcatcgtttc ttaaagcgag atggaccaac caggagaaca ttttgttgat gttggcggct
3841 gttttctttc aaatggctta tcacgatgcc cgccaaattc tgctctggga gatccctgat
3901 gtgttgaatt cactggcggt agcttggatg atactgagag ccataacatt cacaacgaca
3961 tcaaacgtgg ttgttccgct gctagccctg ctaacacccg ggctgagatg cttgaatctg
4021 gatgtgtaca ggatactgct gttgatggtc ggaataggca gcttgatcag ggagaagagg
4081 agtgcagctg caaaaaagaa aggagcaagt ctgctatgct tggctctagc ctcaacagga
4141 cttttcaacc ccatgatcct tgctgctgga ctgattgcat gtgatcccaa ccgtaaacgc
4201 ggatggcccg caactgaagt gatgacagct gtcggcctaa tgtttgccat cgtcggaggg
4261 ctggcagagc ttgacattga ctccatggcc attccaatga ctatcgcggg gctcatgttt
4321 gctgctttcg tgatttctgg gaaatcaaca gatatgtgga ttgagagaac ggcggacatt
4381 tcctgggaaa gtgatgcaga aattacaggc tcgagcgaaa gagttgatgt gcggcttgat
4441 gatgatggaa acttccagct catgaatgat ccaggagcac cttggaagat atggatgctc
4501 agaatggtct gtctcgcgat tagtgcgtac acccctgggg caatcttgcc ctcagtagtt
4561 ggattttgga taactctcca atacacaaag agaggaggcg tgttgtggga cactccctca
4621 ccaaaggagt acaaaaaggg ggacacgacc accggcgtct acaggatcat gactcgtggg
4681 ctgctcggca gttatcaagc aggagcgggc gtgatggttg aaggtgtttt ccacacctt
4741 tggcatacaa caaaggagc cgctttgatg agcggagagg ccgcctgga cccatactgg
4801 ggcagtgtca aggaggatcg actttgttac ggaggaccct ggaaattgca gcacaagtgg
4861 aacgggcagg atgaggtgca gatgattgtg gtggaacctg gcaagaacgt taagaacgtc
4921 cagacgaaac cagggggtgtt caaaacacct gaaggagaaa tcggggccgt gactttggac
4981 ttccccactg gaacatcagg ctcaccaata gtggacaaaa acggtgatgt gattgggctt
5041 tatggcaatg gagtcataat gcccaacggc tcatacataa gcgcgatagt gcagggtgaa
5101 aggatggatg agccaatccc agccggattc gaacctgaga tgctgaggaa aaaacagatc
5161 actgtactgg atctccatcc cggcgccggt aaaacaagga ggattctgcc acagatcatc
5221 aaagaggcca taaacagaag actgagaaca gccgtgctag caccaaccag ggttgtggct
5281 gctgagatgg ctgaagcact gagaggactg cccatccggt accagacatc cgcagtgccc
5341 agagaacata atggaaatga gattgttgat gtcatgtgtc atgctaccct cacccacagg
5401 ctgatgtctc ctcacagggt gccgaactac aacctgttcg tgatggatga ggctcatttc
5461 accgacccag ctagcattgc agcaagaggt tacatttcca caaaggtcga gctaggggag
5521 gcggcggcaa tattcatgac agccaccccca ccaggcactt cagatccatt cccagagtcc
5581 aattcaccaa tttccgactt acagactgag atcccggatc gagcttggaa ctctggatac
5641 gaatggatca cagaatacac cgggaagacg gtttggtttg tgcctagtgt caagatgggg
5701 aatgagattg ccctttgcct acaacgtgct ggaagaaag tagtccaatt gaacagaaag
5761 tcgtacgaga cggagtaccc aaaatgtaag aacgatgatt gggactttgt tatcacaaca
5821 gacatatctg aaatgggggc taacttcaag gcgagcaggg tgattgacag ccggaagagt
5881 gtgaaaccaa ccatcataac agaaggagaa gcgagagtga cctgggagaa accatctgca
5941 gtgacagcag ctagtgccgc ccagagacgt ggacgtatcg gtagaaatcc gtcgcaagtt
6001 ggtgatgagt actgttatgg ggggcacacg aatgaagacg actcgaactt cgccattgg
6061 actgaggcac gaatcatgct ggacaacatc aacatgccaa acggactgat cgctcaattc
6121 taccaaccag agcgtgagaa ggtatatacc atggatgggg aataccggct cagaggagaa
6181 gagagaaaaa actttctgga actgttgagg actgcagatc tgccagtttg ctgcttac
6241 aaggttgcag cggctggagt gtcataccac gaccggaggt ggtgctttga tggtcctagg
6301 acaaacacaa ttttagaaga caacaacgaa gtggaagtca tcacgaagct tggtgaaagg
6361 aagattctga ggccgcgctg gattgacgcc agggtgtact cggatcacca ggcactaaag
```

FIG. 37c

```
6421 gcgttcaagg acttcgcctc gggaaaacgt tctcagatag ggctcattga ggttctggga
6481 aagatgcctg agcacttcat ggggaagaca tgggaagcac ttgacaccat gtacgttgtg
6541 gccactgcag agaaaggagg aagagctcac agaatggccc tggaggaact gccagatgct
6601 cttcagacaa ttgccttgat tgccttattg agtgtgatga ccatgggagt attcttcctc
6661 ctcatgcagc ggaagggcat tggaaagata ggtttgggag gcgctgtctt gggagtcgcg
6721 accttttttct gttggatggc tgaagttcca ggaacgaaga tcgccggaat gttgctgctc
6781 tcccttctct tgatgattgt gctaattcct gagccagaga agcaacgttc gcagacagac
6841 aaccagctag ccgtgttcct gatttgtgtc atgacccttg tgagcgcagt ggcagccaac
6901 gagatgggtt ggctagataa gaccaagagt gacataagca gtttgtttgg gcaaagaatt
6961 gaggtcaagg agaatttcag catgggagag tttcttctgg acttgaggcc ggcaacagcc
7021 tggtcactgt acgctgtgac aacagcggtc ctcactccac tgctaaagca tttgatcacg
7081 tcagattaca tcaacacctc attgacctca ataaacgttc aggcaagtgc actattcaca
7141 ctcgcgcgag gcttcccctt cgtcgatgtt ggagtgtcgg ctctcctgct agcagccgga
7201 tgctggggac aagtcaccct caccgttacg gtaacagcgg caacactcct tttttgccac
7261 tatgcctaca tggttcccgg ttggcaagct gaggcaatgc gctcagccca gcggcggaca
7321 gcggccggaa tcatgaagaa cgctgtagtg gatggcatcg tggccacgga cgtcccagaa
7381 ttagagcgca ccacacccat catgcagaag aaagttggac agatcatgct gatcttggtg
7441 tctctagctg cagtagtagt gaacccgtct gtgaagacag tacgagaagc cggaattttg
7501 atcacggccg cagcggtgac gctttgggag aatggagcaa gctctgtttg gaacgcaaca
7561 actgccatcg gactctgcca catcatgcgt gggggttggt tgtcatgtct atccataaca
7621 tggacactca taagaacat ggaaaaacca ggactaaaaa gaggtggggc aaaaggacgc
7681 accttgggag aggtttggaa agaaagactc aaccagatga caaaagaaga gttcactagg
7741 taccgcaaag aggccatcat cgaagtcgat cgctcagcgg caaaacacgc caggaaagaa
7801 ggcaatgtca ctggagggca tccagtctct aggggcacag caaaactgag atggctggtc
7861 gaacggaggt ttctcgaacc ggtcggaaaa gtgattgacc ttggatgtgg aagaggcggt
7921 tggtgttact atatggcaac ccaaaaaaga gtccaagaag tcagagggta cacaaagggc
7981 ggtcccggac atgaagagcc ccaactagtg caaagttatg gatggaacat tgtcaccatg
8041 aagagtggag tggatgtgtt ctacagacct tctgagtgtt gtgacaccct cctttgtgac
8101 atcggagagt cctcgtcaag tgctgaggtt gaagagcata ggacgattcg ggtccttgaa
8161 atggttgagg actggctgca ccagggcca agggaatttt gcgtgaaggt gctctgcccc
8221 tacatgccga aagtcataga gaagatggag ctgctccaac gccggtatgg ggggggactg
8281 gtcagaaacc cactctcacg gaattccacg cacgagatgt attgggtgag tcgagcttca
8341 ggcaatgtgg tacattcagt gaatatgacc agccaggtgc tcctaggaag aatggaaaaa
8401 aggacctgga agggacccca atacgaggaa gacgtaaact gggaagtgg aaccagggcg
8461 gtgggaaaac ccctgctcaa ctcagacacc agtaaaatca gaacaggat tgaacgactc
8521 aggcgtgagt acagttcgac gtggcaccac gatgagaacc acccatatag aacctggaac
8581 tatcacggca gttatgatgt gaagcccaca ggctccgcca gttcgctggt caatggagtg
8641 gtcaggctcc tctcaaaacc atgggacacc atcacgaatg ttaccaccat ggccatgact
8701 gacactactc ccttcgggca gcagcgagtg ttcaaagaga aggtggacac gaaagctcct
8761 gaaccgccag aaggagtgaa gtacgtgctc aacgagacca ccaactggtt gtgggcgttt
8821 ttggccagag aaaaacgtcc cagaatgtgc tctcgagagg aattcataag aaaggtcaac
8881 agcaatgcag ctttgggtgc catgtttgaa gagcagaatc aatggaggag cgccagagaa
8941 gcagttgaag atccaaaatt tgggagatg gtggatgagg agcgcgaggc acatctgcgg
9001 ggggaatgtc acacttgcat ttacaacatg atgggaaaga gagaaaaaa acccggagag
9061 ttcggaaagg ccaagggaag cagagccatt tggttcatgt ggctcggagc tcgctttctg
9121 gagttcgagg ctctgggttt tctcaatgaa gaccactggc ttggaagaaa gaactcagga
9181 ggaggtgtcg agggcttggg cctccaaaaa ctgggttaca tcctgcgtga gttggcacc
9241 cggcctgggg gcaagatcta tgctgatgac acagctggct gggacacccg catcacgaga
9301 gctgacttgg aaaatgaagc taaggtgctt gagctgcttg atggggaaca tcggcgtctt
9361 gccagggcca tcattgagct cacctatcgt cacaaagttg tgaaagtgat gcgccggct
9421 gctgatggaa gaaccgtcat ggatgttatc tccagagaag atcagagggg agtggacaa
9481 gttgtcacct acgccctaaa cactttcacc aacctggccg tccagctggt gaggatgatg
9541 gaaggggaag gagtgattgg cccagatgat gtggagaaac tcacaaaagg gaaggaccc
9601 aaagtcagga cctggctgtt tgagaatggg gaagaaagac tcagccgcat ggctgtcagt
9661 ggagatgact gtgtggtaaa gccctggac gatcgctttg ccacctcgct ccacttcctc
```

FIG. 37d

```
 9721 aatgctatgt caaaggttcg caaagacatc caagagtgga aaccgtcaac tggatggtat
 9781 gattggcagc aggttccatt ttgctcaaac catttcactg aattgatcat gaaagatgga
 9841 agaacactgg tggttccatg ccgaggacag gatgaattgg taggcagagc tcgcatatct
 9901 ccaggggccg gatggaacgt ccgcgacact gcttgtctgg ctaagtctta tgcccagatg
 9961 tggctgcttc tgtacttcca cagaagagac ctgcggctca tggccaacgc catttgctcc
10021 gctgtccctg tgaattgggt ccctaccgga agaaccacgt ggtccatcca tgcaggagga
10081 gagtggatga caacagagga catgttggag gtctggaacc gtgtttggat agaggagaat
10141 gaatggatgg aagacaaaac cccagtggag aaatggagtg acgtcccata ttcaggaaaa
10201 cgagaggaca tctggtgtgg cagcctgatt ggcacaagag cccgagccac gtgggcagaa
10261 aacatccagg tggctatcaa ccaagtcaga gcaatcatcg gagatgagaa gtatgtggat
10321 tacatgagtt cactaaagag atatgaagac acaactttgg ttgaggacac agtactgtag
10381 atatttaatt aattgtaaat agacaatata agtatgcata aaagtgtagt tttatagtag
10441 tatttagtgg tgttagtgta aatagttaag aaaatttga ggagaaagtc aggccgggaa
10501 gttcccgcca ccggaagttg agtagacggt gctgcctgcg actcaaccc aggaggactg
10561 ggtgaacaaa gccgcgaagt gatccatgta agccctcaga accgtctcgg aaggaggacc
10621 ccacatgttg taacttcaaa gcccaatgtc agaccacgct acggcgtgct actctgcgga
10681 gagtgcagtc tgcgatagtg ccccaggagg actgggttaa caaaggcaaa ccaacgcccc
10741 acgcggccct agccccggta atggtgttaa ccagggcgaa aggactagag gttagaggag
10801 accccgcggt ttaaagtgca cggcccagcc tggctgaagc tgtaggtcag gggaaggact
10861 agaggttagt ggagaccccg tgccacaaaa caccacaaca aaacagcata ttgacacctg
10921 ggatagacta ggagatcttc tgctctgcac aaccagccac acggcacagt gcgcc
```

FIG. 38a

```
   1 agtagttcgc ctgtgtgagc tgacaaactt agtagtgttt gtgaggatta acaacaatta
  61 acacagtgcg agctgtttct tagcacgaag atctcgatgt ctaagaaacc aggagggccc
 121 ggcaagagcc gggctgtcaa tatgctaaaa cgcggaatgc cccgcgtgtt gtccttgatt
 181 ggactgaaga gggctatgtt gagcctgatc gacggcaagg ggccaatacg atttgtgttg
 241 gctctcttgg cgttcttcag gttcacagca attgctccga cccgagcagt gctggatcga
 301 tggagaggtg tgaacaaaca aacagcgatg aaacaccttc tgagttttaa gaaggaacta
 361 gggaccttga ccagtgctat caatcggcgg agctcaaaac aaaagaaaag aggaggaaag
 421 accggaattg cagtcatgat tggcctgatc gccagcgtag gagcagttac cctctctaac
 481 ttccaaggga aggtgatgat gacggtaaat gctactgacg tcacagatgt catcacgatt
 541 ccaacagctg ctggaaagaa cctatgcatt gtcagagcaa tggatgtggg atacatgtgc
 601 gatgatacta tcacttatga atgcccagtg ctgtcggctg taatgatcc agaagacatc
 661 gactgttggt gcacaaagtc agcagtctac gtcaggtatg aagatgcac caagacacgc
 721 cactcaagac gcagtcggag gtcactgaca gtgcagacac acggagaaag cactctagcg
 781 aacaagaagg gggcttggat ggacagcacc aaggccacaa ggtatttggt aaaaacagaa
 841 tcatggatct tgaggaaccc tggatatgcc ctggtggcag ccgtcattgg ttggatgctt
 901 gggagcaaca ccatgcagag agttgtgttt gtcgtgctat tgcttttggt ggccccagct
 961 tacagcttca actgccttgg aatgagcaac agagacttct tggaaggagt gtctggagca
1021 acatgggtgg atttggttct cgaaggcgac agctgcgtga ctatcatgtc taaggacaag
1081 cctaccatcg atgtgaagat gatgaatatg gaggcggcca acctggcaga ggtccgcagt
1141 tattgctatt tggctaccgt cagcgatctc tccaccaaag ctgcgtgccc gaccatggga
1201 gaagctcaca atgacaaacg tgctgaccca gcttttgtgt gcagacaagg agtggtggac
1261 aggggctggg gcaacggctg cggattattt ggcaaaggaa gcattgacac atgcgccaaa
1321 tttgcctgct ctaccaaggc aataggaaga accatcttga aagagaatat caagtacgaa
1381 gtggccattt tgtccatgg accaactact gtggagtcgc acggaaacta ctccacacag
1441 gttggagcca ctcaggcagg gagattcagc atcactcctg cggcgccttc atacacacta
1501 aagcttggag aatatggaga ggtgacagtg gactgtgaac cacggtcagg gattgacacc
1561 aatgcatact acgtgatgac tgttggaaca aagacgttct tggtccatcg tgagtggttc
1621 atggacctca acctcccttg gagcagtgct ggaagtactg tgtggaggaa cagagagacg
1681 ttaatggagt ttgaggaacc acacgccacg aagcagtctg tgatagcatt gggctcacaa
1741 gagggagctc tgcatcaagc tttggctgga gccattcctg tggaattttc aagcaacact
1801 gtcaagttga cgtcgggtca tttgaagtgt agagtgaaga tggaaaaatt gcagttgaag
1861 ggaacaacct atggcgtctg ttcaaaggct ttcaagtttc ttgggactcc cgcagacaca
1921 ggtcacggca ctgtggtgtt ggaattgcag tacactggca cggatggacc ttgtaaagtt
1981 cctatctcgt cagtggcttc attgaacgac ctaacgccag tgggcagatt ggtcactgtc
2041 aacccttttg tttcagtggc cacggccaac gctaaggtcc tgattgaatt ggaaccaccc
2101 tttggagact catacatagt ggtgggcaga ggagaacaac agatcaatca ccattggcac
2161 aagtctggaa gcagcattgg caaagccttt acaaccaccc tcaaaggagc gcagagacta
2221 gccgctctag agacacagc ttgggacttt ggatcagttg gaggggtgtt cacctcagtt
2281 gggaaggctg tccatcaagt gttcggagga gcattccgct tactgttcgg aggcatgtcc
2341 tggataacgc aaggattgct gggggctctc ctgttgtgga tgggcatcaa tgctcgtgat
2401 aggtccatag ctctcacgtt tctcgcagtt ggaggagttc tgctcttcct ctccgtgaac
2461 gtgcacgctg acactgggtg tgccatagac atcagccgg aagagctgag atgtggaagt
2521 ggagtgttca tacacaatga tgtggaggct tggatggacc gatacaagta ttaccctgaa
2581 acgccacaag gcctagccaa gatcattcag aaagctcata aggaaggagt gtgcggtcta
2641 cgatcagttt ccagactgga gcatcaaatg tgggaagcag tgaaggacga gctgaacact
2701 cttttgaagg agaatggtgt ggaccttagt gtcgtggttg agaaacagga gggaatgtac
2761 aagtcagcac ctaaacgcct caccgccacc acggaaaaat tggaaattgg ctggaaggcc
2821 tggggaaaga gtatttatt tgcaccagaa ctcgccaaca cacctttgt ggttgatggt
2881 ccggagacca aggaatgtcc gactcagaat cgcgcttgga atagcttaga agtggaggat
2941 tttggatttg gtctcaccag cactcggatg ttcctgaagg tcagagagag caacacaact
3001 gaatgtgact cgaagatcat tggaacggct gtcaagaaca cttggcgat ccacagtgac
3061 ctgtcctatt ggattgaaag caggctcaat gatacgtgga agcttgaaag ggcagttctg
3121 ggtgaagtca aatcatgtac gtggcctgag acgcatacct gtggggcga tggaatcctt
3181 gagagtgact tgataatacc agtcacactg gcgggaccac gaagcaatca caatcggaga
```

FIG. 38b

```
3241 cctgggtaca agacacaaaa ccagggccca tgggacgaag gccgggtaga gattgacttc
3301 gattactgcc caggaactac ggtcaccctg agtgagagct gcggacaccg tggacctgcc
3361 actcgcacca ccacagagag cggaaagttg ataacagatt ggtgctgcag gagctgcacc
3421 ttaccaccac tgcgctacca aactgacagc ggctgttggt atggtatgga gatcagacca
3481 cagagacatg atgaaaagac cctcgtgcag tcacaagtga atgcttataa tgctgatatg
3541 attgacccttt tcagttgggg ccttctggtc gtgttcttgg ccacccagga ggtccttcgc
3601 aagaggtgga cagccaagat cagcatgcca gctatactga ttgctctgct agtcctggtg
3661 tttggggggca ttacttacac tgatgtgtta cgctatgtca tcttggtggg ggcagctttc
3721 gcagaatcta attcgggagg agacgtggta cacttggcgc tcatggcgac cttcaagata
3781 caaccagtgt ttatggtggc atcgtttctc aaagcgagat ggaccaacca ggagaacatt
3841 tgttgatgt tggcggctgt tttctttcaa atggcttatc acgatgcccg ccaaattctg
3901 ctctgggaga tccctgatgt gttgaattca ctggcggtag cttggatgat actgagagcc
3961 ataacattca caacgacatc aaacgtggtt gttccgctgc tagccctgct aacacccggg
4021 ctgagatgct tgaatctgga tgtgtacagg atactgctgt tgatggtcgg aataggcagc
4081 ttgatcaggg agaagaggag tgcagctgca aaaagaaag gagcaagtct gctatgcttg
4141 gctctagcct caacaggact tttcaacccc atgatccttg ctgctggact gattacatgt
4201 gatcccaacc gtaaacgcgg atggcccgca actgaagtga tgacagctgt cggcctgatg
4261 tttgccatcg tcggagggct ggcagagctt gacattgact ccatggccat tccaatgact
4321 atcgcggggc tcatgtttgc tgctttcgtg atttctggga aatcaacaga tatgtggatt
4381 gagagaacgg cggacatttc ctgggaaagt gatgcagaaa ttacaggctc gagcgaaaga
4441 gttgatgtgc ggcttgatga tgatggaaac ttccagctca tgaatgatcc aggagcacct
4501 tggaagatat ggatgctcag aatggtctgt ctcgcgatta gtgcgtacac ccctgggca
4561 atcttgccct cagtagttgg attttggata actctccaat acacaaagag aggaggcgtg
4621 ttgtgggaca ctccctcacc aaaggagtac aaaaagggg acacgaccac cggcgtctac
4681 aggatcatga ctcgtgggct gctcggcagt tatcaagcag gagcgggcgt gatggttgaa
4741 ggtgttttcc acacccttg gcatacaaca aaaggagccg ctttgatgag cggagagggc
4801 cgcctggacc catactgggg cagtgtcaag gaggatcgac tttgttacgg aggaccctgg
4861 aaattgcagc acaagtggaa cgggcaggat gaggtgcaga tgattgtggt ggaacctggc
4921 aagaacgtta agaacgtcca gacgaaacca ggggtgttca aaacacctga aggagaaatc
4981 ggggccgtga ctttggactt ccccactgga acatcaggct caccaatagt ggacaaaaac
5041 ggtgatgtga ttgggcttta tggcaatgga gtcataatgc caacggctc atacataagc
5101 gcgatagtgc agggtgaaag gatggatgag ccaatcccag ccggattcga acctgagatg
5161 ctgaggaaaa aacagatcac tgtactggat ctccatcccg gcgccggtaa acaaggagg
5221 attctgccac agatcatcaa agaggccata aacagaagac tgagaacagc cgtgctagca
5281 ccaaccaggg ttgtggctgc tgagatggct gaagcactga gaggactgcc catccggtac
5341 cagacatccg cagtgcccag agaacataat ggaaatgaga ttgttgatgt catgtgtcat
5401 gctaccctca cccacaggct gatgtctcct cacagggtgc cgaactacaa cctgttcgtg
5461 atggatgagg ctcatttcac cgaccagct agcattgcag caagaggtta catttccaca
5521 aaggtcgagc taggggaggc ggcggcaata ttcatgacag ccaccccacc aggcacttca
5581 gatccattcc cagagtccaa ttccaatt tccgacttac agactgagat cccggatcga
5641 gcttggaact ctggatacga atggatcaca gaatacaccg gaagacggtt tggtttgtg
5701 cctagtgtca agatggggaa tgagattgcc ctttgcctac aacgtgctgg aaagaaagta
5761 gtccaattga acagaaagtc gtacgagacg gagtacccaa aatgtaagaa cgatgattgg
5821 gactttgtta tcacaacaga catatctgaa atggggggcta actttaaggc gagcagggtg
5881 attgacagcc ggaagagtgt gaaaccaacc atcataacag aaggagaagg gagagtgatc
5941 ctgggagaac catctgcagt gacagcagct agtgccgccc agagacgtgg acgtatcggt
6001 agaaatccgt cgcaagttgg tgatgagtac tgttatgggg ggcacacgaa tgaagacgac
6061 tcgaacttcg cccattggac tgaggcacga atcatgctgg acaacatcaa catgccaaac
6121 ggactgatcg ctcaattcta ccaaccagag cgtgagaagg tatataccat ggatgggaa
6181 taccggctca gaggagaaga gagaaaaaac tttctggaac tgttaggac tgcagatctg
6241 ccagtttggc tggcttacaa ggttgcagcg gctggagtgt cataccacga ccggaggtgg
6301 tgctttgatg gtcctaggac aaacacaatt ttagaagaca acaacgaagt ggaagtcatc
6361 acgaagcttg gtgaaaggaa gattctgagg ccgcgctgga tgacgccag ggtgtactcg
6421 gatcaccagg cactaaaggc gttcaaggac ttcgcctcgg aaaacgttc tcagataggg
6481 ctcattgagg ttctgggaaa gatgcctgag cacttcatgg ggaagacatg ggaagcactt
```

FIG. 38c

```
6541 gacaccatgt acgttgtggc cactgcagag aaaggaggaa gagctcacag aatggccctg
6601 gaggaactgc cagatgctct tcagacaatt gccttgattg ccttattgag tgtgatgacc
6661 atgggagtat tcttcctcct catgcagcgg aagggcattg gaaagatagg tttgggaggc
6721 gctgtcttgg gagtcgcgac cttttctgt tggatggctg aagttccagg aacgaagatc
6781 gccggaatgt tgctgctctc ccttctcttg atgattgtgc taattcctga gccagagaag
6841 caacgttcgc agacagacaa ccagctagcc gtgttcctga tttgtgtcat gacccttgtg
6901 agcgcagtgg cagccaacga gatgggttgg ctagataaga ccaagagtga cataagcagt
6961 ttgtttgggc aaagaattga ggtcaaggag aatttcagca tgggagagtt tcttctggac
7021 ttgaggccgg caacagcctg gtcactgtac gctgtgacaa cagcggtcct cactccactg
7081 ctaaagcatt tgatcacgtc agattacatc aacacctcat tgacctcaat aaacgttcag
7141 gcaagtgcac tattcacact cgcgcgaggc ttcccccttcg tcgatgttgg agtgtcggct
7201 ctcctgctag cagccggatg ctggggacaa gtcaccctca ccgttacggt aacagcggca
7261 acactccttt tttgccacta tgcctacatg gttcccggtt ggcaagctga ggcaatgcgc
7321 tcagcccagc ggcggacagc ggccggaatc atgaagaacg ctgtagtgga tggcatcgtg
7381 gccacggacg tcccagaatt agagcgcacc acacccatca tgcagaagaa agttggacag
7441 atcatgctga tcttggtgtc tctagctgca gtagtagtga cccgtctgt gaagacagta
7501 cgagaagccg gaattttgat cacggccgca gcggtgacgc tttgggagaa tggagcaagc
7561 tctgtttgga acgcaacaac tgccatcgga ctctgccaca tcatgcgtgg gggttggttg
7621 tcatgtctat ccataacatg gacactcata aagaacatgg aaaaaccagg actaaaaaga
7681 ggtggggcaa aaggacgcac cttgggagag gtttggaaag aaagactcaa ccagatgaca
7741 aaagaagagt tcactaggta ccgcaaagag gccatcatcg aagtcgatcg ctcagcagca
7801 aaacacgcca ggaaagaagg caatgtcact ggagggcatc cagtctctag gggcacagca
7861 aaactgagat ggctggtcga acggaggttt ctcgaaccgg tcggaaaagt gattgacctt
7921 ggatgtggaa gaggcggttg tgttactat atggcaaccc aaaaaagagt ccaagaagtc
7981 agagggtaca caaagggcgg tcccggacat gaagagcccc aactagtgca aagttatgga
8041 tggaacattg tcaccatgaa gagtggggtg gatgtgttct acagaccttc tgagtgttgt
8101 gacaccctcc tttgtgacat cggagagtcc tcgtcaagtg ctgaggttga agagcatagg
8161 acgattcggg tccttgaaat ggttgaggac tggctgcacc gagggccaag ggaattttgc
8221 gtgaaggtgc tctgcccta catgccgaaa gtcatagaga agatggagct gctccaacgc
8281 cggtatgggg ggggactggt cagaaaccca ctctcacgga attccacgca cgagatgtat
8341 tgggtgagtc gagcttcagg caatgtggta cattcagtga atatgaccag ccaggtgctc
8401 ctaggaagaa tggaaaaaag gacctggaag ggacccaat acgaggaaga tgtaaacttg
8461 ggaagtggaa ccagggcggt gggaaaaccc ctgctcaact cagacaccag taaaatcaag
8521 aacaggattg aacgactcag gcgtgagtac agttcgacgt ggcaccacga tgagaaccac
8581 ccatatagaa cctggaacta tcacggcagt tatgatgtga agcccacagg ctccgccagt
8641 tcgctggtca atggagtggt caggctcctc tcaaaaccat gggacaccat cacgaatgtt
8701 accaccatgg ccatgactga cactactccc ttcgggcagc agcgagtgtt caaagagaag
8761 gtggacacga agctcctga ccgccagaa ggagtgaagt acgtgctcaa cgagaccacc
8821 aactggttgt gggcgttttt ggccagagaa aaacgtccca gaatgtgctc tcgagaggaa
8881 ttcataagaa aggtcaacag caatgcagct ttgggtgcca tgtttgaaga gcagaatcaa
8941 tggaggagcg ccagagaggc agttgaagat ccaaaatttt gggagatggt ggatgaggag
9001 cgcgaggcac atctgcgggg ggaatgtcac acttgcattt acaacatgat gggaaagaga
9061 gagaaaaaac ccggagagtt cggaaaggcc aagggaagca gagccatttg gttcatgtgg
9121 ctcggagctc gctttctgga gttcgaggct ctgggttttc tcaatgaaga ccactggctt
9181 ggaagaaaga actcaggagg aggtgtcgag ggcttggggcc tccaaaaact gggttacatc
9241 ctgcgtgaag ttggcacccg gcctggggc aagatctatg ctgatgacac agctggctgg
9301 gacacccgca tcacgagagc tgacttggaa aatgaagcta aggtgcttga gctgcttgat
9361 ggggaacatc ggcgtcttgc cagggccatc attgagctca cctatcgtca caagttgtg
9421 aaagtgatgc gcccggctgc tgatggaaga accgtcatgg atgttatctc cagagaagat
9481 cagaggggga gtgacaagt tgtcacctac gccctaaaca ctttcaccaa cctggccgtc
9541 cagctggtga ggatgatgga aggggaagga gtgattggcc cagatgatgt ggagaaactc
9601 acaaaaggga aaggacccaa agtcaggacc tggctgtttg agaatgggga agaaagactc
9661 agccgcatgg ctgtcagtgg agatgactgt gtggtaaagc ccctggacga tcgctttgcc
9721 acctcgctcc acttcctcaa tgctatgtca aaggttcgca aagacatcca agagtggaaa
9781 ccgtcaactg gatggtatga ttggcagcag gttccatttt gctcaaacca tttcactgaa
```

FIG. 38d

```
 9841 ttgatcatga aagatggaag aacactggtg gttccatgcc gaggacagga tgaattggta
 9901 ggcagagctc gcatatctcc aggggccgga tggaacgtcc gcgacactgc ttgtctggct
 9961 aagtcttatg cccagatgtg gctgcttctg tacttccaca gaagagacct gcggctcatg
10021 gccaacgcca tttgctccgc tgtccctgtg aattgggtcc ctaccggaag aaccacgtgg
10081 tccatccatg caggaggaga gtggatgaca acagaggaca tgttggaggt ctggaaccgt
10141 gtttggatag aggagaatga atggatggaa gacaaaaccc cagtggagaa atggagtgac
10201 gtcccatatt caggaaaacg agaggacatc tggtgtggca gcctgattgg cacaagagcc
10261 cgagccacgt gggcagaaaa catccaggtg gctatcaacc aagtcagagc aatcatcgga
10321 gatgagaagt atgtggatta catgagttca ctaaagagat atgaagacac aactttggtt
10381 gaggacacag tactgtagat atttaatcaa ttgtaaatag acaatataag tatgcataaa
10441 agtgtagttt tatagtagta tttagtggtg ttagtgtaaa tagttaagaa aattttgagg
10501 agaaagtcag gccgggaagt tcccgccacc ggaagttgag tagacggtgc tgcctgcgac
10561 tcaaccccag gaggactggg tgaacaaagc cgcgaagtga tccatgtaag ccctcagaac
10621 cgtctcggaa ggaggacccc acatgttgta acttcaaagc ccaatgtcag accacgctac
10681 ggcgtgctac tctgcggaga gtgcagtctg cgatagtgcc ccaggaggac tgggttaaca
10741 aaggcaaacc aacgccccac gcggccctag ccccggtaat ggcgttaacc agggcgaaag
10801 gactagaggt tagaggagac cccgcggttt aaagtgcacg gcccagcctg gctgaagctg
10861 taggtcaggg gaaggactag aggttagtgg agaccccgtg ccacaaaaca ccacaacaaa
10921 acagcatatt gacacctggg atagactagg agatcttctg ctctgcacaa ccagccacac
10981 ggcacagtgc gccgacaatg gtggctggtg gtgcgagaac acaggatct
```

FIG. 39a

```
   1 agttgttagt ctacgtggac cgacaagaac agtttcgaat cggaagcttg cttaacgtag
  61 ttctaacagt tttttattag agagcagatc tctgatgaac aaccaacgga aaaagacggg
 121 tcgaccgtct ttcaatatgc tgaaacgcgc gagaaaccgc gtgtcaactg tttcacagtt
 181 ggcgaagaga ttctcaaaag gattgctttc aggccaagga cccatgaaat tggtgatggc
 241 ttttatagca ttcctaagat ttctagccat acctccaaca gcaggaattt tggctagatg
 301 gggctcattc aagaagaatg gagcgatcaa agtgttacgg ggtttcaaga agaaatctc
 361 aaacatgttg aacataatga acaggaggaa aagatctgtg accatgctcc tcatgctgct
 421 gcccacagcc ctggcgttcc atctgaccac ccgaggggga gagccgcaca tgatagttag
 481 caagcaggaa agaggaaaat cacttttgtt taagacctct gcaggtgtca acatgtgcac
 541 ccttattgca atggatttgg gagagttatg tgaggacaca atgacctaca aatgccccg
 601 gatcactgag acggaaccag atgacgttga ctgttggtgc aatgccacgg agacatggt
 661 gacctatgga acatgttctc aaactggtga acaccgacga gacaaacgtt ccgtcgcact
 721 ggcaccacac gtagggcttg tctagaaac aagaaccgaa acgtggatgt cctctgaagg
 781 cgcttggaaa caaatacaaa aagtggagac ctgggctctg agacacccag gattcacggt
 841 gatagccctt tttctagcac atgccatagg aacatccatc cccagaaag ggatcatttt
 901 tattttgctg atgctggtaa ctccatccat ggccatgcgg tgcgtgggaa taggcaacag
 961 agacttcgtg gaaggactgt caggagctac gtgggtggat gtggtactgg agcatggaag
1021 ttgcgtcact accatggcaa aagacaaacc aacactggac attgaactct tgaagacgga
1081 ggtcacaaac cctgccgtcc tgcgcaaact gtgcattgaa gctaaaatat caaacaccac
1141 caccgattcg agatgtccaa cacaaggaga agccacgctg gtggaagaac aggacacgaa
1201 ctttgtgtgt cgacgaacgt tcgtggacag aggctggggc aatggttgtg ggctattcgg
1261 aaaaggtagc ttaataacgt gtgctaagtt taagtgtgtg acaaaactgg aaggaaagat
1321 agtccaatat gaaaacttaa aatattcagt gatagtcacc gtacacactg gagaccagca
1381 ccaagttgga aatgagacca cagaacatgg aacaactgca accataacac ctcaagctcc
1441 cacgtcggaa atacagctga cagactacgg agctctaaca ttggattgtt cacctagaac
1501 agggctagac tttaatgaga tggtgttgtt gacaatggaa aaaaatcat ggctcgtcca
1561 caaacaatgg tttctagact accactgcc ttggaccctcg ggggcttcaa catcccaaga
1621 gacttggaat agacaagact tgctggtcac atttaagaca gctcatgcaa aaaagcagga
1681 agtagtcgta ctaggatcac aagaaggagc aatgcacact gcgttgactg gagcgacaga
1741 aatccaaacg tctggaacga caacaatttt tgcaggacac ctgaaatgca gactaaaaat
1801 ggataaactg actttaaaag ggatgtcata tgtaatgtgc acagggtcat tcaagttaga
1861 gaaggaagtg gctgagaccc agcatggaac tgttctagtg caggttaaat acgaaggaac
1921 agatgcacca tgcaagatcc ccttctcgtc ccaagatgag aagggagtaa cccagaatgg
1981 gagattgata acagccaacc ccatagtcac tgacaaagaa aaaccagtca acattgaagc
2041 ggagccacct tttggtgaga gctacattgt ggtaggagca ggtgaaaaag ctttgaaact
2101 aagctggttc aagaagggaa gcagtatagg gaaaatgttt gaagcaactg cccgtgagc
2161 acgaaggatg gccatcctgg gagacactgc atgggacttc ggttctatag gagggtgtt
2221 cacgtctgtg ggaaaactga tacaccagat ttttgggact gcgtatggag ttttgttcag
2281 cggtgtttct tggaccatga agataggaat agggattctg ctgacatggc taggattaaa
2341 ctcaaggagc acgtcccttt caatgacgtg tatcgcagtt ggcatggtca cgctgtacct
2401 aggagtcatg gttcaggcgg actcgggatg tgtaatcaac tggaaaggca gagaactcaa
2461 atgtggaagc ggcattttg tcaccaatga agtccacacc tggacagagc aatataatt
2521 ccaggccgac tcccctaaga gactatcagc ggccattggg aaggcatggg aggagggtgt
2581 gtgtggaatt cgatcagcca ctcgtctcga acatcatg tggaagcaaa tatcaaatga
2641 attaaaccac atcttacttg aaaatgacat gaaattaca gtggtcgtag gagacgttag
2701 tggaatcttg gcccaaggaa agaaaatgat taggccacaa cccatggaac acaaatactc
2761 gtggaaaagc tggggaaaag ccaaaatcat aggagcagat gtacagaata ccaccttcat
2821 catcgacggc ccaaacaccc cagaatgccc tgataaccaa agagcatgga acatttggga
2881 agttgaagac tatggatttg aatttcac gacaaacata tggttgaaat tgcgtgactc
2941 ctacactcaa gtgtgtgacc accggctaat gtcagctgcc atcaaggata gcaaagcagt
3001 ccatgctgac atgggtact ggatagaaag tgaaagaac gagacttgga agttggcaag
3061 agcctccttc atagaagtta gacatgcat ctggccaaaa tcccacactc tatggagcaa
3121 tgagtcctg gaaagtgaga tgataatccc aaagatatat ggaggaccaa tatctcagca
3181 caactacaga ccaggatatt tcacacaaac agcagggccg tggcacttgg gcaagttaga
```

FIG. 39b

```
3241 actagatttt gatttatgtg aaggtaccac tgttgttgtg gatgaacatt gtggaaatcg
3301 aggaccatct cttagaacca caacagtcac aggaaagaca atccatgaat ggtgctgtag
3361 atcttgcacg ttaccccccc tacgtttcaa aggagaagac gggtgctggt acggcatgga
3421 aatcagacca gtcaaggaga aggaagagaa cctagttaag tcaatggtct ctgcagggtc
3481 aggagaagtg gacagttttt cactaggact gctatgcata tcaataatga tcgaagaggt
3541 aatgagatcc agatggagca gaaaaatgct gatgactgga acattggctg tgttcctcct
3601 tctcacaatg ggacaattga catggaatga tctgatcagg ctatgtatca tggttggagc
3661 caacgcttca gacaagatgg ggatgggaac aacgtaccta gctttgatgg ccactttcag
3721 aatgagacca atgttcgcag tcgggctact gtttcgcaga ttaacatcta gagaagttct
3781 tcttcttaca gttggattga gtctggtggc atctgtagaa ctaccaaatt ccttagagga
3841 gctaggggat ggacttgcaa tgggcatcat gatgttgaaa ttactgactg attttcagtc
3901 acatcagcta tgggctacct tgctgtcttt aacatttgtc aaaacaactt tttcattgca
3961 ctatgcatgg aagacaatgg ctatgatact gtcaattgta tctctcttcc ctttatgcct
4021 gtccacgact tctcaaaaaa caacatggct tccggtgttg ctgggatctc ttggatgcaa
4081 accactaacc atgtttctta taacagaaaa caaaatctgg ggaaggaaaa gctggcctct
4141 caatgaagga attatggctg ttgaatagt tagcattctt ctaagttcac ttctcaagaa
4201 tgatgtgcca ctagctggcc cactaatagc tggaggcatg ctaatagcat gttatgtcat
4261 atctggaagc tcggccgatt tatcactgga gaaagcggct gaggtctcct gggaagaaga
4321 agcagaacac tctggtgcct cacacaacat actagtggag gtccaagatg atggaaccat
4381 gaagataaag gatgaagaga gagatgacac actccaccatt ctcctcaaag caactctgct
4441 agcaatctca ggggtatacc caatgtcaat accggcgacc ctctttgtgt ggtattttg
4501 gcagaaaaag aaacagagat caggagtgct atgggacaca cccagccctc cagaagtgga
4561 aagagcagtc cttgatgatg gcatttatag aattctccaa agaggattgt tgggcaggtc
4621 tcaagtagga gtaggagttt ttcaagaagg cgtgttccac acaatgtggc acgtcaccag
4681 gggagctgtc ctcatgtacc aagggaagag actggaacca agttgggcca gtgtcaaaaa
4741 agacttgatc tcatatggag gaggttggag gtttcaagga tcctggaacg cgggagaaga
4801 agtgcaggtg attgctgttg aaccggggaa gaaccccaaa aatgtacaga cagcgccggg
4861 taccttcaag acccctgaag gcgaagttgg agccatagct ctagacttaa acccggcac
4921 atctggatct cctatcgtga acagagaggg aaaaatagta ggtctttatg gaaatggagt
4981 ggtgacaaca agtggtacct acgtcagcgc catagctcaa gctaaagcat cacaagaagg
5041 gcctctacca gagattgagg acgaggtgtt taggaaaaga aacttaacaa taatggacct
5101 acatccagga tcgggaaaa caagaagata tcttccagcc atagtccgtg aggccataag
5161 aaggaacgtg cgcacgctag tcttagctcc cacaagagtt gtcgcttctg aaatggcaga
5221 ggcgctcaag ggaatgccaa taaggtatca gacaacagca gtgaagagtg aacacacagg
5281 aaaagagata gttgaccttaa tgtgtcacgc cactttcact atgcgtctcc tgtctcctgt
5341 gagagttccc aattataata tgattatcat ggatgaagca catttaccg atccagccag
5401 catagcagcc agagggtata tctcaacccg agtgggtatg ggtgaagcag ctgcgatttt
5461 catgacagcc actcccccg gatcggtgga ggcctttcca cagagcaatg cagttatcca
5521 agatgaggaa agagacattc ctgaaagatc atggaactca ggctatgact ggatcactga
5581 tttcccaggt aaaacagtct ggtttgttcc aagcatcaaa tcaggaaatg acattgccaa
5641 ctgtttaaga aagaatggga acggggtggt ccaattgagc agaaaaactt tgacactga
5701 gtaccagaaa acaaaaaata cgactggga ctatgttgtc acaacagaca tatccgaaat
5761 gggagcaaac ttccgagccg acagggtaat agacccgagg cggtgcctga accggtaat
5821 actaaaagat ggcccagagc gtgtcattct agccggaccg atgccagtga ctgtggctag
5881 cgccgcccag aggagaggaa gaattggaag gaaccaaaat aaggaaggcg atcagtatat
5941 ttacatggga cagcctctaa acaatgatga ggaccacgcc cattggacag aagcaaaaat
6001 gctccttgac aacataaaca caccagaagg gattatccca gccctctttg agccggagag
6061 agaaaagagt gcagcaatag acggggaata cagactacgg ggtgaagcga ggaaaacgtt
6121 cgtggagctc atgagaagag gagatctacc tgtctggcta tcctacaaag ttgcctcaga
6181 aggcttccag tactccgaca aggtggtg ctttgatggg gaaaggaaca accaggtgtt
6241 ggaggagaac atggacgtgg agatctggac aaaagaagga gaaagaaga actacgacc
6301 ccgctggctg gatgccagaa catactctga cccactggct ctgcgcgaat caaagagtt
6361 cgcagcagga agaagaagcg tctcaggtga cctaatatta gaaatagga aacttccaca
6421 acatttaacg caaagggccc agaacgcctt ggacaatctg gttatgttgc acaactctga
6481 acaaggagga aaagcctata gacacgccat ggaagaacta ccagacacca tagaaacgtt
```

FIG. 39c

```
6541 aatgctccta gctttgatag ctgtgctgac tggtggagtg acgttgttct tcctatcagg
6601 aagggtcta ggaaaaacat ccattggcct actctgcgtg attgcctcaa gcgcactgct
6661 atggatggcc agtgtggaac cccattggat agcggcctct atcatactgg agttctttct
6721 gatggtgttg cttattccag agccggacag acagcgcact ccacaagaca accagctagc
6781 atacgtggtg ataggtctgt tattcatgat attgacagcg gcagccaatg agatgggatt
6841 actggaaacc acaaagaagg acctggggat tggtcatgca gctgctgaaa accaccatca
6901 tgctgcaatg ctggacgtag acctacatcc agcttcagcc tggactctct atgcagtggc
6961 cacaacaatt atcactccca tgatgagaca cacaattgaa aacacaacgg caaatatttc
7021 cctgacagct attgcaaacc aggcagctat attgatggga cttgacaagg gatggccaat
7081 atcaaagatg gacataggag ttccacttct cgccttgggg tgctattctc aggtgaaccc
7141 gctgacgctg acagcggcgg tatttatgct agtggctcat tatgccataa ttggacccgg
7201 actgcaagca aaagctacta gagaagctca aaaaggaca gcagccggaa taatgaaaaa
7261 cccaactgtc gacgggatcg ttgcaataga tttggaccct gtggtttacg atgcaaaatt
7321 tgaaaaacag ctaggccaaa taatgttgtt gatactttgc acatcacaga tcctcctgat
7381 gcggaccaca tgggccttgt gtgaatccat cacactagcc actggacctc tgactacgct
7441 ttgggaggga tctccaggaa aattctggaa caccacgata gcggtgtcca tggcaaacat
7501 ttttagggga agttatctag caggagcagg tctggccttt tcattaatga aatctctagg
7561 aggaggtagg agaggcacgg gagcccaagg ggaaacactg ggagaaaaat ggaaaagaca
7621 gctaaaccaa ttgagcaagt cagaattcaa cacttacaaa aggagtggga ttatagaggt
7681 ggatagatct gaagccaaag aggggttaaa aagaggagaa ccgactaaac acgcagtgtc
7741 gagaggaacg gccaaactga ggtggtttgt ggagaggaac cttgtgaaac cagaagggaa
7801 agtcatagac ctcggttgtg gaagaggtgg ctggtcatat tattgcgctg ggctgaagaa
7861 agtcacagaa gtgaaaggat acacgaaagg aggacctgga catgaggaac caatcccaat
7921 ggcaacctat ggatggaacc tagtaaagct atactccggg aaagatgtat tctttacacc
7981 acctgagaaa tgtgacaccc tcttgtgtga tattggtgag tcctctccga acccaactat
8041 agaagaagga agaacgttac gtgttctaaa gatggtggaa ccatggctca gaggaaacca
8101 attttgcata aaaattctaa atccctatat gccgagtgtg gtagaaactt tggagcaaat
8161 gcaaagaaaa catggaggaa tgctagtgcg aaatccactc tcaagaaact ccactcatga
8221 aatgtactgg gtttcatgtg gaacaggaaa cattgtgtca gcagtaaaca tgacatctag
8281 aatgttgcta aatcgattca atggctca caggaagcca acatatgaaa gagacgtgga
8341 cttaggcgct ggaacaagac atgtggcagt agaaccagag gtggccaacc tagatatcat
8401 tggccagagg atagagaata taaaaaatgg acacaaatca acatggcact atgatgagga
8461 caatccatac aaaacatggg cctatcatgg atcatatgag gtcaagccat caggatcagc
8521 ctcatccatg gtcaatggtg tggtgagact gctaaccaaa ccatgggatg tcattcccat
8581 ggtcacacaa atagccatga ctgacaccac ccccttggga aacagaggg tgtttaaaga
8641 gaaagttgac acgcgtacac caaaagcgaa acgaggcaca gcacaaatta tggaggtgac
8701 agccaggtgg ttatggggtt ttctctctag aaacaaaaaa cccagaatct gcacaagaga
8761 ggagttcaca agaaaagtca ggtcaaacgc agctattgga gcagtgttcg ttgatgaaaa
8821 tcaatggaac tcagcaaaag aggcagtgga agatgaacgg ttctggacc ttgtgcacag
8881 agagagggag cttcataaac aaggaaaatg tgccacgtgt gtctacaaca tgatgggaaa
8941 gagagagaaa aaattaggag agttcggaaa ggcaaaagga agtcgcgcaa tatggtacat
9001 gtggttggga gcgcgctttt tagagtttga agcccttggt ttcatgaatg aagatcactg
9061 gttcagcaga gagaattcac tcagtggagt ggaaggagaa ggactccaca acttggata
9121 catactcaga gacatatcaa agattccagg gggaaatatg tatgcagatg acacagccgg
9181 atgggacaca gaataacag aggatgatct tcagaatgag gccaaaatca ctgacatcat
9241 ggaacctgaa catgccctat tggccacgtc aatctttaag ctaacctacc aaaacaaggt
9301 agtaagggtg cagagaccag cgaaaatgg aaccgtgatg gatgtcatat ccagacgtga
9361 ccagagagga agtggacagg ttggaaccta tggcttaaac accttcacca acatggaggc
9421 ccaactaata agacaaatgg agtctgaggg aatcttttca cccagcgaat ggaaaccccc
9481 aaatctagcc gaaagagtcc tcgactggtt gaaaaacat ggcaccgaga ggctgaaaag
9541 aatggcaatc agtggagatg actgtgtggt gaaaccaatc gatgacagat tgcaacagc
9601 cttaacagct ttgaatgaca tgggaaaggt aagaaagac ataccgcaat gggaaccttc
9661 aaaaggatgg aatgattggc aacaagtgcc tttctgttca caccatttcc accagctgat
9721 tatgaaggat gggagggaga tagtggtgcc atgccgcaac caagatgaac ttgtaggtag
9781 ggccagagta tcacaaggcg ccggatggag cttgagagaa actgcatgcc taggcaagtc
```

FIG. 39d

```
 9841 atatgcacaa atgtggcagc tgatgtactt ccacaggaga gacttgagat tagcggctaa
 9901 tgctatctgt tcagccgttc cagttgattg ggtcccaacc agccgtacca cctggtcgat
 9961 ccatgcccac catcaatgga tgacaacaga agacatgttg tcagtgtgga atagggtttg
10021 gatagaggaa aacccatgga tggaggacaa gactcatgtg tccagttggg aagacgttcc
10081 atacctagga aaaagggaag atcgatggtg tggatcccta ataggcttaa cagcacgagc
10141 cacctgggcc accaacatac aagtggccat aaaccaagtg agaaggctca ttgggaatga
10201 gaattatcta gacttcatga catcaatgaa gagattcaaa aacgagagtg atcccgaagg
10261 ggcactctgg taagccaact cattcacaaa ataaggaaa ataaaaaatc aaacaaggca
10321 agaagtcagg ccggattaag ccatagcacg gtaagagcta tgctgcctgt gagccccgtc
10381 caaggacgta aaatgaagtc aggccgaaag ccacggttcg agcaagccgt gctgcctgta
10441 gctccatcgt ggggatgtaa aaacccggga ggctgcaaac catggaagct gtacgcatgg
10501 ggtagcagac tagtggttag aggagacccc tcccaagaca caacgcagca gcggggccca
10561 acaccagggg aagctgtacc ctggtggtaa ggactagagg ttagaggaga ccccccgcac
10621 aacaacaaac agcatattga cgctgggaga gaccagagat cctgctgtct ctacagcatc
10681 attccaggca cagaacgcca aaaaatggaa tggtgctgtt gaatcaacag gttct
```

FIG. 40a

```
   1 agttgttagt ctacgtggac cgacaaagac agattctttg agggagctaa gctcaacgta
  61 gttctaacag tttttaatt agagagcaga tctctgatga ataaccaacg aaaaaaggcg
 121 agaaataccc ctttcaatat gctgaaacgc gagagaaacc gcgtgtcgac tgtacaacag
 181 ctgacaaaga gattctcact tggaatgctg cagggacgag gaccattaaa actgttcatg
 241 gccctggtgg cgttccttcg tttcctaaca atcccaccaa cagcagggat actgaagaga
 301 tggggaacaa ttaaaaaatc aaaagccatt aatgttttga gagggttcag gaaagagatt
 361 ggaaggatgc tgaacatctt gaacaggaga cgcagaactg caggcatgat cattatgctg
 421 attccaacag tgatggcgtt ccatttaacc acacgtaacg gagaaccaca catgatcgtc
 481 agtagacaag agaaagggaa aagtcttctg tttaaaacag aggatggtgt gaacatgtgt
 541 accctcatgg ccatggacct tggtgaattg tgtgaagata caatcacgta caagtgtcct
 601 tttctcaggc agaatgaacc agaagacata gattgttggt gcaactctac gtccacatgg
 661 gtaacttatg ggacgtgtac caccacagga gaacacagaa gagaaaaaag atcagtggca
 721 ctcgttccac atgtgggaat gggactggag acacgaactg aaacatggat gtcatcagaa
 781 ggggcctgga acatgccca gagaattgaa acttggatct tgagacatcc aggctttacc
 841 ataatggcag caatcctggc ataccata ggaacgacac atttccaaag agccctgatt
 901 ttcatcttac tgacagctgt cgctccttca atgacaatgc gttgcatagg aatatcaaat
 961 agagactttg tagaaggggt ttcaggagga agctgggttg acatagtctt agaacatgga
1021 agctgtgtga cgacgatggc aaaaaacaaa ccaacattgg attttgaact gataaaaaca
1081 gaagccaaac aacctgccac tctaaggaag tactgtatag aggcaaagct gaccaacaca
1141 acaacagatt ctcgctgccc aacacaagga gaacccagcc taaatgaaga gcaggacaaa
1201 aggttcgtct gcaaacactc catggtggac agaggatggg gaaatggatg tggattattt
1261 ggaaaaggag gcattgtgac ctgtgctatg ttcacatgca aaaagaacat gaaaggaaaa
1321 gtcgtgcaac cagaaaactt ggaatacacc attgtgataa cacctcactc aggggaagag
1381 catgcagtcg gaaatgacac aggaaaacat ggcaaggaaa tcaaaataac accacagt
1441 tccatcacag aagcagagtt gacaggctat ggcactgtca cgatggagtg ctctccgaga
1501 acgggcctcg acttcaatga gatggtgttg ctgcaaatgg aaaataaagc ttggctggtg
1561 cacaggcaat ggttcctaga cctgccgttg ccatggctgc ccggagcgga cacacaagga
1621 tcaaattgga tacagaaaga gacattggtc actttcaaaa atccccatgc gaagaaacag
1681 gatgttgttg ttttgggatc ccaagaaggg gccatgcaca cagcactcac aggggccaca
1741 gaaatccaga tgtcatcagg aaacttactg ttcacaggac atctcaagtg caggctgagg
1801 atggacaaac tacagctcaa aggaatgtca tactctatgt gcacaggaaa gtttaaagtt
1861 gtgaaggaaa tagcagaaac acaacatgga acaatagtta tcagagtaca atatgaaggg
1921 gacggttctc catgtaagat cccttttgag ataatggatt tggaaaaaag acatgtttta
1981 ggtcgcctga ttacagtcaa cccaatcgta acagaaaaag atagcccagt caacatagaa
2041 gcagaacctc cattcggaga cagctacatc atcataggag tagagccggg acaattgaag
2101 ctcaactggt ttaagaaagg aagttctatc ggccaaatga ttgagacaac aatgaggggga
2161 gcgaagagaa tggccatttt aggtgacaca gcttgggatt ttggatccct ggggagagtg
2221 tttacatcta taggaaaggc tctccaccaa gttttcggag caatctatgg gctgccttc
2281 agtggggtct catggactat gaaaatactc ataggagtca ttatcacatg gataggaatg
2341 aattcacgca gcacctcact gtctgtgtca ctagtattgg tgggagtcgt gacgctgtat
2401 ttgggagtta tggtgcaggc cgatagtggt tgcgttgtga ctggaaaaa caaagaactg
2461 aagtgtggca gtgggatttt catcacagac aacgtgcaca catggacaga acaatacaag
2521 ttccaaccag aatccccttc aaagctagct tcagctatcc agaaagctca tgaagagggc
2581 atttgtggaa tccgctcagt aacaagactg gaaaatctga tgtggaaaca ataacacca
2641 gaattgaatc acattctatc agaaatgag gtgaagttga ctattatgac aggagacatc
2701 aaaggaatca tgcaggcagg aaaacgatct ctgcagcccc agcccactga gctgaagtat
2761 tcatggaaaa catggggcaa agcgaaaatg ctctctacag agtctcataa ccagacctt
2821 ctcattgatg gccccgaaac agcagaatgc cccaacacaa acagagcttg gaattcgctg
2881 gaagttgaag actatggctt tggagtattc accaccaata tatggctaaa gttgagagaa
2941 aagcaggatg tattctgcga ctcaaaactc atgtcagcgg ccataaaaga caacagagcc
3001 gtccatgccg atatgggtta ttggatagaa agtgcactca atgacacatg aagatagag
3061 aaagcctctt tcatcgaagt aaaagctgc cactggccaa agtcacacac cctctggagt
3121 aatggagtgt agaaagtga atgataatt ccaaagaatt tcgctggacc agtgtcacaa
3181 cacaactaca gaccaggcta ccatacacaa acagcaggac catggcatct aggtaagctt
```

FIG. 40b

```
3241 gagatggact tgatttctg cgaaggaacc acagtggtgg tgactgagga ctgtggaaat
3301 agaggaccct ctttaagaac aactactgcc tctgaaaac tcataacaga atggtgctgc
3361 cgatcttgca cattaccacc gctaagatac agaggtgagg acggatgctg gtacgggatg
3421 gaaatcagac cattgaaaga gaaagaagag aatttggtca actccttggt cacagccgga
3481 catgggcaga ttgacaactt tcactagga gtcttgggaa tggcattgtt cctggaagaa
3541 atgctcagga cccgagtagg aacgaaacat gcaatactac tagttgcagt ttcttttgtg
3601 acattgatca cagggaacat gtcctttaga gacctgggaa gagtgatggt tatggtgggc
3661 gctactatga cggatgacat aggtatgggc gtgacttatc ttgccctact agcagccttc
3721 aaagtcagac caacttttgc agctggacta ctcttgagaa agttgacctc caaggaattg
3781 atgatgacta ccataggaat cgtactcctc tcccagagca ccataccaga gaccattctt
3841 gaactgactg atgcgttagc cttgggcatg atggtcctta aaatggtgag aaaaatggaa
3901 aagtatcaat tggcagtgac tatcatggct atcttgtgcg tcccaaatgc agtgatatta
3961 caaaacgcat ggaaagtgag ttgcacaata ttggcagtgg tgtccgtttc cccactgttc
4021 ttaacatcct cacagcagaa agcggattgg ataccattag cattgacgat caagggtctc
4081 aatccaacag ctatttttct aacaaccctt tcaagaacca acaagaaaag gagctggcca
4141 ctaaatgagg ctatcatggc agtcgggatg gtgagcattt tggccagttc actcctaaag
4201 aatgacattc ccatgacagg accattagtg gctggagggc tcctcactgt gtgctacgtg
4261 ctcactggac gatcggccga tttggaactg gagagagccg ccgatgtcaa atgggaagat
4321 caggcagaga tatcaggaag cagtccaatc ctgtcaataa caatatcaga agatggtagc
4381 atgtcgataa aaaacgaaga ggaagaacaa acactgacca tactcattag aacaggattg
4441 ctggtgatct caggactttt tcctgtatca ataccaatca cggcagcagc atggtacctg
4501 tgggaagtga agaaacaacg ggctggagta ttgtgggatg tcccttcacc cccacccgtg
4561 ggaaaggctg aactggaaga tggagcctat agaatcaagc aaaaagggat tcttggatat
4621 tcccagatcg gagccggagt ttacaaagaa gaacattcc atacaatgtg gcatgtcaca
4681 cgcggcgctg ttctaatgca taaggaaag aggattgaac catcatgggc ggacgttaag
4741 aaagacctaa tatcatatgg aggaggctgg aagctagaag gagaatggaa ggaaggagaa
4801 gaagtccagg tcttggcatt ggagcctgga aaaaatccaa gagccgtcca aacaaaacct
4861 ggtctttta aaaccaacgc cggaaccata ggtgccgtat ctctggactt ttctcctgga
4921 acctcaggat ctccaatcat cgacaaaaaa ggaaaagttg tgggtctta tggtaatggt
4981 gttgttacaa ggagtggagc atatgtgagt gctatagccc agactgaaaa aagtattgaa
5041 gacaatccag agatcgaaga tgatatttt cgaaagagaa aattgaccat catggaccct
5101 cacccaggag cgggaaagac gaagagatac cttccggcca tagtcagaga ggctataaaa
5161 cggggcctga ggacattaat cctggcccc actagagtcg tggcagctga aatggaggaa
5221 gccctaagag gacttccaat aagataccaa accccagcca tcagagctga gcacaccggg
5281 cgggagattg tggacctaat gtgtcatgcc acattcacta tgaggctgct atcaccagtt
5341 agagtgccaa attacaacct gatcatcatg gacgaagccc atttcacaga cccagcaagt
5401 atagcggcta gaggatacat ctcaactcga gtagagatgg gtgaggcagc tgggatttc
5461 atgacagcca ctcctccggg aagcagagac ccattccctc agagcaatgc accaatcatg
5521 gatgaagaaa gagaaatccc tgaacgttcg tggagttctg acatgagtg ggtcacggat
5581 tttaaggga agactgtttg gttcgttcca agtataaaag caggaaatga tatagcagct
5641 tgcctgagaa aaaatggaaa gaaagtgata caactcagta ggaagacctt tgattctgag
5701 tatgtcaaga ctagaaccaa tgattgggac ttcgtggtca caactgacat ttcagaaatg
5761 ggtgccaact tcaaggctga gagggttata gaccccagac gctgcatgaa accagttata
5821 ctaacagatg gtgaagagcg ggtgatcctg caggaccta tgccagtgac ccactctagt
5881 gcagcacaaa gaaagagggag aataggaaga aatccaaaaa atgaaaatga ccagtacata
5941 tacatggggg aacctctgga aaatgatgaa gactgtgcac actggaaaga gctaaaatg
6001 ctcctagata acatcaacac acctgaagga atcattccta gcatgttcga accagagcgt
6061 gaaaaggtgg atgccattga tggtgaatac cgcttgagag gagaagcaag gaaaaccttt
6121 gtggacctaa tgagaagagg agacctacca gtctggttgg cctacagagt ggcagctgaa
6181 ggcatcaact acgcagacag aaggtggtgt tttgatggaa ttaagaacaa ccaaatcttg
6241 gaagaaaatg tggaggtgga atctggaca aaagaagggg aaggaagaa attaaaaccc
6301 agatggttgg atgccaggat ctactctgac ccactgacgc taaggaatt caaggagttt
6361 gcagctggaa gaaagtccct gaccctgaac ctaatcacag aaatgggtag cttccaact
6421 ttcatgactc agaaggcaag agacgcactg gacaacttag cagtgctgca cacggctgaa
6481 gcaggtggaa gggcgtacaa tcatgctctc agtgaactgc cggagaccct ggagacattg
```

FIG. 40c

```
6541 cttttactga cacttctggc tacagtcaca ggaggaatct ttttattctt gatgagcgga
6601 aggggtatag ggaagatgac cctgggaatg tgctgcataa tcacggctag tattctccta
6661 tggtacgcac aaatacagcc acactggata gcagcttcaa taatactgga gttttttctc
6721 atagttttgc ttattccaga accagaaaag cagagaacac cccaagataa ccaattgacc
6781 tacgttgtca tagccatcct cacagtggtg ccgcaacca tggcaaacga gatgggtttc
6841 ctggaaaaaa cgaagaaaga tctcggattg ggaagcatta caacccagca acccgagagc
6901 aacatcctgg acatagatct acgtcccgca tcagcatgga cgctgtatgc tgtggccaca
6961 acatttgtca caccaatgtt gagacacagc attgaaaatt cctcagtgaa cgtgtcccta
7021 acagctattg ccaaccaagc cacagtgtta atgggtcttg ggaaaggatg ccattgtca
7081 aagatggaca tcggagttcc ccttctcgcc attggatgct actcacaagt caaccccata
7141 actctcacag cagctctttt cttactggta gcacattatg ccatcatagg gccaggactc
7201 caagcaaaag caaccaggga agctcagaaa agagcagcag cgggcatcat gaaaaaccca
7261 actgtcgatg gaataacagt gattgaccta gatccaatac cctatgatcc aaagtttgaa
7321 aagcagttgg gacaagtaat gctcctagtc tctgcgtga ctcaagtgtt gatgatgagg
7381 actacatggg ctctgtgtga ggctttaacc ttagcgaccg ggcctatctc acattgtgg
7441 gaaggaaatc cagggaggtt ttggaacact accattgcag tgtcaatggc taacattttt
7501 agagggagtt acttggccgg agctggactt ctcttttcca tcatgaagaa cacaaccaac
7561 acgagaaggg gaactggcaa cataggagag acgcttggag agaaatggaa aagccgattg
7621 aacgcattgg ggaaaagtga attccagatc tacaagaaaa gtggaatcca ggaagtggat
7681 agaaccttag caaaagaagg cattaaaaga ggagaaacgg accatcacgc tgtgtcgcga
7741 ggctcagcaa aactgagatg gttcgtcgag agaaatatgg tcacaccaga agggaaagta
7801 gtggacctcg gttgcggcag aggaggctgg tcatactatt gtgggggact aaagaatgta
7861 agagaagtca aaggcctgac aaaaggagga ccaggacatg aagaaccat ccccatgtca
7921 acatatgggt ggaatctagt acgtcttcaa agtggagttg acgttttctt cactccgcca
7981 gaaaagtgtg acacattgtt gtgtgacata ggggagtcgt caccaaatcc acggtagaa
8041 gcaggacgaa cactcagagt ccttaactta gtggaaaatt ggttgaacaa caacacccaa
8101 ttttgcataa aggttctcaa cccatacatg ccctcagtca tagaaaaaat ggaagcacta
8161 caaaggaaat atggaggagc cttagtgagg aatccactct cacgaaactc cacacatgag
8221 atgtactggg tatccaatgc ctccgggaac atagtgtcat cagtgaacat gatttcaagg
8281 atgttgatca acagattcac aatgagacac aagaaagcca cttacgagcc agatgtagac
8341 ctcggaagcg gaacccgcaa catcggaatt gaaagtgaga taccaaacct agacataatc
8401 gggaaaagaa tagaaaaaat aaaacaagag catgaaacat catggcacta tgaccaagac
8461 cacccataca aacgtgggc ttaccatggc agctatgaaa caaaacaaac tggatcagca
8521 tcatccatgg tgaacggagt ggtcagactg ctgacaaaac cttgggacgt cgtccccatg
8581 gtgacacaga tggcaatgac agacacgact ccatttggac aacagcgcgt ttttaaagaa
8641 aaagtggaca cgagaaccca agaaccgaaa gaaggcacaa agaaactaat gaaaatcacg
8701 gcagagtggc tttggaaaga actagggaag aaaaagacac taggatgtg cactagagaa
8761 gaattcacaa gaaaggtgag aagcaatgca gccttgggg ccatattcac tgatgagaac
8821 aagtggaagt cggcacgtga ggctgttgaa gatagtaggt tttgggagct ggttgacaag
8881 gaaaggaatc tccatcttga aggaaagtgt gaaacatgtg tgtataacat gatgggaaaa
8941 agagagaaga agctagggga gttcggcaag gcaaaaggca gcagccat atggtacatg
9001 tggcttggag cacgcttctt agagtttgaa gccctaggat tcttgaatga agatcactgg
9061 ttctccagag agaactcctt gagtggagtg gaaggagaag gctgcacaa gctaggttac
9121 attttaagag acgtgagcaa aaagaggga ggagcaatgt atgccgatga caccgcagga
9181 tgggacacaa gatcacact agaagaccta aaaatgaag aatggtaac aaaccacatg
9241 gaaggagaac acaagaaact agccgaggcc attttcaaat taacgtacca aaacaaggtg
9301 gtgcgtgtgc aaagaccaac accaagaggc acagtaatgg atatcatatc gagaagagac
9361 caaagaggta gtggacaagt tggtacctat ggactcaata cttttcaccaa tatggaagcc
9421 caactaatca gacagatgga gggagaagga gtcttcaaaa gcattcagca cctgacagtc
9481 acagaagaaa tcgccgtgca aactggtta gcaagagtag gcgcgaaag gttatcaaga
9541 atggccatca gtggagatga ttgtgttgtg aaacctttag atgacaggtt cgcaagcgct
9601 ttaacagctc taaatgacat gggaaaggtt aggaaagaca tacaacaatg gaaccttca
9661 agaggatgga acgattggac acaagtgccc ttctgttcac accatttcca tgagttaatc
9721 atgaaagacg gccgcgtact tgtagttcca tgcagaaacc aagatgaact gattggtaga
9781 gcccgaattt cccaaggagc tgggtggtct ttgcgagaga cggcctgttt ggggaagtcc
```

FIG. 40d

```
 9841 tacgcccaaa tgtggagctt gatgtacttc cacagacgtg acctcaggct ggcggctaat
 9901 gctatttgct cggcagtccc atcacattgg gttccaacaa gtagaacaac ctggtccata
 9961 cacgccaaac atgaatggat gacaacggaa gacatgctga cagtctggaa cagggtgtgg
10021 attcaagaaa acccatggat ggaagacaaa actccagtgg aatcatggga ggaaatccca
10081 tacttgggga aaagagaaga ccaatggtgc ggctcattga ttgggctaac aagcagggcc
10141 acctgggcaa agaacatcca acagcaata aatcaagtta gatcccttat aggcaatgag
10201 gaatacacag attacatgcc atccatgaaa agattcagaa gagaagagga agaggcagga
10261 gtcctgtggt agaaggcaaa actaacatga aacaaggcta gaagtcaggt cggattaagc
10321 tatagtacgg aaaaaactat gctacctgtg agccccgtcc aaggacgtta aaagaagtca
10381 ggccattaca aatgccatag cttgagtaaa ctgtggcagc ctgtagctcc acctgagaag
10441 gtgtaaaaaa tctgggaggc cacaaaccat ggaagctgta cgcatggcgt agtggactag
10501 cggttagagg agacccctcc cttacaaatc gcagcaacaa tgggggccca aggtgagatg
10561 aagctgtagt ctcactggaa ggactagagg ttagaggaga ccccccaaa acaaaaaaca
10621 gcatattgac gctgggaaag accagagatc ctgctgtctc ctcagcatca ttccaggcac
10681 agaacgccag aaaatggaat ggtgctgttg aatcaacagg ttct
```

```
 982 ttggaagga gtgtctggag caacatgggt ggatttggtt
1021 ctcgaaggcg acagctgcgt gactatcatg tctaaggaca agcctaccat cgatgtgaag
1081 atgatgaata tggaggcggc caacctggca gaggtccgca gttattgcta tttggctacc
1141 gtcagcgatc tctccaccaa agctgcgtgc ccgaccatgg gagaagctca caatgacaaa
1201 cgtgctgacc cagcttttgt gtgcagacaa ggagtggtgg acaggggctg gggcaacggc
1261 tgcggactat ttggcaaagg aagcattgac acatgcgcca aatttgcctg ctctaccaag
1321 gcaataggaa gaaccatctt gaaagagaat atcaagtacg aagtggccat ttttgtccat
1381 ggaccaacta ctgtggagtc gcacggaaac tactccacac aggttggagc cactcaggca
1441 gggagattca gcatcactcc tgcagcgcct tcatacacac taaagcttgg agaatatgga
```

FIG. 41

Amino-terminus-
LEGVSGATWVDLVLEGDSCVTIMSKDKPTIDVKMMNMEAANLAEVRSYCYLATVSDLSTKAACPT
MGEAHNDKRADPAFVCRQGVVDRGWGNGCGLFGKGSIDTCAKFACSTKAIGRTILKENIKYEVAI
FVHGPTTVESHGNYSTQVGATQAGRFSITPAAPSYTLKLGE
-carboxy terminus (171 amino acids)

FIG. 42

```
 7681 ggtggggcaa aaggacgcac cttgggagag gtttggaaag aaagactcaa ccagatgaca
 7741 aaagaagagt tcactaggta ccgcaaagag gccatcatcg aagtcgatcg ctcagcagca
 7801 aaacacgcca ggaaagaagg caatgtcact ggagggcatc cagtctctag gggcacagca
 7861 aaactgagat ggctggtcga acggaggttt ctcgaaccgg tcggaaaagt gattgacctt
 7921 ggatgtggaa gaggcggttg gtgttactat atggcaaccc aaaaaagagt ccaagaagtc
 7981 agagggtaca caaagggcgg tcccggacat gaagagcccc aactagtgca agttatgga
 8041 tggaacattg tcaccatgaa gagtggggtg gatgtgttct acagaccttc tgagtgttgt
 8101 gacaccctcc tttgtgacat cggagagtcc tcgtcaagtg ctgaggttga agagcatagg
 8161 acgattcggg tccttgaaat ggttgaggac tggctgcacc gagggccaag ggaattttgc
 8221 gtgaaggtgc tctgcccta catgccgaaa gtcatagaga agatggagct gctccaacgc
 8281 cggtatgggg ggggactggt cagaaaccca ctctcacgga attccacgca cgagatgtat
 8341 tgggtgagtc gagcttcagg caatgtggta cattcagtga atatgaccag ccaggtgctc
 8401 ctaggaagaa tggaaaaaag gacctggaag ggacccaat acgaggaaga tgtaaacttg
 8461 ggaagtggaa ccagggcggt gggaaaacgc ctgctcaact cagacaccag taaaatcaag
 8521 aacaggattg aacgactcag gcgtgagtac agttcgacgt ggcaccacga tgagaaccac
 8581 ccatatagaa cctggaacta tcacggcagt tatgatgtga gcccacagg ctccgccagt
 8641 tcgctggtca atggagtggt caggctcctc tcaaaaccat gggacaccat cacgaatgtt
 8701 accaccatgg ccatgactga cactactccc ttcgggcagc agcgagtgtt caaagagaag
 8761 gtggacacga agctcctga accgccagaa ggagtgaagt acgtgctcaa cgagaccacc
 8821 aactggttgt gggcgttttt ggccagagaa aaacgtccca gaatgtgctc tcgagaggaa
 8881 ttcataagaa aggtcaacag caatgcagct ttgggtgcca tgtttgaaga gcagaatcaa
 8941 tggaggagcg ccagagaggc agttgaagat ccaaaatttt gggagatggt ggatgaggag
 9001 cgcgaggcac atctgcgggg ggaatgtcac acttgcattt acaacatgat gggaaagaga
 9061 gagaaaaaac cggagagtt cggaaaggcc aagggaagca gagccatttg gttcatgtgg
 9121 ctcggagctc gctttctgga gttcgaggct ctgggttttc tcaatgaaga ccactggctt
 9181 ggaagaaaga actcaggagg aggtgtcgag ggcttgggcc tccaaaaact gggttacatc
 9241 ctgcgtgaag ttggcacccg gcctggggc aagatctatg ctgatgacac agctggctgg
 9301 gacacccgca tcacgagagc tgacttggaa aatgaagcta aggtgcttga gctgcttgat
 9361 ggggaacatc ggcgtcttgc caggccatc attgagctca cctatcgtca caagttgtg
 9421 aaagtgatgc gcccggctgc tgatggaaga accgtcatgg atgttatctc cagagaagat
 9481 cagaggggga gtggacaagt tgtcacctac gccctaaaca ctttcaccaa cctggccgtc
 9541 cagctggtga ggatgatgga aggggaagga gtgattggcc cagatgatgt ggagaaactc
 9601 acaaagggga aaggacccaa agtcaggacc tggctgtttg agaatgggga agaaagactc
 9661 agccgcatgg ctgtcagtgg agatgactgt gtggtaaagc ccctggacga tcgctttgcc
 9721 acctcgctcc acttcctcaa tgctatgtca aaggttcgca agacatcca agagtggaaa
 9781 ccgtcaactg gatggtatga ttggcagcag gttccatttt gctcaaacca tttcactgaa
 9841 ttgatcatga aagatggaag aacactggtg gttccatgcc gaggacagga tgaattggta
 9901 ggcagagctc gcatatctcc aggggccgga tggaacgtcc gcgacactgc ttgtctggct
 9961 aagtcttatg cccagatgtg gctgcttctg tacttccaca agagagacct gcggctcatg
10021 gccaacgcca tttgctccgc tgtccctgtg aattgggtcc ctaccggaag aaccacgtgg
10081 tccatccatg caggaggaga gtggatgaca acagaggaca tgttggaggt ctggaaccgt
10141 gtttggatag aggagaatga atggatggaa gacaaaaccc cagtggagaa atggagtgac
10201 gtcccatatt caggaaaacg agaggacatc tggtgtggca gcctgattgg cacaagagcc
10261 cgagccacgt gggcagaaaa catccaggtg ctatcaacc aagtcagagc aatcatcgga
10321 gatgagaagt atgtggatta catgagttca ctaaagagat atgaagacac aacttggtt
10381 gaggacacag tactg
```

FIG. 43

```
Amino terminus-
GGAKGRTLGEVWKERLNQMTKEEFTRYRKEAIIEVDRSAAKHARKEGNVTGGHPVSRGTA
KLRWLVERRFLEPVGKVIDLGCGRGGWCYYMATQKRVQEVRGYTKGGPGHEEPQLVQSYG
WNIVTMKSGVDVFYRPSECCDTLLCDIGESSSSAEVEEHRTIRVLEMVEDWLHRGPREFC
VKVLCPYMPKVIEKMELLQRRYGGGLVRNPLSRNSTHEMYWVSRASGNVVHSVNMTSQVL
LGRMEKRTWKGPQYEEDVNLGSGTRAVGKPLLNSDTSKIKNRIERLRREYSSTWHHDENH
PYRTWNYHGSYDVKPTGSASSLVNGVVRLLSKPWDTITNVTTMAMTDTTPFGQQRVFKEK
VDTKAPEPPEGVKYVLNETTNWLWAFLAREKRPRMCSREEFIRKVNSNAALGAMFEEQNQ
WRSAREAVEDPKFWEMVDEEREAHLRGECHTCIYNMMGKREKKPGEFGKAKGSRAIWFMW
LGARFLEFEALGFLNEDHWLGRKNSGGGVEGLGLQKLGYILREVGTRPGGKIYADDTAGW
DTRITRADLENEAKVLELLDGEHRRLARAIIELTYRHKVVKVMRPAADGRTVMDVISRED
QRGSGQVVTYALNTFTNLAVQLVRMMEGEGVIGPDDVEKLTKGKGPKVRTWLFENGEERL
SRMAVSGDDCVVKPLDDRFATSLHFLNAMSKVRKDIQEWKPSTGWYDWQQVPFCSNHFTE
LIMKDGRTLVVPCRGQDELVGRARISPGAGWNVRDTACLAKSYAQMWLLLYFHRRDLRLM
ANAICSAVPVNWVPTGRTTWSIHAGGEWMTTEDMLEVWNRVWIEENEWMEDKTPVEKWSD
VPYSGKREDIWCGSLIGTRARATWAENIQVAINQVRAIIGDEKYVDYMSSLKRYEDTTLV
EDTVL
-carboxy terminus (905 amino acids)
```

FIG. 44

```
7574                ggcacgg gagcccaagg ggaaacactg ggagaaaaat ggaaaagaca
 7621 gctaaaccaa ttgagcaagt cagaattcaa cacttacaaa aggagtggga ttatagaggt
 7681 ggatagatct gaagccaaag aggggttaaa aagaggagaa ccgactaaac acgcagtgtc
 7741 gagaggaacg gccaaactga ggtggtttgt ggagaggaac cttgtgaaac cagaagggaa
 7801 agtcatagac ctcggttgtg gaagaggtgg ctggtcatat tattgcgctg ggctgaagaa
 7861 agtcacagaa gtgaaaggat acacgaaagg aggacctgga catgaggaac caatcccaat
 7921 ggcaacctat ggatggaacc tagtaaagct atactccggg aaagatgtat tctttacacc
 7981 acctgagaaa tgtgacaccc tcttgtgtga tattggtgag tcctctccga acccaactat
 8041 agaagaagga agaacgttac gtgttctaaa gatggtggaa ccatggctca gaggaaacca
 8101 attttgcata aaaattctaa atccctatat gccgagtgtg gtagaaactt tggagcaaat
 8161 gcaaagaaaa catggaggaa tgctagtgcg aaatccactc tcaagaaact ccactcatga
 8221 aatgtactgg gtttcatgtg gaacaggaaa cattgtgtca gcagtaaaca tgacatctag
 8281 aatgttgcta aatcgattca caatggctca caggaagcca acatatgaaa gagacgtgga
 8341 cttaggcgct ggaacaagac atgtggcagt agaaccagag gtggccaacc tagatatcat
 8401 tggccagagg atagagaata taaaaaatgg acacaaatca acatggcact atgatgagga
 8461 caatccatac aaaacatggg cctatcatgg atcatatgag gtcaagccat caggatcagc
 8521 ctcatccatg gtcaatggtg tggtgagact gctaaccaaa ccatgggatg tcattcccat
 8581 ggtcacacaa atagccatga ctgacaccac acccttgga caacagaggg tgtttaaaga
 8641 gaaagttgac acgcgtacac caaaagcgaa acgaggcaca gcacaaatta tggaggtgac
 8701 agccaggtgg ttatggggtt ttctctctag aaacaaaaaa cccagaatct gcacaagaga
 8761 ggagttcaca agaaaagtca ggtcaaacgc agctattgga gcagtgttcg ttgatgaaaa
 8821 tcaatggaac tcagcaaaag aggcagtgga agatgaacgg ttctggaccc ttgtgcacag
 8881 agagagggag cttcataaac aaggaaaatg tgccacgtgt gtctacaaca tgatgggaaa
 8941 gagagagaaa aaattaggag agttcggaaa ggcaaaagga agtcgcgcaa tatggtacat
 9001 gtggttggga gcgcgctttt tagagtttga agcccttggt ttcatgaatg aagatcactg
 9061 gttcagcaga gagaattcac tcagtggagt ggaaggagaa ggactccaca aacttggata
 9121 catactcaga gacatatcaa agattccagg gggaaatatg tatgcagatg acacagccgg
 9181 atgggacaca gaataacag aggatgatct tcagaatgag gccaaaatca ctgacatcat
 9241 ggaacctgaa catgccctat tggccacgtc aatctttaag ctaacctacc aaaacaaggt
 9301 agtaagggtg cagagaccag cgaaaaatgg aaccgtgatg gatgtcatat ccagacgtga
 9361 ccagagagga agtggacagg ttggaaccta tggcttaaac accttcacca acatggaggc
 9421 ccaactaata agacaaatgg agtctgaggg aatcttttca cccagcgaat ggaaacccc
 9481 aaatctagcc gaaagagtcc tcgactggtt gaaaaaacat ggcaccgaga ggctgaaaag
 9541 aatggcaatc agtggagatg actgtgtggt gaaaccaatc gatgacagat tgcaacagc
 9601 cttaacagct ttgaatgaca tgggaaaggt aagaaaagac ataccgcaat gggaaccttc
 9661 aaaaggatgg aatgattggc aacaagtgcc tttctgttca ccacatttcc accagctgat
 9721 tatgaaggat gggagggaga tagtggtgcc atgccgcaac caagatgaac ttgtaggtag
 9781 ggccagagta tcacaaggcg ccggatggag cttgagagaa actgcatgcc taggcaagtc
 9841 atatgcacaa atgtggcagc tgatgtactt ccacaggaga gacttgagat tagcggctaa
 9901 tgctatctgt tcagccgttc cagttgattg ggtcccaacc agccgtacca cctggtcgat
 9961 ccatgcccac catcaatgga tgacaacaga agacatgttg tcagtgtgga ataggtttg
10021 gatagaggaa aacccatgga tggaggacaa gactcatgtg tccagttggg aagacgttcc
10081 atacctagga aaaagggaag atcgatggtg tggatcccta ataggcttaa cagcacgagc
10141 cacctgggcc accaacatac aagtggccat aaaccaagtg agaaggctca ttgggaatga
10201 gaattatcta gacttcatga catcaatgaa gagattcaaa aacgagagtg atcccgaagg
10261 ggcactctgg
```

FIG. 45

Amino terminus-
GTGAQGETLGEKWKRQLNQLSKSEFNTYKRSGIIEVDRSEAKEGLKRGEPTKHAVSRGTA
KLRWFVERNLVKPEGKVIDLGCGRGGWSYYCAGLKKVTEVKGYTKGGPGHEEPIPMATYG
WNLVKLYSGKDVFFTPPEKCDTLLCDIGESSPNPTIEEGRTLRVLKMVEPWLRGNQFCIK
ILNPYMPSVVETLEQMQRKHGGMLVRNPLSRNSTHEMYWVSCGTGNIVSAVNMTSRMLLN
RFTMAHRKPTYERDVDLGAGTRHVAVEPEVANLDIIGQRIENIKNGHKSTWHYDEDNPYK
TWAYHGSYEVKPSGSASSMVNGVVRLLTKPWDVIPMVTQIAMTDTTPFGQQRVFKEKVDT
RTPKAKRGTAQIMEVTARWLWGFLSRNKKPRICTREEFTRKVRSNAAIGAVFVDENQWNS
AKEAVEDERFWDLVHRERELHKQGKCATCVYNMMGKREKKLGEFGKAKGSRAIWYMWLGA
RFLEFEALGFMNEDHWFSRENSLSGVEGEGLHKLGYILRDISKIPGGNMYADDTAGWDTR
ITEDDLQNEAKITDIMEPEHALLATSIFKLTYQNKVVRVQRPAKNGTVMDVISRRDQRGS
GQVGTYGLNTFTNMEAQLIRQMESEGIFSPSELETPNLAERVLDWLKKHGTERLKRMAIS
GDDCVVKPIDDRFATALTALNDMGKVRKDIPQWEPSKGWNDWQQVPFCSHHFHQLIMKDG
REIVVPCRNQDELVGRARVSQGAGWSLRETACLGKSYAQMWQLMYFHRRDLRLAANAICS
AVPVDWVPTSRTTWSIHAHHQWMTTEDMLSVWNRVWIEENPWMEDKTHVSSWEDVPYLGK
REDRWCGSLIGLTARATWATNIQVAINQVRRLIGNENYLDFMTSMKRFKNESDPEGALW
-carboxy terminus (899 amino acids)

FIG. 46

```
 7561          g gaactggcaa cataggagag acgcttggag agaaatggaa aagccgattg
 7621 aacgcattgg ggaaaagtga attccagatc tacaagaaaa gtggaatcca ggaagtggat
 7681 agaaccttag caaaagaagg cattaaaaga ggagaaacgg accatcacgc tgtgtcgcga
 7741 ggctcagcaa aactgagatg gttcgtcgag agaaatatgg tcacaccaga agggaaagta
 7801 gtggacctcg gttgcggcag aggaggctgg tcatactatt gtgggggact aaagaatgta
 7861 agagaagtca aaggcctgac aaaaggagga ccaggacatg aagaacccat ccccatgtca
 7921 acatatgggt ggaatctagt acgtcttcaa agtggagttg acgttttctt cactccgcca
 7981 gaaaagtgtg acacattgtt gtgtgacata ggggagtcgt caccaaatcc cacggtagaa
 8041 gcaggacgaa cactcagagt ccttaactta gtggaaaatt ggttgaacaa caacacccaa
 8101 ttttgcataa aggttctcaa cccatacatg ccctcagtca tagaaaaaat ggaagcacta
 8161 caaaggaaat atggaggagc cttagtgagg aatccactct cacgaaactc cacacatgag
 8221 atgtactggg tatccaatgc ctccgggaac atagtgtcat cagtgaacat gatttcaagg
 8281 atgttgatca acagattcac aatgagacac aagaaagcca cttacgagcc agatgtagac
 8341 ctcggaagcg gaacccgcaa catcggaatt gaaagtgaga taccaaacct agacataatc
 8401 gggaaaagaa tagaaaaaat aaaacaagag catgaaacat catggcacta tgaccaagac
 8461 cacccataca aaacgtgggc ttaccatggc agctatgaaa caaaacaaac tggatcagca
 8521 tcatccatgg tgaacggagt ggtcagactg ctgacaaaac cttgggacgt cgtccccatg
 8581 gtgacacaga tggcaatgac agacacgact ccatttggac aacagcgcgt ttttaaagaa
 8641 aaagtggaca cgagaaccca agaaccgaaa gaaggcacaa agaaactaat gaaaatcacg
 8701 gcagagtggc tttggaaaga actagggaag aaaaagacac taggatgtg cactagagaa
 8761 gaattcacaa gaaaggtgag aagcaatgca gccttggggg ccatattcac tgatgagaac
 8821 aagtggaagt cggcacgtga ggctgttgaa gatagtaggt tttgggagct ggttgacaag
 8881 gaaaggaatc tccatcttga aggaaagtgt gaaacatgtg tgtataacat gatgggaaaa
 8941 agagagaaga agctagggga gttcggcaag gcaaaaggca gcagccat atggtacatg
 9001 tggcttggag cacgcttctt agagtttgaa gccctaggat tcttgaatga agatcactgg
 9061 ttctccagag agaactcctt gagtggagtg gaaggagaag gctgcacaa gctaggttac
 9121 attttaagag acgtgagcaa gaaagaggga ggagcaatgt atgccgatga caccgcagga
 9181 tgggacacaa gaatcacact agaagaccta aaaaatgaag aatggtaac aaaccacatg
 9241 gaaggagaac acaagaaact agccgaggcc attttcaaat taacgtacca aaacaaggtg
 9301 gtgcgtgtgc aaagaccaac accaagaggc acagtaatgg atatcatatc gagaagagac
 9361 caaagaggta gtggacaagt tggtacctat ggactcaata ctttcaccaa tatggaagcc
 9421 caactaatca gacagatgga gggagaagga gtcttcaaaa gcattcagca cctgacagtc
 9481 acagaagaaa tcgccgtgca aaactggtta gcaagagtag gcgcgaaag gttatcaaga
 9541 atggccatca gtggagatga ttgtgttgtg aaacctttag atgacaggtt cgcaagcgct
 9601 ttaacagctc taaatgacat gggaaaggtt aggaaagaca taacaatg ggaaccttca
 9661 agaggatgga acgattggac acaagtgccc ttctgttcac accatttcca tgagttaatc
 9721 atgaaagacg ccgcgtact tgtagttcca tgcagaaacc aagatgaact gattggtaga
 9781 gcccgaattt cccaaggagc tgggtgtct ttgcgagaga cggcctgttt ggggaagtcc
 9841 tacgcccaaa tgtggagctt gatgtacttc cacagacgtg acctcaggct ggcggctaat
 9901 gctatttgct cggcagtccc atcacattgg gttccaacaa gtagaacaac ctggtccata
 9961 cacgccaaac atgaatggat gacaacggaa gacatgctga cagtctggaa cagggtgtgg
10021 attcaagaaa acccatggat ggaagacaaa actccagtgg aatcatggga ggaaatccca
10081 tacttgggga aaagagaaga ccaatggtgc ggctcattga ttgggctaac aagcagggcc
10141 acctgggcaa agaacatcca aacagcaata aatcaagtta gatcccttat aggcaatgag
10201 gaatacacag attacatgcc atccatgaaa agattcagaa gagaagagga gaggcagga
10261 gtcctgtggt
```

FIG. 47

Amino terminus-
GTGNIGETLGEKWKSRLNALGKSEFQIYKKSGIQEVDRTLAKEGIKRGETDHHAVSRGSA
KLRWFVERNMVTPEGKVVDLGCGRGGWSYYCGGLKNVREVKGLTKGGPGHEEPIPMSTYG
WNLVRLQSGVDVFFTPPEKCDTLLCDIGESSPNPTVEAGRTLRVLNLVENWLNNNTQFCI
KVLNPYMPSVIEKMEALQRKYGGALVRNPLSRNSTHEMYWVSNASGNIVSSVNMISRMLI
NRFTMRHKKATYEPDVDLGSGTRNIGIESEIPNLDIIGKRIEKIKQEHETSWHYDQDHPY
KTWAYHGSYETKQTGSASSMVNGVVRLLTKPWDVVPMVTQMAMTDTTPFGQQRVFKEKVD
TRTQEPKEGTKKLMKITAEWLWKELGKKKTPRMCTREEFTRKVRSNAALGAIFTDENKWK
SAREAVEDSRFWELVDKERNLHLEGKCETCVYNMMGKREKKLGEFGKAKGSRAIWYMWLG
ARFLEFEALGFLNEDHWFSRENSLSGVEGEGLHKLGYILRDVSKKEGGAMYADDTAGWDT
RITLEDLKNEEMVTNHMEGEHKKLAEAIFKLTYQNKVVRVQRPTPRGTVMDIISRRDQRG
SGQVGTYGLNTFTNMEAQLIRQMEGEGVFKSIQHLTVTEEIAVQNWLARVGRERLSRMAI
SGDDCVVKPLDDRFASALTALNDMGKVRKDIQQWEPSRGWNDWTQVPFCSHHFHELIMKD
GRVLVVPCRNQDELIGRARISQGAGWSLRETACLGKSYAQMWSLMYFHRRDLRLAANAIC
SAVPSHWVPTSRTTWSIHAKHEWMTTEDMLTVWNRVWIQENPWMEDKTPVESWEEIPYLG
KREDQWCGSLIGLTSRATWAKNIQTAINQVRSLIGNEEYTDYMPSMKRFRREEEEAGVLW
-carboxy terminus (900 amino acids)

FIG. 48

SEQUENCE LISTING

<160> NUMBER OF SEQ ID NOS: 20

<210> SEQ ID NO 1
<211> LENGTH: 10975
<212> TYPE: DNA
<213> ORGANISM: West Nile virus

<400> SEQUENCE: 1

```
gctgacaaac ttagtagtgt ttgtgaggat taacaacaat taacacagtg cgagctgttt      60
cttagcacga agatctcgat gtctaagaaa ccaggagggc ccggcaagag ccgggctgtc     120
aatatgctaa aacgcggaat gccccgcgtg ttgtccttga ttggactgaa gagggctatg     180
ttgagcctga tcgacggcaa ggggccaata cgatttgtgt tggctctctt ggcgttcttc     240
aggttcacag caattgctcc gacccgagca gtgctggatc gatggagagg tgtgaacaaa     300
caaacagcga tgaaacacct tctgagtttt aagaaggaac tagggacctt gaccagtgct     360
atcaatcggc ggagctcaaa acaaaagaaa agaggaggaa agaccggaat tgcagtcatg     420
attggcctga tcgccagcgt aggagcagtt accctctcta acttccaagg gaaggtgatg     480
atgacggtaa atgctactga cgtcacagat gtcatcacga ttccaacagc tgctggaaag     540
aacctatgca ttgtcagagc aatggatgtg ggatacatgt gcgatgatac tatcacttat     600
gaatgcccag tgctgtcggc tggtaatgat ccagaagaca tcgactgttg gtgcacaaag     660
tcagcagttt acgtcaggta tggaagatgc accaagacac gccactcaag acgcagtcgg     720
aggtcactga cagtgcagac acacggagaa agcactctag cgaacaagaa ggggcttgg     780 atggacagca ccaaggccac aaggtacttg gtaaaaacag aatcatggat cttgaggaac     840
cctggatatg ccctggtggc agccgtcatt ggttggatgc ttgggagcaa caccatgcag     900
agagttgtgt ttgtcgtgct attgcttttg gtggccccag cttacagctt caactgcctt     960
ggaatgagca acagagactt cttggaagga gtgtctggag caacatgggt ggatttggtt    1020
ctcgaaggcg acagctgcgt gactatcatg tctaaggaca gcctaccat cgatgtgaag    1080 atgatgaata tggaggcggc caacctggca gaggtccgca gttattgcta tttggctacc    1140
gtcagcgatc tctccaccaa agctgcgtgc ccgaccatgg gagaagctca caatgacaaa    1200
cgtgctgacc cagcttttgt gtgcagacaa ggagtggtgg acaggggctg gggcaacggc    1260
tgcggactat ttggcaaagg aagcattgac acatgcgcca aatttgcctg ctctaccaag    1320
gcaataggaa gaaccatctt gaaagagaat atcaagtacg aagtggccat tttttgtccat    1380 ggaccaacta ctgtggagtc gcacggaaac tactccacac aggttggagc cactcaggca    1440
gggagattca gcatcactcc tgcagcgcct tcatacacac taaagcttgg agaatatgga    1500
gaggtgacag tggactgtga accacggtca gggattgaca ccaatgcata ctacgtgatg    1560
actgttggaa caaagacgtt cttggtccat cgtgagtggt tcatggacct caacctccct    1620
```

```
tggagcagtg ctggaagtac tgtgtggagg aacagagaga cgttaatgga gtttgaggaa    1680
ccacacgcca cgaagcagtc tgtgatagca ttgggctcac aagagggagc tctgcatcaa    1740
gctttggctg gagccattcc tgtggaattt tcaagcaaca ctgtcaagtt gacgtcgggt    1800
catttgaagt gtagagtgaa gatggaaaaa ttgcagttga agggaacaac ctatggcgtc    1860
tgttcaaagg ctttcaagtt tcttgggact cccgcagaca caggtcacgg cactgtggtg    1920
ttggaattgc agtacactgg cacgatgga ccttgcaaag ttcctatctc gtcagtggct     1980
tcattgaacg acctaacgcc agtgggcaga ttggtcactg tcaacccttt tgtttcaatg    2040
gccacggcca acgctaaggt cctgattgaa ttggaaccac cctttggaga ctcatacata    2100
gtggtgggca gaggagaaca acagatcaat caccattggc acaagtctgg aagcagcatt    2160
ggcaaagcct ttacaaccac cctcaaagga gcgcagagac tagccgctct aggagacaca    2220
gcttgggact ttgatcagt tggagggggtg ttcacctcag ttgggaaggc tgtccatcaa    2280
gtgttcggag gagcattccg ctcactgttc ggaggcatgt cctggataac gcaaggattg    2340 ctggggctc tcctgttgtg gatgggcatc aatgctcgtg ataggtccat agctctcacg    2400
tttctcgcag ttgaggagt tctgctcttc ctctccgtga acgtgcacgc tgacactggg    2460
tgtgccatag acatcagccg gcaagagctg agatgtggaa gtggagtgtt catacacaat    2520
gatgtggagg cttggatgga ccggtacaag tattaccctg aaacgccaca aggcctagcc    2580
aagatcattc agaaagctca taaggaagga gtgtgcggtc tacgatcagt ttccagactg    2640
gagcatcaaa tgtgggaagc agtgaaggac gagctgaaca ctcttttgaa ggagaatggt    2700 gtggaccta gtgtcgtggt tgagaaacag gagggaatgt acaagtcagc acctaaacgc    2760
ctcaccgcca ccacgaaaaa attggaaatt ggctggaagg cctggggaaa gagtattta    2820 tttgcaccag aactcgccaa caacaccttt gtggttgatg gtccggagac caaggaatgt    2880
ccgactcaga atcgcgcttg gaatagctta gaagtggagg attttggatt tggtctcacc    2940
agcactcgga tgttcctgaa ggtcagagag agcaacacaa ctgaatgtga ctcgaagatc    3000
attggaacgc ctgtcaagaa caacttggcg atccacagtg acctgtccta ttggattgaa    3060
agcaggctca atgatacgtg gaagcttgaa agggcagttc tgggtgaagt caaatcatgt    3120
acgtggcctg agacgcatac cttgtggggc gatggaatcc ttgagagtga cttgataata    3180
ccagtcacac tggcgggacc acgaagcaat cacaatcgga gacctgggta caagacacaa    3240
aaccagggcc catgggacga aggccgggta gagattgact tcgattactg cccaggaact    3300
acggtcaccc tgagtgagag ctgcggacac cgtggacctg ccactcgcac caccacagag    3360
agcggaaagt tgataacaga ttggtgctgc aggagctgca cccttaccac actgcgctac    3420
caaactgaca gcggctgttg gtatggtatg gagatcagac acagagaca tgatgaaaag    3480 accctcgtgc agtcacaagt gaatgcttat aatgctgata tgattgaccc ttttcagttg    3540
ggccttctgg tcgtgttctt ggccacccag gaggtccttc gcaagaggtg gacagccaag    3600
atcagcatgc cagctatact gattgctctg ctagtcctgg tgtttgggg cattacttac    3660 actgatgtgt tacgctatgt catcttggtg ggggcagctt cgcagaatc taattcggga    3720 ggagacgtgg tacacttggc gctcatggcg accttcaaga tacaaccagt gtttatggtg    3780
gcatcgtttc ttaaagcgag atggaccaac caggagaaca ttttgttgat gttggcggct    3840
gttttctttc aaatggctta tcacgatgcc cgccaaattc tgctctggga gatccctgat    3900
gtgttgaatt cactggcggt agcttggatg atactgagag ccataacatt cacaacgaca    3960
```

```
tcaaacgtgg ttgttccgct gctagccctg ctaacacccg ggctgagatg cttgaatctg    4020
gatgtgtaca ggatactgct gttgatggtc ggaataggca gcttgatcag ggagaagagg    4080
agtgcagctg caaaaaagaa aggagcaagt ctgctatgct tggctctagc ctcaacagga    4140
cttttcaacc ccatgatcct tgctgctgga ctgattgcat gtgatcccaa ccgtaaacgc    4200
ggatggcccg caactgaagt gatgacagct gtcggcctaa tgtttgccat cgtcggaggg    4260
ctggcagagc ttgacattga ctccatggcc attccaatga ctatcgcggg gctcatgttt    4320
gctgctttcg tgatttctgg gaaatcaaca gatatgtgga ttgagagaac ggcggacatt    4380
tcctgggaaa gtgatgcaga aattacaggc tcgagcgaaa gagttgatgt gcggcttgat    4440
gatgatggaa acttccagct catgaatgat ccaggagcac cttggaagat atggatgctc    4500
agaatggtct gtctcgcgat tagtgcgtac accccctggg caatcttgcc ctcagtagtt    4560
ggattttgga taactctcca atacacaaag agaggaggcg tgttgtggga cactccctca    4620
ccaaaggagt acaaaagggg ggacacgacc accggcgtct acaggatcat gactcgtggg    4680
ctgctcggca gttatcaagc aggagcgggc gtgatggttg aaggtgtttt ccacacccct    4740
tggcatacaa caaaggagc cgcttttgatg agcggagagg gccgcctgga cccatactgg    4800
ggcagtgtca aggaggatcg actttgttac ggaggaccct ggaaattgca gcacaagtgg    4860
aacgggcagg atgaggtgca gatgattgtg gtggaacctg gcaagaacgt taagaacgtc    4920
cagacgaaac caggggtgtt caaaacacct gaaggagaaa tcggggccgt gactttggac    4980 ttcccccactg gaacatcagg ctcaccaata gtggacaaaa acggtgatgt gattgggctt    5040
tatggcaatg gagtcataat gcccaacggc tcatacataa gcgcgatagt gcagggtgaa    5100
aggatggatg agccaatccc agccggattc gaacctgaga tgctgaggaa aaaacagatc    5160
actgtactgg atctccatcc cggcgccggt aaaacaagga ggattctgcc acagatcatc    5220
aaagaggcca taaacagaag actgagaaca gccgtgctag caccaaccag ggttgtggct    5280
gctgagatgg ctgaagcact gagaggactg cccatccggt accagacatc cgcagtgccc    5340
agagaacata tggaaatga gattgttgat gtcatgtgtc atgctaccct cacccacagg    5400
ctgatgtctc ctcacagggt gccgaactac aacctgttcg tgatggatga ggctcatttc    5460
accgacccag ctagcattgc agcaagaggt tacatttcca caaaggtcga gctaggggag    5520
gcggcggcaa tattcatgac agccacccca ccaggcactt cagatccatt cccagagtcc    5580
aattcaccaa tttccgactt acagactgag atcccggatc gagcttggaa ctctggatac    5640
gaatggatca cagaatacac cgggaagacg gtttggtttg tgcctagtgt caagatgggg    5700
aatgagattg cccttttgcct acaacgtgct ggaaagaaag tagtccaatt gaacagaaag    5760
tcgtacgaga cggagtaccc aaaatgtaag aacgatgatt gggactttgt tatcacaaca    5820
gacatatctg aaatgggggc taacttcaag gcgagcaggg tgattgacag ccggaagagt    5880
gtgaaaccaa ccatcataac agaaggagaa gcgagagtga tcctgggaga accatctgca    5940
gtgacagcag ctagtgccgc ccagagacgt ggacgtatcg gtagaaatcc gtcgcaagtt    6000
ggtgatgagt actgttatgg ggggcacacg aatgaagacg actcgaactt cgcccattgg    6060
actgaggcac gaatcatgct ggacaacatc aacatgccaa acggactgat cgctcaattc    6120
taccaaccag agcgtgagaa ggtatatacc atggatgggg aataccggct cagaggagaa    6180
gagagaaaaa actttctgga actgttgagg actgcagatc tgccagtttg gctggcttac    6240
aaggttgcag cggctggagt gtcataccac gaccggaggt ggtgcttgga tggtcctagg    6300
acaaacacaa ttttagaaga caacaacgaa gtggaagtca tcacgaagct tggtgaaagg    6360
```

```
aagattctga ggccgcgctg gattgacgcc agggtgtact cggatcacca ggcactaaag    6420
gcgttcaagg acttcgcctc gggaaaacgt tctcagatag ggctcattga ggttctggga    6480
aagatgcctg agcacttcat ggggaagaca tgggaagcac ttgacaccat gtacgttgtg    6540
gccactgcag agaaggagg aagagctcac agaatggccc tggaggaact gccagatgct    6600
cttcagacaa ttgccttgat tgccttattg agtgtgatga ccatgggagt attcttcctc    6660
ctcatgcagc ggaagggcat tggaaagata ggtttgggag gcgctgtctt gggagtcgcg    6720
acctttttct gttggatggc tgaagttcca ggaacgaaga tcgccggaat gttgctgctc    6780
tcccttctct tgatgattgt gctaattcct gagccagaga agcaacgttc gcagacagac    6840
aaccagctag ccgtgttcct gatttgtgtc atgacccttg tgagcgcagt ggcagccaac    6900
gagatgggtt ggctagataa gaccaagagt gacataagca gtttgtttgg gcaaagaatt    6960
gaggtcaagg agaatttcag catgggagag tttcttctgg acttgaggcc ggcaacagcc    7020
tggtcactgt acgctgtgac aacagcggtc ctcactccac tgctaaagca tttgatcacg    7080
tcagattaca tcaacacctc attgacctca ataaacgttc aggcaagtgc actattcaca    7140
ctcgcgcgag gcttcccctt cgtcgatgtt ggagtgtcgg ctctcctgct agcagccgga    7200
tgctggggac aagtcaccct caccgttacg gtaacagcgg caacactcct tttttgccac    7260
tatgcctaca tggttcccgg ttggcaagct gaggcaatgc gctcagccca gcggcggaca    7320
gcggccggaa tcatgaagaa cgctgtagtg gatggcatcg tggccacgga cgtcccagaa    7380
ttagagcgca ccacacccat catgcagaag aaagttggac agatcatgct gatcttggtg    7440
tctctagctg cagtagtagt gaacccgtct gtgaagacag tacgagaagc cggaattttg    7500 atcacgccg cagcggtgac gctttgggag aatggagcaa gctctgtttg gaacgcaaca    7560
actgccatcg gactctgcca catcatgcgt gggggttggt tgtcatgtct atccataaca    7620
tggacactca taaagaacat ggaaaaacca ggactaaaaa gaggtggggc aaaaggacgc    7680
accttgggag aggtttggaa agaaagactc aaccagatga caaaagaaga gttcactagg    7740
taccgcaaag aggccatcat cgaagtcgat cgctcagcgg caaacacgc caggaaagaa    7800 ggcaatgtca ctggagggca tccagtctct aggggcacag caaaactgag atggctggtc    7860
gaacggaggt ttctcgaacc ggtcggaaaa gtgattgacc ttggatgtgg aagaggcggt    7920
tggtgttact atatggcaac ccaaaaaaga gtccaagaag tcagagggta cacaaagggc    7980
ggtcccggac atgaagagcc ccaactagtg caaagttatg gatggaacat tgtcaccatg    8040
aagagtggag tggatgtgtt ctacagacct tctgagtgtt gtgacaccct cctttgtgac    8100
atcggagagt cctcgtcaag tgctgaggtt gaagagcata ggacgattcg ggtccttgaa    8160
atggttgagg actggctgca ccgagggcca agggaatttt gcgtgaaggt gctctgcccc    8220
tacatgccga aagtcataga gaagatggag ctgctccaac gccggtatgg gggggactg    8280 gtcagaaacc cactctcacg gaattccacg cacgagatgt attgggtgag tcgagcttca    8340
ggcaatgtgg tacattcagt gaatatgacc agccaggtgc tcctaggaag aatggaaaaa    8400
aggacctgga agggacccca atacgaggaa gacgtaaact tgggaagtgg aaccagggcg    8460
gtgggaaaac ccctgctcaa ctcagacacc agtaaaatca agaacaggat tgaacgactc    8520
aggcgtgagt acagttcgac gtggcaccac gatgagaacc acccatatag aacctggaac    8580
tatcacggca gttatgatgt gaagcccaca ggctccgcca gttcgctggt caatggagtg    8640
gtcaggctcc tctcaaaacc atgggacacc atcacgaatg ttaccaccat ggccatgact    8700
```

-continued

```
gacactactc ccttcgggca gcagcgagtg ttcaaagaga aggtggacac gaaagctcct    8760
gaaccgccag aaggagtgaa gtacgtgctc aacgagacca ccaactggtt gtgggcgttt    8820
ttggccagag aaaaacgtcc cagaatgtgc tctcgagagg aattcataag aaaggtcaac    8880
agcaatgcag ctttgggtgc catgtttgaa gagcagaatc aatggaggag cgccagagaa    8940
gcagttgaag atccaaaatt ttgggagatg gtggatgagg agcgcgaggc acatctgcgg    9000
ggggaatgtc acacttgcat ttacaacatg atgggaaaga gagagaaaaa acccggagag    9060
ttcggaaagg ccaagggaag cagagccatt tggttcatgt ggctcggagc tcgctttctg    9120
gagttcgagg ctctgggttt tctcaatgaa gaccactggc ttggaagaaa gaactcagga    9180
ggaggtgtcg agggcttggg cctccaaaaa ctgggttaca tcctgcgtga agttggcacc    9240
cggcctgggg gcaagatcta tgctgatgac acagctggct gggacacccg catcacgaga    9300
gctgacttgg aaaatgaagc taaggtgctt gagctgcttg atggggaaca tcggcgtctt    9360
gccagggcca tcattgagct cacctatcgt cacaaagttg tgaaagtgat gcgcccggct    9420
gctgatggaa gaaccgtcat ggatgttatc tccagagaag atcagagggg gagtggacaa    9480
gttgtcacct acgccctaaa cactttcacc aacctggccg tccagctggt gaggatgatg    9540
gaaggggaag gagtgattgg cccagatgat gtggagaaac tcacaaaagg gaaaggaccc    9600
aaagtcagga cctggctgtt tgagaatggg gaagaaagac tcagccgcat ggctgtcagt    9660
ggagatgact gtgtggtaaa gcccctggac gatcgctttg ccacctcgct ccacttcctc    9720
aatgctatgt caaaggttcg caaagacatc aagagtggaa aaccgtcaac tggatggtat    9780
gattggcagc aggttccatt ttgctcaaac catttcactg aattgatcat gaaagatgga    9840
agaacactgg tggttccatg ccgaggacag gatgaattgg taggcagagc tcgcatatct    9900
ccaggggccg gatggaacgt ccgcgacact gcttgtctgg ctaagtctta tgcccagatg    9960
tggctgcttc tgtacttcca cagaagagac ctgcggctca tggccaacgc catttgctcc    10020
gctgtccctg tgaattgggt ccctaccgga agaaccacgt ggtccatcca tgcaggagga    10080
gagtggatga caacagagga catgttggag gtctggaacc gtgtttggat agaggagaat    10140
gaatggatgg aagacaaaac cccagtggag aaatggagtg acgtcccata ttcaggaaaa    10200
cgagaggaca tctggtgtgg cagcctgatt ggcacaagag cccgagccac gtgggcagaa    10260
aacatccagg tggctatcaa ccaagtcaga gcaatcatcg gagatgagaa gtatgtggat    10320
tacatgagtt cactaaagag atatgaagac acaactttgg ttgaggacac agtactgtag    10380
atatttaatt aattgtaaat agacaatata agtatgcata aaagtgtagt tttatagtag    10440
tatttagtgg tgttagtgta aatagttaag aaaattttga ggagaaagtc aggccgggaa    10500
gttcccgcca ccggaagttg agtagacggt gctgcctgcg actcaacccc aggaggactg    10560
ggtgaacaaa gccgcgaagt gatccatgta agccctcaga accgtctcgg aaggaggacc    10620
ccacatgttg taacttcaaa gcccaatgtc agaccacgct acggcgtgct actctgcgga    10680
gagtgcagtc tgcgatagtg ccccaggagg actgggttaa caaaggcaaa ccaacgcccc    10740
acgcggccct agccccggta atggtgttaa ccagggcgaa aggactagag gttagaggag    10800
accccgcggt ttaaagtgca cggcccagcc tggctgaagc tgtaggtcag gggaaggact    10860
agaggttagt ggagacccca tgccacaaaa caccacaaca aaacagcata ttgacacctg    10920
ggatagacta ggagatcttc tgctctgcac aaccagccac acggcacagt gcgcc          10975
```

<210> SEQ ID NO 2
<211> LENGTH: 11029

<212> TYPE: DNA
<213> ORGANISM: West Nile virus

<400> SEQUENCE: 2

| | | | | | |
|---|---|---|---|---|---|
| agtagttcgc | ctgtgtgagc | tgacaaactt | agtagtgttt | gtgaggatta | acaacaatta      60 |
| acacagtgcg | agctgtttct | tagcacgaag | atctcgatgt | ctaagaaacc | aggagggccc     120 |
| ggcaagagcc | gggctgtcaa | tatgctaaaa | cgcggaatgc | cccgcgtgtt | gtccttgatt     180 |
| ggactgaaga | gggctatgtt | gagcctgatc | gacggcaagg | ggccaatacg | atttgtgttg     240 |
| gctctcttgg | cgttcttcag | gttcacagca | attgctccga | cccgagcagt | gctggatcga     300 |
| tggagaggtg | tgaacaaaca | aacagcgatg | aaacaccttc | tgagttttaa | gaaggaacta     360 |
| gggaccttga | ccagtgctat | caatcggcgg | agctcaaaac | aaaagaaaag | aggaggaaag     420 |
| accggaattg | cagtcatgat | tggcctgatc | gccagcgtag | gagcagttac | cctctctaac     480 |
| ttccaaggga | aggtgatgat | gacggtaaat | gctactgacg | tcacagatgt | catcacgatt     540 |
| ccaacagctg | ctggaaagaa | cctatgcatt | gtcagagcaa | tggatgtggg | atacatgtgc     600 |
| gatgatacta | tcacttatga | atgcccagtg | ctgtcggctg | gtaatgatcc | agaagacatc     660 |
| gactgttggt | gcacaaagtc | agcagtctac | gtcaggtatg | aagatgcac | caagacacgc     720 |
| cactcaagac | gcagtcggag | gtcactgaca | gtgcagacac | acggagaaag | cactctagcg     780 |
| aacaagaagg | gggcttggat | ggacagcacc | aaggccacaa | ggtatttggt | aaaaacagaa     840 |
| tcatggatct | tgaggaaccc | tggatatgcc | ctggtggcag | ccgtcattgg | ttggatgctt     900 |
| gggagcaaca | ccatgcagag | agttgtgttt | gtcgtgctat | tgcttttggt | ggccccagct     960 |
| tacagcttca | actgccttgg | aatgagcaac | agagacttct | tggaaggagt | gtctggagca    1020 |
| acatgggtgg | atttggttct | cgaaggcgac | agctgcgtga | ctatcatgtc | taaggacaag    1080 |
| cctaccatcg | atgtgaagat | gatgaatatg | gaggcggcca | acctggcaga | ggtccgcagt    1140 |
| tattgctatt | tggctaccgt | cagcgatctc | tccaccaaag | ctgcgtgccc | gaccatggga    1200 |
| gaagctcaca | atgacaaacg | tgctgaccca | gcttttgtgt | gcagacaagg | agtggtggac    1260 |
| aggggctggg | gcaacggctg | cggattattt | ggcaaaggaa | gcattgacac | atgcgccaaa    1320 |
| tttgcctgct | ctaccaaggc | aataggaaga | accatcttga | aagagaatat | caagtacgaa    1380 |
| gtggccattt | ttgtccatgg | accaactact | gtggagtcgc | acggaaacta | ctccacacag    1440 |
| gttggagcca | ctcaggcagg | agattcagc | atcactcctg | cggcgccttc | atacacacta    1500 |
| aagcttggag | aatatggaga | ggtgacagtg | gactgtgaac | cacggtcagg | gattgacacc    1560 |
| aatgcatact | acgtgatgac | tgttggaaca | aagacgttct | tggtccatcg | tgagtggttc    1620 |
| atggacctca | acctcccttg | gagcagtgct | ggaagtactg | tgtggaggaa | cagagagacg    1680 |
| ttaatggagt | ttgaggaacc | acacgccacg | aagcagtctg | tgatagcatt | gggctcacaa    1740 |
| gagggagctc | tgcatcaagc | tttggctgga | gccattcctg | tggaattttc | aagcaacact    1800 |
| gtcaagttga | cgtcgggtca | tttgaagtgt | agagtgaaga | tggaaaaatt | gcagttgaag    1860 |
| ggaacaacct | atgccgtctg | ttcaaaggct | ttcaagtttc | ttgggactcc | cgcagacaca    1920 |
| ggtcacggca | ctgtggtgtt | ggaattgcag | tacactggca | cggatggacc | ttgtaaagtt    1980 |
| cctatctcgt | cagtggcttc | attgaacgac | ctaacgccag | tgggcagatt | ggtcactgtc    2040 |
| aacccttttg | tttcagtggc | cacggccaac | gctaaggtcc | tgattgaatt | ggaaccaccc    2100 |
| tttggagact | catacatagt | ggtgggcaga | ggagaacaac | agatcaatca | ccattggcac    2160 |
| aagtctggaa | gcagcattgg | caaagccttt | acaaccaccc | tcaaaggagc | gcagagacta    2220 |

```
gccgctctag gagacacagc ttgggacttt ggatcagttg gagggtgtt caccctcagtt   2280 gggaaggctg tccatcaagt gttcggagga gcattccgct tactgttcgg aggcatgtcc   2340
tggataacgc aaggattgct gggggctctc ctgttgtgga tgggcatcaa tgctcgtgat   2400
aggtccatag ctctcacgtt tctcgcagtt ggaggagttc tgctcttcct ctccgtgaac   2460
gtgcacgctg acactgggtg tgccatagac atcagccggc aagagctgag atgtggaagt   2520
ggagtgttca tacacaatga tgtggaggct tgatggacc gatacaagta ttaccctgaa    2580
acgccacaag gcctagccaa gatcattcag aaagctcata aggaaggagt gtgcggtcta   2640
cgatcagttt ccagactgga gcatcaaatg tgggaagcag tgaaggacga gctgaacact   2700
cttttgaagg agaatggtgt ggaccttagt gtcgtggttg agaaacagga gggaatgtac   2760
aagtcagcac ctaaacgcct caccgccacc acggaaaaat tggaaattgg ctggaaggcc   2820
tggggaaaga gtattttatt tgcaccagaa ctcgccaaca cacctttgt ggttgatggt    2880 ccggagacca aggaatgtcc gactcagaat cgcgcttgga atagcttaga agtggaggat   2940
tttggatttg gtctcaccag cactcggatg ttcctgaagg tcagagagag caacacaact   3000
gaatgtgact cgaagatcat tggaacggct gtcaagaaca acttggcgat ccacagtgac   3060
ctgtcctatt ggattgaaag caggctcaat gatacgtgga agcttgaaag gcagttctg    3120 ggtgaagtca atcatgtac gtggcctgag acgcatacct tgtggggcga tggaatcctt    3180
gagagtgact tgataatacc agtcacactg gcgggaccac gaagcaatca caatcggaga   3240
cctgggtaca agacacaaaa ccagggccca tgggacgaag gccgggtaga gattgacttc   3300
gattactgcc caggaactac ggtcaccctg agtgagagct gcggacaccg tggacctgcc   3360
actcgcacca ccacagagag cggaaagttg ataacagatt ggtgctgcag gagctgcacc   3420
ttaccaccac tgcgctacca aactgacagc ggctgttggt atggtatgga gatcagacca   3480
cagagacatg atgaaaagac cctcgtgcag tcacaagtga atgcttataa tgctgatatg   3540 attgacccctt ttcagttggg ccttctggtc gtgttcttgg ccacccagga ggtccttcgc   3600
aagaggtgga cagccaagat cagcatgcca gctatactga ttgctctgct agtcctggtg   3660
tttgggggca ttacttacac tgatgtgtta cgctatgtca tcttggtggg ggcagcttc    3720 gcagaatcta attcgggagg agacgtggta cacttggcgc tcatggcgac cttcaagata   3780
caaccagtgt ttatggtggc atcgtttctc aaagcgagat ggaccaacca ggagaacatt   3840
ttgttgatgt tggcggctgt tttctttcaa atggcttatc acgatgcccg ccaaattctg   3900
ctctgggaga tccctgatgt gttgaattca ctggcggtag cttggatgat actgagagcc   3960
ataacattca caacgacatc aaacgtggtt gttccgctgc tagccctgct aacacccggg   4020
ctgagatgct tgaatctgga tgtgtacagg atactgctgt tgatggtcgg aataggcagc   4080
ttgatcaggg agaagaggag tgcagctgca aaaagaaag gagcaagtct gctatgcttg   4140
gctctagcct caacaggact tttcaacccc atgatccttg ctgctggact gattacatgt   4200
gatcccaacc gtaaacgcgg atggcccgca actgaagtga tgacagctgt cggcctgatg   4260
tttgccatcg tcgagggct ggcagagctt gacattgact ccatggccat tccaatgact   4320
atcgcggggc tcatgtttgc tgctttcgtg atttctggga aatcaacaga tatgtggatt   4380
gagagaacgc cggacatttc ctgggaaagt gatgcagaaa ttacaggctc gagcgaaaga   4440
gttgatgtgc ggcttgatga tgatggaaac ttccagctca tgaatgatcc aggagcacct   4500
tggaagatat ggatgctcag aatggtctgt ctcgcgatta gtgcgtacac ccctgggca    4560 atcttgcct cagtagttgg atttggata actctccaat acacaaagag aggaggcgtg     4620
```

```
ttgtgggaca ctccctcacc aaaggagtac aaaaagggg  acacgaccac cggcgtctac   4680
aggatcatga ctcgtgggct gctcggcagt tatcaagcag gagcgggcgt gatggttgaa   4740
ggtgttttcc acacccttg  gcatacaaca aaaggagccg cttgatgag  cggagagggc   4800 cgcctggacc catactgggg cagtgtcaag gaggatcgac tttgttacgg aggaccctgg   4860
aaattgcagc acaagtggaa cgggcaggat gaggtgcaga tgattgtggt ggaacctggc   4920
aagaacgtta agaacgtcca gacgaaacca ggggtgttca aaacacctga aggagaaatc   4980
ggggccgtga cttggactt  ccccactgga acatcaggct caccaatagt ggacaaaaac   5040
ggtgatgtga ttgggcttta tggcaatgga gtcataatgc ccaacggctc atacataagc   5100
gcgatagtgc agggtgaaag gatggatgag ccaatcccag ccggattcga acctgagatg   5160
ctgaggaaaa aacagatcac tgtactggat ctccatcccg gcgccggtaa acaaggagg   5220 attctgccac agatcatcaa agaggccata aacagaagac tgagaacagc cgtgctagca   5280
ccaaccaggg ttgtggctgc tgagatggct gaagcactga gaggactgcc catccggtac   5340
cagacatccg cagtgcccag agaacataat ggaaatgaga ttgttgatgt catgtgtcat   5400
gctaccctca cccacaggct gatgtctcct cacagggtgc cgaactacaa cctgttcgtg   5460
atggatgagg ctcatttcac cgacccagct agcattgcag caagaggtta catttccaca   5520
aaggtcgagc taggggaggc ggcggcaata ttcatgacag ccaccccacc aggcacttca   5580
gatccattcc cagagtccaa ttcaccaatt ccgacttac  agactgagat cccggatcga   5640
gcttggaact ctggatacga atggatcaca gaatacaccg ggaagacggt ttggttgtg   5700 cctagtgtca agatggggaa tgagattgcc ctttgcctac aacgtgctgg aaagaaagta   5760
gtccaattga acagaaagtc gtacgagacg gagtacccaa aatgtaagaa cgatgattgg   5820
gactttgtta tcacaacaga catatctgaa atggggcta  actttaaggc gagcagggtg   5880
attgacagcc ggaagagtgt gaaaccaacc atcataacag aaggagaagg gagagtgatc   5940
ctgggagaac catctgcagt gacagcagct agtgccgccc agagacgtgg acgtatcggt   6000
agaaatccgt cgcaagttgg tgatgagtac tgttatgggg gcacacgaa  tgaagacgac   6060 tcgaacttcg cccattggac tgaggcacga atcatgctgg acaacatcaa catgccaaac   6120
ggactgatcg ctcaattcta ccaaccagag cgtgagaagg tatataccat ggatgggga   6180 taccggctca gaggagaaga gagaaaaaac tttctggaac tgttgaggac tgcagatctg   6240
ccagtttggc tggcttacaa ggttgcagcg gctggagtgt cataccacga ccggaggtgg   6300
tgctttgatg gtcctaggac aaacacaatt ttagaagaca caacgaagt  ggaagtcatc   6360 acgaagcttg gtgaaaggaa gattctgagg ccgcgctgga ttgacgccag ggtgtactcg   6420
gatcaccagg cactaaaggc gttcaaggac ttcgcctcgg gaaaacgttc tcagataggg   6480
ctcattgagg ttctgggaaa gatgcctgag cacttcatgg ggaagacatg ggaagcactt   6540
gacaccatgt acgttgtggc cactgcagag aaaggaggaa gagctcacag aatggcctg   6600 gaggaactgc cagatgctct tcagacaatt gccttgattg ccttattgag tgtgatgacc   6660
atgggagtat tcttcctcct catgcagcgg aagggcattg aaagatagg  tttgggaggc   6720 gctgtcttgg gagtcgcgac cttttctgt  tggatggctg aagttccagg aacgaagatc   6780
gccggaatgt tgctgctctc ccttctcttg atgattgtgc taattcctga gccagaaag   6840 caacgttcgc agacagacaa ccagctagcc gtgttcctga tttgtgtcat gaccctgtg   6900 agcgcagtgg cagccaacga gatgggttgg ctagataaga ccaagagtga cataagcagt   6960
```

```
ttgtttgggc aaagaattga ggtcaaggag aatttcagca tgggagagtt tcttctggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttccccttcg tcgatgttgg agtgtcggct    7200
ctcctgctag cagccggatg ctggggacaa gtcaccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcatcgtg    7380
gccacggacg tcccagaatt agagcgcacc acacccatca tgcagaagaa agttggacag    7440
atcatgctga tcttggtgtc tctagctgca gtagtagtga acccgtctgt gaagacagta    7500
cgagaagccg aattttgat cacgccgca gcggtgacgc tttgggagaa tggagcaagc    7560
tctgtttgga acgcaacaac tgccatcgga ctctgccaca tcatgcgtgg gggttggttg    7620
tcatgtctat ccataacatg gacactcata agaacatgg aaaaaccagg actaaaaaga    7680
ggtggggcaa aaggacgcac cttgggagag gtttggaaag aaagactcaa ccagatgaca    7740
aaagaagagt tcactaggta ccgcaaagag gccatcatcg aagtcgatcg ctcagcagca    7800
aaacacgcca ggaaagaagg caatgtcact ggagggcatc cagtctctag ggcacagca    7860 aaactgagat ggctggtcga acggaggttt ctcgaaccgg tcggaaaagt gattgacctt    7920
ggatgtggaa gaggcggttg gtgttactat atggcaaccc aaaaaagagt ccaagaagtc    7980
agagggtaca caaagggcgg tcccggacat gaagagcccc aactagtgca aagttatgga    8040
tggaacattg tcaccatgaa gagtgggtg gatgtgttct acagaccttc tgagtgttgt    8100
gacaccctcc tttgtgacat cggagagtcc tcgtcaagtg ctgaggttga agagcatagg    8160
acgattcggg tccttgaaat ggttgaggac tggctgcacc gagggccaag ggaattttgc    8220
gtgaaggtgc tctgccccta catgccgaaa gtcatagaga agatggagct gctccaacgc    8280
cggtatgggg gggactggt cagaaaccca ctctcacgga attccacgca cgagatgtat    8340
tgggtgagtc gagcttcagg caatgtggta cattcagtga atatgaccag ccaggtgctc    8400
ctaggaagaa tggaaaaaag gacctggaag ggaccccaat acgaggaaga tgtaaacttg    8460
ggaagtggaa ccagggcggt gggaaaaccc ctgctcaact cagacaccag taaaatcaag    8520
aacaggattg aacgactcag gcgtgagtac agttcgacgt ggcaccacga tgagaaccac    8580
ccatatagaa cctggaacta tcacggcagt tatgatgtga agcccacagg ctccgccagt    8640
tcgctggtca atggagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa cgagaccacc    8820
aactggtttg gggcgttttt ggccagagaa aaacgtccca gaatgtgctc tcgagaggaa    8880
ttcataagaa aggtcaacag caatgcagct ttgggtgcca tgtttgaaga gcagaatcaa    8940
tggaggagcg ccagagaggc agttgaagat ccaaaatttt gggagatggt ggatgaggag    9000
cgcgaggcac atctgcgggg ggaatgtcac acttgcattt acaacatgat gggaaagaga    9060
gagaaaaaac ccggagagtt cggaaaggcc aagggaagca gagccatttg gttcatgtgg    9120
ctcggagctc gctttctgga gttcgaggct ctggtttttc tcaatgaaga ccactggctt    9180
ggaagaaaga actcaggagg aggtgtcgag ggcttgggcc tccaaaaact gggttacatc    9240
ctgcgtgaag ttggcacccg gcctgggggc aagatctatg ctgatgacac agctggctgg    9300
gacacccgca tcacgagagc tgacttggaa aatgaagcta aggtgcttga gctgcttgat    9360
```

| gggaacatc | ggcgtcttgc | cagggccatc | attgagctca | cctatcgtca | caaagttgtg | 9420 |
| aaagtgatgc | gcccggctgc | tgatggaaga | accgtcatgg | atgttatctc | cagagaagat | 9480 |
| cagaggggga | gtggacaagt | tgtcacctac | gccctaaaca | ctttcaccaa | cctggccgtc | 9540 |
| cagctggtga | ggatgatgga | agggaagga | gtgattggcc | cagatgatgt | ggagaaactc | 9600 |
| acaaaaggga | aaggacccaa | agtcaggacc | tggctgtttg | agaatgggga | agaaagactc | 9660 |
| agccgcatgg | ctgtcagtgg | agatgactgt | gtggtaaagc | ccctggacga | tcgctttgcc | 9720 |
| acctcgctcc | acttcctcaa | tgctatgtca | aaggttcgca | aagacatcca | agagtggaaa | 9780 |
| ccgtcaactg | gatggtatga | ttggcagcag | gttccatttt | gctcaaacca | tttcactgaa | 9840 |
| ttgatcatga | agatggaag | aacactggtg | gttccatgcc | gaggacagga | tgaattggta | 9900 |
| ggcagagctc | gcatatctcc | aggggccgga | tggaacgtcc | gcgacactgc | ttgtctggct | 9960 |
| aagtcttatg | cccagatgtg | gctgcttctg | tacttccaca | gaagagacct | gcggctcatg | 10020 |
| gccaacgcca | tttgctccgc | tgtccctgtg | aattgggtcc | taccggaag | aaccacgtgg | 10080 |
| tccatccatg | caggaggaga | gtggatgaca | acagaggaca | tgttggaggt | ctggaaccgt | 10140 |
| gtttggatag | aggagaatga | atggatggaa | gacaaaaccc | cagtggagaa | atggagtgac | 10200 |
| gtcccatatt | caggaaaacg | agaggacatc | tggtgtggca | gcctgattgg | cacaagagcc | 10260 |
| cgagccacgt | gggcagaaaa | catccaggtg | gctatcaacc | aagtcagagc | aatcatcgga | 10320 |
| gatgagaagt | atgtggatta | catgagttca | ctaaagagat | atgaagacac | aactttggtt | 10380 |
| gaggacacag | tactgtagat | atttaatcaa | ttgtaaatag | acaatataag | tatgcataaa | 10440 |
| agtgtagttt | tatagtagta | tttagtggtg | ttagtgtaaa | tagttaagaa | aattttgagg | 10500 |
| agaaagtcag | gccgggaagt | tcccgccacc | ggaagttgag | tagacggtgc | tgcctgcgac | 10560 |
| tcaaccccag | gaggactggg | tgaacaaagc | cgcgaagtga | tccatgtaag | ccctcagaac | 10620 |
| cgtctcggaa | ggaggacccc | acatgttgta | acttcaaagc | ccaatgtcag | accacgctac | 10680 |
| ggcgtgctac | tctgcggaga | gtgcagtctg | cgatagtgcc | ccaggaggac | tgggttaaca | 10740 |
| aaggcaaacc | aacgccccac | gcggccctag | ccccggtaat | ggcgttaacc | agggcgaaag | 10800 |
| gactagaggt | tagaggagac | cccgcggttt | aaagtgcacg | gcccagcctg | gctgaagctg | 10860 |
| taggtcaggg | gaaggactag | aggttagtgg | agaccccgtg | ccacaaaaca | ccacaacaaa | 10920 |
| acagcatatt | gacacctggg | atagactagg | agatcttctg | ctctgcacaa | ccagccacac | 10980 |
| ggcacagtgc | gccgacaatg | gtggctggtg | gtgcgagaac | acaggatct | | 11029 |

```
<210> SEQ ID NO 3
<211> LENGTH: 10735
<212> TYPE: DNA
<213> ORGANISM: Dengue virus type 1

<400> SEQUENCE: 3
```

| agttgttagt | ctacgtggac | cgacaagaac | agtttcgaat | cggaagcttg | cttaacgtag | 60 |
| ttctaacagt | tttttattag | agagcagatc | tctgatgaac | aaccaacgga | aaaagacggg | 120 |
| tcgaccgtct | ttcaatatgc | tgaaacgcgc | gagaaaccgc | gtgtcaactg | tttcacagtt | 180 |
| ggcgaagaga | ttctcaaaag | gattgctttc | aggccaagga | cccatgaaat | tggtgatggc | 240 |
| ttttatagca | ttcctaagat | ttctagccat | acctccaaca | gcaggaattt | tggctagatg | 300 |
| gggctcattc | aagaagaatg | gagcgatcaa | agtgttacgg | ggtttcaaga | agaaaatctc | 360 |
| aaacatgttg | aacataatga | acaggaggaa | aagatctgtg | accatgctcc | tcatgctgct | 420 |

```
gcccacagcc ctggcgttcc atctgaccac ccgagggga gagccgcaca tgatagttag      480
caagcaggaa agaggaaaat cacttttgtt taagacctct gcaggtgtca acatgtgcac      540
ccttattgca atggatttgg gagagttatg tgaggacaca atgacctaca aatgcccccg      600
gatcactgag acggaaccag atgacgttga ctgttggtgc aatgccacgg agacatgggt      660
gacctatgga acatgttctc aaactggtga acaccgacga acaaacgtt ccgtcgcact       720 ggcaccacac gtagggcttg gtctagaaac aagaaccgaa acgtggatgt cctctgaagg      780
cgcttggaaa caaatacaaa aagtggagac ctgggctctg agacacccag gattcacggt      840
gatagccctt tttctagcac atgccatagg aacatccatc acccagaaag ggatcatttt     900
tattttgctg atgctggtaa ctccatccat ggccatgcgg tgcgtgggaa taggcaacag      960
agacttcgtg gaaggactgt caggagctac gtgggtggat gtggtactgg agcatggaag     1020
ttgcgtcact accatggcaa aagacaaacc aacactggac attgaactct gaagacgga      1080 ggtcacaaac cctgccgtcc tgcgcaaact gtgcattgaa gctaaaatat caaacaccac     1140
caccgattcg agatgtccaa cacaaggaga agccacgctg gtggaagaac aggacacgaa     1200
ctttgtgtgt cgacgaacgt tcgtggacag aggctgggc aatggttgtg ggctattcgg      1260
aaaaggtagc ttaataacgt gtgctaagtt taagtgtgtg acaaaactgg aaggaaagat     1320
agtccaatat gaaaacttaa aatattcagt gatagtcacc gtacacactg agaccagca     1380 ccaagttgga aatgagacca cagaacatgg aacaactgca accataacac ctcaagctcc     1440
cacgtcggaa atacagctga cagactacgg agctctaaca ttggattgtt cacctagaac     1500
agggctagac tttaatgaga tggtgttgtt gacaatggaa aaaaaatcat ggctcgtcca     1560
caaacaatgg tttctagact taccactgcc ttggacctcg gggcttcaa catcccaaga     1620 gacttggaat agacaagact tgctggtcac atttaagaca gctcatgcaa aaaagcagga    1680
agtagtcgta ctaggatcac aagaaggagc aatgcacact gcgttgactg gagcgacaga    1740
aatccaaacg tctgaacga caacaatttt tgcaggacac ctgaaatgca gactaaaaat     1800
ggataaactg actttaaaag gatgtcata tgtaatgtgc acagggtcat tcaagttaga      1860
gaaggaagtg gctgagaccc agcatggaac tgttctagtg caggttaaat acgaaggaac    1920
agatgcacca tgcaagatcc ccttctcgtc ccaagatgag aagggagtaa cccagaatgg    1980
gagattgata acagccaacc ccatagtcac tgacaaagaa aaaccagtca acattgaagc    2040
ggagccacct tttggtgaga gctacattgt ggtaggagca ggtgaaaaag cttttgaaact    2100 aagctggttc aagaagggaa gcagtatagg gaaaatgttt gaagcaactg cccgtggagc    2160
acgaaggatg gccatcctgg gagacactgc atgggactc ggttctatag gaggggtgtt     2220
cacgtctgtg ggaaaactga tacaccagat ttttgggact gcgtatggag ttttgttcag   2280
cggtgtttct tggaccatga agataggaat agggattctg ctgacatggc taggattaaa    2340
ctcaaggagc acgtcccttt caatgacgtg tatcgcagtt ggcatggtca cgctgtacct    2400
aggagtcatg gttcaggcgg actcgggatg tgtaatcaac tggaaaggca gagaactcaa    2460
atgtggaagc ggcatttttg tcaccaatga agtccacacc tggacagagc aatataaatt    2520
ccaggccgac tccctaaga gactatcagc ggccattggg aaggcatggg aggagggtgt    2580
gtgtggaatt cgatcagcca ctcgtctcga aacatcatg tggaagcaaa tatcaaatga     2640
attaaaccac atcttacttg aaaatgacat gaaatttaca gtggtcgtag agacgttag    2700 tggaatcttg gcccaaggaa agaaaatgat taggccacaa cccatggaac acaaatactc    2760
gtggaaaagc tggggaaaag ccaaaatcat aggagcagat gtacagaata ccaccttcat    2820
```

```
catcgacggc ccaaacaccc cagaatgccc tgataaccaa agagcatgga acatttggga    2880
agttgaagac tatggatttg aattttcac  gacaaacata tggttgaaat tgcgtgactc    2940
ctacactcaa gtgtgtgacc accggctaat gtcagctgcc atcaaggata gcaaagcagt    3000
ccatgctgac atggggtact ggatagaaag tgaaagaac  gagacttgga agttggcaag    3060
agcctccttc atagaagtta agacatgcat ctggccaaaa tcccacactc tatggagcaa    3120
tggagtcctg gaaagtgaga tgataatccc aaagatatat ggaggaccaa tatctcagca    3180
caactacaga ccaggatatt tcacacaaac agcagggccg tggcacttgg gcaagttaga    3240
actagatttt gatttatgtg aaggtaccac tgttgttgtg gatgaacatt gtggaaatcg    3300
aggaccatct cttagaacca caacagtcac aggaaagaca atccatgaat ggtgctgtag    3360
atcttgcacg ttaccccccc tacgtttcaa aggagaagac gggtgctggt acggcatgga    3420
aatcagacca gtcaaggaga aggaagagaa cctagttaag tcaatggtct ctgcagggtc    3480
aggagaagtg gacagttttt cactaggact gctatgcata tcaataatga tcgaagaggt    3540
aatgagatcc agatggagca gaaaaatgct gatgactgga acattggctg tgttcctcct    3600
tctcacaatg ggacaattga catggaatga tctgatcagg ctatgtatca tggttggagc    3660
caacgcttca gacaagatgg ggatgggaac aacgtaccta gctttgatgg ccactttcag    3720
aatgagacca atgttcgcag tcgggctact gtttcgcaga ttaacatcta gagaagttct    3780
tcttcttaca gttggattga gtctggtggc atctgtagaa ctaccaaatt ccttagagga    3840 gctagggggat ggacttgcaa tgggcatcat gatgttgaaa ttactgactg attttcagtc    3900
acatcagcta tgggctacct tgctgtcttt aacatttgtc aaaacaactt tttcattgca    3960
ctatgcatgg aagacaatgg ctatgatact gtcaattgta tctctcttcc ctttatgcct    4020
gtccacgact tctcaaaaaa caacatggct tccggtgttg ctgggatctc ttggatgcaa    4080
accactaacc atgtttctta aacagaaaaa caaaatctgg ggaaggaaaa gctggcctct    4140
caatgaagga attatggctg ttggaatagt tagcattctt ctaagttcac ttctcaagaa    4200
tgatgtgcca ctagctggcc cactaatagc tggaggcatg ctaatagcat gttatgtcat    4260
atctggaagc tcggccgatt tatcactgga gaaagcggct gaggtctcct gggaagaaga    4320
agcagaacac tctggtgcct cacacaacat actagtggag gtccaagatg atggaaccat    4380
gaagataaag gatgaagaga gagatgacac actcaccatt ctcctcaaag caactctgct    4440
agcaatctca ggggtatacc aatgtcaat  accggcgacc ctctttgtgt ggtatttttg    4500
gcagaaaaag aaacagagat caggagtgct atgggacaca cccagccctc cagaagtgga    4560
aagagcagtc cttgatgatg gcatttatag aattctccaa agaggattgt ggggcaggtc    4620
tcaagtagga gtaggagttt ttcaagaagg cgtgttccac acaatgtggc acgtcaccag    4680
gggagctgtc ctcatgtacc aagggaagag actggaacca agttgggcca gtgtcaaaaa    4740
agacttgatc tcatatggag gaggttggag gtttcaagga tcctggaacg cgggagaaga    4800
agtgcaggtg attgctgttg aaccggggaa gaacccaaaa aatgtacaga cagcgccggg    4860
taccttcaag accctgaag  gcgaagttgg agccatagct ctagacttta aacccggcac    4920
atctggatct cctatcgtga acagagaggg aaaaatagta ggtctttatg gaaatggagt    4980
ggtgacaaca agtggtacct acgtcagcgc catagctcaa gctaaagcat cacaagaagg    5040
gcctctacca gagattgagg acgaggtgtt taggaaaaga aacttaacaa taatggacct    5100
acatccagga tcggggaaaa caagaagata tcttccagcc atagtccgtg aggccataag    5160
```

```
aaggaacgtg cgcacgctag tcttagctcc cacaagagtt gtcgcttctg aaatggcaga    5220
ggcgctcaag ggaatgccaa taaggtatca gacaacagca gtgaagagtg aacacacagg    5280
aaaagagata gttgacctta tgtgtcacgc cactttcact atgcgtctcc tgtctcctgt    5340
gagagttccc aattataata tgattatcat ggatgaagca cattttaccg atccagccag    5400
catagcagcc agagggtata tctcaacccg agtgggtatg ggtgaagcag ctgcgatttt    5460
catgacagcc actcccccg gatcggtgga ggcctttcca cagagcaatg cagttatcca    5520
agatgaggaa agagacattc ctgaaagatc atggaactca ggctatgact ggatcactga    5580
tttcccaggt aaaacagtct ggtttgttcc aagcatcaaa tcaggaaatg acattgccaa    5640
ctgtttaaga aagaatggga aacgggtggt ccaattgagc agaaaaactt ttgacactga    5700
gtaccagaaa acaaaaaata cgactgggac tatgttgtc acaacagaca tatccgaaat    5760
gggagcaaac ttccgagccg acagggtaat agacccgagg cggtgcctga accggtaat    5820 actaaaagat ggcccagagc gtgtcattct agccggaccg atgccagtga ctgtggctag    5880
cgccgcccag aggagaggaa gaattggaag gaaccaaaat aaggaaggcg atcagtatat    5940
ttacatggga cagcctctaa acaatgatga ggaccacgcc cattggacag aagcaaaaat    6000
gctccttgac aacataaaca caccagaagg gattatccca gccctctttg agccggagag    6060
agaaaagagt gcagcaatag acggggaata cagactacgg ggtgaagcga ggaaaacgtt    6120
cgtggagctc atgagaagag gagatctacc tgtctggcta tcctacaaag ttgcctcaga    6180
aggcttccag tactccgaca gaaggtggtg ctttgatggg gaaaggaaca accaggtgtt    6240
ggaggagaac atggacgtgg agatctggac aaaagaagga gaaagaaaga aactacgacc    6300
ccgctggctg gatgccagaa catactctga cccactggct ctgcgcgaat caaagagtt    6360 cgcagcagga agaagaagcg tctcaggtga cctaatatta gaaatagggga aacttccaca    6420 acatttaacg caaagggccc agaacgcctt ggacaatctg gttatgttgc acaactctga    6480
acaaggagga aaagcctata gacacgccat ggaagaacta ccagacacca tagaaacgtt    6540
aatgctccta gctttgatag ctgtgctgac tggtggagtg acgttgttct tcctatcagg    6600 aagggggtcta ggaaaaacat ccattggcct actctgcgtg attgcctcaa gcgcactgct    6660
atggatggcc agtgtggaac cccattggat agcggcctct atcatactgg agttctttct    6720
gatggtgttg cttattccag agccggacag acagcgcact ccacaagaca accagctagc    6780
atacgtggtg ataggtctgt tattcatgat attgacagcg gcagccaatg agatgggatt    6840
actggaaacc acaagaaagg acctgggat tggtcatgca gctgctgaaa accaccatca    6900
tgctgcaatg ctggacgtag acctacatcc agcttcagcc tggactctct atgcagtggc    6960
cacaacaatt atcactccca tgatgagaca cacaattgaa aacacaacgg caaatatttc    7020
cctgacagct attgcaaacc aggcagctat attgatggga cttgacaagg gatggccaat    7080
atcaaagatg gacataggag ttccacttct cgccttgggg tgctattctc aggtgaaccc    7140
gctgacgctg acagcggcgg tatttatgct agtggctcat tatgccataa ttggacccgg    7200
actgcaagca aaagctacta gagaagctca aaaaaggaca gcagccggaa taatgaaaaa    7260
cccaactgtc gacgggatcg ttgcaataga tttggaccct gtggtttacg atgcaaaatt    7320
tgaaaaacag ctaggccaaa taatgttgtt gatactttgc acatcacaga tcctcctgat    7380
gcggaccaca tgggccttgt gtgaatccat cacactagcc actggacctc tgactacgct    7440 ttgggagggga tctccaggaa aattctggaa caccacgata gcggtgtcca tggcaaacat    7500 ttttaggggga agttatctag caggagcagg tctggccttt tcattaatga aatctctagg    7560
```

```
aggaggtagg agaggcacgg gagcccaagg ggaaacactg ggagaaaaat ggaaaagaca      7620
gctaaaccaa ttgagcaagt cagaattcaa cacttacaaa aggagtggga ttatagaggt      7680
ggatagatct gaagccaaag aggggttaaa aagaggagaa ccgactaaac acgcagtgtc      7740
gagaggaacg gccaaactga ggtggtttgt ggagaggaac cttgtgaaac cagaagggaa      7800
agtcatagac ctcggttgtg gaagaggtgg ctggtcatat tattgcgctg ggctgaagaa      7860
agtcacagaa gtgaaggat acacgaaagg aggacctgga catgaggaac caatcccaat       7920
ggcaacctat ggatggaacc tagtaaagct atactccggg aaagatgtat tctttacacc      7980
acctgagaaa tgtgacaccc tcttgtgtga tattggtgag tcctctccga acccaactat      8040
agaagaagga agaacgttac gtgttctaaa gatggtggaa ccatggctca gaggaaacca      8100
attttgcata aaaattctaa atccctatat gccgagtgtg gtagaaactt tggagcaaat      8160
gcaaagaaaa catggaggaa tgctagtgcg aaatccactc tcaagaaact ccactcatga      8220
aatgtactgg gtttcatgtg gaacaggaaa cattgtgtca gcagtaaaca tgacatctag      8280
aatgttgcta aatcgattca caatggctca caggaagcca acatatgaaa gagacgtgga      8340
cttaggcgct ggaacaagac atgtggcagt agaaccagag gtggccaacc tagatatcat      8400
tggccagagg atagagaata taaaaaatgg acacaaatca acatggcact atgatgagga      8460
caatccatac aaaacatggg cctatcatgg atcatatgag gtcaagccat caggatcagc      8520
ctcatccatg gtcaatggtg tggtgagact gctaaccaaa ccatgggatg tcattcccat      8580
ggtcacacaa atagccatga ctgacaccac acccttttgga caacagaggg tgtttaaaga     8640
gaaagttgac acgcgtacac caaaagcgaa acgaggcaca gcacaaatta tggaggtgac      8700
agccaggtgg ttatggggtt ttctctctag aaacaaaaaa cccagaatct gcacaagaga      8760
ggagttcaca agaaaagtca ggtcaaacgc agctattgga gcagtgttcg ttgatgaaaa      8820
tcaatggaac tcagcaaaag aggcagtgga agatgaacgg ttctgggacc ttgtgcacag      8880
agagagggag cttcataaac aaggaaaatg tgccacgtgt gtctacaaca tgatgggaaa      8940
gagagagaaa aaattaggag agttcggaaa ggcaaaagga agtcgcgcaa tatggtacat      9000
gtggttggga gcgcgctttt tagagtttga agcccttggt ttcatgaatg aagatcactg      9060
gttcagcaga gagaattcac tcagtggagt ggaaggagaa ggactccaca acttggata        9120
catactcaga gacatatcaa agattccagg gggaaatatg tatgcagatg acacagccgg      9180
atgggacaca gaataacag aggatgatct tcagaatgag gccaaaatca ctgacatcat       9240
ggaacctgaa catgccctat tggccacgtc aatctttaag ctaacctacc aaaacaaggt      9300
agtaagggtg cagagaccag cgaaaaatgg aaccgtgatg gatgtcatat ccagacgtga      9360
ccagagagga agtggacagg ttggaaccta tggcttaaac accttcacca acatggaggc      9420
ccaactaata agacaaatgg agtctgaggg aatcttttca cccagcgaat ggaaaccccc      9480
aaatctagcc gaaagagtcc tcgactggtt gaaaaaacat ggcaccgaga ggctgaaaag      9540
aatggcaatc agtggagatg actgtgtggt gaaaccaatc gatgacagat ttgcaacagc      9600
cttaacagct ttgaatgaca tgggaaaggt aagaaaagac ataccgcaat gggaaccttc      9660
aaaaggatgg aatgattggc aacaagtgcc tttctgttca caccatttcc accagctgat      9720
tatgaaggat gggagggaga tagtggtgcc atgccgcaac caagatgaac ttgtaggtag      9780
ggccagagta tcacaaggcg ccggatggag cttgagagaa actgcatgcc taggcaagtc      9840
atatgcacaa atgtggcagc tgatgtactt ccacaggaga gacttgagat tagcggctaa      9900
```

| | | | | |
|---|---|---|---|---|
| tgctatctgt | tcagccgttc | cagttgattg | ggtcccaacc | agccgtacca  cctggtcgat | 9960 |
| ccatgcccac | catcaatgga | tgacaacaga | agacatgttg | tcagtgtgga  atagggtttg | 10020 |
| gatagaggaa | aacccatgga | tggaggacaa | gactcatgtg | tccagttggg  aagacgttcc | 10080 |
| atacctagga | aaagggaag | atcgatggtg | tggatcccta | taggcttaa  cagcacgagc | 10140 |
| cacctgggcc | accaacatac | aagtggccat | aaaccaagtg | agaaggctca  ttgggaatga | 10200 |
| gaattatcta | gacttcatga | catcaatgaa | gagattcaaa | aacgagagtg  atcccgaagg | 10260 |
| ggcactctgg | taagccaact | cattcacaaa | ataaggaaa | ataaaaaatc  aaacaaggca | 10320 |
| agaagtcagg | ccgattaag | ccatagcacg | gtaagagcta | tgctgcctgt  gagccccgtc | 10380 |
| caaggacgta | aaatgaagtc | aggccgaaag | ccacggttcg | agcaagccgt  gctgcctgta | 10440 |
| gctccatcgt | ggggatgtaa | aaacccggga | ggctgcaaac | catggaagct  gtacgcatgg | 10500 |
| ggtagcagac | tagtggttag | aggagacccc | tcccaagaca | caacgcagca  gcggggccca | 10560 |
| acaccagggg | aagctgtacc | ctggtggtaa | ggactagagg | ttagaggaga  ccccccgcac | 10620 |
| aacaacaaac | agcatattga | cgctgggaga | gaccagagat | cctgctgtct  ctacagcatc | 10680 |
| attccaggca | cagaacgcca | aaaaatggaa | tggtgctgtt | gaatcaacag  gttct | 10735 |

```
<210> SEQ ID NO 4
<211> LENGTH: 10724
<212> TYPE: DNA
<213> ORGANISM: Dengue virus type 2

<400> SEQUENCE: 4
```

| | | | | |
|---|---|---|---|---|
| agttgttagt | ctacgtggac | cgacaaagac | agattctttg | agggagctaa  gctcaacgta | 60 |
| gttctaacag | ttttttaatt | agagagcaga | tctctgatga | ataaccaacg  aaaaaaggcg | 120 |
| agaaatacccc | ctttcaatat | gctgaaacgc | gagagaaacc | gcgtgtcgac  tgtacaacag | 180 |
| ctgacaaaga | gattctcact | tggaatgctg | cagggacgag | gaccattaaa  actgttcatg | 240 |
| gccctggtgg | cgttccttcg | tttcctaaca | atcccaccaa | cagcagggat  actgaagaga | 300 |
| tggggaacaa | ttaaaaaatc | aaaagccatt | aatgtttga | gagggttcag  gaaagagatt | 360 |
| ggaaggatgc | tgaacatctt | gaacaggaga | cgcagaactg | caggcatgat  cattatgctg | 420 |
| attccaacag | tgatggcgtt | ccatttaacc | acacgtaacg | agaaccaca  catgatcgtc | 480 |
| agtagacaag | agaaagggaa | aagtcttctg | tttaaaacag | aggatggtgt  gaacatgtgt | 540 |
| accctcatgg | ccatgacct | tggtgaattg | tgtgaagata | caatcacgta  caagtgtcct | 600 |
| tttctcaggc | agaatgaacc | agaagacata | gattgttggt | gcaactctac  gtccacatgg | 660 |
| gtaacttatg | ggacgtgtac | caccacagga | gaacacagaa | gagaaaaaag  atcagtggca | 720 |
| ctcgttccac | atgtgggaat | gggactggag | acacgaactg | aaacatggat  gtcatcagaa | 780 |
| ggggcctgga | acatgcccca | gagaattgaa | acttggatct | tgagacatcc  aggctttacc | 840 |
| ataatggcag | caatcctggc | atacaccata | ggaacgacac | atttccaaag  agccctgatt | 900 |
| ttcatcttac | tgacagctgt | cgctccttca | atgacaatgc | gttgcatagg  aatatcaaat | 960 |
| agagactttg | tagaagggt | ttcaggagga | agctggttg | acatagtctt  agaacatgga | 1020 |
| agctgtgtga | cgacgatggc | aaaaaacaaa | ccaacattgg | attttgaact  gataaaaaca | 1080 |
| gaagccaaac | aacctgccac | tctaaggaag | tactgtatag | aggcaaagct  gaccaacaca | 1140 |
| acaacagatt | ctcgctgccc | aacacaagga | gaacccagcc | taatgaaga  gcaggacaaa | 1200 |
| aggttcgtct | gcaaacactc | catggtggac | agaggatggg | gaaatggatg  tggattatt | 1260 |
| ggaaaaggag | gcattgtgac | ctgtgctatg | ttcacatgca | aaaagaacat  gaaaggaaaa | 1320 |

```
gtcgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagagtt gacaggctat ggcactgtca cgatggagtg ctctccgaga    1500
acgggcctcg acttcaatga gatggtgttg ctgcaaatgg aaaataaagc ttggctggtg    1560
cacaggcaat ggttcctaga cctgccgttg ccatggctgc ccggagcgga cacacaagga    1620
tcaaattgga tacagaaaga gacattggtc actttcaaaa atccccatgc gaagaaacag    1680
gatgttgttg ttttgggatc ccaagaaggg gccatgcaca cagcactcac aggggccaca    1740
gaaatccaga tgtcatcagg aaacttactg ttcacaggac atctcaagtg caggctgagg    1800
atggacaaac tacagctcaa aggaatgtca tactctatgt gcacaggaaa gtttaaagtt    1860
gtgaaggaaa tagcagaaac acaacatgga acaatagtta tcagagtaca atatgaaggg    1920
gacggttctc catgtaagat ccctttgag ataatggatt tggaaaaaag acatgtttta    1980
ggtcgcctga ttacagtcaa cccaatcgta acagaaaaag atagcccagt caacatagaa    2040
gcagaacctc cattcggaga cagctacatc atcataggag tagagccggg acaattgaag    2100
ctcaactggt ttaagaaagg aagttctatc ggccaaatga ttgagacaac aatgagggga    2160
gcgaagagaa tggccatttt aggtgacaca gcttgggatt ttggatccct gggaggagtg    2220
tttacatcta taggaaaggc tctccaccaa gttttcggag caatctatgg ggctgccttc    2280 agtgggggtct catggactat gaaaatactc ataggagtca ttatcacatg gataggaatg    2340
aattcacgca gcacctcact gtctgtgtca ctagtattgg tgggagtcgt gacgctgtat    2400
ttgggagtta tggtgcaggc cgatagtggt tgcgttgtga ctggaaaaaa caaagaactg    2460
aagtgtggca gtgggatttt catcacagac aacgtgcaca catggacaga acaatacaag    2520
ttccaaccag aatccccttc aaagctagct tcagctatcc agaaagctca tgaagagggc    2580
atttgtggaa tccgctcagt aacaagactg gaaaatctga tgtggaaaca aataacacca    2640
gaattgaatc acattctatc agaaaatgag gtgaagttga ctattatgac aggagacatc    2700
aaaggaatca tgcaggcagg aaaacgatct ctgcagcccc agcccactga gctgaagtat    2760
tcatggaaaa catggggcaa agcgaaaatg ctctctacag agtctcataa ccagaccttt    2820
ctcattgatg gccccgaaac agcagaatgc cccaacacaa acagagcttg gaattcgctg    2880
gaagttgaag actatggctt tggagtattc accaccaata tatggctaaa gttgagagaa    2940
aagcaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcatcgaagt taaaagctgc cactggccaa agtcacacac cctctggagt    3120
aatggagtgt agaaagtga gatgataatt ccaaagaatt tcgctggacc agtgtcacaa    3180
cacaactaca gaccaggcta ccatacacaa acagcaggac catggcatct aggtaagctt    3240
gagatggact ttgatttctg cgaaggaacc acagtggtgg tgactgagga ctgtggaaat    3300
agaggaccct ctttaagaac aactactgcc tctggaaaac tcataacaga atggtgctgc    3360
cgatcttgca cattaccacc gctaagatac agaggtgagg acggatgctg gtacgggatg    3420
gaaatcagac cattgaaaga aaagaagag aatttggtca actccttggt cacagcggga    3480
catgggcaga ttgacaactt ttcactagga gtcttgggaa tggcattgtt cctggaagaa    3540
atgctcagga cccgagtagg aacgaaacat gcaatactac tagttgcagt ttcttttgtg    3600
acattgatca caggaacat gtcctttaga gacctgggaa gagtgatggt tatggtgggc    3660
```

```
gctactatga cggatgacat aggtatgggc gtgacttatc ttgccctact agcagccttc    3720
aaagtcagac caacttttgc agctggacta ctcttgagaa agttgacctc caaggaattg    3780
atgatgacta ccataggaat cgtactcctc tcccagagca ccataccaga gaccattctt    3840
gaactgactg atgcgttagc cttgggcatg atggtcctta aaatggtgag aaaaatggaa    3900
aagtatcaat tggcagtgac tatcatggct atcttgtgcg tcccaaatgc agtgatatta    3960
caaaacgcat ggaaagtgag ttgcacaata ttggcagtgg tgtccgtttc cccactgttc    4020
ttaacatcct cacagcagaa agcggattgg ataccattag cattgacgat caagggtctc    4080
aatccaacag ctattttct aacaacccctt tcaagaaccca acaagaaaag gagctggcca    4140
ctaaatgagg ctatcatggc agtcgggatg gtgagcattt tggccagttc actcctaaag    4200
aatgacattc ccatgacagg accattagtg gctggagggc tcctcactgt gtgctacgtg    4260
ctcactggac gatcggccga tttggaactg gagagagccg ccgatgtcaa atgggaagat    4320
caggcagaga tatcaggaag cagtccaatc ctgtcaataa caatatcaga agatggtagc    4380
atgtcgataa aaaacgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggctggagta ttgtgggatg tccttcacc cccacccgtg    4560 ggaaaggctg aactggaaga tggagcctat agaatcaagc aaaagggat tcttggatat    4620 tcccagatcg gagccggagt ttacaaagaa ggaacattcc atacaatgtg gcatgtcaca    4680
cgcggcgctg ttctaatgca taaggaaaag aggattgaac catcatgggc ggacgttaag    4740
aaagacctaa tatcatatgg aggaggctgg aagctagaag gagaatggaa ggaaggagaa    4800
gaagtccagg tcttggcatt ggagcctgga aaaaatccaa gagccgtcca aacaaaacct    4860
ggtcttttca aaccaacgc cggaaccata ggtgccgtat ctctggactt ttctcctgga    4920
acctcaggat ctccaatcat cgacaaaaaa ggaaaagttg tgggtcttta tggtaatggt    4980
gttgttacaa ggagtggagc atatgtgagt gctatagccc agactgaaaa aagtattgaa    5040
gacaatccag agatcgaaga tgatatttt cgaaagagaa aattgaccat catggacctc    5100
cacccaggag cgggaaagac gaagagatac cttccggcca tagtcagaga ggctataaaa    5160
cggggcctga gacattaat cctggccccc actagagtcg tggcagctga atggaggaa    5220 gccctaagag gacttccaat aagataccaa accccagcca tcagagctga gcacaccggg    5280
cgggagattg tggacctaat gtgtcatgcc acattcacta tgaggctgct atcaccagtt    5340
agagtgccaa attcaacct gatcatcatg gacgaagccc atttcacaga cccagcaagt    5400
atagcggcta gaggatacat ctcaactcga gtagagatgg gtgaggcagc tgggatttc    5460 atgacagcca ctcctccggg aagcagagac ccattccctc agagcaatgc accaatcatg    5520
gatgaagaaa gagaaatccc tgaacgttcg tggagttctg gacatgagtg ggtcacggat    5580
tttaaaggga agactgtttg gttcgttcca agtataaaag caggaaatga tatagcagct    5640
tgcctgagaa aaaatggaaa gaaagtgata caactcagta ggaagacctt tgattctgag    5700
tatgtcaaga ctagaaccaa tgattgggac ttcgtggtca caactgacat ttcagaaatg    5760
ggtgccaact tcaaggctga gagggttata gacccagac gctgcatgaa accagttata    5820
ctaacgatgt gtgaagagcg ggtgatcctg cagggaccta tgccagtgac ccactctagt    5880
gcagcacaaa gaagagggag aataggaaga aatccaaaaa atgaaaatga ccagtacata    5940
tacatggggg aacctctgga aaatgatgaa gactgtgcac actggaaaga agctaaaatg    6000
ctcctagata acatcaacac acctgaagga atcattccta gcatgttcga accagagcgt    6060
```

```
gaaaaggtgg atgccattga tggtgaatac cgcttgagag gagaagcaag gaaaacctt      6120 gtggacctaa tgagaagagg agacctacca gtctggttgg cctacagagt ggcagctgaa     6180
ggcatcaact acgcagacag aaggtggtgt tttgatggaa ttaagaacaa ccaaatcttg     6240
gaagaaaatg tggaggtgga aatctggaca aaagaagggg aaaggaagaa attaaaaccc    6300
agatggttgg atgccaggat ctactctgac ccactgacgc taaaggaatt caaggagttt    6360
gcagctggaa gaaagtccct gaccctgaac ctaatcacag aaatgggtag gcttccaact   6420
ttcatgactc agaaggcaag agacgcactg acaacttag cagtgctgca cacggctgaa    6480
gcaggtggaa gggcgtacaa tcatgctctc agtgaactgc cggagaccct ggagacattg   6540
cttttactga cacttctggc tacagtcaca ggaggaatct ttttattctt gatgagcgga    6600 agggtatag ggaagatgac cctgggaatg tgctgcataa tcacggctag tattctccta    6660
tggtacgcac aaatacagcc acactggata gcagcttcaa taatactgga gttttttctc    6720
atagttttgc ttattccaga accagaaaag cagagaacac cccaagataa ccaattgacc   6780
tacgttgtca tagccatcct cacagtggtg gccgcaacca tggcaaacga gatgggttc    6840 ctggaaaaaa cgaagaaaga tctcggattg ggaagcatta caacccagca acccgagagc   6900
aacatcctgg acatagatct acgtcccgca tcagcatgga cgctgtatgc tgtggccaca    6960
acatttgtca caccaatgtt gagacacagc attgaaaatt cctcagtgaa cgtgtcccta   7020
acagctattg ccaaccaagc cacagtgtta atgggtcttg ggaaaggatg gccattgtca   7080
aagatggaca tcgagttcc ccttctcgcc attggatgct actcacaagt caaccccata    7140
actctcacag cagctctttt cttactggta gcacattatg ccatcatagg gccaggactc   7200
caagcaaaag caaccaggga agctcagaaa agagcagcag cgggcatcat gaaaaaccca   7260
actgtcgatg gaataacagt gattgaccta gatccaatac cctatgatcc aaagtttgaa    7320
aagcagttgg acaagtaat gctcctagtc tctgcgtga ctcaagtgtt gatgatgagg    7380
actacatggg ctctgtgtga ggctttaacc ttagcgaccg gcctatctc cacattgtgg    7440 gaaggaaatc cagggaggtt ttggaacact accattgcag tgtcaatggc taacattttt    7500
agagggagtt acttggccgg agctggactt ctcttttcca tcatgaagaa cacaaccaac    7560
acgagaaggg gaactggcaa cataggagag acgcttggag agaaatggaa aagccgattg    7620
aacgcattgg ggaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgtcgag agaaatatgg tcacaccaga agggaaagta    7800
gtggacctcg gttgcggcag aggaggctgg tcatactatt gtgggggact aaagaatgta    7860
agagaagtca aaggcctgac aaaaggagga ccaggacatg aagaacccat ccccatgtca    7920
acatatgggt ggaatctagt acgtcttcaa agtggagttg acgttttctt cactccgcca    7980
gaaaagtgtg acacattgtt gtgtgacata ggggagtcgt caccaaatcc cacggtagaa    8040
gcaggacgaa cactcagagt ccttaactta gtggaaaatt ggttgaacaa caacacccaa    8100
ttttgcataa aggttctcaa cccatacatg ccctcagtca tagaaaaaat ggaagcacta    8160
caaaggaaat atggaggagc cttagtgagg aatccactct cacgaaactc cacacatgag    8220
atgtactggg tatccaatgc ctccgggaac atagtgtcat cagtgaacat gatttcaagg    8280
atgttgatca acagattcac aatgagacac aagaaagcca ttacgagcc agatgtagac    8340 ctcggaagcg gaacccgcaa catcggaatt gaaagtgaga taccaaacct agacataatc    8400
```

```
gggaaaagaa tagaaaaaat aaaacaagag catgaaacat catggcacta tgaccaagac    8460
cacccataca aaacgtgggc ttaccatggc agctatgaaa caaaacaaac tggatcagca    8520
tcatccatgg tgaacggagt ggtcagactg ctgacaaaac cttggacgt cgtccccatg     8580 gtgacacaga tggcaatgac agacacgact ccatttggac aacagcgcgt ttttaaagaa    8640
aaagtggaca cgagaaccca agaaccgaaa gaaggcacaa agaaactaat gaaaatcacg    8700
gcagagtggc tttggaaaga actagggaag aaaaagacac ctaggatgtg cactagaaaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtataacat gatgggaaaa    8940
agagagaaga agctagggga gttcggcaag gcaaaaggca gcagagccat atggtacatg    9000
tggcttggag cacgcttctt agagtttgaa gccctaggat tcttgaatga agatcactgg    9060
ttctccagag agaactcctt gagtggagtg gaaggagaag gctgcacaa gctaggttac     9120 attttaagag acgtgagcaa aaagagggga ggagcaatgt atgccgatga caccgcagga    9180
tgggacacaa gaatcacact agaagaccta aaaaatgaag aaatggtaac aaaccacatg    9240
gaaggagaac acaagaaact agccgaggcc attttcaaat taacgtacca aaacaaggtg    9300
gtgcgtgtgc aaagaccaac accaagaggc acagtaatgg atatcatatc gagaagagac    9360
caaagaggta gtggacaagt tggtacctat ggactcaata cttttcaccaa tatggaagcc    9420 caactaatca gacagatgga gggagaagga gtcttcaaaa gcattcagca cctgacagtc    9480
acagaagaaa tcgccgtgca aaactggtta gcaagagtag ggcgcgaaag gttatcaaga    9540
atggccatca gtggagatga ttgtgttgtg aaacctttag atgacaggtt cgcaagcgct    9600
ttaacagctc taaatgacat gggaaaggtt aggaaagaca tacaacaatg gaaccttca     9660 agaggatgga acgattggac acaagtgccc ttctgttcac accatttcca tgagttaatc    9720
atgaaagacg gccgcgtact tgtagttcca tgcagaaacc aagatgaact gattggtaga    9780
gcccgaattt cccaaggagc tgggtggtct ttgcgagaga cggcctgttt ggggaagtcc    9840
tacgcccaaa tgtggagctt gatgtacttc cacagacgtg acctcaggct ggcggctaat    9900
gctatttgct cggcagtccc atcacattgg gttccaacaa gtagaacaac ctggtccata    9960
cacgccaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aaagagaaga ccaatggtgc ggctcattga ttgggctaac aagcagggcc   10140
acctgggcaa agaacatcca aacagcaata aatcaagtta gatcccttat aggcaatgag   10200
gaatacacag attacatgcc atccatgaaa agattcagaa gagaagagga agaggcagga   10260
gtcctgtggt agaaggcaaa actaacatga aacaaggcta gaagtcaggt cggattaagc   10320
tatagtacgg aaaaaactat gctacctgtg agccccgtcc aaggacgtta aaagaagtca   10380
ggccattaca aatgccatag cttgagtaaa ctgtggcagc ctgtagctcc acctgagaag   10440
gtgtaaaaaa tctgggaggc cacaaaccat ggaagctgta cgcatggcgt agtggactag   10500
cggttagagg agacccctcc cttacaaatc gcagcaacaa tgggggccca aggtgagatg   10560
aagctgtagt ctcactggaa ggactagagg ttagaggaga ccccccaaa acaaaaaaca    10620 gcatattgac gctgggaaag accagagatc ctgctgtctc ctcagcatca ttccaggcac   10680
agaacgccag aaaatggaat ggtgctgttg aatcaacagg ttct                    10724
```

<210> SEQ ID NO 5
<211> LENGTH: 519
<212> TYPE: DNA
<213> ORGANISM: West Nile virus

<400> SEQUENCE: 5

| | | | | | |
|---|---|---|---|---|---|
| ttggaaggag | tgtctggagc | aacatgggtg | gatttggttc | tcgaaggcga | cagctgcgtg | 60 |
| actatcatgt | ctaaggacaa | gcctaccatc | gatgtgaaga | tgatgaatat | ggaggcggcc | 120 |
| aacctggcag | aggtccgcag | ttattgctat | ttggctaccg | tcagcgatct | ctccaccaaa | 180 |
| gctgcgtgcc | cgaccatggg | agaagctcac | aatgacaaac | gtgctgaccc | agcttttgtg | 240 |
| tgcagacaag | gagtggtgga | cagggctgg | ggcaacggct | gcggactatt | tggcaaagga | 300 |
| agcattgaca | catgcgccaa | atttgcctgc | tctaccaagg | caataggaag | aaccatcttg | 360 |
| aaagagaata | tcaagtacga | agtggccatt | tttgtccatg | gaccaactac | tgtggagtcg | 420 |
| cacggaaact | actccacaca | ggttggagcc | actcaggcag | ggagattcag | catcactcct | 480 |
| gcagcgcctt | catacacact | aaagcttgga | gaatatgga | | | 519 |

<210> SEQ ID NO 6
<211> LENGTH: 171
<212> TYPE: PRT
<213> ORGANISM: West Nile virus

<400> SEQUENCE: 6

Leu Glu Gly Val Ser Gly Ala Thr Trp Val Asp Leu Val Leu Glu Gly
 1               5                  10                  15

Asp Ser Cys Val Thr Ile Met Ser Lys Asp Lys Pro Thr Ile Asp Val
                20                  25                  30

Lys Met Met Asn Met Glu Ala Ala Asn Leu Ala Glu Val Arg Ser Tyr
            35                  40                  45

Cys Tyr Leu Ala Thr Val Ser Asp Leu Ser Thr Lys Ala Ala Cys Pro
        50                  55                  60

Thr Met Gly Glu Ala His Asn Asp Lys Arg Ala Asp Pro Ala Phe Val
    65                  70                  75                  80

Cys Arg Gln Gly Val Val Asp Arg Gly Trp Gly Asn Gly Cys Gly Leu
                85                  90                  95

Phe Gly Lys Gly Ser Ile Asp Thr Cys Ala Lys Phe Ala Cys Ser Thr
            100                 105                 110

Lys Ala Ile Gly Arg Thr Ile Leu Lys Glu Asn Ile Lys Tyr Glu Val
        115                 120                 125

Ala Ile Phe Val His Gly Pro Thr Thr Val Glu Ser His Gly Asn Tyr
    130                 135                 140

Ser Thr Gln Val Gly Ala Thr Gln Ala Gly Arg Phe Ser Ile Thr Pro
145                 150                 155                 160

Ala Ala Pro Ser Tyr Thr Leu Lys Leu Gly Glu
                165                 170

<210> SEQ ID NO 7
<211> LENGTH: 2715
<212> TYPE: DNA
<213> ORGANISM: West Nile virus

<400> SEQUENCE: 7

| | | | | | |
|---|---|---|---|---|---|
| ggtggggcaa | aaggacgcac | cttgggagag | gtttggaaag | aaagactcaa | ccagatgaca | 60 |
| aaagaagagt | tcactaggta | ccgcaaagag | gccatcatcg | aagtcgatcg | ctcagcagca | 120 |
| aaacacgcca | ggaaagaagg | caatgtcact | ggagggcatc | cagtctctag | ggcacagca | 180 |

```
aaactgagat ggctggtcga acggaggttt ctcgaaccgg tcggaaaagt gattgacctt     240
ggatgtggaa gaggcggttg gtgttactat atggcaaccc aaaaaagagt ccaagaagtc     300
agagggtaca caaagggcgg tcccggacat gaagagcccc aactagtgca agttatgga      360 tggaacattg tcaccatgaa gagtggggtg gatgtgttct acagaccttc tgagtgttgt     420
gacaccctcc tttgtgacat cggagagtcc tcgtcaagtg ctgaggttga agagcatagg     480
acgattcggg tccttgaaat ggttgaggac tggctgcacc gagggccaag ggaattttgc     540
gtgaaggtgc tctgccccta catgccgaaa gtcatagaga gatgagct gctccaacgc       600 cggtatgggg gggactggt cagaaaccca ctctcacgga attccacgca cgagatgtat      660
tgggtgagtc gagcttcagg caatgtggta cattcagtga atatgaccag ccaggtgctc    720
ctaggaagaa tggaaaaaag gacctggaag ggaccccaat acgaggaaga tgtaaacttg    780
ggaagtggaa ccagggcggt gggaaaaccc ctgctcaact cagacaccag taaaatcaag    840
aacaggattg aacgactcag gcgtgagtac agttcgacgt ggcaccacga tgagaaccac    900
ccatatagaa cctggaacta tcacggcagt tatgatgtga agcccacagg ctccgccagt    960
tcgctggtca atggagtggt caggctcctc tcaaaaccat gggacaccat cacgaatgtt   1020
accaccatgg ccatgactga cactactccc ttcgggcagc agcgagtgtt caaagagaag   1080
gtggacacga aagctcctga accgccagaa ggagtgaagt acgtgctcaa cgagaccacc   1140
aactggttgt gggcgttttt ggccagaaa aaacgtccca gaatgtgctc tcgagaggaa    1200
ttcataagaa aggtcaacag caatgcagct ttgggtgcca tgtttgaaga gcagaatcaa   1260
tggaggagcg ccagagaggc agttgaagat ccaaaatttt gggagatggt ggatgaggag   1320
cgcgaggcac atctgcgggg ggaatgtcac acttgcattt acaacatgat gggaagaga    1380 gagaaaaaac ccggagagtt cggaaaggcc aagggaagca gagccatttg gttcatgtgg   1440 ctcgagctc gctttctgga gttcgaggct ctgggttttc tcaatgaaga ccactggctt    1500
ggaagaaaga actcaggagg aggtgtcgag ggcttgggcc tccaaaaact gggttacatc   1560
ctgcgtgaag ttggcacccg gcctgggggc aagatctatg ctgatgacac agctggctgg   1620
gacacccgca tcacgagagc tgacttggaa aatgaagcta aggtgcttga gctgcttgat   1680
ggggaacatc ggcgtcttgc cagggccatc attgagctca cctatcgtca caaagttgtg   1740
aaagtgatgc gcccggctgc tgatggaaga accgtcatgg atgttatctc cagagaagat   1800 cagagggga gtggacaagt tgtcacctac gccctaaaca cttttcaccaa cctggccgtc   1860 cagctggtga ggatgatgga aggggaagga gtgattggcc cagatgatgt ggagaaactc   1920
acaaagggga aaggacccaa agtcaggacc tggctgtttg agaatgggga agaaagactc   1980
agccgcatgg ctgtcagtgg agatgactgt gtggtaaagc ccctggacga tcgctttgcc   2040
acctcgctcc acttcctcaa tgctatgtca aaggttcgca aagacatcca agagtggaaa   2100
ccgtcaactg gatggtatga ttggcagcag gttccatttt gctcaaacca tttcactgaa    2160
ttgatcatga aagatggaag aacactggtg gttccatgcc gaggacagga tgaattggta     2220
ggcagagctc gcatatctcc agggggccgga tggaacgtcc gcgacactgc ttgtctggct   2280
aagtcttatg cccagatgtg gctgcttctg tacttccaca gaagagacct gcggctcatg     2340
gccaacgcca tttgctccgc tgtccctgtg aattgggtcc ctaccggaag aaccacgtgg    2400
tccatccatg caggaggaga gtggatgaca acagaggaca tgttggaggt ctggaaccgt    2460
gttgggatag aggagaatga atggatggaa gacaaaaccc cagtggagaa atggagtgac    2520
```

```
gtcccatatt caggaaaacg agaggacatc tggtgtggca gcctgattgg cacaagagcc    2580
cgagccacgt gggcagaaaa catccaggtg gctatcaacc aagtcagagc aatcatcgga    2640
gatgagaagt atgtggatta catgagttca ctaaagagat atgaagacac aactttggtt    2700
gaggacacag tactg                                                      2715
```

<210> SEQ ID NO 8
<211> LENGTH: 905
<212> TYPE: PRT
<213> ORGANISM: West Nile virus

<400> SEQUENCE: 8

```
Gly Gly Ala Lys Gly Arg Thr Leu Gly Glu Val Trp Lys Glu Arg Leu
  1               5                  10                  15

Asn Gln Met Thr Lys Glu Glu Phe Thr Arg Tyr Arg Lys Glu Ala Ile
             20                  25                  30

Ile Glu Val Asp Arg Ser Ala Ala Lys His Ala Arg Lys Glu Gly Asn
         35                  40                  45

Val Thr Gly Gly His Pro Val Ser Arg Gly Thr Ala Lys Leu Arg Trp
     50                  55                  60

Leu Val Glu Arg Arg Phe Leu Glu Pro Val Gly Lys Val Ile Asp Leu
 65                  70                  75                  80

Gly Cys Gly Arg Gly Gly Trp Cys Tyr Tyr Met Ala Thr Gln Lys Arg
                 85                  90                  95

Val Gln Glu Val Arg Gly Tyr Thr Lys Gly Gly Pro Gly His Glu Glu
            100                 105                 110

Pro Gln Leu Val Gln Ser Tyr Gly Trp Asn Ile Val Thr Met Lys Ser
        115                 120                 125

Gly Val Asp Val Phe Tyr Arg Pro Ser Glu Cys Cys Asp Thr Leu Leu
    130                 135                 140

Cys Asp Ile Gly Glu Ser Ser Ser Ala Glu Val Glu Glu His Arg
145                 150                 155                 160

Thr Ile Arg Val Leu Glu Met Val Glu Asp Trp Leu His Arg Gly Pro
                165                 170                 175

Arg Glu Phe Cys Val Lys Val Leu Cys Pro Tyr Met Pro Lys Val Ile
            180                 185                 190

Glu Lys Met Glu Leu Leu Gln Arg Arg Tyr Gly Gly Leu Val Arg
        195                 200                 205

Asn Pro Leu Ser Arg Asn Ser Thr His Glu Met Tyr Trp Val Ser Arg
    210                 215                 220

Ala Ser Gly Asn Val Val His Ser Val Asn Met Thr Ser Gln Val Leu
225                 230                 235                 240

Leu Gly Arg Met Glu Lys Arg Thr Trp Lys Gly Pro Gln Tyr Glu Glu
                245                 250                 255

Asp Val Asn Leu Gly Ser Gly Thr Arg Ala Val Gly Lys Pro Leu Leu
            260                 265                 270

Asn Ser Asp Thr Ser Lys Ile Lys Asn Arg Ile Glu Arg Leu Arg Arg
        275                 280                 285

Glu Tyr Ser Ser Thr Trp His His Asp Glu Asn His Pro Tyr Arg Thr
    290                 295                 300

Trp Asn Tyr His Gly Ser Tyr Asp Val Lys Pro Thr Gly Ser Ala Ser
305                 310                 315                 320

Ser Leu Val Asn Gly Val Val Arg Leu Leu Ser Lys Pro Trp Asp Thr
                325                 330                 335
```

-continued

```
Ile Thr Asn Val Thr Thr Met Ala Met Thr Asp Thr Thr Pro Phe Gly
            340                 345                 350

Gln Gln Arg Val Phe Lys Glu Lys Val Asp Thr Lys Ala Pro Glu Pro
            355                 360                 365

Pro Glu Gly Val Lys Tyr Val Leu Asn Glu Thr Thr Asn Trp Leu Trp
            370                 375                 380

Ala Phe Leu Ala Arg Glu Lys Arg Pro Arg Met Cys Ser Arg Glu Glu
385                 390                 395                 400

Phe Ile Arg Lys Val Asn Ser Asn Ala Ala Leu Gly Ala Met Phe Glu
                405                 410                 415

Glu Gln Asn Gln Trp Arg Ser Ala Arg Glu Ala Val Glu Asp Pro Lys
            420                 425                 430

Phe Trp Glu Met Val Asp Glu Glu Arg Glu Ala His Leu Arg Gly Glu
            435                 440                 445

Cys His Thr Cys Ile Tyr Asn Met Met Gly Lys Arg Glu Lys Lys Pro
            450                 455                 460

Gly Glu Phe Gly Lys Ala Lys Gly Ser Arg Ala Ile Trp Phe Met Trp
465                 470                 475                 480

Leu Gly Ala Arg Phe Leu Glu Phe Glu Ala Leu Gly Phe Leu Asn Glu
                485                 490                 495

Asp His Trp Leu Gly Arg Lys Asn Ser Gly Gly Gly Val Glu Gly Leu
            500                 505                 510

Gly Leu Gln Lys Leu Gly Tyr Ile Leu Arg Glu Val Gly Thr Arg Pro
            515                 520                 525

Gly Gly Lys Ile Tyr Ala Asp Asp Thr Ala Gly Trp Asp Thr Arg Ile
            530                 535                 540

Thr Arg Ala Asp Leu Glu Asn Glu Ala Lys Val Leu Glu Leu Leu Asp
545                 550                 555                 560

Gly Glu His Arg Arg Leu Ala Arg Ala Ile Ile Glu Leu Thr Tyr Arg
                565                 570                 575

His Lys Val Val Lys Val Met Arg Pro Ala Ala Asp Gly Arg Thr Val
            580                 585                 590

Met Asp Val Ile Ser Arg Glu Asp Gln Arg Gly Ser Gly Gln Val Val
            595                 600                 605

Thr Tyr Ala Leu Asn Thr Phe Thr Asn Leu Ala Val Gln Leu Val Arg
            610                 615                 620

Met Met Glu Gly Glu Gly Val Ile Gly Pro Asp Asp Val Glu Lys Leu
625                 630                 635                 640

Thr Lys Gly Lys Gly Pro Lys Val Arg Thr Trp Leu Phe Glu Asn Gly
                645                 650                 655

Glu Glu Arg Leu Ser Arg Met Ala Val Ser Gly Asp Asp Cys Val Val
            660                 665                 670

Lys Pro Leu Asp Asp Arg Phe Ala Thr Ser Leu His Phe Leu Asn Ala
            675                 680                 685

Met Ser Lys Val Arg Lys Asp Ile Gln Glu Trp Lys Pro Ser Thr Gly
            690                 695                 700

Trp Tyr Asp Trp Gln Gln Val Pro Phe Cys Ser Asn His Phe Thr Glu
705                 710                 715                 720

Leu Ile Met Lys Asp Gly Arg Thr Leu Val Val Pro Cys Arg Gly Gln
                725                 730                 735

Asp Glu Leu Val Gly Arg Ala Arg Ile Ser Pro Gly Ala Gly Trp Asn
            740                 745                 750

Val Arg Asp Thr Ala Cys Leu Ala Lys Ser Tyr Ala Gln Met Trp Leu
```

```
                755                 760                 765
Leu Leu Tyr Phe His Arg Arg Asp Leu Arg Leu Met Ala Asn Ala Ile
        770                 775                 780

Cys Ser Ala Val Pro Val Asn Trp Val Pro Thr Gly Arg Thr Thr Trp
785                 790                 795                 800

Ser Ile His Ala Gly Gly Glu Trp Met Thr Thr Glu Asp Met Leu Glu
                805                 810                 815

Val Trp Asn Arg Val Trp Ile Glu Glu Asn Glu Trp Met Glu Asp Lys
            820                 825                 830

Thr Pro Val Glu Lys Trp Ser Asp Val Pro Tyr Ser Gly Lys Arg Glu
        835                 840                 845

Asp Ile Trp Cys Gly Ser Leu Ile Gly Thr Arg Ala Arg Ala Thr Trp
    850                 855                 860

Ala Glu Asn Ile Gln Val Ala Ile Asn Gln Val Arg Ala Ile Ile Gly
865                 870                 875                 880

Asp Glu Lys Tyr Val Asp Tyr Met Ser Ser Leu Lys Arg Tyr Glu Asp
                885                 890                 895

Thr Thr Leu Val Glu Asp Thr Val Leu
            900                 905

<210> SEQ ID NO 9
<211> LENGTH: 2697
<212> TYPE: DNA
<213> ORGANISM: Dengue virus type 1

<400> SEQUENCE: 9
ggcacgggag cccaagggga aacactggga gaaaaatgga aaagacagct aaaccaattg    60
agcaagtcag aattcaacac ttacaaaagg agtgggatta tagaggtgga tagatctgaa   120
gccaaagagg ggttaaaaag aggagaaccg actaaacacg cagtgtcgag aggaacggcc   180
aaactgaggt ggtttgtgga gaggaacctt gtgaaaccag aagggaaagt catagacctc   240
ggttgtggaa gaggtggctg gtcatattat tgcgctgggc tgaagaaagt cacagaagtg   300
aaaggataca cgaaaggagg acctggacat gaggaaccaa tcccaatggc aacctatgga   360
tggaacctag taaagctata ctccgggaaa gatgtattct ttacaccacc tgagaaatgt   420
gacaccctct tgtgtgatat tggtgagtcc tctccgaacc caactataga agaaggaaga   480
acgttacgtg ttctaaagat ggtggaacca tggctcagag aaaccaattt tgcataaaa    540 attctaaatc cctatatgcc gagtgtggta gaaactttgg agcaaatgca agaaaaacat   600
ggaggaatgc tagtgcgaaa tccactctca agaaactcca ctcatgaaat gtactgggtt   660
tcatgtggaa caggaaacat tgtgtcagca gtaaacatga catctagaat gttgctaaat   720
cgattcacaa tggctcacag gaagccaaca tatgaaagag acgtggactt aggcgctgga   780
acaagacatg tggcagtaga accagaggtg gccaacctag atatcattgg ccagaggata   840
gagaatataa aaaatggaca caatcaaca tggcactatg atgaggacaa tccatacaaa   900
acatgggcct atcatggatc atatgaggtc aagccatcag gatcagcctc atccatggtc   960
aatggtgtgg tgagactgct aaccaaacca tgggatgtca ttcccatggt cacacaaata  1020
gccatgactg acaccacacc ctttggacaa cagagggtgt ttaaagagaa agttgacacg  1080
cgtacaccaa aagcgaaacg aggcacagca caaattatgg aggtgacagc caggtggtta  1140
tgggggtttc tctctagaaa caaaaaaccc agaatctgca caagagagga gttcacaaga  1200
aaagtcaggt caaacgcagc tattggagca gtgttcgttg atgaaaatca atggaactca  1260
```

-continued

```
gcaaaagagg cagtggaaga tgaacggttc tgggaccttg tgcacagaga gagggagctt  1320
cataaacaag gaaatgtgc cacgtgtgtc tacaacatga tgggaaagag agagaaaaaa  1380
ttaggagagt tcggaaaggc aaaaggaagt cgcgcaatat ggtacatgtg gttgggagcg  1440
cgcttttag agtttgaagc ccttggtttc atgaatgaag atcactggtt cagcagagag  1500
aattcactca gtggagtgga aggagaagga ctccacaaac ttggatacat actcagagac  1560
atatcaaaga ttccagggggg aaatatgtat gcagatgaca cagccggatg ggacacaaga  1620
ataacagagg atgatcttca gaatgaggcc aaaatcactg acatcatgga acctgaacat  1680
gccctattgg ccacgtcaat ctttaagcta acctaccaaa acaaggtagt aagggtgcag  1740
agaccagcga aaatggaac cgtgatggat gtcatatcca cgtgacca gagaggaagt  1800
ggacaggttg gaacctatgg cttaaacacc ttcaccaaca tggaggccca actaataaga  1860
caaatggagt ctgagggaat ctttcaccc agcgaattgg aaaccccaaa tctagccgaa  1920
agagtcctcg actggttgaa aaacatggc accgagaggc tgaaaagaat ggcaatcagt  1980
ggagatgact gtgtggtgaa accaatcgat gacagatttg caacagcctt aacagctttg  2040
aatgacatgg gaaggtaag aaaagacata ccgcaatggg aaccttcaaa aggatggaat  2100
gattggcaac aagtgccttt ctgttcacac catttccacc agctgattat gaaggatggg  2160
agggagatag tggtgccatg ccgcaaccaa gatgaacttg taggtagggc cagagtatca  2220
caaggcgccg gatggagctt gagagaaact gcatgcctag gcaagtcata tgcacaaatg  2280
tggcagctga tgtacttcca caggagagac ttgagattag cggctaatgc tatctgttca  2340
gccgttccag ttgattgggt cccaaccagc cgtaccacct ggtcgatcca tgcccaccat  2400
caatggatga caacagaaga catgttgtca gtgtggaata gggtttggat agaggaaaac  2460
ccatggatgg aggacaagac tcatgtgtcc agttgggaag acgttccata cctaggaaaa  2520
agggaagatc gatggtgtgg atccctaata ggcttaacag cacgagccac ctgggccacc  2580
aacatacaag tggccataaa ccaagtgaga aggctcattg ggaatgagaa ttatctagac  2640
ttcatgacat caatgaagag attcaaaaac gagagtgatc ccgaaggggc actctgg    2697
```

<210> SEQ ID NO 10
<211> LENGTH: 899
<212> TYPE: PRT
<213> ORGANISM: Dengue virus type 1

<400> SEQUENCE: 10

```
Gly Thr Gly Ala Gln Gly Glu Thr Leu Gly Glu Lys Trp Lys Arg Gln
 1               5                  10                  15

Leu Asn Gln Leu Ser Lys Ser Glu Phe Asn Thr Tyr Lys Arg Ser Gly
            20                  25                  30

Ile Ile Glu Val Asp Arg Ser Glu Ala Lys Glu Gly Leu Lys Arg Gly
        35                  40                  45

Glu Pro Thr Lys His Ala Val Ser Arg Gly Thr Ala Lys Leu Arg Trp
    50                  55                  60

Phe Val Glu Arg Asn Leu Val Lys Pro Glu Gly Lys Val Ile Asp Leu
65                  70                  75                  80

Gly Cys Gly Arg Gly Gly Trp Ser Tyr Tyr Cys Ala Gly Leu Lys Lys
                85                  90                  95

Val Thr Glu Val Lys Gly Tyr Thr Lys Gly Gly Pro Gly His Glu Glu
            100                 105                 110

Pro Ile Pro Met Ala Thr Tyr Gly Trp Asn Leu Val Lys Leu Tyr Ser
        115                 120                 125
```

```
Gly Lys Asp Val Phe Phe Thr Pro Pro Glu Lys Cys Asp Thr Leu Leu
    130                 135                 140
Cys Asp Ile Gly Glu Ser Ser Pro Asn Pro Thr Ile Glu Glu Gly Arg
145                 150                 155                 160
Thr Leu Arg Val Leu Lys Met Val Glu Pro Trp Leu Arg Gly Asn Gln
                165                 170                 175
Phe Cys Ile Lys Ile Leu Asn Pro Tyr Met Pro Ser Val Val Glu Thr
            180                 185                 190
Leu Glu Gln Met Gln Arg Lys His Gly Gly Met Leu Val Arg Asn Pro
        195                 200                 205
Leu Ser Arg Asn Ser Thr His Glu Met Tyr Trp Val Ser Cys Gly Thr
    210                 215                 220
Gly Asn Ile Val Ser Ala Val Asn Met Thr Ser Arg Met Leu Leu Asn
225                 230                 235                 240
Arg Phe Thr Met Ala His Arg Lys Pro Thr Tyr Glu Arg Asp Val Asp
                245                 250                 255
Leu Gly Ala Gly Thr Arg His Val Ala Val Glu Pro Glu Val Ala Asn
            260                 265                 270
Leu Asp Ile Ile Gly Gln Arg Ile Glu Asn Ile Lys Asn Gly His Lys
        275                 280                 285
Ser Thr Trp His Tyr Asp Glu Asp Asn Pro Tyr Lys Thr Trp Ala Tyr
    290                 295                 300
His Gly Ser Tyr Glu Val Lys Pro Ser Gly Ser Ala Ser Ser Met Val
305                 310                 315                 320
Asn Gly Val Val Arg Leu Leu Thr Lys Pro Trp Asp Val Ile Pro Met
                325                 330                 335
Val Thr Gln Ile Ala Met Thr Asp Thr Thr Pro Phe Gly Gln Gln Arg
            340                 345                 350
Val Phe Lys Glu Lys Val Asp Thr Arg Thr Pro Lys Ala Lys Arg Gly
        355                 360                 365
Thr Ala Gln Ile Met Glu Val Thr Ala Arg Trp Leu Trp Gly Phe Leu
    370                 375                 380
Ser Arg Asn Lys Lys Pro Arg Ile Cys Thr Arg Glu Glu Phe Thr Arg
385                 390                 395                 400
Lys Val Arg Ser Asn Ala Ala Ile Gly Ala Val Phe Val Asp Glu Asn
                405                 410                 415
Gln Trp Asn Ser Ala Lys Glu Ala Val Glu Asp Glu Arg Phe Trp Asp
            420                 425                 430
Leu Val His Arg Glu Arg Glu Leu His Lys Gln Gly Lys Cys Ala Thr
        435                 440                 445
Cys Val Tyr Asn Met Met Gly Lys Arg Glu Lys Lys Leu Gly Glu Phe
    450                 455                 460
Gly Lys Ala Lys Gly Ser Arg Ala Ile Trp Tyr Met Trp Leu Gly Ala
465                 470                 475                 480
Arg Phe Leu Glu Phe Glu Ala Leu Gly Phe Met Asn Glu Asp His Trp
                485                 490                 495
Phe Ser Arg Glu Asn Ser Leu Ser Gly Val Glu Gly Glu Gly Leu His
            500                 505                 510
Lys Leu Gly Tyr Ile Leu Arg Asp Ile Ser Lys Ile Pro Gly Gly Asn
        515                 520                 525
Met Tyr Ala Asp Asp Thr Ala Gly Trp Asp Thr Arg Ile Thr Glu Asp
    530                 535                 540
```

-continued

```
Asp Leu Gln Asn Glu Ala Lys Ile Thr Asp Ile Met Glu Pro Glu His
545                 550                 555                 560

Ala Leu Leu Ala Thr Ser Ile Phe Lys Leu Thr Tyr Gln Asn Lys Val
                565                 570                 575

Val Arg Val Gln Arg Pro Ala Lys Asn Gly Thr Val Met Asp Val Ile
            580                 585                 590

Ser Arg Arg Asp Gln Arg Gly Ser Gly Gln Val Gly Thr Tyr Gly Leu
        595                 600                 605

Asn Thr Phe Thr Asn Met Glu Ala Gln Leu Ile Arg Gln Met Glu Ser
    610                 615                 620

Glu Gly Ile Phe Ser Pro Ser Glu Leu Glu Thr Pro Asn Leu Ala Glu
625                 630                 635                 640

Arg Val Leu Asp Trp Leu Lys Lys His Gly Thr Glu Arg Leu Lys Arg
                645                 650                 655

Met Ala Ile Ser Gly Asp Asp Cys Val Val Lys Pro Ile Asp Asp Arg
            660                 665                 670

Phe Ala Thr Ala Leu Thr Ala Leu Asn Asp Met Gly Lys Val Arg Lys
        675                 680                 685

Asp Ile Pro Gln Trp Glu Pro Ser Lys Gly Trp Asn Asp Trp Gln Gln
    690                 695                 700

Val Pro Phe Cys Ser His His Phe His Gln Leu Ile Met Lys Asp Gly
705                 710                 715                 720

Arg Glu Ile Val Val Pro Cys Arg Asn Gln Asp Glu Leu Val Gly Arg
                725                 730                 735

Ala Arg Val Ser Gln Gly Ala Gly Trp Ser Leu Arg Glu Thr Ala Cys
            740                 745                 750

Leu Gly Lys Ser Tyr Ala Gln Met Trp Gln Leu Met Tyr Phe His Arg
        755                 760                 765

Arg Asp Leu Arg Leu Ala Ala Asn Ala Ile Cys Ser Ala Val Pro Val
    770                 775                 780

Asp Trp Val Pro Thr Ser Arg Thr Thr Trp Ser Ile His Ala His His
785                 790                 795                 800

Gln Trp Met Thr Thr Glu Asp Met Leu Ser Val Trp Asn Arg Val Trp
                805                 810                 815

Ile Glu Glu Asn Pro Trp Met Glu Asp Lys Thr His Val Ser Ser Trp
            820                 825                 830

Glu Asp Val Pro Tyr Leu Gly Lys Arg Glu Asp Arg Trp Cys Gly Ser
        835                 840                 845

Leu Ile Gly Leu Thr Ala Arg Ala Thr Trp Ala Thr Asn Ile Gln Val
    850                 855                 860

Ala Ile Asn Gln Val Arg Arg Leu Ile Gly Asn Glu Asn Tyr Leu Asp
865                 870                 875                 880

Phe Met Thr Ser Met Lys Arg Phe Lys Asn Glu Ser Asp Pro Glu Gly
                885                 890                 895

Ala Leu Trp
```

<210> SEQ ID NO 11
<211> LENGTH: 2701
<212> TYPE: DNA
<213> ORGANISM: Dengue virus type 2

<400> SEQUENCE: 11

```
ggaactggca acataggaga gacgcttgga gagaaatgga aaagccgatt gaacgcattg      60
gggaaaagtg aattccagat ctacaagaaa agtggaatcc aggaagtgga tagaacctta     120
```

```
gcaaaagaag gcattaaaag aggagaaacg gaccatcacg ctgtgtcgcg aggctcagca      180
aaactgagat ggttcgtcga gagaaatatg gtcacaccag aagggaaagt agtggacctc      240
ggttgcggca gaggaggctg gtcatactat tgtgggggac taaagaatgt aagagaagtc      300
aaaggcctga caaaggagg accaggacat gaagaaccca tccccatgtc aacatatggg       360
tggaatctag tacgtcttca aagtggagtt gacgttttct tcactccgcc agaaaagtgt      420
gacacattgt tgtgtgacat aggggagtcg tcaccaaatc ccacggtaga agcaggacga      480
acactcagag tccttaactt agtggaaaat tggttgaaca acaacaccca attttgcata      540
aaggttctca acccatacat gccctcagtc atagaaaaaa tggaagcact acaaaggaaa      600
tatggaggag ccttagtgag gaatccactc tcacgaaact ccacacatga gatgtactgg      660
gtatccaatg cctccgggaa catagtgtca tcagtgaaca tgatttcaag gatgttgatc      720
aacagattca caatgagaca caagaaagcc acttacagag cagatgtaga cctcggaagc      780
ggaacccgca acatcggaat tgaaagtgag ataccaaacc tagacataat cgggaaaaga      840
atagaaaaaa taaacaaga gcatgaaaca tcatggcact atgaccaaga ccacccatac       900
aaaacgtggg cttaccatgg cagctatgaa acaaaacaaa ctggatcagc atcatccatg      960
gtgaacggaa tggtcagact gctgacaaaa ccttgggacg tcgtcccat ggtgacacag       1020 atggcaatga cagacacgac tccatttgga caacagcgcg tttttaaaga aaaagtggac      1080
acgagaaccc aagaaccgaa agaaggcaca aagaaactaa tgaaaatcac ggcagagtgg      1140 cttttggaaag aactagggaa gaaaaagaca cctaggatgt gcactagaga agaattcaca      1200
agaaaggtga gaagcaatgc agccttgggg gccatattca ctgatgagaa caagtggaag      1260
tcggcacgtg aggctgttga agatagtagg ttttgggagc tggttgacaa ggaaaggaat      1320
ctccatcttg aaggaaagtg tgaaacatgt gtgtataaca tgatgggaaa aagagagaag      1380
aagctagggg agttcggcaa ggcaaaaggc agcagagcca tatggtacat gtggcttgga      1440
gcacgcttct tagagtttga agccctagga ttcttgaatg aagatcactg gttctccaga      1500
gagaactcct tgagtggagt ggaaggagaa gggctgcaca agctaggtta catttttaaga     1560 gacgtgagca agaaagaggg aggagcaatg tatgccgatg acaccgcagg atgggacaca      1620
agaatcacac tagaagacct aaaaaatgaa gaaatggtaa caaaccacat ggaaggagaa      1680
cacaagaaac tagccgaggc cattttcaaa ttaacgtacc aaaacaaggt ggtgcgtgtg      1740
caaagaccaa caccaagagg cacagtaatg gatatcatat cgagaagaga ccaaagaggt      1800
agtggacaag ttggtaccta tggactcaat actttcacca atatggaagc ccaactaatc      1860
agacagatgg agggagaagg agtcttcaaa agcattcagc acctgacagt cacagaagaa      1920
atcgccgtgc aaaactggtt agcaagagta gggcgcgaaa ggttatcaag aatggccatc      1980
agtggagatg attgtgttgt gaaacctta tgatgacagg tcgcaagcgc tttaacagct       2040
ctaaatgaca tgggaaaggt taggaaagac atacaacaat gggaaccttc aagaggatgg      2100
aacgattgga cacaagtgcc cttctgttca caccattcc atgagttaat catgaaagac       2160
ggccgcgtac ttgtagttcc atgcagaaac caagatgaac tgattggtag agcccgaatt      2220
tcccaaggag ctggggtc tttgcgagag acggcctgtt ggggaagtc ctacgcccaa         2280 atgtggagct tgatgtactt ccacagacgt gacctcaggc tggcggctaa tgctatttgc      2340
tcggcagtcc catcacattg ggttccaaca agtagaacaa cctggtccat acacgccaaa      2400
catgaatgga tgacaacgga agacatgctg acagtctgga acagggtgtg gattcaagaa      2460
```

```
aacccatgga tggaagacaa aactccagtg gaatcatggg aggaaatccc atacttgggg    2520
aaaagagaag accaatggtg cggctcattg attgggctaa caagcagggc cacctgggca    2580
aagaacatcc aaacagcaat aaatcaagtt agatccctta taggcaatga ggaatacaca    2640
gattacatgc catccatgaa aagattcaga agagaagagg aagaggcagg agtcctgtgg    2700
t                                                                    2701
```

<210> SEQ ID NO 12
<211> LENGTH: 900
<212> TYPE: PRT
<213> ORGANISM: Dengue virus type 2

<400> SEQUENCE: 12

```
Gly Thr Gly Asn Ile Gly Glu Thr Leu Gly Glu Lys Trp Lys Ser Arg
  1               5                  10                  15

Leu Asn Ala Leu Gly Lys Ser Glu Phe Gln Ile Tyr Lys Lys Ser Gly
             20                  25                  30

Ile Gln Glu Val Asp Arg Thr Leu Ala Lys Glu Gly Ile Lys Arg Gly
         35                  40                  45

Glu Thr Asp His His Ala Val Ser Arg Gly Ser Ala Lys Leu Arg Trp
     50                  55                  60

Phe Val Glu Arg Asn Met Val Thr Pro Glu Gly Lys Val Val Asp Leu
 65                  70                  75                  80

Gly Cys Gly Arg Gly Gly Trp Ser Tyr Tyr Cys Gly Gly Leu Lys Asn
                 85                  90                  95

Val Arg Glu Val Lys Gly Leu Thr Lys Gly Gly Pro Gly His Glu Glu
            100                 105                 110

Pro Ile Pro Met Ser Thr Tyr Gly Trp Asn Leu Val Arg Leu Gln Ser
        115                 120                 125

Gly Val Asp Val Phe Phe Thr Pro Pro Glu Lys Cys Asp Thr Leu Leu
    130                 135                 140

Cys Asp Ile Gly Glu Ser Ser Pro Asn Pro Thr Val Glu Ala Gly Arg
145                 150                 155                 160

Thr Leu Arg Val Leu Asn Leu Val Glu Asn Trp Leu Asn Asn Asn Thr
                165                 170                 175

Gln Phe Cys Ile Lys Val Leu Asn Pro Tyr Met Pro Ser Val Ile Glu
            180                 185                 190

Lys Met Glu Ala Leu Gln Arg Lys Tyr Gly Gly Ala Leu Val Arg Asn
        195                 200                 205

Pro Leu Ser Arg Asn Ser Thr His Glu Met Tyr Trp Val Ser Asn Ala
    210                 215                 220

Ser Gly Asn Ile Val Ser Ser Val Asn Met Ile Ser Arg Met Leu Ile
225                 230                 235                 240

Asn Arg Phe Thr Met Arg His Lys Lys Ala Thr Tyr Glu Pro Asp Val
                245                 250                 255

Asp Leu Gly Ser Gly Thr Arg Asn Ile Gly Ile Glu Ser Glu Ile Pro
            260                 265                 270

Asn Leu Asp Ile Ile Gly Lys Arg Ile Glu Lys Ile Lys Gln Glu His
        275                 280                 285

Glu Thr Ser Trp His Tyr Asp Gln Asp His Pro Tyr Lys Thr Trp Ala
    290                 295                 300

Tyr His Gly Ser Tyr Glu Thr Lys Gln Thr Gly Ser Ala Ser Ser Met
305                 310                 315                 320

Val Asn Gly Val Val Arg Leu Leu Thr Lys Pro Trp Asp Val Val Pro
```

-continued

```
                325                 330                 335
Met Val Thr Gln Met Ala Met Thr Asp Thr Thr Pro Phe Gly Gln Gln
                340                 345                 350

Arg Val Phe Lys Glu Lys Val Asp Thr Arg Thr Gln Glu Pro Lys Glu
                355                 360                 365

Gly Thr Lys Lys Leu Met Lys Ile Thr Ala Glu Trp Leu Trp Lys Glu
                370                 375                 380

Leu Gly Lys Lys Lys Thr Pro Arg Met Cys Thr Arg Glu Glu Phe Thr
385                 390                 395                 400

Arg Lys Val Arg Ser Asn Ala Ala Leu Gly Ala Ile Phe Thr Asp Glu
                405                 410                 415

Asn Lys Trp Lys Ser Ala Arg Glu Ala Val Glu Asp Ser Arg Phe Trp
                420                 425                 430

Glu Leu Val Asp Lys Glu Arg Asn Leu His Leu Glu Gly Lys Cys Glu
                435                 440                 445

Thr Cys Val Tyr Asn Met Met Gly Lys Arg Glu Lys Lys Leu Gly Glu
                450                 455                 460

Phe Gly Lys Ala Lys Gly Ser Arg Ala Ile Trp Tyr Met Trp Leu Gly
465                 470                 475                 480

Ala Arg Phe Leu Glu Phe Glu Ala Leu Gly Phe Leu Asn Glu Asp His
                485                 490                 495

Trp Phe Ser Arg Glu Asn Ser Leu Ser Gly Val Glu Gly Glu Gly Leu
                500                 505                 510

His Lys Leu Gly Tyr Ile Leu Arg Asp Val Ser Lys Lys Glu Gly Gly
                515                 520                 525

Ala Met Tyr Ala Asp Asp Thr Ala Gly Trp Asp Thr Arg Ile Thr Leu
                530                 535                 540

Glu Asp Leu Lys Asn Glu Glu Met Val Thr Asn His Met Glu Gly Glu
545                 550                 555                 560

His Lys Lys Leu Ala Glu Ala Ile Phe Lys Leu Thr Tyr Gln Asn Lys
                565                 570                 575

Val Val Arg Val Gln Arg Pro Thr Pro Arg Gly Thr Val Met Asp Ile
                580                 585                 590

Ile Ser Arg Arg Asp Gln Arg Gly Ser Gly Gln Val Gly Thr Tyr Gly
                595                 600                 605

Leu Asn Thr Phe Thr Asn Met Glu Ala Gln Leu Ile Arg Gln Met Glu
                610                 615                 620

Gly Glu Gly Val Phe Lys Ser Ile Gln His Leu Thr Val Thr Glu Glu
625                 630                 635                 640

Ile Ala Val Gln Asn Trp Leu Ala Arg Val Gly Arg Glu Arg Leu Ser
                645                 650                 655

Arg Met Ala Ile Ser Gly Asp Asp Cys Val Val Lys Pro Leu Asp Asp
                660                 665                 670

Arg Phe Ala Ser Ala Leu Thr Ala Leu Asn Asp Met Gly Lys Val Arg
                675                 680                 685

Lys Asp Ile Gln Gln Trp Glu Pro Ser Arg Gly Trp Asn Asp Trp Thr
                690                 695                 700

Gln Val Pro Phe Cys Ser His His Phe His Glu Leu Ile Met Lys Asp
705                 710                 715                 720

Gly Arg Val Leu Val Val Pro Cys Arg Asn Gln Asp Glu Leu Ile Gly
                725                 730                 735

Arg Ala Arg Ile Ser Gln Gly Ala Gly Trp Ser Leu Arg Glu Thr Ala
                740                 745                 750
```

-continued

```
Cys Leu Gly Lys Ser Tyr Ala Gln Met Trp Ser Leu Met Tyr Phe His
            755                 760                 765
Arg Arg Asp Leu Arg Leu Ala Ala Asn Ala Ile Cys Ser Ala Val Pro
        770                 775                 780
Ser His Trp Val Pro Thr Ser Arg Thr Thr Trp Ser Ile His Ala Lys
785                 790                 795                 800
His Glu Trp Met Thr Thr Glu Asp Met Leu Thr Val Trp Asn Arg Val
                805                 810                 815
Trp Ile Gln Glu Asn Pro Trp Met Glu Asp Lys Thr Pro Val Glu Ser
            820                 825                 830
Trp Glu Glu Ile Pro Tyr Leu Gly Lys Arg Glu Asp Gln Trp Cys Gly
        835                 840                 845
Ser Leu Ile Gly Leu Thr Ser Arg Ala Thr Trp Ala Lys Asn Ile Gln
    850                 855                 860
Thr Ala Ile Asn Gln Val Arg Ser Leu Ile Gly Asn Glu Glu Tyr Thr
865                 870                 875                 880
Asp Tyr Met Pro Ser Met Lys Arg Phe Arg Arg Glu Glu Glu Glu Ala
                885                 890                 895
Gly Val Leu Trp
            900

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Arg Val Lys Met Glu Lys Leu Gln Leu Lys Gly Thr Thr
  1               5                  10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Gln Leu Leu Met Arg Glu Val Lys Thr Gly Thr Lys Lys
  1               5                  10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Ser Thr Lys Ala Ile Gly Arg Thr Ile Leu Lys Glu Asn Ile Lys
  1               5                  10                  15
Tyr Glu Val

<210> SEQ ID NO 16
<211> LENGTH: 23
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 16
gactgaagag ggcaatgttg agc                                           23

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaataactg cggacytctg c                                             21

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaattcttca actgccttgg aatgagc                                       27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgcagttat ttgccaatgc tgcttcc                                       27

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 20

His His His His His His
  1               5
```

DIAGNOSTIC TEST FOR WEST NILE VIRUS

REFERENCE TO RELATED APPLICATIONS

A claim of priority is made to U.S. Provisional Application No. 60/422,755, filed Oct. 31, 2002 and No. 60/476,513, filed Jun. 6, 2003. Reference is also made to: PCT application PCT/US02/09036, filed on Mar. 11, 2002 and published as WO 02/072036 on Sep. 19, 2002, which claims priority to U.S. Provisional Application No. 60/275,025, filed Mar. 12, 2001, and U.S. Provisional Application No. 60/281,947, filed Apr. 5, 2001; and reference is made to U.S. Provisional Application No. 60/402,860, filed Aug. 8, 2002, the disclosures of which are hereby incorporated by reference in their entireties. Each of the documents cited herein (herein cited documents), and each of the documents cited in each of the herein cited documents, together with any manufacturer's specifications, data sheets, descriptions, product literature, instructions and the like for any products mentioned herein or in herein cited documents or in documents cited in herein cited documents, is hereby incorporated herein by reference. None of the documents incorporated by reference into this text is admitted to be prior art with respect to the present invention, but, documents incorporated by reference into this text may be employed in the practice of the invention.

FIELD OF THE INVENTION

The instant invention relates generally to the field of diagnostic assays for the detection of viruses, infectious organisms, antibodies, and autoimmune diseases. More in particular, this invention relates to compositions and methods for diagnosing a flavivirus infection. Even more in particular, this invention relates to the use of isolated and/or purified polypeptides of West Nile virus (WNV), which includes recombinant, synthetic and fusion proteins comprising the polypeptides or a nucleic acid molecule encoding a WNV polypeptide, whereby the WNV polypeptide is substantially pure and of authentic conformation and is reactive with antibodies against WNV and strongly cross-reactive with antibodies against one or more members of the genus Flavivirus, advantageously Japanese encephalitis virus (JEV), St. Louis encephalitis virus (SLEV), and Dengue virus (DENV); and are useful to detect a flavivirus infection or exposure in a subject capable of being infected by a flavivirus or capable of mounting an immune response (e.g. production of antibodies) against a flavivirus or a flavivirus antigen, without needing to specify as to which flavivirus is the source of infection or exposure, e.g., to rapidly determine whether a subject has a flavivirus infection or has been exposed to a flavivirus.

The instant invention is further directed to a novel method for the rapid detection of antibodies to a flavivirus or an antigen thereof using a microsphere immunoassay under conditions that provide enhanced reaction kinetics to provide a more cost-effective, rapid, and sensitive approach to detecting antibodies in a biological specimen against a substantially pure WNV polypeptide of authentic conformation which reacts with antibodies against WNV and strongly cross-reacts with antibodies against a flavivirus, advantageously JEV, SLEV, and/or DENV. In one embodiment, the instant invention further provides a method to detect a recent or acute infection utilizing an immunodepletion step to remove a subpopulation of antibodies, such as IgG or IgM antibodies, raised against the WNV polypeptide of the instant invention.

Also within the scope of this invention are diagnostic kits comprising reagents and including an isolated and/or substantially purified WNV polypeptide of authentic conformation or a nucleic acid encoding the said WNV polypeptide, for the detection of a recent, current or prior flavivirus infection or exposure to a flavivirus antigen or polypeptide in a subject susceptible thereto.

The present invention also relates to the use of isolated and/or purified nonstructural polypeptides of WNV, which includes recombinant, synthetic and fusion proteins comprising the nonstructural polypeptides or a nucleic acid molecule encoding a WNV nonstructural polypeptide, whereby the WNV nonstructural (NS) polypeptide is substantially pure and of authentic conformation and is reactive with WNV antibodies with specificity wherein the WNV NS polypeptide is not substantially cross-reactive with antibodies against one or more members of the genus Flavivirus, such as, for example, JEV, SLEV, or DENV.

The nonstructural polypeptides of the present invention are useful for specifically detecting a WNV infection or exposure in a subject capable of being infected by a WNV or capable of mounting an immune response (e.g. production of antibodies) against a WNV or a WNV antigen in a time-efficient manner, i.e., to rapidly determine whether a subject has a WNV infection or has been exposed to a WNV.

The nonstructural polypeptides of WNV which are reactive with WNV antibodies with specificity but are not substantially cross-reactive with antibodies against another Flavivirus, such as, for example, JEV, SLEV, or DENV, may also be used to identify recently acquired WNV infections within a period of up to approximately a year or less post-infection. Also within the scope of the invention is the use of the nonstructural polypeptides of WNV to discriminate between vaccination with a killed virus vaccine and a natural infection with WNV. For example, such an application of the present invention can be used to determine which members of a population of horses are vaccinated and which are infected or carriers of WNV.

The present invention also relates to the use of isolated and/or purified nonstructural (NS) polypeptides of the four known strains of DENV, namely, DENV-1, DENV-2, DENV-3, and DENV-4, (a) to rapidly detect a DENV infection with specificity as to the which strain is the source of infection, (b) to rapidly discriminate between past DENV infections and current DENV infections, and (c) to discriminate between a general flavivirus infection and a DENV infection. The isolated and/or purified NS polypeptides of the invention include recombinant, synthetic and fusion polypeptides comprising the DENV NS polypeptides or a nucleic acid molecule encoding the DENV NS polypeptide, whereby the DENV NS polypeptides may be substantially pure and of authentic conformation.

For the purposes of this invention, a "serospecific DENV" refers to a single strain of DENV, namely DENV-1, DENV-2, DENV-3, or DENV-4. Further, a "serospecific" protein or antigen is such that the protein/antigen has been obtained from a specific strain DENV, namely a protein/antigen obtained from DENV-1, DENV-2, DENV-3, or DENV-4.

DENV NS polypeptides of a first particular strain show specificity for antibodies raised against the same first DENV strain and are not cross-reactive with antibodies against other DENV strains. For example, NS of DENV-1 will show specificity to anti-DENV-1 sera, but will not be reactive with sera raised against DENV-2, -3, or -4. In addition, like WNV NS proteins, the DENV NS polypeptides are not substantially cross-reactive with antibodies against one or more members of the genus Flavivirus, such as, for example, JEV, SLEV, or WNV. Thus, the DENV NS can be used to discriminate between a general flavivirus infection and a DENV infection. In addition, since the antibodies to DENV NS proteins are not persistent, the DENV NS proteins can be used to detect recently acquired infections or current infections.

The present invention also contemplates diagnostic kits comprising reagents and including an isolated and/or substantially purified WNV nonstructural polypeptide of authentic conformation or a nucleic acid encoding the said WNV nonstructural polypeptide, for the detection of a recent or current WNV infection or exposure to a WNV antigen or polypeptide in a subject susceptible thereto.

BACKGROUND OF THE INVENTION

In the summer of 1999, an outbreak of encephalitis in humans that was associated with mosquitoes occurred in New York City (CDC, *MMWR,* 48, pp. 845-9 (1999); CDC, *MMWR,* 48, pp. 944-6 (1999); D. S. Asnis et al., *Clin Infect Dis,* 30, pp. 413-8 (2000)). At approximately the same time, American crows began dying in the Northeastern United States, many in Fairfield County, Conn. Two reports in December of 1999 demonstrated that these outbreaks in birds and humans were actually due to WNV virus transmitted by mosquitoes (R. S. Lanciotti et al., *Science,* 286, pp. 2333-7 (1999); J. F. Anderson et al., *Science,* 286, pp. 2331-3 (1999)). It is clear from these reports that WNV was the cause of the 1999 outbreak of fatal encephalitis in the Northeastern United States. This is the first reported appearance of WNV in the Western Hemisphere.

Future outbreaks of WNV in the United States are a new and important public health concern. To date, the only method for preventing WNV infection is spraying large geographic areas with insecticide to kill mosquito vectors. Spraying is difficult, potentially toxic to humans, requires repeated applications and is incompletely effective. There is no known vaccine for use in humans against WNV.

WNV is a member of the family Flaviviridae, genus *Flavivirus* belonging to the Japanese Encephalitis antigenic complexes of viruses. This sero-complex includes JEV, SLEV, Alfuy, Koutango, Kunjin, Cacipacore, Yaounde, and Murray Valley Encephalitis viruses. This Flaviviridae family also includes the Tick-borne encephalitis virus (TBEV), Dengue virus (including the four strains of: DENV-1, DENV-2, DENV-3, and DENV-4), and the family prototype, Yellow Fever virus (YFV). WNV infections generally have mild symptoms, although infections can be fatal in elderly and immunocompromised patients. Typical symptoms of mild WNV infections include fever, headache, body aches, rash and swollen lymph glands. Severe disease with encephalitis is typically found in elderly patients (D. S. Asnis et al., supra). For the most part, treatment of a subject having a flavivirus infection is a symptomatic treatment, i.e. the general symptoms of a flavivirus infection are treated, such that for initial treatment, mere knowledge of the infection being a flavivirus infection may be sufficient. However, in certain other cases rapid and accurate diagnosis of the specific flavivirus, particularly WNV, is critical such that the most appropriate treatment can be initiated.

Moreover, with respect to the blood suppy (e.g., donor blood to be supplied to patients), and donor organs (e.g., organs to be supplied to patients), there is a need to rapidly determine whether the blood or organs are contaminated by a flavivirus, e.g., determine whether the donor suffers from a flavivirus infection, without needing to know specifically which flavivirus is the source of infection. Conversely, there is also a need for rapid and accurate detection of a specific flavivirus such as WNV since it may be important in some cases to delimit the spread of WNV through the blood supply.

Flavivirus infections are a global public health problem (C. G. Hayes, in *The Arboviruses: Epidemiology and Ecology*, T. P. Monath, ed., CRC, Boca Raton, Fla., vol. 5, chap. 49 (1989); M. J. Cardosa, *Br Med Bull,* 54, pp. 395-405 (1998); Z. Hubalek and J. Halouzka, *Emerg Infect Dis,* 5, pp. 643-50 (1999)) with about half of the flaviviruses causing human diseases. These viruses are normally maintained in a natural cycle between mosquito vectors and birds, where humans and horses are considered dead-end hosts. Birds, including the American crow, *Corvus brachyrhynchos*, can serve as non-human reservoirs for the virus. In the case of WNV, the virus is transmitted to man by mosquitoes, which in the Northeastern United States are primarily of the genera *Culex* and *Aedes*, in particular *C. pipiens* and *A. vexans.*

Flaviviruses are the most significant group of arthropod-transmitted viruses in terms of global morbidity and mortality. An estimated one hundred million cases coupled with the lack of sustained mosquito control measures, has distributed the mosquito vectors of flaviviruses throughout the tropics, subtropics, and some temperate areas. As a result, over half the world's population is at risk for flaviviral infection. Further, modern jet travel and human migration have raised the potential for global spread of these pathogens. Thus, in certain cases, early and rapid detection of a flavivirus infection or of exposure to a flavivirus antigen, without needing to be specific as to which flavivirus, is important. Conversely, it may also be critical to accurately and confidently know the identity of the specific flavivirus causing the infection.

The WNV, like other flaviviruses, is enveloped by host cell membrane and contains the three structural proteins capsid (C), membrane (M), and envelope glycoprotein (E glycoprotein). The E glycoprotein and M proteins are found on the surface of the virion where they are anchored in the membrane. Mature E glycoprotein is glycosylated, whereas M is not, although its precursor, prM, is a glycoprotein. In other flaviviruses, E glycoprotein is the largest structural protein and contains functional domains responsible for cell surface attachment and intraendosomal fusion activities. In some flaviviruses, E glycoprotein has been reported to be a major target of the host immune system during a natural infection.

In general, the flavivirus genome which is replicated in the cytoplasm of the infected cell is a single positive-stranded RNA of approximately 10,500 nucleotides containing short 5' and 3' untranslated regions, a single long open reading frame (ORF), a 5' cap, and a nonpolyadenylated 3' terminus. The flavivirus genome encodes a single polyprotein which is co- and post-translationally processed by viral and cellular proteases into the three structural proteins, C (capsid), prM/M (premembrane/membrane), and envelope (E glycoprotein) and seven nonstructural proteins, NS1 (nonstructural protein 1), NS2A, NS2B, NS3, NS4A, NS4B, and NS5 (T. J. Chambers et al., *Ann Rev Microbiol,* 44, pp. 649-88 (1990)).

With respect to post-translational processing of the polyprotein, the sites of proteolytic cleavage in the YFV, which is likely to be predictive of the sites of cleavage in all flaviviruses, have been determined by comparing the nucleotide sequence and the amino terminal sequences of the viral proteins. Subsequent to initial processing of the polyprotein, prM is converted to M during virus release (G. Wengler at al., *J Virol,* 63, pp. 2521-6 (1989)), and anchored C is processed during virus maturation (Nowak et al., *Virology*, 156, pp. 127-37 (1987)). In some flaviviruses, the E glycoprotein is the major virus antigen involved in virus neutralization by specific antibodies (Martin D. A., et al. 2002, Clin Diagn Lab Immunol. 9:544-9).

The complete or partial genomes of a number of WNV isolates from the outbreak in the Northeastern United States have been sequenced. The complete sequence of WNV isolated from a dead Chilean flamingo (WN-NY99) at the Bronx Zoo was deposited in GenBank™ (accession number AF196835) (R. S. Lanciotti et al., supra). The genome of a WNV isolate from human victims of the New York outbreak (WNV-NY1999) was sequenced and deposited as GenBank™ accession number AF202541 (X-Y. Jia et al., *The Lancet*, 354, pp. 1971-2 (1999)). Partial sequences of isolates from two species of mosquito, a crow and a hawk from Connecticut are deposited as GenBank™ accession numbers AF206517-AF206520, respectively (J. F. Anderson et al., supra). Comparative phylogenetic analysis of the NY sequences with previously reported WNV sequences indicated a high degree of sequence similarity between the NY isolates and two isolates from Romania and one from Israel (J. F. Anderson et al., supra; X.-Y. Jia et al., supra; R. S. Lanciotti et al., supra). Furthermore, PCT WO 02/072056 relates to the WNV E glycoprotein and its use in diagnostics of WNV infections. Importantly, the referenced PCT does not at any timerecognize that this antigen is strongly cross-reactive among flaviviruses, such as, JEV, SLEV, and DENV; rather, this PCT publication attempts to advance the proposition that the WNV E glycoprotein is specific for WNV and hence useful to diagnose or detect only WNV or to immunize or vaccinate against only WNV, contrary to the herein inventor's discoveries.

While flaviviruses such as JEV, SLEV, and DENV exhibit similar structural features and components, the individual viruses are significantly different at both the sequence and antigenic levels. Indeed, antigenic distinctions have been used to define four different strains within just the DENV subgroup of the flaviviruses. Infection of an individual with one DENV strain does not provide long-term immunity against the other strains and secondary infections with heterologous strains are becoming increasingly prevalent as multiple strains co-circulate in a geographic area. Such secondary infections indicate that vaccination or prior infection with any one flavivirus may not to provide generalized protection against other flaviviruses.

Serodiagnosis of WNV and other flavivirus infections currently requires a series of enzyme-linked immunosorbant assays (ELISA) and viral plaque reduction neutralization (PRN) tests. Specifically, the recommended assays for the identification of WNV infection of humans are the immunoglobulin M (IgM) antibody capture enzyme linked immunosorbent assay (MAC ELISA), the IgG ELISA (Martin, D. A., 2000, J. Clin. Microbiol. 38:1823-1826; Johnson, A. J., 2000, J. Clin. Microbiol. 38:1827-1831), detection of antibodies in cerebrospinal fluid or serum using a plaque assay (PRN test), isolation of the virus, and RT-PCR. Most public health laboratories in the United States are performing these assays according to protocols recommended by the Centers of Disease Control and Prevention (CDC).

However, the currently available ELISA assays, while not precisely specific for WNV, do not provide for a general diagnostic assay for flavivirus infections (or exposure thereto) with other members of the JEV serogroup (including JEV and SLEV) and DENV because the cross reactivity of the assay to other flaviviruses is unreliable and inconsistent. Further, the currently used ELISA assays according to the CDC do not provide rapid results. Separate assays are currently used to properly and reliably diagnose flavivirus infections other than WNV, such as, JEV, SLEV, and DENV and there is no available assay to reliably, consistently and rapidly detect a flavivirus infection, especially WNV, JEV, SLEV, or DENV. Accordingly, an antigen that is strongly cross-reactive to antibodies against JEV serogroup flaviviruses, especially JEV, SLEV, and DENV for use in a rapid diagnostic assay providing rapid results thereof would be an advance in the art since it would enable a general flavivirus detection assay when knowledge of the specific flavivirus is not necessarily needed. Further, in addition to the current assays that are used to diagnose specific flavivirus infections, antigens for use in new rapid diagnostic assay procedures for the specific diagnosis of a specific flavivirus, such as WNV, that are more accurate, reliable, and sensitive than those currently available would be an important advance in the art.

When rapid, accurate, and sensitive detection of a flavivirus is desired wherein knowledge of the specific flavivirus is not required, an antigen with strong cross-reactivity between flaviviruses is desirable. Further, the antigens currently known in the art lack a sufficient cross-reactivity to allow for reliable, consistent, and accurate testing of a flavivirus infection. One reason limiting the cross-reactivity of current assays in the art, such as, the CDC ELISA assay for the detection of WNV, may relate to the impurity of the antigens used in the assays. The assays used in the art for the detection of WNV and other flaviviruses typically utilize somewhat impure antigens that are contaminated with proportionally high levels of cellular protein and other macromolecules as a result of the purification process. In some cases, the concentration of contaminating protein, such as bovine serum albumin, is greater than the concentration of the antigen being prepared. These impurities can cause a significant reduction in the sensitivity of a given assay (i.e., higher levels of background signals relative to true detection signals) in detecting antibodies against a virus or pathogen of interest from a biological sample. For example, as a control reaction aimed at determining the relative level of background inherent with a given supplied antigen, a separate test of the tissue culture supernatant from which the antigen was obtained may be required. Thus, an antigen that is substantially pure, i.e., one that is not contaminated with unwanted protein or other macromolecules, would be useful for screening for flavivirus infections or exposure thereto since it would provide for a more sensitive diagnosis.

Further, the antigens currently used in the art for the detection of flaviviruses typically are damaged with respect to their three-dimensional structure. For example, damage may occur at specific protein domains or epitopes. Such structural damage is usually introduced during antigen purification and/or isolation wherein the antigen is often treated under harsh and/or destructive conditions that result in damage to an antigen's three-dimensional form. For example, the antigens currently prepared in the art may be treated with the chemical, polyethylene glycol ("PEG") to help carry out the precipitation of the antigen from solution for the purpose of increasing its concentration. This process can be harmful to a given antigen and may introduce irreversible damage to its structure. Additionally during purification, the antigens can be extracted using acetone. However, acetone extraction can lead to full and/or partial denaturation of the antigen, which, in turn, can result in an antigen having lost its authentic and/or native conformation. Further still, the extent, predictability, reliability, and consistency of cross-reactivity of an antigen is typically greater in the case of an antigen having a authentic and/or native conformation. Thus, it would be useful to have a WNV polypeptide (i.e., antigen) that is of authentic conformation to allow for a stronger, more predictable, more reliable and more consistent cross-reactivity to other flaviviruses, especially, JEV, SLEV and DENV.

In contrast, in situations where cross-reactivity to multiple flaviviruses is undesirable, it would also be an improvement in the art to have available one or more polypeptides (i.e., antigens) that could be used to specifically detect antibodies against a specific flavivirus infection, especially WNV, more accurately, reliably, and rapidly without cross-reactivity with antibodies against other Flaviviruses, such as, for example, JEV, SLEV, or DENV. In other word, in addition to the utility of a polypeptide for the general detection of a flavivirus infection without regard as to which flavivirus, it would also be useful to detect a specific flavivirus infection, such as a WNV infection, using a specific antigen such that the detection of the WNV infection is more reliable, more rapid, and more accurate than currently known methods.

A number of serologic assays are routinely used for laboratory diagnosis of flavivirus infections: IgM antibody capture enzyme immunoassay (MAC-ELISA), indirect IgG ELISA, indirect fluorescent antibody assay (IFAT), hemagglutination inhibition (HIT), and serum dilution cross-species plaque reduction neutralization tests (PRNTs)—each varying markedly in sensitivity, technical difficulty, turnaround time, and clinical utility of the results.

A specific example of a current assay method to detect a flavivirus infection is an assay available from the CDC for the detection of a WNV infection using the COS-1 WNV recombinant antigen (NRA) (Davis, B. S. et al., 2001, J. Virology 75:4040-4047). This antigen can be used in an ELISA procedure to test biological samples for antibodies against WNV. Positive ELISA results are typically confirmed by plaque reduction neutralization (PRN) tests performed in a biosafety level 3 facility. Although this combination of assays is highly sensitive and specific, it requires several days to weeks and specialized facilities to perform the complete panel of tests. For example, the recommended ELISA procedure considered separately takes two to three working days to complete, as overnight incubations are deemed necessary to enhance sensitivity (Martin, D. A., 2000, J. Clin. Microbiol. 38:1823-1826; Johnson, A. J., 2000, J. Clin. Microbiol. 38:1827-1831). Accordingly, the assays currently used in the art to test for WNV and/or other flavivirus infections, such as the COS-1-based assay, are slow and do not provide rapid results. Thus, an assay for determining the presence of a flavivirus infection that is more rapid than those currently available in the art would be useful.

Flavivirus infections occur globally and represent a continued health problem around the world. For example, WNV has recently reached the United States and presently constitutes a growing concern for health officials. Accordingly, surveillance is rapidly becoming more common and widespread. As a result of the increased surveillance, the demand by local health departments and state public health laboratories for critical serologic reagents is far exceeding the supply. Further, the current assays used for WNV detection, such as the CDC-recommended assays mentioned above, are slow and inefficient and do not meet the growing needs of the general health community to rapidly identify infections and to effectively assess WNV epidemiology. Further, current assay methods for detecting WNV are not sufficient to meet growing needs for quicker, more efficient and more sensitive analysis of blood and organ supplies for flavivirus contamination, such as, contamination by WNV and other flavivirus species, including, JEV, SLEV, and DENV. Further still, there exists a need for new diagnostic assays directed to the detection of flavivirus infections in animals to faciliate the handling of infected animal populations or animal populations at-risk of infection. Such diagnostic assays could be in the form of a general flavivirus test wherein knowledge of the specific flavivirus in not required or of a specific flavivirus test, such as a specific test for WNV.

Accordingly, there is a need in the art for methods and kits for improved diagnostic assays for the detection of infections by WNV and other flaviviruses in animals and humans, including JEV, SLEV, and DENV, that are more rapid, cost-effective, efficient and sensitive than the current diagnostic assays available in the art. Further, there is a need for a single assay to enable the general detection of a flavivirus, especially WNV, JEV, SLEV, and DENV, without the requirement of knowing exactly which species is the source of infection. Further still, there is a need in the art for an efficient, sensitive and cost-effective high-throughput diagnostic assay for large-scale detection of flaviviruses to allow for public health control over flaviviral diseases, for example, improving the study of flaviviral-disease epidemiology or improving the ability to analyze blood and organ supplies. In addition to the need for a general flavivirus detection method, there also exists a need for improved methods to enable the rapid and reliable detection of a specific flavivirus, such as WNV and DENV, without substantial cross-reaction to other flaviviruses. Moreover, with respect to DENV, there exists a further need for a method to reliably and rapidly descriminate between the different strains of DENV, including DENV-1, DENV-2, DENV-3, and DENV-4. Further still, a need exists for a method that is capable also of discriminating reliably between a recent and/or current flavivirus infection and a previous infection of a flavivirus in a manner that is either specific or nonspecific as to the flavivirus of the infection.

OBJECTS AND SUMMARY OF THE INVENTION

It is an object of the present invention to provide an improved method for the diagnosis of a flavivirus infection, especially WNV, JEV, SLEV, and DENV, which is more sensitive, easier to use, and less expensive than methods used in the prior art; and further, wherein the improved method enables one to determine whether there is a flavivirus infection, for instance, infection by any of WNV, JEV, SLEV, or DENV, by a single assay.

Another object of the present invention is to reduce the window between initial infection by a flavivirus, especially WNV, JEV, SLEV, and DENV, and initial detection of IgM and/or IgG antibodies against the infective flavivirus by providing a more sensitive and rapid assay which can separately determine IgG and IgM antibody levels.

Yet another object of the present invention is to significantly reduce the time it takes to diagnose a flavivirus infection by providing a novel method for the rapid detection of a flavivirus using a microsphere immunoassay and conditions that enhance the reaction kinetics.

Another object of the present invention is to significantly reduce the time it takes to diagnose a WNV infection by providing a novel method for the rapid and specific detection of WNV using a microsphere immunoassay and a WNV nonstructural antigen, such as NS5, which is reactive with antibodies against WNV with specificity but which does not significantly cross-react with antibodies against other flaviviruses.

Yet another object of the present invention is to significantly reduce the time it takes to diagnose a flavivirus infection by providing a novel method for the rapid and specific detection of flavivirus, such as, but not limited to WNV and DENV, using a microsphere immunoassay and a flavivirus nonstructural antigen, especially NS5, which is reactive with antibodies against a specific type of flavivirus, such as WNV or DENV, with specificity but which does not significantly cross-react with antibodies against other flaviviruses.

Still another object of the present invention is to significantly reduce the time it takes to diagnose a flavivirus infection by providing a novel method for the rapid and specific detection of flavivirus, such as, but not limited to WNV and DENV, using an immunochromatographic (also known as "lateral flow test" or "membrane strip test") and a flavivirus nonstructural antigen, especially NS5, which is reactive with antibodies against a specific type of flavivirus, such as WNV or DENV, with specificity but which does not significantly cross-react with antibodies against other flaviviruses.

A further object of the present invention is to significantly reduce the time it takes to diagnose a DENV-1 infection by providing a novel method for the rapid and specific detection of DENV-1 using a microsphere immunoassay and a DENV-1 nonstructural antigen, such as NS5, which is reactive with antibodies against DENV-1 with specificity but which does not significantly cross-react with antibodies against other DENV strains, including DENV-2, DENV-3, and DENV-4 or other flaviviruses.

A still further object of the present invention is to significantly reduce the time it takes to diagnose a DENV-2 infection by providing a novel method for the rapid and specific detection of DENV-2 using a microsphere immunoassay and a DENV-2 nonstructural antigen, such as NS5, which is reactive with antibodies against DENV-2 with specificity but which does not significantly cross-react with antibodies against other DENV strains, including DENV-1, DENV-3, and DENV-4 or other flaviviruses.

Yet another object of the present invention is to significantly reduce the time it takes to diagnose a DENV-3 infection by providing a novel method for the rapid and specific detection of DENV-3 using a microsphere immunoassay and a DENV-3 nonstructural antigen, such as NS5, which is reactive with antibodies against DENV-3 with specificity but which does not significantly cross-react with antibodies against other DENV strains, including DENV-1, DENV-2, and DENV-4 or other flaviviruses.

Still another object of the present invention is to significantly reduce the time it takes to diagnose a DENV-4 infection by providing a novel method for the rapid and specific detection of DENV-4 using a microsphere immunoassay and a DENV-4 nonstructural antigen, such as NS5, which is reactive with antibodies against DENV-4 with specificity but which does not significantly cross-react with antibodies against other DENV strains, including DENV-1, DENV-2, and DENV-3 or other flaviviruses.

Another object of the present invention is to permit the broad application of the WNV E glycoprotein to the non-specific detection of flaviviruses, such as WNV, DENV, JEV, and SLEV through the inventor's own discovery that a substantially purified WNV E glycoprotein having an authentic conformation is reactive with antibodies against WNV and strongly, reliably, predictably and consistently cross-reactive with antibodies against various other flaviviruses, especially DENV, JEV, and SLEV.

Still another object of the present invention is to provide a novel method to detect a recent or ongoing infection by WNV or a flavivirus, especially JEV, SLEV, and DENV, utilizing a microsphere immunoassay in combination with an immunodepletion step to remove IgG antibodies to enable the specific detection of IgM antibodies against the WNV E glycoprotein, which would be indicative of a likely recent or ongoing infection.

Yet another object of the present invention is to provide a novel method to detect a protective immune response to an infection by WNV or a flavivirus, especially JEV, SLEV, and DENV, utilizing a microsphere immunoassay in combination with an immunodepletion step to remove IgM antibodies to enable the specific detection of IgG antibodies against the WNV E glycoprotein, which would be indicative of a protective immune response.

A further object of the present invention is to provide a flavivirus antigen, especially, WNV E glycoprotein, WNV NS protein, such as NS5, or DENV NS proteins, such as NS5, coupled to a microsphere to be used in an immunoassay to detect anti-flavivirus antibodies in a biological specimen wherein the coupled antigen is highly stable over time such that 90% or more of the antigen's reactivity is preserved following 3 months or more of storage.

Yet another object of the present invention is to provide a WNV nonstructural antigen, especially, the NS5 antigen, a nonstructural protein that forms a key enzyme in flavivirus RNA replication, that is reactive with WNV antibodies with specificity but which does not significantly cross-react with antibodies against other flaviviruses.

Yet another object of the present invention is to provide a DENV nonstructural antigen from a specific strain of DENV, especially, the NS5 antigen, a nonstructural protein that forms a key enzyme in flavivirus RNA replication, that is reactive with DENV antibodies raised to the same DENV strain with specificity but which does not significantly cross-react with antibodies against other DENV strains or other flaviviruses.

Still a further object of the present invention is to provide a WNV nonstructural antigen, especially, the NS5 antigen, for use in a rapid diagnostic test to specifically detect WNV infection in humans and animals without any significant cross-reactivity with other Flavivirus infections.

Another object of the present invention is to provide a DENV nonstructural antigen of a specific DENV strain, especially, the NS5 antigen, for use in a rapid diagnostic test to specifically detect an infection in animals, especially humans and monkeys (e.g. chimpanzees), by the same specific DENV strain without any significant cross-reactivity with other DENV strains or other flaviviruses.

Another object of the present invention is to provide a flavivirus nonstructural antigen, especially, the WNV NS5 antigen and DENV NS5 antigens of each strain, for the use in a rapid diagnostic test to discriminate between vaccination with a killed virus vaccine and a natural infection with the flavivirus, especially WNV or DENV.

Yet another object of the instant invention is to provide an assay utilizing a flavivirus nonstructural antigen, especially the WNV NS5 antigen and DENV NS5 antigens of each strain, to reliably discriminate an infection with a specific flavivirus, especially WNV or DENV, and infections of other fFlaviviruses, such as, for example JEV or SLEV.

Yet a further object of the present invention is to significantly reduce the time it takes to diagnose a WNV infection by providing a novel method for the detection of a WNV infection using a microsphere immunoassay and conditions that enhance the reaction kinetics.

Another object of the present invention is to provide a novel method to detect a recent or ongoing infection in humans and animals, including but not limited to birds, mice, and horses, by a flavivirus, especially WNV.

Yet another object of the present invention is to provide a WNV antigen, especially WNV NS5 antigen, coupled to a microsphere to (i) reliably discriminate between WNV infections and infections of other flaviviruses such as DENV or SLEV; (ii) differentiate between vaccination with inactivated flavivirus and natural WNV infection; and (iii) indicate recent infections in animals, including in particular, humans, birds, horses, cats and dogs.

Still another object of the present invention is to provide a DENV antigen, especially DENV NS5 antigen from one of the four known strains of DENV, namely, DENV-1, DENV-2, DENV-3, and DENV-4, coupled to a microsphere (a) to rapidly detect a DENV infection with specificity as to the which strain is the source of infection, (b) to rapidly discriminate between past DENV infections, and current DENV infections, and (c) to discriminate between a general flavivirus infection and a DENV infection.

Another object of the present invention is to provide a method of using a NS5-based immunoassay, especially WNV NS5, to determine whether animals, in particular, humans, birds, horses, cats and dogs, who have previously been vaccinated with a killed-flavivirus vaccine also have sustained new exposure to a flavivirus, especially WNV.

Still another object of the present invention is to provide a sensitive, reproducible, rapid, and inexpensive diagnostic assay to detect the presence of antibodies to WNV in a sample using the WNV nonstructural protein NS5 antigen as a probe.

The present invention endeavors to address the need in the art for a more rapid, efficient, cost effective and sensitive diagnostic assay for detecting WNV and/or other flavivirus infections in subjects suspected of carrying a WNV and/or flavivirus infection, such as subjects with encephalitis, meningitis, or fever of unknown origin. More in particular, this invention provides compositions and methods using purified WNV polypeptides, fragments or derivatives thereof for the rapid specific detection of an infection by WNV or the rapid detection of an infection by a flavivirus, advantageously, WNV, JEV, SLEV, and DENV, without needing to be specific as to the flavivirus.

Moreover, and as herein demonstrated, the present invention relates to a novel use for the WNV E glycoprotein as an antigen to be used for the detection of antibodies against certain species of flaviviruses relevant to human disease, such as, WNV, JEV, SLEV, DENV, using a single assay to take the place of a multitude of assays currently used in the art for the detection of these flaviviruses. Thus, by the present invention, one can determine whether there is a flavivirus infection, for instance, infection by any of WNV, JEV, SLEV, or DENV, by a single assay. The inventor has discovered that a substantially purified WNV E glycoprotein antigen having a substantially authentic conformation is reliably, consistently, predictably, and strongly cross-reactive to antibodies against any of WNV, JEV, SLEV, and DENV, and is therefore useful to broadly assay or test for flavivirus infection, non-specifically, e.g., in subjects, donors, blood, organs, etc. In contrast, antigens currently available in the art for the detection of DENV, SLEV, JEV, and WNV infections are often concentrated by polyethylene glycol and/or extracted with acetone, treatments which are likely to alter the structural domains of a given antigen.

Another aspect of the present invention relates to a novel use for the WNV nonstructural protein, NS5 or a specific antigenic determinant or specific epitope thereof, as an antigen for the specific detection of antibodies against WNV. Importantly, the NS5 antigen is not cross-reactive to other Flaviviruses, such as, for example, JEV, SLEV, or DENV. Thus, in accordance with the present aspect of the invention, one can consistently, reliably, and accurately determine whether there is a WNV infection with the confidence and assurance that the detection signal is not due to cross-reactivity with other flaviviruses.

In one aspect of the invention, it has been discovered that a substantially purified WNV NS5 antigen is reliably, consistently, predictably, and strongly reactive to antibodies against a WNV without having substantial cross-reactivity with other flaviviruses, such as, for example, JEV, SLEV, and DENV. Therefore, NS5 antigen is useful to specifically assay or test for WNV infection, e.g., in subjects, donors, blood, organs, etc. In contrast, current serologic diagnoses of WNV infection is based on detection of antibodies against viral structural proteins, such as the E protein. Although, the cross-reactivity of the E protein among flaviviruses, as also discovered by the instant inventors, is certainly advantageous with respect to its use as a rapid diagnostic for detecting a general flavivirus infection when knowing the identity of the flavivirus is not critical, it would also be desirable to have a rapid test that could confidently, accurately, and correctly identify a WNV infection with specificity and without cross-reactivity with other types of flaviviruses.

The methods currently available in the art are neither optimized for the detection of a general flavivirus infection nor are they optimized for specific detection of a particular flavivirus, such as WNV or DENV. For example, many of the currently available antigens are highly, but inconsistently, cross-reactive with multiple flaviviruses. Thus, the positive sera or spinal fluids detected by current methods must be verified by cross-species plaque reduction neutralization tests to exclude the possibility of infection with cross-reactive viruses such as SLEV and DENV. Further, these confirmatory plaque reduction tests have to be performed in level 3 biocontainment for many flaviviruses, which substantially lengthens the overall time required for a definitive serologic test. Thus, in contrast to the current methods used in the art, the advantages of the instant invention relate to, inter alia, the increased efficiency, speed, reliability and predictability of the specific detection of a WNV infection without significant cross-reactivity to other flaviviruses.

In certain embodiments, the WNV polypeptides of the instant invention are derived from WNV isolates from the Northeastern United States, in particular from isolate 2741 (GenBank accession No. AF206518; see FIGS. 37*a-d*) or from WNV 3356 from kidney of a New York crow used in the infectious cDNA clone developed by Dr. Pei-Yong Shi, GenBank accession no. AF404756 (see FIGS. 38*a-d*) (Shi et al., 2002. Infectious cDNA Clone of the epidemic West Nile Virus from New York City, J. Virology 76:5847-5856.) More in particular, the WNV isolates of the present invention contain a WNV E glycoprotein (e.g. encoded by nucleotide positions 949-2451 of GenBank accession No. AF206518 of FIGS. 37*a-d*) or an immunogenic fragment thereof or alternatively a WNV NS5 nonstructural protein (e.g. encoded by nucleotide positions 7681-10395 of GenBank accession No. AF404756 shown in FIGS. 38*a-d*) or an immunogenic fragment thereof. This invention further provides methods for the production and isolation of said WNV polypeptides, such as E glycoprotein or NS5 protein, preferably by either recombinant or synthetic production methods, especially for use in flavivirus or WNV assays, respectively. One of ordinary skill in the art will certainly appreciate that the methods of the instant invention could be applied to corresponding proteins from other flaviviruses, especially DENV, and are not meant to be particularly limited to the E glycoprotein and NS proteins of WNV or DENV. For example, the present invention contemplates the use of DENV NS5 antigen from any known strain, including DENV-1, -2, -3, and -4. In particular, the invention relates to the use of NS5 of DENV-1 "WestPac", encoded by nucleotide positions 7574-10270 of GenBank accession No. U88535 (see FIGS. 39*a-d*) and NS5 of DENV-2 "New Guinea", encoded by nucleotide positions 7570-10269 of GenBank accession No. AF038403 (see FIGS. 40*a-d*).

In a further embodiment, the instant invention provides a novel method of a microsphere immunoassay comprising microspheres that are coupled to substantially purified WNV E glycoprotein in an authentic conformation for use in detecting antibodies in a biological sample (e.g., bodily fluid, blood, serum, plasma, saliva, tears, feces, semen, mucous, tissue, tissue homogenate, cellular extract, or spinal fluid, inter alia) against flaviviruses, especially WNV, JEV, SLEV, and DENV. In this embodiment, a biological specimen, for example, bodily fluid, blood, serum, plasma, saliva, tears, feces, semen, mucous, tissue, tissue homogenate, cellular extract, or spinal fluid, inter alia, is contacted with microspheres coupled to WNV E glycoprotein which is strongly, reliably, predictably and consistently cross-reactive to antibodies against any of WNV, JEV, SLEV, and DENV under conditions sufficient to form a complex between the WNV E glycoprotein and any antibodies capable of recognizing and specifically binding thereto. The bound antibodies are then detected using a detection reagent, such as a secondary antibody coupled to a detectable fluorescent tag or to an enzyme, such as horseradish peroxidase.

In another embodiment, the biological sample (e.g., bodily fluid, blood, serum, plasma, saliva, tears, feces, semen, mucous, tissue, tissue homogenate, cellular extract, or spinal fluidinter alia) may first be immunodepleted in order to remove or block a functional site of a specific antibody population, such as an IgM or IgG antibody population. Immunodepletion can be carried out by contacting the biological sample with a second antibody against the specific antibody subpopulation to be removed to form an insoluble complex, comprising the second antibody and antibody subpopulation to be removed, that can be subsequently removed by a separation process, such as centrifugation.

Accordingly, the instant invention can be used to specifically detect a recent or ongoing infection, for example, following IgG removal, or to specifically detect a protective immune response, for example, following IgM removal.

In another embodiment, the present invention provides a novel method relating to a microsphere immunoassay comprising microspheres that are coupled to substantially purified WNV NS5 antigen for use in detecting in a biological sample (e.g., bodily fluid, blood, serum, plasma, saliva, tears, feces, semen, mucous, tissue, tissue homogenate, cellular extract, or spinal fluid, inter alia) antibodies specific to WNV wherein the NS5 antigen is not substantially cross-reactive with antibodies against other Flaviviruses, including WNV, JEV, SLEV, and DENV. In this embodiment, a biological specimen, for example, blood, plasma, serum, or spinal fluid, is contacted with the microspheres coupled to NS5 antigen which is strongly, reliably, predictably, consistently, and specifically reactive to antibodies against a WNV yet is not substantiallly cross-reactive against antibodies to other Flaviviruses, such as JEV, SLEV, and DENV. Subsequently, conditions are provided that allow for a complex to form between the NS5 antigen and anti-WNV antibodies capable of recognizing and specifically binding thereto. The bound antibodies are then detected using a detection reagent, such as a secondary antibody coupled to a detectable fluorescent tag or to an enzyme, such as horseradish peroxidase.

Also within the scope of this invention are diagnostic kits and methods for detecting antibodies against WNV and other flaviviruses, especially JEV, SLEV, and DENV, characterized by the compositions of the present invention comprising at least one isolated and substantially purified polypeptide comprising a WNV E glycoprotein or an immunogenic fragment/derivative thereof in an authentic conformation whereby the WNV E glycoprotein or the immunogenic fragment/derivative thereof is reactive with antibodies against WNV and strongly, reliably, predictably and consistently cross-reactive with antibodies against flaviviruses, especially JEV, SLEV, and DENV. The cross-reactivity of the WNV E glycoprotein or immunogenic fragment/derivative thereof, is the inventor's own discovery which permits the broad application of the WNV E glycoprotein to the non-specific detection of flaviviruses, such as WNV, DENV, JEV, and SLEV. Prior to the instant invention, one of ordinary skill in the art would not have unequivocally and/or reliably known WNV E glycoprotein having an authentic conformation strongly cross-reacts with antibodies against various flaviviruses, in addition to antibodies against WNV.

In one embodiment, the diagnostic kits alternatively comprise at least one isolated and substantially purified polypeptide comprising a WNV NS5 antigen or an immunogenic fragment/derivative thereof whereby the WNV NS5 antigen or the immunogenic fragment/derivative thereof, especially of humans, birds, horses, cats, dogs, any animal or mammal, is specifically, strongly, reliably, predictably and consistently reactive with antibodies against WNV but is not substantially or detectably cross-reactive with antibodies against other flaviviruses, such as JEV, SLEV, and DENV. The specificity of the WNV NS5 antigen towards WNV antibodies and the lack of cross-reactivity of NS5 with antibodies against other Flaviviruses permits the application of the WNV NS5 to the detection method of WNV as taught by the present application. As it is used herein, the phrase "detectably cross-reactive" is meant to refer to an antigen-antibody interaction that can be substantiated by measuring or detecting a binding complex formed from the interaction between the antigen and antibody. Thus, the recitation "not substantially or detectably cross-reactive" is meant to exclude antigen-antibody interactions that are non-specific, i.e. background "noise".

The diagnostic kits and methods according to the present invention are also useful for detecting a protective immune response to WNV infection or infection by various flaviviruses, especially JEV, SLEV, and DENV. Further, the methods of the instant invention are also useful in monitoring the course of immunization against WNV and various flaviviruses. In patients previously inoculated with the vaccines against WNV or various flaviviruses, the detection means and methods disclosed herein are also useful for determining if booster inoculations are appropriate. The neutralizing antibodies which develop are primarily IgG antibodies, which are readily detectable in the microsphere immunoassay format of the present invention.

In an embodiment, the instant invention relates to a novel method for detecting a non-specific flavivirus infection, especially WNV, DENV, JEV, or SLEV, comprising the step of contacting a biological sample from a subject suspected of having said infection with an isolated and substantially purified polypeptide comprising a WNV E glycoprotein or an immunogenic fragment/derivative thereof having an authentic conformation wherein the E glycoprotein or the immunogenic fragment/derivative thereof is reactive with antibodies against WNV and strongly, reliably, predictably and consistently cross-reactive with antibodies against a flavivirus, especially JEV, SLEV, and DENV.

In yet another embodiment, the present invention relates to a method for detecting a protective immune response in a subject comprising the step of contacting a biological sample from said subject with an isolated and substantially purified polypeptide comprising a WNV E glycoprotein or an immunogenic fragment thereof having an authentic conformation wherein the E glycoprotein or the immunogenic fragment thereof is reactive with protective antibodies against WNV and strongly, reliably, predictably and consistently cross-reactive with protective antibodies against a flavivirus, especially JEV, SLEV, and DENV.

Also within the scope of the present invention is a method for detecting a first antibody to a flavivirus from a biological specimen of a subject suspected of being infected by said flavivirus comprising the steps of contacting the biological specimen with a substantially purified WNV E glycoprotein or an immunogenic fragment/derivative thereof having an authentic conformation under conditions to form a complex between the WNV E glycoprotein and the first antibody, if present, that recognizes and binds the WNV E glycoprotein followed by detecting the first antibody of said complex, wherein the WNV E glycoprotein is reactive to an antibody against a WNV and strongly, reliably, predictably and consistently cross-reactive to an antibody against a flavivirus, especially JEV, DENV, and SLEV.

The instant invention further relates to a method for rapidly detecting a recent or ongoing flavivirus infection using a microsphere immunoassay to detect an IgM antibody against a flavivirus in a biological specimen by first contacting the biological specimen with anti-IgG antibodies to form IgG immune complexes followed by the removal of the IgG complexes to form a biological specimen comprising IgM antibodies and lacking IgG antibodies. Next, the biological specimen is contacted with a microsphere comprising a substantially purified WNV E glycoprotein antigen or immunogenic fragment/derivative thereof having an authentic conformation to form a microsphere mixture under conditions sufficient to form a binding complex between the WNV E glycoprotein antigen and a IgM antibody whereby the WNV E glycoprotein antigen is reactive to antibodies against WNV and strongly, reliably, predictably and consistently cross-reactive to antibodies against a flavivirus, especially JEV, DENV, and SLEV. Next, the microsphere mixture is contacted with a detection reagent capable of detecting a IgM antibody. Finally, the detection reagent is detected wherein detecting the detection reagent indicates a recent or ongoing flavivirus infection.

Also within the scope of the invention is a diagnostic kit comprising at least one isolated and purified polypeptide comprising a WNV NS5 protein or an immunogenic fragment thereof having an native conformation or non-denatured structure whereby the NS5 protein or the immunogenic fragment thereof is specifically reactive with antibodies against WNV but not detectably cross-reactive with antibodies against a flavivirus other than WNV. The invention also provides a method for detecting a WNV infection in a subject suspected of having said infection comprising the steps of (a) contacting a biological sample (e.g., bodily fluid, blood, serum, plasma, saliva, tears, feces, semen, mucous, tissue, tissue homogenate, cellular extract, or spinal fluid, inter alia) from the subject with an isolated and substantially purified polypeptide comprising a WNV NS5 protein or an immunogenic fragment thereof having a native conformation or non-denatured structure whereby the NS5 protein or the immunogenic fragment thereof is specifically reactive with anti-WNV antibodies but not detectably cross-reactive with antibodies against a flavivirus other than WNV, and (b) detecting anti-WNV antibodies that have reacted with the WNV NS5 protein, wherein detection of the anti-WNV antibodies indicates a WNV infection.

The present invention further relates to methods for detecting a protective immune response in a subject comprising the step of contacting a biological sample from said subject with an isolated and substantially purified polypeptide comprising a WNV NS5 protein or an immunogenic fragment thereof whereby the WNV NS5 protein or the immunogenic fragment thereof having a native conformation or non-denatured structure is specifically reactive with protective antibodies against WNV with no detectable cross-reactivity with protective antibodies against a flavivirus other than WNV. While antibodies to NS5 would not neutralize against infection, they could be effective in rapidly decreasing the spread of the infection.

Also within the scope of the present invention is a method for detecting a first antibody to a WNV from a biological specimen of a subject suspected of being infected by said WNV comprising the steps of: (a) contacting the biological specimen with a substantially pure WNV NS5 protein or an immunogenic fragment thereof having a native conformation and non-denatured structure under conditions to form a complex between the NS5 protein and the first antibody, if present, that recognizes and binds the NS5 protein, (b) detecting the first antibody of said complex, wherein the NS5 protein is not detectably cross-reactive to an antibody against a flavivirus other than a WNV.

The invention further relates to a method for rapidly detecting an anti-WNV antibody comprising the steps of: (a) contacting a biological sample (e.g., bodily fluid, blood, serum, plasma, saliva, tears, feces, semen, mucous, tissue, tissue homogenate, cellular extract, or spinal fluid, inter alia) with a microsphere suspension, each microsphere coupled to a substantially pure WNV NS5 protein having a native conformation or non-denatured structure whereby each NS5 protein is specifically reactive to antibodies against WNV but not detectably cross-reactive with antibodies against a flavivirus other than WNV, (b) incubating the microsphere suspension under conditions sufficient to increase reaction kinetics to promote the binding of an anti-WNV antibody to the NS5 proteins, (c) contacting the microsphere suspension with a detection reagent capable of detecting an anti-WNV antibody, (d) detecting the detection reagent, wherein detection of the detection reagent indicates the presence an anti-WNV in the biological sample.

The instant invention also contemplates a method for the detection of a WNV infection in a biological specimen comprising the steps of: (a) obtaining a suspension of microspheres each coupled to a substantially pure WNV NS5 protein having a native conformation or non-denatured structure wherein the WNV NS5 protein is specifically reactive with anti-WNV antibodies but not detectably cross-reactive with antibodies against a flavivirus; (b) performing a microsphere immunoassay; (c) obtaining a result indicating either the presence or absence of an anti-WNV antibody, wherein the presence of an anti-WNV antibody indicates a WNV infection.

In another embodiment, the present invention relates to a method for discriminating between whether (1) a host has an ongoing WNV infection or (2) a host has been vaccinated with a killed-flavivirus vaccine wherein the host in the case of (1) has both anti-E glycoprotein antibodies and anti-NS5 antibodies but in the case of (2) has anti-E glycoprotein but not anti-NS5 antibodies comprising the steps of: (a) carrying out a first reaction comprising the steps of (i) contacting a biological sample (e.g., bodily fluid, blood, serum, plasma, saliva, tears, feces, semen, mucous, tissue, tissue homogenate, cellular extract, or spinal fluid, inter alia) from the host with a first detection reagent for the detection of anti-E glycoprotein antibodies, (ii) detecting said first detection reagent to provide either a positive or negative signal wherein a positive signal indicates the presence of anti-E glycoprotein antibodies and a negative signal indicates the absence of anti-E glycoprotein antibodies; (b) carrying out a second reaction comprising the steps of (i) contacting a biological sample from the host with a second detection reagent for the detection of anti-NS5 antibodies, (ii) detecting said second detection reagent to provide either a positive or negative signal wherein a positive signal indicates the presence of anti-NS5 antibodies and a negative signal indicates the absence of anti-NS5 antibodies; and (c) comparing the results of the first and second reactions wherein the following may be true: (i) a positive signal for anti-E glycoprotein antibody and a positive signal for anti-NS5 antibody indicates that the host has an ongoing WNV infection and (ii) a positive signal for anti-E glycoprotein antibody and a negative signal for anti-NS5 antibody indicates that the host does not have an ongoing WNV infection but may have been vaccinated with a killed-flavivirus vaccine.

In yet another embodiment, ther instant invention relates to a method for detecting a recent or ongoing WNV infection in a host comprising the steps of: (a) carrying out a first reaction comprising the steps of (i) contacting a biological sample from the host with a first detection reagent for the detection of anti-E glycoprotein antibodies, (ii) detecting said first detection reagent to provide either a positive or negative signal wherein a positive signal indicates the presence of anti-E glycoprotein antibodies and a negative signal indicates the absence of anti-E glycoprotein antibodies; (b) carrying out a second reaction comprising the steps of (i) contacting a biological sample from the host with a second detection reagent for the detection of anti-NS5 antibodies, (ii) detecting said second detection reagent to provide either a positive or negative signal wherein a positive signal indicates the presence of anti-NS5 antibodies and a negative signal indicates the absence of anti-NS5 antibodies; and (c) comparing the results of the first and second reactions wherein the following may be true: (i) a positive signal for anti-E glycoprotein antibody and a positive signal for anti-NS5 antibody indicates that the host has a recent or ongoing WNV infection and (ii) a positive signal for anti-E glycoprotein antibody but a negative signal for anti-NS5 antibody indicates that the host does not have an recent or ongoing WNV infection.

The present invention also endeavors to address the need in the art for a more rapid, efficient, cost effective and sensitive diagnostic assay for detecting DENV infections in subjects suspected of carrying a DENV infection. More in particular, this invention provides compositions and methods using purified DENV polypeptides, fragments or derivatives thereof for the rapid specific detection of an infection by DENV, advantageously where the the different strains, namely DENV-1, DENV-2, DENV-3, and DENV-4 can be discriminated.

Another aspect of the present invention relates to a novel use for the DENV nonstructural protein, NS5 or a specific antigenic determinant or specific epitope thereof, as an antigen for the specific detection of antibodies against DENV. Importantly, the NS5 antigen is not cross-reactive to other flaviviruses, such as, for example, JEV, SLEV, or DENV. Also, the NS5 antigen shows specificity with antibodies to the particular strain (also referred to as "strain"), namely DENV-1, DENV-2, DENV-3, or DENV-4, from which is sourced from and is not measurably cross-reactive with the remaining DENV strains. Thus, in accordance with the present aspect of the invention, one can consistently, reliably, and accurately determine whether there is a DENV infection and the identity of the specific strain thereof with the confidence and assurance that the detection signal is not due to cross-reactivity with other flaviviruses or to other DENV strains.

In one aspect of the invention, it has been discovered that a substantially purified DENV NS5 antigen is reliably, consistently, predictably, and strongly reactive to antibodies against a DENV without having substantial cross-reactivity with other flaviviruses, such as, for example, JEV, SLEV, and WNV. Therefore, DENV NS5 antigen is useful to specifically assay or test for DENV infection, e.g., in subjects, donors, blood, organs, etc. In contrast, current serologic diagnoses of DENV infection is based on detection of antibodies against viral structural proteins, such as the E protein. Although, the cross-reactivity of the E protein among flaviviruses, as also discovered by the instant inventors, is certainly advantageous with respect to its use as a rapid diagnostic for detecting a general flavivirus infection when knowing the identity of the flavivirus is not critical, it would also be desirable to have a rapid test that could confidently, accurately, and correctly identify a WNV infection with specificity and without cross-reactivity with other types of flaviviruses.

In another embodiment, the present invention provides a novel method relating to a microsphere immunoassay comprising microspheres that are coupled to substantially purified DENV NS5 antigen for use in detecting in a biological sample (e.g., bodily fluid, blood, serum, plasma, saliva, tears, feces, semen, mucous, tissue, tissue homogenate, cellular extract, or spinal fluid, inter alia) antibodies specific to DENV wherein the NS5 antigen is not substantially cross-reactive with antibodies against other flaviviruses, including WNV, JEV, and SLEV. In this embodiment, a biological specimen, for example, blood, plasma, serum, or spinal fluid, is contacted with microspheres coupled to DENV NS5 antigen which is strongly, reliably, predictably, consistently, and specifically reactive to antibodies against its specific corresponding DENV strain yet is not substantially cross-reactive against antibodies to other flaviviruses, such as WNV, JEV, and SLEV. Subsequently, conditions are provided that allow for a complex to form between the NS5 antigen and anti-DENV antibodies capable of recognizing and specifically binding thereto. The bound antibodies are then detected using a detection reagent, such as a secondary antibody coupled to a detectable fluorescent tag or to an enzyme, such as horseradish peroxidase.

In one embodiment, the diagnostic kits of the invention alternatively comprise at least one isolated and substantially purified polypeptide comprising a DENV NS5 antigen of a specific strain thereof or an immunogenic fragment/derivative thereof whereby the DENV NS5 antigen or the immunogenic fragment/derivative thereof, especially of humans or birds, is specifically, strongly, reliably, predictably and consistently reactive with antibodies against DENV but is not substantially or detectably cross-reactive with antibodies against other flaviviruses, such as JEV, SLEV, and WNV. Further, the NS5 antigen is specific as to the particular DENV strain isolated therefrom and is not cross-reactive to the remaining DENV strains. The specificity of the DENV NS5 antigen towards DENV antibodies and the lack of cross-reactivity of DENV NS5 with antibodies against other flaviviruses (and to other DENV strains) permits the application of the DENV NS5 to the detection method as taught by the present invention. As it is used herein, the phrase "detectably cross-reactive" is meant to refer to an antigen-antibody interaction that can be substantiated by measuring or detecting a binding complex formed from the interaction between the antigen and antibody. Thus, the recitation "not substantially or detectably cross-reactive" is meant to exclude antigen-antibody interactions that are non-specific, i.e. background "noise".

The present invention further relates to methods for detecting a protective DENV immune response in a subject comprising the step of contacting a biological sample from said subject with an isolated and substantially purified polypeptide comprising a DENV NS5 protein or an immunogenic fragment thereof whereby the DENV NS5 protein or the immunogenic fragment thereof having a native conformation or non-denatured structure is specifically reactive with protective antibodies against DENV with no detectable cross-reactivity with protective antibodies against a flavivirus other than DENV. While antibodies to DENV NS5 would not neutralize against infection, they could be effective in rapidly decreasing the spread of the infection.

Also within the scope of the present invention is a method for detecting a first antibody to a DENV from a biological specimen of a subject suspected of being infected by said DENV comprising the steps of: (a) contacting the biological specimen with a substantially pure DENV NS5 protein or an immunogenic fragment thereof having a native conformation and non-denatured structure under conditions to form a complex between the NS5 protein and the first antibody, if present, that recognizes and binds the NS5 protein, (b) detecting the first antibody of said complex, wherein the NS5 protein is not detectably cross-reactive to an antibody against a flavivirus other than DENV. Further, a DENV NS5 protein isolated from a specific strain of DENV will be specific for antibodies to that DENV strain and not cross-reactive to antibodies against the remaining strains of DENV.

The invention further relates to a method for rapidly detecting an anti-DENV antibody comprising the steps of: (a) contacting a biological sample (e.g., bodily fluid, blood, serum, plasma, saliva, tears, feces, semen, mucous, tissue, tissue homogenate, cellular extract, or spinal fluid, inter alia) with a microsphere suspension, each microsphere coupled to a substantially pure DENV NS5 protein having a native conformation or non-denatured structure whereby each DENV NS5 protein is specifically reactive to antibodies against DENV but not detectably cross-reactive with antibodies against a flavivirus other than DENV, (b) incubating the microsphere suspension under conditions sufficient to increase reaction kinetics to promote the binding of an anti-DENV antibody to the NS5 proteins, (c) contacting the microsphere suspension with a detection reagent capable of detecting an anti-DENV antibody, (d) detecting the detection reagent, wherein detection of the detection reagent indicates the presence an anti-DENV in the biological sample.

The instant invention also contemplates a method for the detection of a DENV infection in a biological specimen comprising the steps of: (a) obtaining a suspension of microspheres each coupled to a substantially pure DENV NS5 protein having a native conformation or non-denatured structure wherein the DENV NS5 protein is specifically reactive with anti-DENV antibodies but not detectably cross-reactive with antibodies against a flavivirus; (b) performing a microsphere immunoassay; (c) obtaining a result indicating either the presence or absence of an anti-DENV antibody, wherein the presence of an anti-DENV antibody indicates a DENV infection. Further, a DENV NS5 protein isolated from a specific strain of DENV will be specific for antibodies to that DENV strain and not cross-reactive to antibodies against the remaining strains of DENV. It will be appreciated that four DENV strains are known, namely, DENV-1, DENV-2, DENV-3, and DENV-4.

Throughout this specification and claims, the word "comprise," or variations such as "comprises" or "comprising," will be understood to imply the inclusion of a stated integer or group of integers but not the exclusion of any other integer or group of integers.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference.

FIG. 1 is the amino acid sequence of the WNV-288-301 fragment (SEQ ID NO: 13), (peptide 1).

FIG. 2 is the amino acid sequence of the random 288-301 fragment (SEQ ID NO: 14), (peptide 2).

FIG. 3 is the amino acid sequence of the WNV-121-139 peptide (SEQ ID NO: 15), (peptide 3).

FIG. 4 is a diagrammatic representation of the 71 kDa Tr-env fusion protein. Tr, thioredoxin domain; EK, enterokinase cleavage site; WNV, 55 kDa full length sequence of WNV envelope glycoprotein; V5, V5 epitopes; His, 3 kDa six histidine-tag sequence; 1, location of WNE-288-301 fragment; 3, location of WNE-121-139 fragment.

FIG. 10A demonstrates the greater sensitivity of the WNV E glycoprotein microsphere immunoassay (WNV E MI) over ELISA testing in detecting antibodies against WNV in two of three sera from WNV patients. The figure further shows that WNV E MI detected no WNV antibodies in 7 sera, which was consistent with the negative PRN test results for the same 7 sera. Similarly, WNV E MI identified WNV antibodies in the three WNV sera that had positive PRN test results (PRN titers of 160 and 320).

FIG. 10B demonstrates the ability of the WNV E glycoprotein microsphere immunoassay (WNV E MI) to detect antibodies against SLEV in sera of four of six SLEV patients. The P/N value of the WNV E MI results were substantially higher than ELISA P/N values for sera from 2 patients. Two sera from SLEV patients were missed by the microsphere assay, which were collected on day 0 and day 2 after onset.

FIG. 10C demonstrates the greater sensitivity of the WNV E glycoprotein microsphere immunoassay (WNV E MI) over ELISA testing in detecting antibodies against DENV in three sera from Dengue patients. The results show that the WNV E MI identified correctly the three sera from Dengue fever patients with much higher P/N values (range 15.00 to 55.23) than the traditional ELISA tests with an IgG P/N range of 4.95 and IgM P/N range from 2.98 to 8.67.

FIGS. 11A and 11B show scatter plots comparing the P/N values between the WNV E glycoprotein microsphere immunoassay using the polyvalent (IgG/IgM/IgA) detection reagent and either the WN IgG ELISA (A) or the WN IgM ELISA (B) with trendline according to Example 12.

FIG. 12, as outlined in Example 11, shows two plots comparing the P/N values measured by either standard ELISA methods (A) or the WNV E microsphere immunoassay (B). Serum was obtained sequentially over time at 3 days prior to infection with WNV and then 2, 18, 72 and 260 days post-infection. The serum in 11B was untreated or treated with antibodies to remove either the IgM or the IgG antibody subpopulations. These immunodepleted serum samples were tested using the microsphere immunoassay. The microsphere immunoassay shows that, unlike the IgM and IgG ELISAs, there is a greater IgM P/N than a IgG P/N for early serum samples, which may indicate that the patient had an active or recent infection.

FIG. 13, according to Example 13, shows the P/N value as determined by carrying out the WNV E glycoprotein microsphere immunoassay on sera from twelve persons having received a flavivirus vaccine (and four sera from non-vaccinated persons). The sera was either immunodepleted of IgM antibodies (B) or the sera was not depleted of IgM antibodies (A). The assay demonstrated that the microsphere immunoassay could detect antibodies to JEV, as well as WNV, SLEV, and DENV.

FIG. 15 shows the results of WNV-E microsphere immunoassay in comparison to results of the MAC ELISA test on spinal fluids of patients with diagnosed encephalitis due to flavivirus infection. Confirmation of diagnosis was by plaque reduction neutralization tests including WNV, DENV, and SLEV.

FIG. 16 shows the results of testing seven pairs of serum along with same-day collected spinal fluid specimens from seven patients using the recombinant WNV-E microsphere immunoassay along with both the polyvalent antibody reagent and the "IgM" serum (anti-IgG treated serum). The seven patients were chosen on the basis of having been tested positive for WNV by either an IgM and/or an IgG ELISA using the reagents and protocol recommended by the CDC. The data are presented in the table shows both the MFI and the P/N values. The results show that the WNV-E assay has a greater sensitivity than the standard ELISA since 5 patients who were shown to test negative for a WNV infection by MAC ELISA were shown to be strongly positive by the WNV-E assay.

FIG. 18 shows the median fluorescence intensity (MFI) data for mouse sera tested by the microsphere immunoassay (MIA) using WNV E glycoprotein (column 1), WNV NS3 antigen (column 2), and WNV NS5 antigen (column 3) as detected with goat antimouse polyvalent conjugate. The data demonstrates that WNV NS5 (column 3) is equivalent to superior to WNV E glycoprotein (column 1) as an antigen to detect WNV infection in mice.

FIG. 19 shows MFI data for human sera tested by MIA using WNV E glycoprotein, WNV NS3 antigen, and WNV NS5 antigen. While the negative range for normal non-infected subjects was higher, the overall MFI for infected patients was 2.5 to 3 fold higher than the MFI signal to the WNV E glycoprotein.

FIG. 20 demonstrates that WNV NS5 can be used to discriminate between infection by DENV and WNV. The data shows that all the sera from the DENV patients examined were highly reactive (positive) to the WNV E glycoprotein in the MIA, but conversely each were negative to the WNV NS5 antigen. All the convalescent dengue sera were positive and 11 of 17 acute sera were positive by MIA. Data were fully concordant with Dengue ELISA and Hemagglutination inhibition results. It is likely that the polymerase structures of the DENV and the WNV are significantly different. DENV polymerase did not induce antibodies that recognized the WNV NS5 antigen.

FIG. 21 demonstrates that NS5 can be used to discriminate between vaccination and active infection. Sera from employees who received JEV vaccine (a series of three shots), who developed neutralizing antibodies, each developed an increase in antibody to the envelope protein. However, the sera of the JEV recipients were all non-reactive to the NS5 antigen. This result is intuitive since the polymerase (NS5 protein) would not be expressed by the killed virus of the JEV killed-virus vaccine. The data also demonstrates that NS5 is more specific as a reagent in immunoassay than the WNV E glycoprotein since one of ten sera from HIV-infected patients was positive to NS5 and each remaining sera sample including the negative control were negative to NS5.

FIG. 22 demonstrates that antibodies to NS5 disappear before antibodies to WNV E glycoprotein. Since the level of anti-NS5 drops prior to the levels of anti-E antibody, NS5 likely is a useful marker to indicate recent WNV infections.

FIG. 25 shows the specificity of a NS5-based MIA as demonstrated by challenging 120 sera from patients with various infections, autoimmune conditions, JEV vaccination, YFV vaccination, or good health.

FIG. 26 shows the cross-reactivity of WNV NS5 and E protein with dengue patient sera. The data indicates that only 8.8% of the total dengue patient sera samples showed a cross-reaction with the WNV NS5 antigen as compared to 71% with WNV E glycoprotein.

FIG. 27 shows the cross-reactivity of WNV NS5 and E protein with St. Louis encephalitis patient sera. The data indicates that only 5% of the total St. Louis encephalitis patient sera samples showed a cross-reaction with the WNV NS5 antigen as compared to 28% with WNV E glycoprotein.

FIG. 28 shows a comparison of MIA values measured for wild bird sera samples using the NS5 antigen as compared to the E glycoprotein.

FIG. 29 shows a comparison of MIA values in sera from humans who received the live-attenuated virus vaccine Yellow Fever vaccine. The data show that 10 out of 19 sera were cross-reactive (above the MIA cutoff value) to the WNV E glycoprotein whereas only 1 out of 19 sera were cross-reactive (above the MIA cutoff value) to the WNV NS5 protein. The data indicate that the recipients of Yellow Fever vaccine are negative in assays using WNV NS5 protein. Accordingly, the data demonstrate that the WNV NS5 is useful for discriminating between sera of humans vaccinated with Yellow Fever vaccine and sera of humans infected with WNV.

FIG. 30(A) shows a comparison of MIA values measured for various horse sera samples tested against WNV E glycoprotein, WNV NS5 antigen, and WNV NS3 antigen. (B) shows a of a multiplex assay comparing the MIA values of various horse sera tested with WNV E glycoprotein, WNV NS5, or WNV NS3 protein.

FIG. 34 shows the results of an E protein based microsphere immunoassay (MIA). The assay tested a coded serum panel revealing that the rWNV-E MIA detects human antibodies elicited by SLEV and DENV. FIG. 34 is a tabular form of the data shown in FIG. 10 A, B, and C.

FIG. 35 shows the results of an E protein based microsphere immunoassay (MIA) on sera from patients with various viral infections, bacterial infections, or autoimmune diseases were tested in the rWNV-E MIA. This shows the same data as FIG. 14A.

FIG. 36 compares the results of an E protein based microsphere immunoassay (MIA) on human cerebral spinal fluid samples from patients infected with WNV, DENV, or an unknown flavivirus. Serum samples shown here include those shown in FIG. 15. The data in FIG. 15 is a subset of the data shown in FIG. 36.

FIG. 37 shows the nucleotide sequence of GenBank accession No. AF206518 comprising the genome sequence of WNV isolate 2741 (SEQ ID NO.1).

FIG. 38 shows the nucleotide sequence of GenBank accession No. AF404756 comprising the genome sequence of WNV isolate 3356 (SEQ ID NO.2).

FIG. 39 shows the nucleotide sequence of GenBank accession No. U88535 comprising the genome sequence of DENV-1 isolate "WestPac" (SEQ ID NO.3).

FIG. 40 shows the nucleotide sequence of GenBank accession No. AF038403 comprising the genome sequence of DENV-2 isolate "New Guinea" (SEQ ID NO.4)

FIG. 41 shows the nucleotide sequence for nucleotide positions 982-1494 (SEQ ID NO.5) of GenBank accession No. AF206518 (WNV isolate 2741) corresponding to the amino acid sequence of WNV E glycoprotein.

FIG. 42 shows the amino acid sequence of WNV E glycoprotein (SEQ ID NO.6) corresponding to nucleotide sequence positions 982-1494 of GenBank accession No. AF206518 (WNV isolate 2741).

FIG. 43 shows the nucleotide sequence for nucleotide positions 7681-10395 (SEQ ID NO.7) of GenBank accession No. AF404756 (WNV isolate 3356) corresponding to the amino acid sequence of WNV NS5.

FIG. 44 shows the amino acid sequence of WNV NS5 (SEQ ID NO.8) corresponding to nucleotide sequence positions 7681-10395 of GenBank accession no. AF404756 (WNV isolate 3356).

FIG. 45 shows the nucleotide sequence of nucleotide positions 7574-10270 (SEQ ID NO.9) of GenBank accession No. U88535 (DENV-1 isolate "WestPac") corresponding to the amino acid sequence of DENV-1 NS5.

FIG. 46 shows the amino acid sequence of DENV-1 NS5 (SEQ ID NO.10) corresponding to nucleotide sequence positions 7574-10270 of GenBank accession No. U88535 (DENV isolate "WestPac").

FIG. 47 shows the nucleotide sequence for nucleotide positions 7570-10269 (SEQ ID NO.11) of GenBank accession No. AF038403 (DENV-2 isolate "New Guinea") corresponding to the amino acid sequence of DENV-2 NS5.

FIG. 48 shows the amino acid sequence of DENV-2 NS5 (SEQ ID NO.12) corresponding to nucleotide sequence positions 7570-10269 of GenBank accession No. AF038403 (DENV isolate "New Guinea").

DETAILED DESCRIPTION OF THE INVENTION

Figure 5:
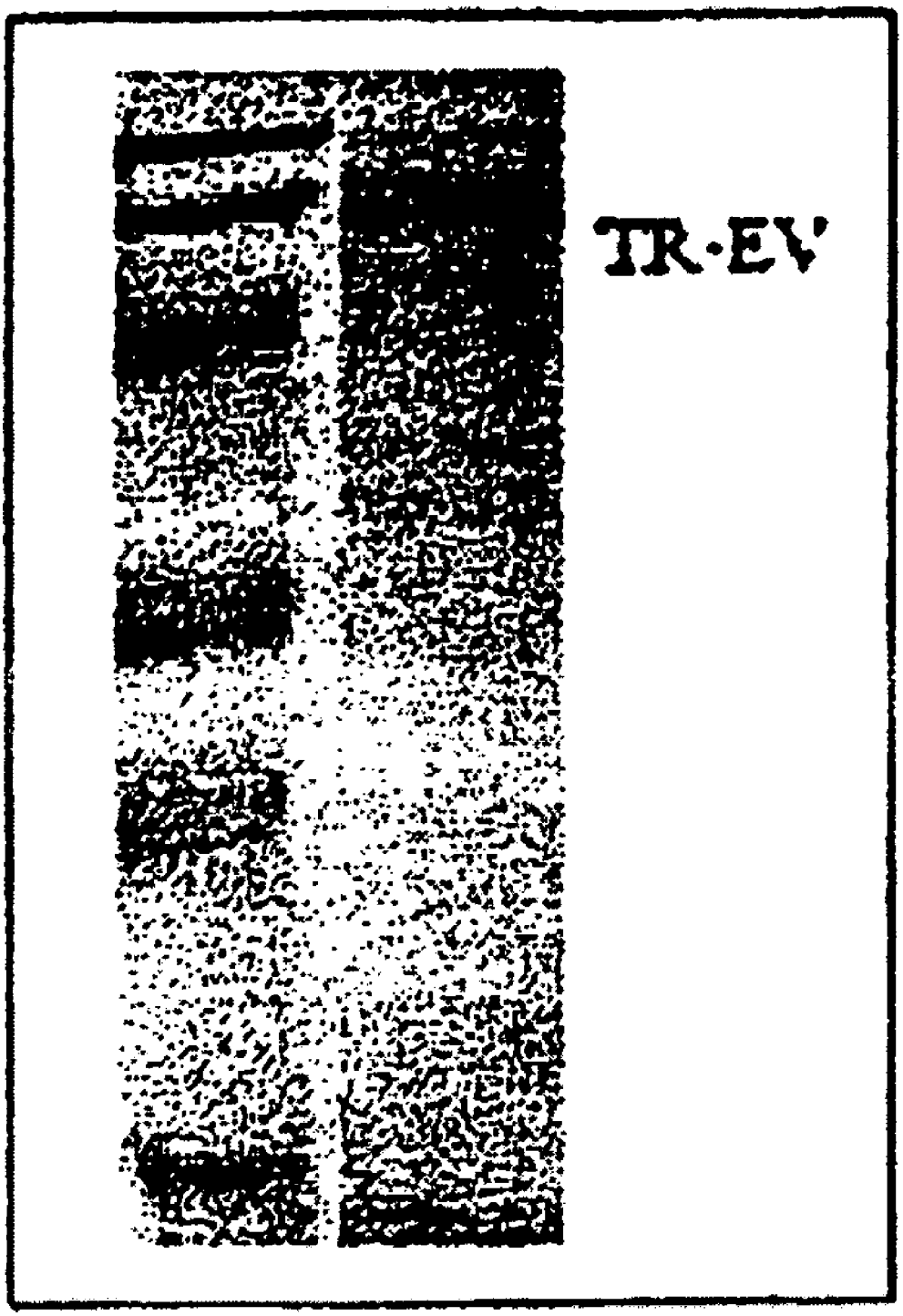
FIG. 5 is a Coomassie-blue stained SDS-PAGE gel showing purified, recombinant TR-env fusion protein.
Figure 6:
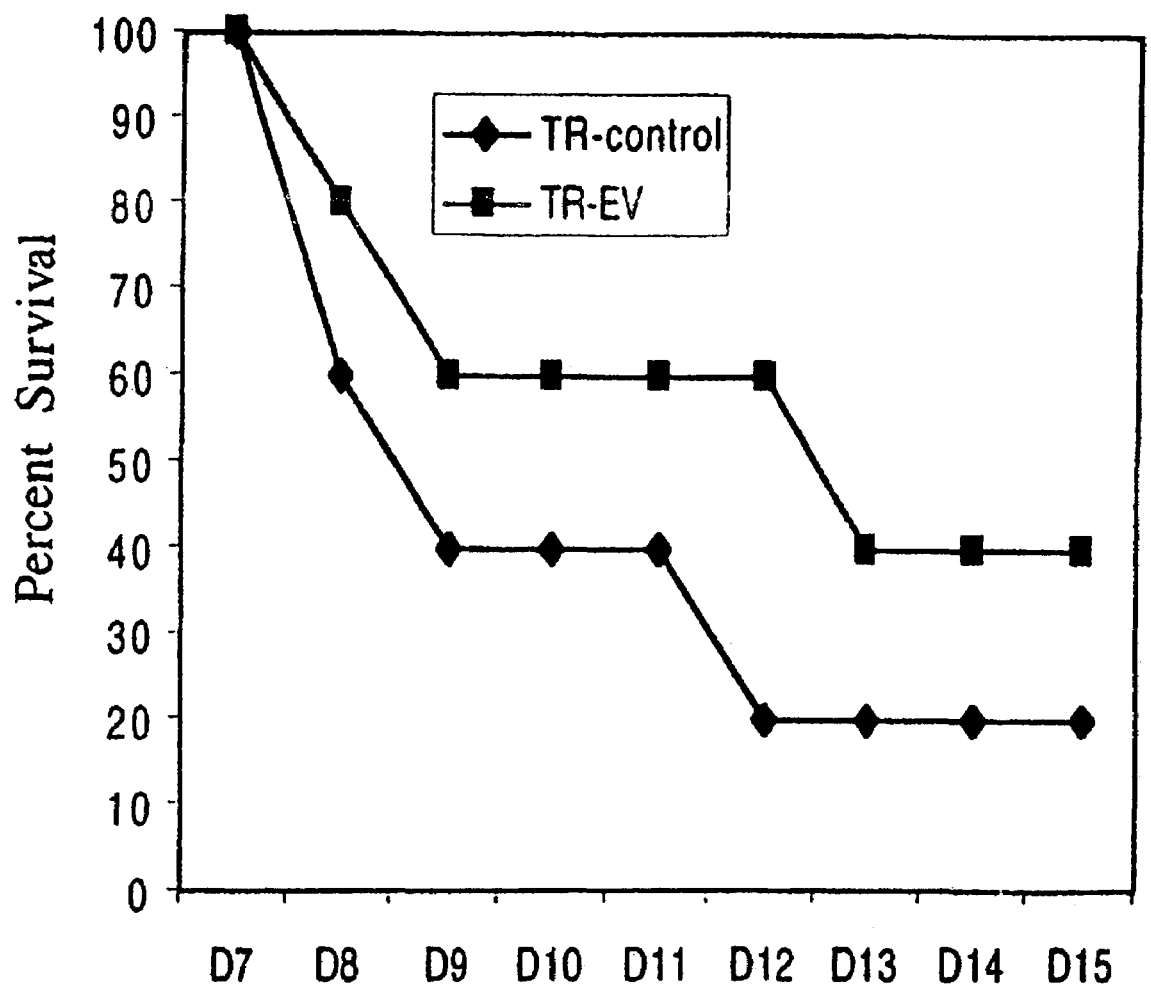
FIG. 6 depicts the utility of mice as an experimental model organism for WNV infection and further demonstrates that the purified Tr-env protein is able to elicit a protective antibody response. C3H mice were immunized with Tr-env protein (upper line), or Tr control protein (lower line) and challenged with WNV. Five mice were in each group.
Figure 7:
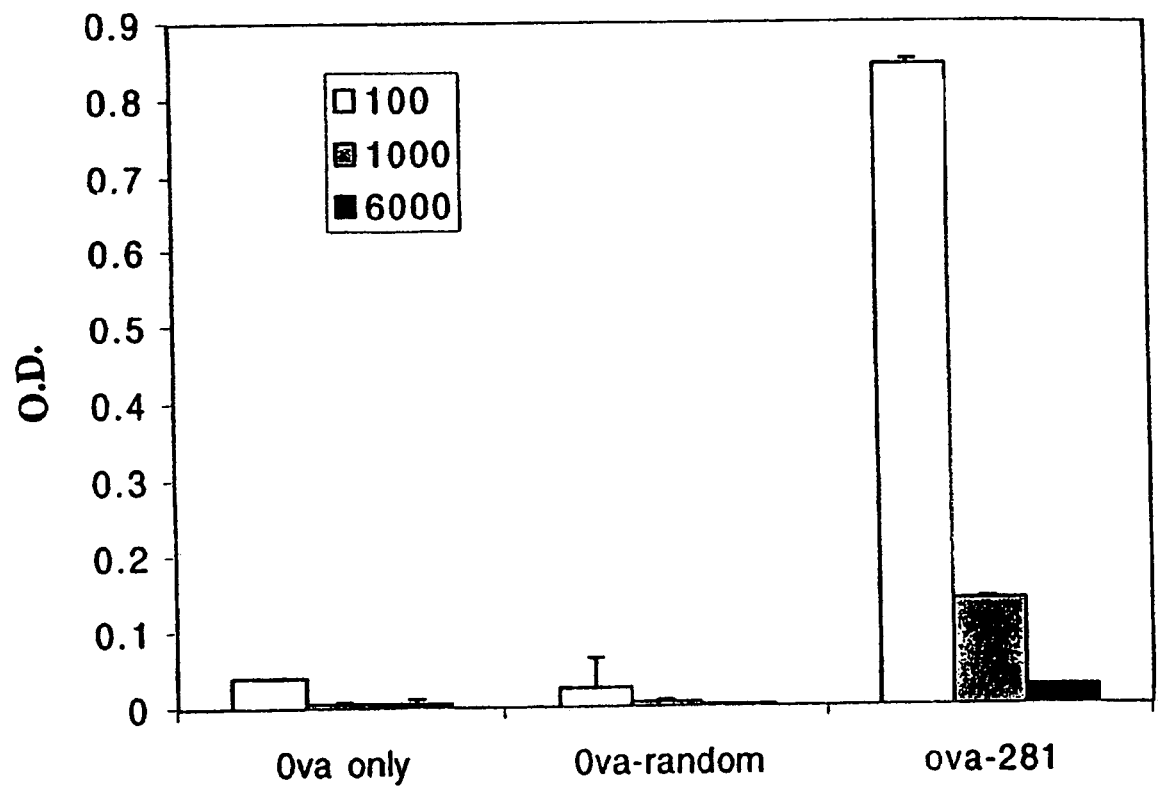
FIG. 7 shows the results of an ELISA demonstrating the specificity of antibodies generated following inoculation of mice with purified Tr-env protein. Ova, ovalbumin; Ova-random, ovalbumin-conjugated random-288-301 peptide (SEQ ID NO: 14); Ova-281, ovalbumin-conjugated WNE-288-301 peptide (SEQ ID NO: 13). 100, 1000, and 6000 represent serum dilutions of 1:100, 1:1000 and 1:6000.
Figure 8:
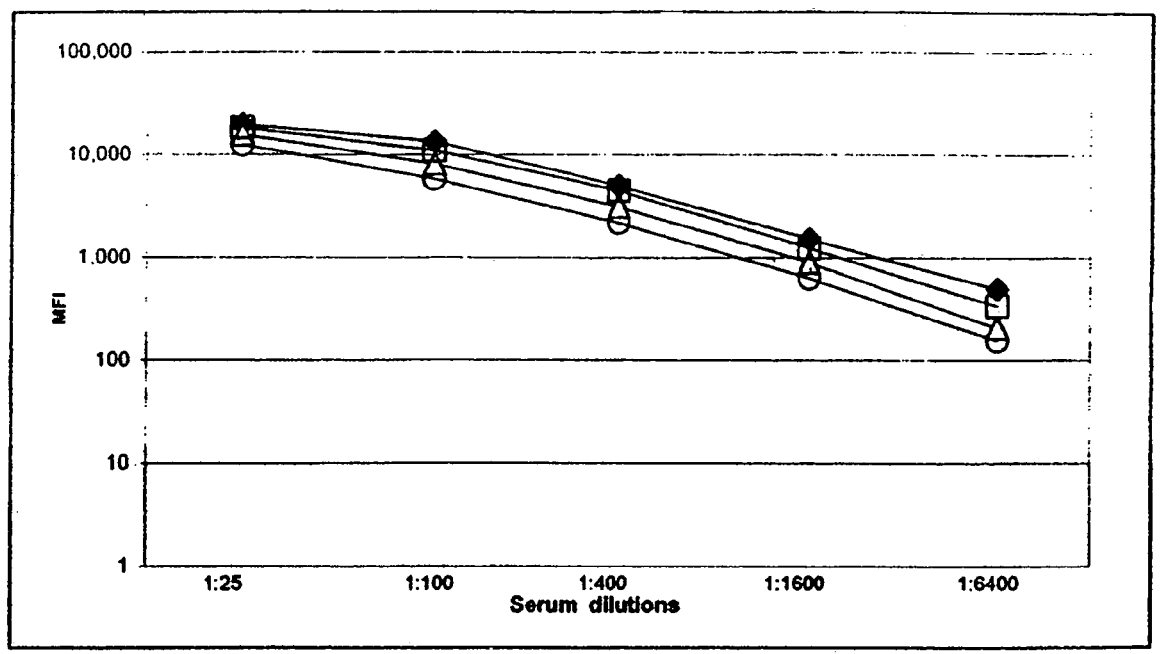
FIG. 8 shows the results of the WNV E microsphere immunoassay testing serum dilutions ranging from 1:25 to 1:6400. The graph shows linear responses for selected (P) positive sera. The graph show that 1:100 dilution of serum provides near maximal MFI. Since 1:25 dilution of serum were shown to be inhibitory in other experiments, 1:100 was chosen as the best screening dilution for subsequent experiments.

The subject invention relates to compositions and methods for diagnosing an infection by a flavivirus, especially WNV, JEV, SLEV, or DENV, in a subject suspected of carrying said infection that are more rapid, efficient, cost effective and sensitive than the methods and compositions currently available in the art. More in particular, this invention relates to the use of an isolated and/or substantially purified polypeptide of WNV, in particular, WNV E glycoprotein, which includes recombinant, synthetic and fusion proteins comprising the polypeptides, subfragments or derivatives thereof, or a nucleic acid molecule encoding a WN polypeptide or subfragment thereof, whereby the WNV polypeptide is of authentic conformation and is reactive to antibodies against WNV and strongly, reliably, predictably and consistently cross-reactive with antibodies against a flavivirus, advantageously, JEV, SLEV, and/or DENV.

Moreover, the present invention relates to a novel use for the WNV E glycoprotein as an antigen for the detection of antibodies against a flavivirus. The inventors have discovered that a substantially purified WNV E glycoprotein antigen having an authentic conformation is strongly, reliably, predictably and consistently cross-reactive among WNV, JEV, SLEV, and DENV, and is therefore useful to broadly assay or test for flavivirus infection, non-specifically, e.g., in subjects, blood donors, organ donors, blood, organs, etc. Accordingly, by the present invention, one can determine whether there is a recent or past flavivirus infection, for instance, infection by any of WNV, JEV, SLEV, or DENV, by a single assay therein providing a faster, simpler, more cost effective approach to broadly assaying for an infection by a flavivirus when the exact identity of the flavivirus is not required.

Another aspect of the present invention includes compositions and methods for consistently and reliably diagnosing an infection specifically by WNV that are more rapid, efficient, cost effective and sensitive than the methods and compositions currently available in the art. More in particular, this aspect of the invention relates to the use of an isolated and/or substantially purified nonstructural polypeptide of WNV, in particular, NS5, which includes recombinant, synthetic and fusion proteins comprising the polypeptides, subfragments or derivatives thereof, or a nucleic acid molecule encoding a nonstructural polypeptide, in particular, NS5, or subfragment thereof, whereby the WNV nonstructural polypeptide is of authentic conformation and is reactive to WNV antibodies with specificity without having substantial cross-reactivity to antibodies against other Flaviviruses, such as JEV, SLEV, and/or DENV.

Moreover, the present aspect of the invention relates to a novel use for the WNV NS5 nonstructural protein as an antigen for the specific detection of antibodies against WNV without substantial cross-reactivity to antibodies against other Flaviviruses, such as JEV, SLEV, and/or DENV. It has been discovered that the WNV NS5 nonstructural protein is strongly, reliably, predictably and consistently reactive to WNV antibodies with high specificity without cross-reactivity with antibodies against other Flaviviruses, such as JEV, SLEV, and DENV, and is therefore useful to assay or test for WNV infection with specificity, e.g., in subjects, blood donors, organ donors, blood, organs, etc. In addition, the present aspect of the invention relates to compostions and methods for differentiating between vaccination with inactivated flavivirus and natural WNV infection. It has been recognized by the inventors that only replicative viruses produce NS proteins. Thus, inactivated flavivirus vaccines do not produce NS proteins since they do not replicate. Accordingly, the WNV NS5 protein can be used according to the instant invention to discriminate between vaccination with inactived flavivirus and a natural WNV infection. Moreover, the present aspect of the invention relates to compositions and methods for indicating the timing of WNV infection and can be used to discriminate between recent and remote WNV infections.

Yet another aspect of the present invention includes compositions and methods for consistent and reliable diagnosis of an infection by DENV that are more rapid, efficient, cost effective and sensitive than the methods and compositions currently available in the art. More in particular, this aspect of the invention relates to the use of an isolated and/or substantially purified nonstructural polypeptide of DENV, in particular, NS5, which includes recombinant, synthetic and fusion proteins comprising the polypeptides, subfragments or derivatives thereof, or a nucleic acid molecule encoding a nonstructural polypeptide, in particular, NS5, or subfragment thereof, whereby the DENV nonstructural polypeptide is of authentic conformation and is reactive to DENV antibodies with specificity without having substantial cross-reactivity to antibodies against other flaviviruses, such as JEV, SLEV, and/or DENV. Further, the DENV NS5 protein of the present invention when isolated from a specific strain of DENV will be specific for antibodies to that same DENV strain and will not be cross-reactive to antibodies against the remaining strains of DENV. It will be appreciated to one of ordinary skill in the art that DENV is comprised of four serologically distinct type, including DENV-1, DENV-2, DENV-3, and DENV-4. Thus, a NS5 of DENV-1 will be specific to antibodies against DENV-1, and not detetectably cross-reactive with antibodies to DENV-2, -3, or -4.

Moreover, the present aspect of the invention relates to a novel use for the DENV NS5 nonstructural protein as an antigen for the specific detection of antibodies against DENV without substantial cross-reactivity to antibodies against other flaviviruses, such as JEV, SLEV, and/or DENV. It has been discovered that the DENV NS5 nonstructural protein is strongly, reliably, predictably and consistently reactive to DENV antibodies with high specificity without cross-reactivity with antibodies against other flaviviruses, such as JEV, SLEV, and WNV, and is therefore useful to assay or test for DENV infection with specificity, e.g., in subjects, blood donors, organ donors, blood, organs, etc. In addition, the present aspect of the invention relates to compostions and methods for differentiating between vaccination with inactivated flavivirus and natural WNV infection. One of skill in the art will appreciate that only replicating viruses produce NS proteins. Thus, inactivated (or "heat-killed") flavivirus vaccines do not produce NS proteins since they do not replicate. Accordingly, the DENV NS5 protein can be used according to the instant invention to discriminate between vaccination with inactivated flavivirus and a natural WNV infection. Moreover, the present aspect of the invention relates to compositions and methods for indicating the timing of DENV infection and can be used to discriminate between recent and remote DENV infections since the antibody response to NS proteins is not sustained. Similarly, one of ordinary skill in the art would appreciate that the methods and compositions of the present invention, in particular, the nonstructural flavivirus antigens, including but not limited to WNV NS5 or DENV NS5, could be used to discriminate a vaccination with a recombinant or subunit flavivirus vaccine, such as a recombinant or subunit WNV, DENV, SLEV, or JEV vaccine, from a recent or ongoing infection with a flavivirus, including but not limited to WNV, DENV, SLEV, and JEV.

In another embodiment, the methods and compositions of the present invention, especially flavivirus nonstructural proteins such as NS5, can be used to distinguish recent or ongoing infections of a flavivirus, such as WNV, DENV, SLEV, or JEV, in a susceptible animal, such as a human, horse, cat, dog, or bird, inter alia, from vaccination by an in vivo flavivirus vaccine, which provides flavivirus structural proteins to an animal to be vaccinated by direct expression to the protein within the animal. It will be appreciated that an in vivo vaccine comprises a DNA molecule coding for one or more structural immunogenic viral polypeptides or portions thereof that are directly administered to a host, such as a human, horse, cat, dog, or bird, inter alia, that is to be vaccinated.

One of ordinary skill in the art would certainly appreciate the numerous benefits of the instant invention, which in one aspect provides a novel method for the broad detection of a flavivirus infection, such as an infection with WNV, JEV, SLEV, and/or DENV, in light of a hypothetical scenario wherein knowledge of the identity of the flavivirus would not be immediately required, but a rapid identification of a putative flaviviral infection would be critical. Such a scenario could involve a patient arriving at a hospital in a geographical region having recently experienced cases of flavivirus infections in patients, such as an infection with WNV, JEV, SLEV, or DENV, wherein the patient arrives with typical flavivirus-like symptoms, such as headache, sudden fever, malaise, and swollen glands. The treating physician would want to know immediately whether or not the symptoms are due to a flavivirus infection, but immediate identification of the flavivirus species or strain is not initially critical. The instant invention provides a rapid diagnostic assay to broadly detect a flavivirus infection, such as an infection with WNV, JEV, SLEV, or DENV, which in one embodiment, can be completed in under 3 hours. Thus, providing a rapid result in the diagnosis of a flavivirus infection is clearly an advantage of the instant invention. Another aspect of the instant invention relates to a novel method for the detection of antibodies to a flavivirus using enhanced reaction kinetics and a microsphere immunoassay that together drastically reduce the time it takes for diagnosis of a WNV infection or a general flavivirus infection from 3 days and up to 3 weeks, to less than 3 hours.

Also within the scope of the instant invention are diagnostic kits and methods for detecting antibodies against a flavivirus, especially WNV, JEV, SLEV, and/or DENV, characterized by the compositions of the present invention comprising a substantially pure WNV polypeptide, fragments, or derivatives thereof, such as WNV E glycoprotein, that are reactive with antibodies against WNV and strongly, reliably, predictably and consistently cross-reactive with antibodies against a flavivirus wherein the WNV polypeptide has an authentic conformation. These diagnostic kits and methods for detecting antibodies against a flavivirus are also useful for detecting a protective immune response to a flavivirus infection, especially by WNV, JEV, SLEV, and/or DENV.

Further, the methods of the instant invention are also useful in monitoring the course of immunization against a flavivirus, especially, WNV, JEV, SLEV, and/or DENV. In patients previously inoculated with the vaccines against a flavivirus, the detection means and methods disclosed herein are also useful for determining if booster inoculations are appropriate.

It will be appreciated by those having ordinary skill in the art based on the teachings and examples set forth herein that the methods of the present invention represent a more reliable, consistent, effective and time efficient approach to detecting in biological samples, including those from humans and animals such as wild or domestic birds, and mammals such as horses, cats or dogs, antibodies to WNV, DENV and other flaviviruses. It will be understood that the various proteins isolated from the various flaviviruses of the invention, especially WNV and DENV, can be used as antigens in the methods of the instant invention to detect in a specific or nonspecific manner, flaviviruses, especially WNV and DENV.

It will be appreciated that the WNV E glycoprotein can be used as an antigen to in the method of the instant invention to detect antibodies against certain species of flaviviruses relevant to human disease, such as, WNV, JEV, SLEV, DENV, using a single assay to take the place of a multitude of assays currently used in the art for the detection of these flaviviruses. Thus, by the present invention, one can determine whether there is a flavivirus infection, for instance, infection by any of WNV, JEV, SLEV, or DENV, by a single assay. It has been discovered here that a substantially purified WNV E glycoprotein antigen having a substantially authentic conformation is reliably, consistently, predictably, and strongly cross-reactive to antibodies against any of WNV, JEV, SLEV, and DENV, and is therefore useful to broadly assay or test for flavivirus infection, non-specifically, e.g., in subjects, donors, blood, organs, etc. In contrast, antigens currently available in the art for the detection of DENV, SLEV, JEV, and WNV infections are often concentrated by polyethylene glycol and/or extracted with acetone, treatments which are likely to alter the structural domains of a given antigen.

It will further be appreciated that a WNV nonstructural protein, especially NS5, or a specific antigenic determinant or specific epitope thereof, can be used as an antigen for the specific detection of antibodies against WNV in the method of the instant invention. Importantly, the NS5 antigen is not cross-reactive to other flaviviruses, such as, for example, JEV, SLEV, or DENV. Thus, in accordance with the present aspect of the invention, one can consistently, reliably, and accurately determine whether there is a WNV infection with the confidence and assurance that the detection signal is not due to cross-reactivity with other flaviviruses.

It will also be appreciated that the substantially purified DENV NS5 antigen of the present invention is reliably, consistently, predictably, and strongly reactive to antibodies against a DENV without having substantial cross-reactivity with other flaviviruses, such as, for example, JEV, SLEV, and WNV. Therefore, DENV NS5 antigen will be useful to specifically assay or test for DENV infection, e.g., in subjects, donors, blood, organs, etc. In contrast, current serologic diagnoses of DENV infection is based on detection of antibodies against viral structural proteins, such as the E protein. Although, the cross-reactivity of the E protein among flaviviruses, as also discovered by the instant inventors, is certainly advantageous with respect to its use as a rapid diagnostic for detecting a general flavivirus infection when knowing the identity of the flavivirus is not critical, it would also be desirable to have a rapid test that could confidently, accurately, and correctly identify a DENV infection with specificity and without cross-reactivity with other types of flaviviruses. Further, the DENV NS5 protein of the present invention when isolated from a specific strain of DENV will be specific for antibodies to that same DENV strain and will not be cross-reactive to antibodies against the remaining strains of DENV.

As one of ordinary skill in the art will understand, prior to the present invention, a number of serologic assays were routinely used for laboratory diagnosis of flavivirus infections, including infections of WNV, DENV, JEV, and SLEV: IgM antibody capture enzyme immunoassay (MAC-ELISA), indirect IgG ELISA, indirect fluorescent antibody assay (IFAT), hemagglutination inhibition (HIT), and serum dilution cross-species plaque reduction neutralization tests (PRNTs). As described below, these assays vary markedly in sensitivity, technical difficulty, turn-around time, and clinical utility of the results.

IgM Antibody Capture ELISA

IgM response to WNV infection occurs earlier than that of IgG, and is often used to indicate recent infections of WNV (G. Tardei et al.). MAC-ELISA is typically performed to detect the IgM level in serum samples, as described by Beaty and coworkers (Martin et al.) with modifications (Martin et al.). Briefly, goat anti-human IgM (PerlImmune Inc., Rockville, Md.) is used as a capture antibody, and is coated onto 96-well flat-bottom plates. After blocking of the plates with nonfat dry milk, diluted human sera are reacted with the anti-human IgM. Viral antigens, either sucrose-acetone extracts of infected suckling mouse brains [32, 33] or recombinant viral structural proteins (B. Davis et al.), are added to the plates. Flavivirus group-reactive SLE monoclonal antibody 6B6C-1 (conjugated to horseradish peroxidase) (Roehrig et al.) is then reacted with the immobilized viral antigen. After addition of substrate 3,3'5,5' tetra methyl benzidine (TMB-ELISA; Neogen, Lexington, Ky.), reactions are measured using a microplate reader at an absorbance of 450 nm. A ratio of 2.0 or greater of the absorbance of the test serum over the absorbance of the negative control serum is usually considered positive. Serial dilutions of positive sera can be evaluated. The maximum dilution that exhibits positive signal is the titer for the serum. The titer of the MAC-ELISA can be compared with the titers of HI and PRN tests. It should be noted that, in the CDC MAC-ELISA, all serum samples are tested on control antigen in addition to viral antigen, to reduce the number of false-positive results due to non-specific binding of the serum or other factors. Any "positive" test result (ratio≧2.0) is deemed un-interpretable if the mean absorbance of the test specimen reacted on viral antigen is <2× the mean absorbance of the test specimen reacted on the control antigen. These samples require testing with an alternate method, generally PRNT.

MAC-ELISA has replaced complement fixation and HIT in most public health laboratories, because of its superior sensitivity in diagnosing early acute infections of flaviviruses. The MAC-ELISA was reported to be more sensitive than PCR-based assay for spinal fluid and blood specimens from patients with symptomatic infection (D Nash et al.). The MAC-ELISA is a more appropriate assay to use for symptomatic patients, because the virus is cleared so efficiently by the immune system in healthy individuals, that it is not usually possible to detect viral nucleic acid once clinical symptoms are observed. Since the 1999 outbreak of WNV in New York, the Centers for Disease Control and Prevention (CDC) have extensively trained public health laboratories to perform this complex 2-day assay. MAC-ELISA is currently the most widely used diagnostic test for acute WNV encephalitis in the United States.

Initially, the ELISA antigen was a sucrose-acetone extract of WNV-infected suckling mouse brain (Martin et al.). The antigen was later replaced by unpurified E and prM proteins secreted from a plasmid-transformed COS cell line (B Davis et al.). The cell line-derived antigens are concentrated by precipitation with polyethylene glycol followed by lyophilization. Several companies have purchased licenses to commercialize the noninfectious recombinant antigens (NRA), including Abbott Laboratories (Abbott Park, Ill.), Focus Technologies (Cypress, Calif.), GenBio (San Diego, Calif.), Hennesy Research Associates (Shawnee, Kans.), Immucor (Atlanta, Ga.), InBIOS (Seattle, Wash.), RMZ Biotech Corporation (Baltimore, Md.), and Rapid Medical Diagnostic Corporation (Miami, Fla.). These products are sold as analyte-specific reagents (ASR) and, as such, must be validated by the user. The FDA recently approved the enzyme immunoassay kit for diagnostic testing from PanBio (Baltimore, Md.).

The IgM response to WNV infection is rapid; most sera and spinal fluids are positive in the MAC-ELISA within 8 days of symptom onset (Roehrig et al.). IgM detected by MAC-ELISA in spinal fluids is directly indicative of recent infection (B. J. Beaty et al.). This is because the detected IgM is synthesized by lymphocytes in the central nervous system, and serum IgM, a pentameric molecule, is too large to pass through an intact blood-brain barrier. However, because anti-WNV IgM in serum persists in many patients for 3 to 6 months after symptom onset, and can persist beyond 15 months (D. A. Martin et al. 2000), caution should be used when interpreting IgM-positive results from early-season WNV IgM-positive patients. Solitary serum IgM positive results must be considered in conjunction with other WNV surveillance data, e.g., evidence of WNV in mosquitoes or in reservoir bird populations. Follow-up testing of paired specimens is recommended. For the same reason, because the duration of the anti-WNV IgM in chickens or rabbits has been not well defined, IgM testing should not be performed as the sole testing modality when these animals are used as sentinels for monitoring WNV activities. In one study, the IgM persistence was reported to vary in chickens from 19 days to greater than 61 days post WNV infection (A. J. Johnson et al.). If the bleeding schedule is less frequent than once every 3 weeks, a recent infection of the sentinel animals may be missed through sole reliance on MAC-ELISA (A. J. Johnson et al.).

Several limitations were previously reported for the MAC-ELISA. First, although human IgM response to WNV and other flaviviruses is more virus-type specific than is the IgG response, cross-reactivities with other JE serogroup viruses, DEN and YF, do occur in the IgM tests (D. A. Martin et al. 2002, T. P. Monath et al., M. Lhullier et al.). Additional information about the patient, such as travel history to regions where WNV or other flaviviruses are active, should be helpful in interpreting the diagnostic results. Second, the sensitivity of the MAC-ELISA may be decreased when patient serum contains IgM molecules in response to infections other than WNV. These non-WNV-IgM molecules can nonspecifically compete against WNV-IgM molecules for binding to the anti-human IgM antibodies coated on the ELISA plate, resulting in reduced sensitivity of the assay. Third, false-positive results of MAC-ELISA may occur due to nonspecific binding of rheumatoid factors, which often exist in sera from healthy individuals (P. P. Mortimer et al.). Rheumatoid factors are well known to confound serological diagnosis through their cross-linking of the capture antibody to the detector antibody in the absence of any WNV antigen (P. P. Mortimer et al.).

Indirect IgG ELISA

Indirect IgG ELISA is a 2-day assay that is often performed in tandem with MAC-ELISA. The protocol for diagnosis of anti-WNV IgG was described by Johnson and coworkers, 2000). A flavivirus E protein cross-reactive monoclonal antibody (Mab) 4G2 (ATCC, Manassas, Va.) (A. J. Johnson et al., 2000) is coated onto 96-well microtiter plates. After blocking of the plates with 3% goat serum in PBS and multiple washes, WNV antigens are reacted with the Mab 4G2. After several washes, diluted human sera are reacted with the immobilized viral antigens. Goat anti-human IgG Fc-alkaline phosphatase conjugate is then reacted with serum-derived IgG. Upon addition of p-nitrophenyl phosphate (Sigma Aldrich, St. Louis, Mo.) to the wells, colorimetric absorbance at 405 nm is measured, and a ratio of 2.0 or greater for the test serum over the negative control serum is considered positive (A. J. Johnson et al., 2003).

The same antigens as used for the MAC-ELISA are used for the IgG ELISA. Because of the cross reactivities of the structural proteins during various flavivirus infections, the identity of the infecting virus can not be determined with certainty. Other assays such as HI and PRNT are routinely performed to verify the identity of the virus. Because the level of IgG remains elevated for many years after an infection, a 4-fold increase in IgG antibody titer between paired sera are considered essential for estimation of a recent, acute infection (D. Gubler et al., 2000). Using inactivated WNV as antigen, Ebel and co-workers recently reported that the IgG ELISA could also be used to detect anti-WNV antibodies in birds.

Indirect Fluorescent Antibody Tests

IFAT is used to detect anti-WNV IgG, IgM, or total antibodies (IgG+IgA+IgM) from suspected WNV-infected sera. The assay can be completed within 2-3 hr. IFAT slides and test kits are commercially available from PanBio (Baltimore, Md.). WNV-infected Vero cells are grown until the appearance of cytopathic effects, mixed with uninfected tissue culture cells, and spotted onto a microscope slide. The slides are then acetone-fixed and stored frozen. Patient sera, starting at a 1:8 dilution, are reacted with the antigens on the slide. After incubations with anti-human immunoglobulins conjugated with fluorescein isothiocyanate (FITC) and washings, the cells are examined under a fluorescent microscope. Positive IgG antibody is indicated by specific apple-green fluorescence in the cytoplasm cells. Since only 30% to 50% of the cells on the slides are infected with WNV, observation of 100% cells of positive fluorescence indicates a non-specific reaction, rather than a serum infected with WNV. Autoantibodies in patient serum can react with cellular antigens, resulting in non-specific fluorescence. This possibility can be excluded by using undiluted serum to react with uninfected tissue culture cells. If positive, the patient serum is likely to have autoantibodies to cellular antigens. The sensitivity of the IFAT is low, with an estimated detection limit of 0.05-1 µg of virus-specific neutralizing antibody (J. Pillot, 1996). The detection limit of the IFAT is about a 1,000-fold lower than that of ELISA. However, IFAT measurement of IgG is slightly more specific than ELISA (P. Koraka et al., 2002).

For detection of virus-specific IgM or IgG, serum specimens are pretreated with rabbit anti-human IgG or IgM, respectively. Complete depletion of IgG in serum is essential for an accurate detection of IgM, because residual IgG can compete with IgM to bind to the antigens on the slide, resulting in inaccurate results. To increase the sensitivity of the IgM assay, overnight incubation of IgG depleted serum with antigen slides is recommended. After binding of the IgM to antigen, anti-human IgM conjugated with FITC is applied to bind to the antigen-bound IgM. Even through the IgM-IFAT is less sensitive than MAC-ELISA, it has been applied to rapid diagnosis of acute serum samples. Because the procedure of IgM-IFAT requires manual pipetting and reviewing of individual wells of the IFAT slides under a fluorescent microscope, this assay does not have the capability to diagnose a large volume of patient specimens. Further, since the concentration of IgM in spinal fluid is nearly a 1,000-fold lower than that in serum, neither can the assay be reliably used to detect IgM in spinal fluid (W. R. Chen et al., 1992). However, the specificity of the IgM IFAT against DEN, JE, YF, and WNV was reported to exceed that of the standard EIA (P. Koraka et al.), with a cross-reactivity that ranged from 4% to 10%, compared to 30% to 44% for the standard EIA. False IgM-IFAT positives can be caused by rheumatoid factor; false IgM-IFAT negatives can be caused by competition from residual IgG molecules remaining after the IgG depletion.

Hemagglutination Inhibition Tests

The HI test is performed essentially as described nearly 60 years ago by Casals and Brown (J. Casals, et al., 1954). Serum is first treated by acetone extraction, followed by adsorption with goose erythrocytes to remove nonspecific inhibitors associated with false-positive results, and to remove hemagglutinins associated with false-negative results. Treated sera are serially diluted and mixed with a known amount of suckling mouse brain WNV antigen for an overnight incubation at 4° C. Goose erythrocytes, preferably from an adult gander, are added to the serum/virus mixture in microtiter plates. The HI titer is read after a 1-hr incubation at room temperature. A thin mat of cells across the well indicates agglutination. A pellet of cells at the bottom of the well indicates inhibition of agglutination. The highest dilution of serum that completely inhibits agglutination of the goose erythrocytes is taken as the HI titer of the serum. HI tests provide higher titers than do standard neutralization tests, but lower titers and lower numbers of positive samples than do micro PRN tests (H. M. Weingartl et al.). HI tests measure both IgM and IgG antibody classes, and are considerably less sensitive than ELISAs. Although HI antibodies appear rapidly, they disappear more quickly than do neutralizing antibodies, which are detected by the IgG ELISAs (B. J. Beaty et al., 1995). Reagents for HI tests are somewhat less stable to long-term storage than are the reagents used in other methods. Agglutination occurs over a narrow pH range. In addition, patient sera must be tested by a panel of viruses known to occur and to cause disease in humans in a given geographic region.

Plaque Reduction Neutralization Tests (PRNT)

PRNT is a 3- to 5-day assay (H. S. Lindsey, 1976). Sera are first heat-inactivated at 56° C. for 30 min. A set of serially diluted sera are added to known amounts of virus. After incubation for 1 hr, the mixture is added to Vero cells, followed by another 1-hr incubation. Nutrient agar is applied, and the plates are incubated for 2-3 days in a $CO_2$ incubator. A second overlay with a neutral red stain is applied. Plates are checked for plaque formation over the next 1-2 days. The titer is the reciprocal of the serum dilution causing a plaque reduction of 90%. PRNT detects antibodies at an earlier time post-infection, with higher mean serum antibody titers, than did HI and ELISA tests, in experimental infections of chickens. PRNT also detects the highest number of positive serum samples at various times post-infection (H. M. Weingartl, et al., 2003).

It will be appreciated that the instant invention provides methods for assaying biological samples for the presence of antibodies against flaviviruses that are distinguished from and advantageous over the previous methods. Several examples of this invention's advantages over prior art methods for detecting anti-flavivirus antibodies include, inter alia, reduced time requirements, greater consistency in results, and enhanced ease of use. More in particular, the traditional serologic assays such as HI or particle agglutination are performed with either antigens or antibodies passively adsorbed onto the surfaces of tanned erythrocytes or latex microspheres. The recent technology of lateral flow immunoassays utilizes antibodies or antigens bound to microspheres and lateral flow immunochromatography to capture zones on nitrocellulose membranes. Recently, antigens have been covalently attached to fluorescent polystyrene microspheres for immunoassays performed in microfilter plates, and the assays are quantified through a flow cytometer such as the Luminex 100 (Luminex, Austin, Tex.).

One embodiment of the instant invention relates to the use of microsphere immunoassays. Although the antigens of the invention, including WNV E glycoprotein and the NS5 protein, can be used essentially in any assay format known to one of ordinary skill in the art, such as the above-mentioned methods, including ELISA formats, certain embodiments of the instant invention are advantageous over others. More in particular, the antigens of the invention, including WNV E glycoprotein and the NS5 protein can be used in connecting with microsphere immunoassays (MIAs). MIAs are more quantitative than prior serological testing methods, including, for example, ELISAs. The microsphere assays have broad dynamic ranges, often exceeding what can be obtained with ELISAs. Reaction times are short, since kinetics are enhanced by shaking of the microspheres in fluid suspension during the incubations. Small specimen volumes can be used in the microsphere assays, and replicate testing is not required because of the high precision of the analyses. Therefore, large specimen volumes of precious specimens, such as spinal fluid, are not required. MIA results can be obtained with small amounts of biological sample, such as, for example, 30 µl of spinal fluid, compared to the 450 µl required for the MAC-ELISA (Wong et al, submitted). In addition, microbeads have more surface area and thus more epitopes available for antigen or antibody binding than do macrobeads, microtiter plates, or nitrocellulose papers, resulting in an increased sensitivity. The preferred reporter fluorochrome, red-phycoerythrin, has an extremely high extinction coefficient, which also enhances the analytical sensitivity. Finally, microsphere immunoassays allow a more cost-effective use of antigen: 1 µg of antigen usually suffices for approximately 50 tests.

In accordance with one embodiment of the present invention, an E-based microsphere immunoassay is provided which consistently, accurately, strongly, and reliably detects a WNV-infection at around day 2-6 post-symptom onset. Retrospective testing as carried out by the present inventors on over 800 sera from patients with suspected viral encephalitis by the polyvalent (anti-IgG+IgA+IgM) microsphere immunoassay exhibited 95% concordance with results obtained with the IgG ELISA. The E-based microsphere immunoassay of the present invention could also be used to detect anti-E IgM antibodies, and to indicate current or recent WNV infection. In addition, the inventors have discovered that a substantially purified WNV E glycoprotein antigen having a substantially authentic conformation is reliably, consistently, predictably, and strongly cross-reactive to antibodies against any of WNV, JEV, SLEV, and DENV, and is therefore useful to broadly assay or test for flavivirus infection, non-specifically, e.g., in subjects, donors, blood, organs, etc. In contrast, antigens currently available in the art for the detection of DENV, SLEV, JEV, and WNV infections are often concentrated by polyethylene glycol and/or extracted with acetone, treatments which are likely to alter the structural domains of a given antigen.

In another embodiment of the present invention, a NS5-based microsphere immunoassay is provided. The NS5-based microsphere immunoassay reliably detects WNV-infection (IgG+IgA+IgM total antibodies) at around day 6 post-symptom onset. The overall reactive pattern derived from the NS5-based assay was shown by the inventors to correlate well with that from the E-based assay. However, the NS5-based assay has two major diagnostic differences over the E-based assay. First, the NS5-based assay can be used to differentiate between WNV infection and vaccinations with either an inactivated JEV or a live attenuated YFV vaccine. In support, sera was collected from the JEV vaccine recipients and reacted with the WNV NS5 antigen. The result was that only 5% of the sera collected from the YFV-vaccine recipients reacted with the WNV NS5 antigen. By contrast, 100% of the JEV-vaccinated sera and 53% of the YFV-vaccinated sera reacted with the E antigen. Second, the NS5-based assay substantially improves discrimination between DENV/SLEV and WNV infections. The inventors show herein through experimentation that only 9% of the DENV sera were marginally positive in the WNV NS5-based assay, whereas 71% of the same sera were reactive in the WNV E-based assay (see Examples and FIG. 26). Further, only 5% of the SLEV sera were positive in the WNV NS5-based assay, whereas 27.5% of the same panel of sera were positive in the WNV E-based assay (see Examples and FIG. 27). The results of the NS5-based immunoassay clearly suggest that NS5 could be used as an antigen for virus type-specific diagnosis of flavivirus infections.

In accordance with one embodiment of the invention, the NS5-based microsphere immunoassay can be used to distinguish between WNV infection and vaccination by inactivated JE. Without being bound by theory, this distinction is possible since only replicative viruses produce NS proteins, while inactivated JE vaccines cannot replicate and thus cannot produce NS proteins. Another reason is that no or very few NS proteins, including NS5, exist in the inactivated JEV vaccines since the vaccines are prepared through an extensive purification procedure.

In another embodiment of the invention, the antigen-based immunoassays of the present application can be useful for determining whether animals, such as horses, previously vaccinated with inactivated WNV have sustained a new exposure to WNV infections. The first documented case of equine WNV infection was in Minnesota in 2003 in a horse that had received a vaccine in 2002, but had not had a booster. Since protective immunity wanes quickly, and there is a chance for reinfection, veterinarians are increasingly challenged to diagnose neurological illness possibly owing to WNV infection in previously WNV-vaccinated horses. Such diagnosis will be problematic for structural protein-based assays, such as assays based on WNV E glycoprotein, due to the presence of preexisting antibodies to the immunodominant E protein as a result of the vaccination. However, WNV infection in previously vaccinated horses could be assessed using the NS5-based immunoassay of the present invention. The NS5-based assay will detect only current or recent WNV infections. It will not show a positive result for an animal that was solely vaccinated with a WNV or flavivirus vaccine since there needs to be viral replication in order to produce NS5 in sufficient quantity to provide an immune response and the production of anti-NS5 antibodies.

As used herein, the term "polypeptide" is taken to encompass all the polypeptides, peptides, and fusion proteins described in this invention and refers to any polymer consisting essentially of amino acids regardless of its size which maintains a comparable level of cross-reactivity to the cross-reactivity of the unmodified polypeptide from which it is derived. Although "protein" is often used in reference to relatively large polypeptides, and "peptide" is often used in reference to small polypeptides, usage of these terms in the art overlaps and varies. The term "polypeptide" as used herein thus refers interchangeably to peptides, polypeptides, or fusion proteins unless otherwise noted. The term "amino acid" refers to a monomeric unit of a peptide, polypeptide or protein.

Further, the term "polypeptide" is meant to encompass any "derivative" thereof. A derivative refers to a modified or altered form of the native or original polypeptide. As used in the present application, a derivative will have a comparable level of cross-reactivity to the cross-reactivity of the unmodified polypeptide from which it is derived. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure.

A "substantially pure" polypeptide is a polypeptide that is free from other WNV components with which it is normally associated. Further, a substantially pure polypeptide is one which is free of other undesired protein contamination, such as bovine serum albumin, which can be carried over from culture medium during antigen preparation.

As used herein, an "authentic conformation" of a polypeptide (e.g. antigen) refers to the native conformation of the polypeptide (e.g. antigen). The native conformation of the polypeptide refers specifically to the three-dimensional form of the molecule as it exists in vivo. Many processes currently used in the art to prepare various polypeptides (e.g. antigens) involve harsh preparatory treatments, such as acetone extraction and/or polyethylene glycol precipitation, both of which are known to deform and/or denature polypeptides (e.g. antigens). A fully or partially denatured polypeptide (e.g. antigen) is not as cross-reactive as the same polypeptide (e.g. antigen) having an authentic conformation since the epitopes of the polypeptide (e.g. antigen) involved in cross-reacting interactions become damaged such that they are no longer or less efficiently recognized by antibodies.

As it is used herein, the terms "NS5", "NS5 protein", or "NS5 antigen" are meant to be synonymous with one another. Further "NS5", "NS5 protein", or "NS5 antigen" are meant to encompass any immunogenic fragment thereof or any specific portion encompassing any unique epitope that is immunogenically distinct from NS5 proteins from other flaviviruses. The instant invention contemplates the use of nonstructural proteins or fragment thereof obtained from any flavivirus, including but not limited to WNV, SLEV, JEV, and DENV, especially WNV and DENV. It was the inventors' discovery that the nonstructural protein NS5 antigen from a first flavivirus, such as WNV or DENV, can be used to specifically detect antibodies against said first flavivirus from a biological sample (e.g. biological fluid, tears, semen, blood, plasma, feces, spinal fluid, saliva, or mucous) wherein the NS5 antigen from the first flavivirus is not detectably cross-reactive with antibodies to other flaviviruses. Moreover, in the case of DENV, the NS5 antigens from a first strain, such as DENV-1, is not cross-reactive with antibodies to the remaining DENV strains. Thus, the DENV NS5 antigens are useful for discriminating DENV strains.

According to various embodiments of the instant invention, the WNV E glycoprotein utilized by the instant invention is prepared by a process that results in a substantially purified WNV E glycoprotein having an authentic conformation. In a further preferred embodiment, the purification method of the instant invention utilizes column chromatography in a manner that does not harshly treat or denature the desired polypeptide to be purified. Specifically, column chromatography as used by the instant invention does not require polyethylene glycol precipitation or acetone extraction.

As used herein, a "protective epitope" is (1) an epitope that is recognized by a protective antibody, and/or (2) an epitope that, when used to immunize a human or animal, elicits an immune response sufficient to confer WNV immunity or to prevent or reduce the severity for some period of time, of the resulting symptoms. A protective epitope may comprise a T cell epitope, a B cell epitope, or combinations thereof.

As used herein, "enhanced reaction kinetics" refers to an antibody-antigen binding reaction that occurs at a rate that exceeds the expected reaction rate when carried out under conditions used in prior art methods. "Conditions" that are suitable for enhanced reaction kinetics according to the present invention are a discovery of the inventor. Such conditions may comprise parameters related to incubation time, temperature, buffers, and pH levels. The conditions further may comprise physical parameters, such as, shaking or moving the components of any given reaction sample. In one embodiment, enhanced reaction kinetics are achieved by incubating together a biological sample and a WNV antigen, such as, WNV E glycoprotein, and at 37° C. for about 30 minutes while keeping the reaction mixture in motion, such as on platform shaker at low speed.

Various compositions and methods of the aforementioned embodiments are characterized by immunogenic polypeptides. As used herein, an "immunogenic polypeptide" is a polypeptide that, when administered to a human or animal, is capable of eliciting a corresponding antibody.

This invention also provides two novel immunogenic fragments of the WNV E glycoprotein and compositions and methods comprising these peptides. More specifically, this invention provides the WNE-121-139 (peptide 3) peptide and WNE-288-301 peptide (peptide 1). It will be appreciated by those of ordinary skill in the art that similar immunogenic fragments of the flavivirus antigens contemplated by the present invention, especially immunogenic fragments of NS5 and E glycoprotein antigens from the flaviviruses of the invention, especially WNV and DENV, can be obtained and used in accordance with the methods of the invention.

Also within the scope of this invention are polypeptides that are at least 75% identical in amino acid sequence to the aforementioned polypeptides. Specifically, the invention includes polypeptides that are at least 80%, 85%, 90% or 95% identical in amino acid sequence to an amino acid sequence set forth herein. The term "percent identity" in the context of amino acid sequence refers to the residues in the two sequences which are the same when aligned for maximum correspondence. There are a number of different algorithms known in the art which can be used to measure sequence similarity or identity. For instance, polypeptide sequences can be compared using NCBI BLASTp. Alternatively, FASTA, a program in GCG version 6.1. FASTA provides alignments and percent sequence identity of the regions of the best overlap between the query and search sequences (Peterson, 1990).

Alternatively, nucleotide sequence similarity or homology or identity can be determined using the "Align" program of Myers and Miller, ("Optimal Alignments in Linear Space", CABIOS 4, 11-17, 1988) and available at NCBI. The terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

Various compositions and methods of the aforementioned embodiments are characterized by WNV polypeptides, such as, for example, WNV E glycoprotein, that elicit in treated humans or animals the formation of an immune response. As used herein, an "immune response" is manifested by the production of antibodies that recognize the corresponding polypeptide. In an especially preferred embodiment, the compositions and methods of the invention are characterized by WNV polypeptides or antibodies that confer protection against WNV infection or disease.

In yet another embodiment, this invention relates to diagnostic means and methods characterized by a WNV polypeptide, such as, for example, WNV E glycoprotein. The inventor has discovered that a substantially pure WNV E glycoprotein having an authentic conformation as described in this application is not only reactive with antibodies against WNV, but is also strongly, reliably, predictably and consistently cross-reactive against other flaviviruses, especially, JEV, SLEV, and DENV.

As used herein, an antigen, such as, WNV E glycoprotein of WNV, is "reactive" with an antibody raised against the antigen when there is a specific binding event/reaction between the antigen and the antibody.

As used herein, a first antigen, such as, WNV E glycoprotein of WNV, is "cross-reactive" with an antibody raised against a second antigen of a second virus, such as, DENV, when there is a specific binding event/reaction between the first antigen and the antibody raised against the second antigen. One of ordinary skill in the art will understand that similar or related viruses may comprise similar proteins, e.g., proteins with similar amino acid sequences and three-dimensional structural features that may provide similar recognition epitopes such that an antibody raised against a first antigen may recognize and bind to the second antigen.

The WNV polypeptides or derivatives thereof described herein are immunologically reactive with antisera produced in response to an infection with WNV. Accordingly, they are useful in methods and compositions to detect both immunity to WNV or prior infection with WNV.

As will be apparent from the disclosure to follow, the polypeptides in the pharmaceutical compositions of this invention may also be prepared with the objective of increasing stability or rendering the molecules more amenable to purification and preparation. One such technique is to express the polypeptides as fusion proteins comprising other WNV sequences.

In accordance with this invention, a derivative of a polypeptide of the invention may be prepared by a variety of methods, including by in vitro manipulation of the DNA encoding the native polypeptides and subsequent expression of the modified DNA, by chemical synthesis of derivatized DNA sequences, or by chemical or biological manipulation of expressed amino acid sequences.

For example, derivatives may be produced by substitution of one or more amino acids with a different natural amino acid, an amino acid derivative or non-native amino acid. Those of skill in the art will understand that conservative substitution is preferred, e.g., 3-methyl-histidine may be substituted for histidine, 4-hydroxy-proline may be substituted for proline, 5-hydroxylysine may be substituted for lysine, and the like.

Furthermore, one of skill in the art will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins* W. H. Freeman and Co.

Conservative substitutions typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions are described by Dayhoff in the Atlas of Protein Sequence and Structure (1988).

Causing amino acid substitutions which are less conservative may also result in desired derivatives, e.g., by causing changes in charge, conformation or other biological properties. Such substitutions would include for example, substitution of a hydrophilic residue for a hydrophobic residue, substitution of a cysteine or proline for another residue, substitution of a residue having a small side chain for a residue having a bulky side chain or substitution of a residue having a net positive charge for a residue having a net negative charge.

In another embodiment of this invention, the WNV polypeptides described herein are prepared as part of a larger fusion protein. For example, a WNV polypeptide used in a composition of this invention may be fused at its N-terminus or C-terminus to a different immunogenic WNV polypeptide, to a non-WNV polypeptide or to combinations thereof, to produce fusion proteins comprising the WNV polypeptide.

In a further embodiment of this invention, fusion proteins comprising a WNV polypeptide used in a composition are constructed comprising B cell and/or T cell epitopes from multiple strains of WNV, each variant differing from another with respect to the locations or sequences of the epitopes within the polypeptide. Such fusion proteins are in particular effective in the induction of immunity against a wide spectrum of WNV strains and can be utilized to modulate the specificity of detection of antibodies against flaviviruses.

In an embodiment of this invention, the WNV polypeptides used in pharmaceutical compositions are fused to moieties, such as immunoglobulin domains, which may increase the stability and prolong the in vivo plasma half-life of the polypeptide. Such fusions may be prepared without undue experimentation according to methods well known to those of skill in the art, for example, in accordance with the teachings of U.S. Pat. No. 4,946,778, or U.S. Pat. No. 5,116,964. The exact site of the fusion is not critical as long as the polypeptide retains the desired biological activity. Such determinations may be made according to the teachings herein or by other methods known to those of skill in the art.

The fusion proteins comprising the WNV polypeptides, according to previous embodiments, may be produced at the DNA level, e.g., by constructing a nucleic acid molecule encoding the fusion protein, transforming host cells with the molecule, inducing the cells to express the fusion protein, and recovering the fusion protein from the cell culture. Alternatively, the fusion proteins may be produced after gene expression according to known methods.

The polypeptides of the invention may also be part of larger multimeric molecules which may be produced recombinantly or may be synthesized chemically. Such multimers may also include the polypeptides fused or coupled to moieties other than amino acids, including lipids and carbohydrates.

It will be readily appreciated by one of ordinary skill in the art that the polypeptides in the pharmaceutical compositions of this invention, as well as fusion proteins and multimeric proteins containing them, may be prepared by recombinant means, chemical means, or combinations thereof.

For example, the polypeptides may be generated by recombinant means using the DNA sequence as set forth in the sequence listing contained herein. DNA encoding variants of the polypeptides in other WNV strains may likewise be cloned, e.g., using PCR and oligonucleotide primers derived from the sequence herein disclosed.

For example, it may be particularly desirable to isolate the genes encoding WNV polypeptides from any isolates that may differ antigenically in order to obtain a broad spectrum of different epitopes which would be useful in the methods and compositions of this invention.

Oligonucleotide primers and other nucleic acid probes derived from the genes encoding the polypeptides in the compositions of this invention may also be used to isolate and clone related proteins from other WNV isolates which may contain regions of DNA sequence homologous to the DNA sequences of the polypeptides described in this invention.

In another embodiment, the polypeptides used in the compositions of this invention are produced recombinantly and may be expressed in unicellular hosts. As is well known to one of skill in the art, in order to obtain high expression levels of foreign DNA sequences in a host, the sequences are generally operably linked to transcriptional and translational expression control sequences that are functional in the chosen host. Preferably, the expression control sequences, and the gene of interest, will be contained in an expression vector that further comprises a selection marker.

The DNA sequences encoding the polypeptides used in the compositions of this invention may or may not encode a signal sequence. If the expression host is eukaryotic, it generally is preferred that a signal sequence be encoded so that the mature glycoprotein is secreted from the eukaryotic host.

An amino terminal methionine may or may not be present on the expressed polypeptides in the compositions of this invention. If the terminal methionine is not cleaved by the expression host, it may, if desired, be chemically removed by standard techniques.

A wide variety of expression host/vector combinations may be employed in expressing the DNA sequences encoding the WNV polypeptides used in the pharmaceutical compositions and vaccines of this invention. Useful expression vectors for eukaryotic hosts, include, for example, vectors comprising expression control sequences from SV40, bovine papilloma virus, adenovirus, adeno-associated virus, cytomegalovirus and retroviruses including lentiviruses. Useful expression vectors for bacterial hosts include bacterial plasmids, such as those from E. coli, including pBluescript®, pGEX-2T, pUC vectors, col E1, pCR1, pBR322, pMB9 and their derivatives, pET-15, wider host range plasmids, such as RP4, phage DNAs, e.g., the numerous derivatives of phage lambda, e.g. λGT10 and λGT11, and other phages. Useful expression vectors for yeast cells include the 2μ plasmid and derivatives thereof. Useful vectors for insect cells include pVL 941.

In addition, any of a wide variety of expression control sequences-sequences that control the expression of a DNA sequence when operably linked to it-may be used in these vectors to express the polypeptides used in the compositions of this invention. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast-mating system and other constitutive and inducible promoter sequences known to control the expression of genes of prokaryotic or eukaryotic cells or their viruses, and various combinations thereof.

In another embodiment, a DNA sequence encoding a WNV polypeptide used in a pharmaceutical composition of this invention is cloned in the expression vector lambda ZAP® II (Stratagene, La Jolla, Calif.), in which expression from the lac promoter may be induced by IPTG.

In yet another embodiment, a DNA sequence encoding a WNV polypeptide, preferably the WNV E glycoprotein, that is used in a composition of this invention is cloned in the pBAD/Thiofusion™ expression vector, in which expression of the resulting thioredoxin fusion protein from the araBAD promoter may be induced by arabinose.

In another preferred embodiment, DNA encoding the WNV polypeptides used in a composition of this invention is inserted in frame into an expression vector that allows high level expression of the polypeptide as a glutathione S-transferase fusion protein. Such a fusion protein thus contains amino acids encoded by the vector sequences as well as amino acids of the WNV polypeptide.

The term "host cell" refers to one or more cells into which a recombinant DNA molecule is introduced. Host cells of the invention include, but need not be limited to, bacterial, yeast, animal, insect and plant cells. Host cells can be unicellular, or can be grown in tissue culture as liquid cultures, monolayers or the like. Host cells may also be derived directly or indirectly from tissues.

In an embodiment of the instant invention, an insect cell line, such as a mosquito cell line, is used in conjuction with an appropriate expression vector to express and produce the WNV E glycoprotein antigen. One of ordinary skill in the art will appreciate that a eukaryotic host line, such as yeast, plant, insect and mammalian cells can be necessary to achieve glycosylation of the WNV polypeptide. Further, since a mosquito is the natural host of WNV, it will be recognized that an insect host for the expression and production of a WNV antigen may be optimal. Although prokaryotic cells provide certain advantages with respect to ease of genetic manipulation, cell growth, and product yield, there is no capacity for glycosylation (at least in naturally-occurring prokaryotic cells). Glycosylation of eukaryotic or viral proteins raised in eukaryotic cells, such as the WNV E glycoprotein, can affect protein folding, sorting, stability, protease resistance, secretion and immunogenicity. Therefore, one of ordinary skill in the art will recognize that glycosylation of the viral antigen of the instant invention can be necessary to achieve an authentic three-dimensional structure, thereby promoting optimal cross-reactivity of the antigen. A discussion of use of various types of host cell lines and corresponding expression vectors for the expression of antigens may be found in J. Schmitt and W. Papisch, *Autoimmunity Reviews*, 1: 79-88 (2002).

A wide variety of unicellular host cells are useful in expressing the DNA sequences encoding the polypeptides used in the pharmaceutical compositions of this invention. These hosts may include well known eukaryotic and prokaryotic hosts, such as strains of *E. coli, Pseudomonas, Bacillus, Streptomyces*, fungi, yeast, insect cells such as *Spodoptera frugiperda* (SF9), animal cells such as CHO and mouse cells, African green monkey cells such as COS 1, COS 7, BSC 1, BSC 40, and BMT 10, and human cells, as well as plant cells.

A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer.

An "expression control sequence" is a nucleic acid sequence which regulates gene expression (i.e., transcription, RNA formation and/or translation). Expression control sequences may vary depending, for example, on the chosen host cell or organism (e.g., between prokaryotic and eukaryotic hosts), the type of transcription unit (e.g., which RNA polymerase must recognize the sequences), the cell type in which the gene is normally expressed (and, in turn, the biological factors normally present in that cell type).

A "promoter" is one such expression control sequence, and, as used herein, refers to an array of nucleic acid sequences which control, regulate and/or direct transcription of downstream (3') nucleic acid sequences. As used herein, a promoter includes necessary nucleic acid sequences near the start site of transcription, such as, in the case of a polymerase II type promoter, a TATA element.

A "constitutive" promoter is a promoter which is active under most environmental and developmental conditions. An "inducible" promoter is a promoter which is inactive under at least one environmental or developmental condition and which can be switched "on" by altering that condition. A "tissue specific" promoter is active in certain tissue types of an organism, but not in other tissue types from the same organism. Similarly, a developmentally-regulated promoter is active during some but not all developmental stages of a host organism.

Expression control sequences also include distal enhancer or repressor elements which can be located as much as several thousand base pairs from the start site of transcription. They also include sequences required for RNA formation (e.g., capping, splicing, 3' end formation and polyadenylation, where appropriate); translation (e.g., ribosome binding site); and post-translational modifications (e.g., glycosylation, phosphorylation, methylation, prenylation, and the like).

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

It should of course be understood that not all vectors and expression control sequences will function equally well to express the WNV polypeptides mentioned herein. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered.

In selecting an expression control sequence, a variety of factors should also be considered. These include, for example, the relative strength of the promoter sequence, its controllability, and its compatibility with the DNA sequence of the peptides described in this invention, in particular with regard to potential secondary structures. Unicellular hosts should be selected by consideration of their compatibility with the chosen vector, the toxicity of the product coded for by the DNA sequences encoding the glycoproteins used in a pharmaceutical composition of this invention, their secretion characteristics, their ability to fold the polypeptide correctly, their fermentation or culture requirements, and the ease of purification from them of the products coded for by the DNA sequences.

Within these parameters, one of skill in the art may select various vector/expression control sequence/host combinations that will express the DNA sequences encoding the products used in the pharmaceutical compositions of this invention on fermentation or in other large scale cultures.

The polypeptides described in this invention may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of ordinary skill in the art may select the most appropriate isolation and purification techniques without departing from the scope of this invention. If the polypeptide is membrane bound or suspected of being a lipoprotein, it may be isolated using methods known in the art for such proteins, e.g., using any of a variety of suitable detergents.

In a preferred embodiment, the WNV E glycoprotein of the instant invention is expressed in an insect cell line, such as a mosquito cell line, using an appropriate vector capable of replicating and expressing cloned genes therefrom. The purification of the WNV E glycoprotein will not utilize harsh techniques that denature or deform the antigen such as polyethylene glycol precipitation or acetone extraction. Instead, the present embodiment relates to the use of column chromatography methods, such as size-exclusion or affinity chromatography, to produce a substantially purified antigen that has an authentic and native conformation and/or three-dimensional structure.

In addition, the polypeptides of the invention may be generated by any of several chemical techniques. For example, they may be prepared using the solid-phase synthetic technique originally described by R. B. Merrifield, *J Am Chem Soc*, 83, pp. 2149-54 (1963), or they may be prepared by synthesis in solution. A summary of peptide synthesis techniques may be found in E. Gross & H. J. Meinhofer, 4 *The Peptides: Analysis, Synthesis, Biology; Modern Techniques Of Peptide And Amino Acid Analysis*, John Wiley & Sons, (1981) and M. Bodanszky, *Principles Of Peptide Synthesis*, Springer-Verlag (1984).

Typically, these synthetic methods comprise the sequential addition of one or more amino acid residues to a growing peptide chain. Often peptide coupling agents are used to facilitate this reaction. For a recitation of peptide coupling agents suitable for the uses described herein see M. Bodansky, supra. Normally, either the amino or carboxyl group of the first amino acid residue is protected by a suitable, selectively removable protecting group. A different protecting group is utilized for amino acids containing a reactive side group, e.g., lysine. A variety of protecting groups known in the field of peptide synthesis and recognized by conventional abbreviations therein, may be found in T. Greene, *Protective Groups In Organic Synthesis*, Academic Press (1981).

To screen the polypeptides or fragments thereof according to this invention for their ability to confer protection against WNV infection or their ability to reduce the severity or duration of the attendant symptoms, mice are preferred as an animal model. Of course, while any animal that is susceptible to WNV infection may be useful, mice are a well-known and particularly convenient model. Thus, by administering a particular WNV polypeptide or anti-WNV polypeptide antibody to mice, one of skill in the art may determine without undue experimentation whether that polypeptide or antibody would be useful in the methods and compositions claimed herein.

The administration of the WNV polypeptide or antibody of this invention to the animal may be accomplished by any of the methods disclosed herein or by a variety of other standard procedures. For a detailed discussion of such techniques, see *Antibodies, A Laboratory Manual*, supra. Preferably, if a polypeptide is used, it will be administered with a pharmaceutically acceptable adjuvant, such as complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

According to yet another embodiment, the WNV polypeptides used in the compositions of this invention, preferably, are useful as diagnostic agents for detecting immunity to WNV, and recent, current, or prior infection by a flavivirus, especially WNV, JEV, SLEV or DENV. The polypeptides are capable of binding to antibody molecules produced in animals, including humans, that have been exposed to a flavivirus, especially WNV, JEV, SLEV or DENV, as a result of infection with said flavivirus or from vaccination. The detection of WNV or flavivirus antigens is evidence of prior exposure to a flavivirus infection or vaccine. Such information is an important aid in the diagnosis of WNV infection.

Such diagnostic agents may be included in a kit which may also comprise instructions for use and other appropriate reagents, preferably a means for detecting when the polypeptide or antibody is bound. For example, the polypeptide may be labeled with a detection means that allows for the detection of the polypeptide when it is bound to an antibody, or for the detection of the antibody when it is bound to WNV or an antigen thereof.

The detection means may be a fluorescent labeling agent such as fluorescein isocyanate (FIC), fluorescein isothiocyanate (FITC), and the like, an enzyme, such as horseradish peroxidase (HRP), glucose oxidase or the like, a radioactive element such as $^{125}I$ or $^{51}Cr$ that produces gamma ray emissions, or a radioactive element that emits positrons which produce gamma rays upon encounters with electrons present in the test solution, such as $^{11}C$, $^{15}O$, or $^{13}N$. Binding may also be detected by other methods, for example via avidin-biotin complexes. Further, the labeling agent may be any enzyme included in the groups oxidases (such as horse radish peroxidase), luciferases, peptidases (such as caspase-3), glycosidases (such as beta-galactosidase) and phosphatases (such as alkaline phosphatase).

The linking of the detection means is well known in the art. For instance, monoclonal antibody molecules produced by a hybridoma can be metabolically labeled by incorporation of radioisotope-containing amino acids in the culture medium, or polypeptides may be conjugated or coupled to a detection means through activated functional groups.

The diagnostic kits of the present invention may be used to detect the presence of antibodies against flaviviruses, especially WNV, JEV, SLEV or DENV, in a body fluid sample such as serum, plasma, urine, or spinal fluid. In various embodiments of the instant invention, a substantially pure WNV polypeptide having an authentic conformation is bound to a solid support typically by adsorption from an aqueous medium. Useful solid matrices are well known in the art, and include crosslinked dextran; agarose; polystyrene; polyvinylchloride; cross-linked polyacrylamide; nitrocellulose or nylon-based materials; tubes, plates or the wells of microtiter plates. The polypeptides of the present invention may be used as diagnostic agents in solution form or as a substantially dry powder, e.g., in lyophilized form. In another preferred embodiment, the instant invention provides an antigen, such as WNV E glycoprotein, coupled to a solid matrix in the form of a bead or microsphere, such as those available from Luminex Corporation (Austin, Tex.). Coupling may be to the surface of the microsphere or to an internal surface that is accessible from the outside surface.

The method of attachment of antigens to microsphere beads are known in the art. Antigens can be coupled to beads such as those provided by Luminex Corporation by a two-step carbodiimide process according to the manufacturer's recommendations. According to the instant invention, 50 micrograms of purified WNV E glycoprotein antigen (WNV-E) is coupled to the surface of $6.25 \times 10^6$ microspheres. Activation is initiated with 50 microliters of 50 mg/ml Sulfo-NHS followed by 50 microliters of 50 mg/ml EDC and a 20 minute incubation at room temperature. Coupling of the recombinant antigen takes place for 2 hours, in the dark, on a rotator at room temperature. Microspheres were washed by centrifugation, twice, in 1.0 ml PBS Azide blocking buffer, (PBN) composed of PBS, 1 BSA, 0.02% $NaN_3$.

In a preferred embodiment of the instant invention, a plurality of antigens can be used, each coupled to separate or the same microsphere beads. It is within the scope of the present invention for additional antigens of WNV or another flavivirus, such as, the membrane (M) protein or a non-structural (NS) protein, to be coupled to the microspheres. It will be recognized that incorporating additional antigens to the microspheres can enable the further ability to distinguish between related flaviviruses, such as WNV, JEV, SLEV, DENV strains, or tick-borne encephalitis virus. Different beads or different regions of beads can be tagged with fluorescent identifier tags, which allows for the coupling of specific antigens to specific fluorescent tag identifiers. This enables the methods of the instant invention to be carried out in a "multiplexing" approach, wherein more than one type of antigen is bound to the microspheres, which enables a multi-antigen assay to be carried out simultaneously. Use of the microsphere immunoassay approach also allows the method of the instant invention to be carried out in a high-throughput manner. High-throughput screening according to the method of the instant invention can be useful for large-scale screeing, such as screening large population sizes for epidemiological studies or screening blood banks or organs for samples contaminated with flaviviruses or WNV.

The present invention also encompasses fragments or portions of WNV polypeptides, which may provide more specific diagnostic reagents than full-length WNV polypeptides and thus may alleviate such pitfalls as false positive and false negative results. According to the inventor's own discoveries, a substantially pure WNV E glycoprotein having an authentic conformation is not only reactive against antibodies against WNV E glycoprotein, but strongly, reliably, predictably and consistently cross-reactive with antibodies against JEV, SLEV and DENV. Thus, in one embodiment, the WNV E glycoprotein is used in a diagnostic method for detecting a current or prior infection of a flavivirus, such as, WNV, DENV, JEV, or SLEV. Prior to the inventor's own research, WNV E glycoprotein was believed mainly to react specifically with antibodies to WNV. It was not reliably known to cross-react with antibodies against other flaviviruses, such as JEV, SLEV, or DENV, with greater sensitivity than JEV, SLEV, or DENV antigens prepared by polyethylene glycol precipitation and/or acetone extraction, which can cause denaturation.

One skilled in the art will realize that it may also be advantageous in the preparation of detection reagents to utilize epitopes from more than one WNV protein or more than one WNV isolate.

One of ordinary skill in the art will recognize that serodiagnosis of a WNV infection currently requires a series of enzyme-linked immunosorbent assays (ELISA) and viral plaque reduction neutralization (PRN) tests. It will be further recognized by one of ordinary skill in the art that currently used diagnostic methods available in the art require between 3 days and 3 weeks to obtain a reliable result. In a preferred embodiment, the instant invention provides a method for presumptive serodiagnosis of a WNV infection using a novel microsphere immunoassay that requires less than about 3 hours to obtain a reliable preliminary result. Further, the method of the instant invention requires as little as 10 microliters of biological sample and thus is not a wasteful method nor does the method require plentiful reaction reagents since the reaction volumes can be kept small.

According to the instant invention, antibodies elicited by WNV and certain other flaviviruses, such as, JEV, SLEV, and DENV, are detected in a recombinant WNV E glycoprotein microsphere immunoassay. "Immunoassay" refers to a method of detection of a specific antigen or a group of related or similar antigens through their ability to be recognized and bound by a specific antibody directed against them. It will be understood that antibody-antigen interactions are very specific and involves the recognition of and binding to specific epitopes of the antigen. One of ordinary skill in the art will appreciate that the bound antibody can be detected in a variety of different ways. In one example, the bound antibody, for example an IgM antibody, that is bound to the antigen being assayed can itself be detected by a second antibody that is capable of binding the first antibody, such as, for example, an anti-IgM antibody. The second antibody can be coupled to a detectable label, such as a fluorescent marker, or an enzyme, such as horse radish peroxidase.

According to one embodiment of the instant invention, the microsphere immunoassay can identify an infection by a flavivirus, such as, WNV, JEV, SLEV, or DENV, from a biological sample from a patient having no evidence of said infection in less than about 3 hours. Further, a recent or current infection can be determined following IgG depletion of and subsequent detection of IgM antibodies to said flaviviruses. Thus, it will be understood by one of ordinary skill in the art that the microsphere assay of the instant invention can used to identify suspect cases of WNV or flavivirus infection within 5 working hours. Accordingly, the microsphere immunoassay according to the instant invention would enable the replacement of eight separate assays, namely, MAC ELISA and IgG ELISA for WNV, JEV, SLEV, or DENV.

Further, results from testing for WNV and certain flavivirus infections would be available within less than one testing day, instead of 3 days as currently taught by the methods available in the art. A cost analysis for a test result on the microsphere immunoassay according to the instant invention, calculated on the basis of supplies and reagents while excluding the cost of the recombinant polypeptide of the instant invention and staff time was $0.24. Conversely, the cost per test result for the MAC ELISA is $4.84 and the cost per test result for the IgG ELISA is $5.25 (exluding antigen and monoclonal antibodies provided by the CDC and labor). Thus, the method of the instant invention provides a much less expensive alternative to current art methods of detection.

The microsphere immunoassay of the instant invention requires less labor and less time to generate 100 test results than the MAC ELISA or the IgG ELISA. The microsphere immunoassay of the instant invention could be combined with a subsequent virus-specific plaque reduction neutralization test used to provide information on the specific flavivirus of the infection.

In another embodiment of the subject invention, a microsphere-based suspension flow cytometric immunoassay is used to detect antibodies to a WNV envelope glycoprotein and antibodies to other certain flaviviruses, such SLEV, JEV, and DENV. The immunoassay uses a low serum volume (about 10 microliters) and exhibits a broad dynamic range of detection over two logarithms of antibody concentration with a high signal to noise ratio. Reaction kinetics are enhanced by incubations with continual shaking at 37° C., which enables the entire assay to be completed within 2.5 hours, depending upon the number of serum samples processed. One of ordinary skill in the art will understand that an optimal dilution of biological sample is about 1:25 to 1:250, preferably a dilution of 1:100.

In preferred embodiments of the present invention, an immunodepletion step is performed prior to testing a biological sample in order to remove a specific antibody population, such as an IgM or IgG antibody population. Immunodepletion can be carried out by contacting the biological sample with an antibody against the specific antibody subpopulation to be removed to form an insoluble complex which can be removed by a separation process, such as centrifugation. Accordingly, the instant invention can be used to determine recent or ongoing infections, for example, following IgG removal, or to detect a protective immune response, for example, following IgM removal.

The subject invention also provides for diagnostic kits, such as ELISAs, capable of detecting a WNV infection and infections by other certain flaviviruses, such as SLEV, JEV and DENV that include a purified and/or isolated polypeptide or fragment thereof from WNV, in particular, WNV E glycoprotein. As determined by the inventor's own research, a substantially purified WNV E glycoprotein having intact conformational epitopes is reactive to antibodies against WNV and also strongly, reliably, predictably and consistently cross-reactive to antibodies against other certain flaviviruses, such as, DENV, SLEV and JEV. In contrast to the methods currently available in the art, ELISA antigens are partially denatured by acetone and contaminated with other proteins from the host cells from which the antigen was expressed or produced. Impure antigen provides more non-specific binding and lower detection signals than the pure antigen used in the assay of the present invention. One of ordinary skill in the art will appreciate the mechanics of an ELISA and further details thereof can be found in numerous scientific literature and protocol books, such as, for example, *The ELISA: Enzyme-Linked Immunosorbent Assay in Veterinary Research and Diagnosis (Current Topics in Veterinary Medicine and Animal Science, V. 22)*, R. C. Wardley (Editor), J. R. Crowther (Editor).

The diagnostic kits and methods for detecting antibodies against WNV and other flaviviruses are also useful for detecting a protective immune response to WNV or flavivirus infection. Further, the methods of the instant invention are also useful in monitoring the course of immunization against WNV and other flaviviruses. In patients previously inoculated with the vaccines against WNV or other flaviviruses, the detection means and methods disclosed herein are also useful for determining if booster inoculations are appropriate.

The diagnostic kit, such as an ELISA, can be self-contained, no laboratory equipment is needed. The advantages of such a kit are apparent, as it facilitates screening for antibodies to WNV or other certain flaviviruses at any time and virtually at any place, including remote geographic areas and those locations lacking a 24 hour testing facility.

The invention also contemplates that the diagnostic kits, such as ELISAs, can include a nonstructural protein of WNV, especially NS5, for the specific detection of WNV without cross-reactivity to other flaviviruses, including for example SLEV, JEV, and DENV. In addition, a nonstructural protein of DENV, especially NS5, is contemplated for the diagnostic kits of the present invention to be used to specifically detect an infection of DENV. DENV NS polypeptides of a first particular strain show specificity for antibodies raised against the same first DENV strain and are not cross-reactive with antibodies against other DENV strains. For example, NS of DENV-1 will show specificity to anti-DENV-1 sera, but will not be reactive with sera raised against DENV-2, -3, or -4. In addition, like WNV NS proteins, the DENV NS polypeptides are not substantially cross-reactive with antibodies against one or more members of the genus *Flavivirus*, such as, for example, JEV, SLEV, or WNV. Thus, the DENV NS can be used to discriminate between a general flavivirus infection and a DENV infection. In addition, since the antibodies to DENV NS proteins are not persistent, the DENV NS proteins can be used to detect recently acquired infections or current infections.

The diagnostic kits and methods for detecting antibodies against WNV, DENV and other flaviviruses are also useful for detecting a protective immune response to WNV or flavivirus infection. Further, the methods of the instant invention are also useful in monitoring the course of immunization against WNV and other flaviviruses. In patients previously inoculated with the vaccines against WNV or other flaviviruses, the detection means and methods disclosed herein are also useful for determining if booster inoculations are appropriate.

The diagnostic kit can be self-contained, no laboratory equipment is needed, such as with ELISAs. The advantages of such a kit are apparent, as it facilitates screening for antibodies to WNV or other certain flaviviruses at any time and virtually at any place, including remote geographic areas and those locations lacking a 24 hour testing facility.

In a further embodiment, the diagnostic methods of the instant invention can be carried out using a lateral flow immunoassay. A lateral flow immunoassay (immunochromatographic test) comprising a simple lateral flow device can be used to rapidly detect antibodies present in a biological sample against a flavivirus antigen, such as WNV E glycoprotein, WNV NS5, or DENV NS5. Such a device consists of a membrane strip, with the membrane typically of nitrocellulose, cellulose acetate or nylon, through which the serum (i.e., biological) sample, buffer, and detection reagent (antigen-coated microparticles) flow by capillary action. The membrane strip further comprises a reagent application pad onto which a biological sample and an antigen-coupled microparticle can be applied. The microparticles can be of known form, size or constitution deemed useful to one of ordinary skill in the art, such as polystyrene, fluorescently-labeled polystryrene, magnetic, latex, or any such polymer.

The membrane strip can be further divided into "zones," which are specific regions of the membrane strip wherein an immunological reaction takes place between an antigen-coated microparticle and an antibody. In a preferred embodiment, the test zones are coated with an anti-immunoglobulin antibody population, such as, anti-human IgG or anti-human IgM antibodies, which can be located at different positions along the test membrane. According to the present embodiment, the membrane strip also comprises a positive control zone containing an antibody against the antigen of interest, such as a monoclonal/polyclonal antibody reactive against WNV E glycoprotein antigen, WNV NS5 antigen, or DENV NS5 antigen. The invention, however, is not meant to be limited to the detection of antibodies against WNV E and NS5 or DENV NS5, but rather antibodies to any flavivivirus antigen, especially a flavivirus E glycoprotein or NS5 antigen, could be detected using the membrane strip method of the invention, such as antibodies against JEV and SLEV antigens.

In another embodiment, an antigen of interest, such as a flavivirus antigen, especially WNV E glycoprotein, WNV NS5, or DENV NS5, are adsorbed or alternately dried to the surface of the membrane strip. The membrane strip can be of any suitable material known in the art, such as, for example nitrocellulose, cellulose acetate or nylon. Preferably, the antigens are adsorbed or dried to the surface of the membrane strip in separate zones to enable separate detection of antibody types, such as IgG or IgM antibodies, that will bind to the antigen during the course of the membrane strip assay. In this embodiment, a biological sample, such as a bodily fluid, blood, serum, plasma, saliva, tears, feces, semen, mucous, tissue, tissue homogenate, cellular extract, or spinal fluid, containing anti-flavivirus antigen antibodies, such as IgG anti-NS5, IgM anti-NS5, IgG anti-WNV E, or IgM anti-WNV E, would be applied to the membrane strip at one end to allow the sample to move through the membrane. Antibodies contained in the biological sample against the flavivirus antigens of the membrane strip, such as IgG or IgM antibodies, will recognize, interact with, and bind to said antigens. One of skill in the art will appreciate that certain biological samples, such as a bodily fluid, blood, serum, plasma, saliva, tears, feces, semen, mucous, tissue, tissue homogenate, cellular extract, or spinal fluid, may require certain preparatory steps prior to applying the the membrane strip to enable the sample to flow through the membrane strip. Such pretreatment includes, but is not limited to, dilution or removal of particulate matter. Once the anti-flavivirus antibodies present in the sample have bound to the flavivirus antigens of the membrane strip, a detection reagent comprising secondary antibody-coupled microparticles, such as anti-human IgG or IgM antibody-coupled microparticles, are applied to the membrane strip to detect the anti-flavivirus antibodies already bound to the flavivirus antigens.

One of ordinary skill in the art will recognize that the key components of one embodiment of a lateral flow device consist of:

1) a membrane strip consisting of modified nitrocellulose, cellulose acetate or nylon to which the detection reagent, consisting of antigen-coupled microparticles and a biological sample containing antibodies that recognize the antigen is applied;
2) a test zone of anti-immunoglobulin capture antibodies, immobilized at a specific zone, or location on the membrane, wherein capture of the detection reagent at this zone gives a colored pattern and indicates the presence of antibodies of interest; and
3) a control zone of antibodies specific for the antigen under study, immobilized in a second zone on the membrane, wherein capture of the detection reagent at this zone gives a visual pattern and shows that the test was successfully completed.

The detection reagent, which consists of antigen-coupled microparticles, such as colored latex or metal beads, can be detected visually. The detection reagent is applied with special releasing agents and dried near the bottom of the membrane strip. The microparticles can be applied directly to the membrane, or they can be applied to an absorbent pad that is in contact with the membrane. When a biological sample is introduced to the antigen-coupled microparticles, anti-antigen antibodies, such as, for example anti-antigen IgG or IgM antibodies, present in the biological sample bind to the antigen-coupled microparticles. The microparticles are then carried through the membrane strip by capillary action and come into contact with the secondary antibodies coupled at each of the zones along the strip, wherein the secondary antibodies recognize the specific types of anti-antigen antibodies bound to the antigen-coupled microparticle, such as anti-human IgG or IgM antibodies. It will be appreciated that the membrane strip can be provided with absorbent pads located at the top of the membrane to act as a reservoirs of buffer or fluid so that the biological sample/antigen-coupled microparticles flow continuously through the membrane coming into contact with each zone of the membrane strip.

One of ordinary skill in the art will understand that all of the components and reagents that go into a lateral flow device must be chosen with care and matched during research and development of the test to ensure adequate sensitivity, stability and reliability of the finished test device. When properly constructed, these tests are sturdy and reliable, but they are delicately balanced, and even minor changes in materials, reagent processing or raw material specifications can cause significant loss in test performance. A discussion of lateral flow methodology may be found in L. B. Bangs, Manual for The Latex Course, Bangs Laboratories, Inc., Carmel, Ind. (1996).

Figure 17:
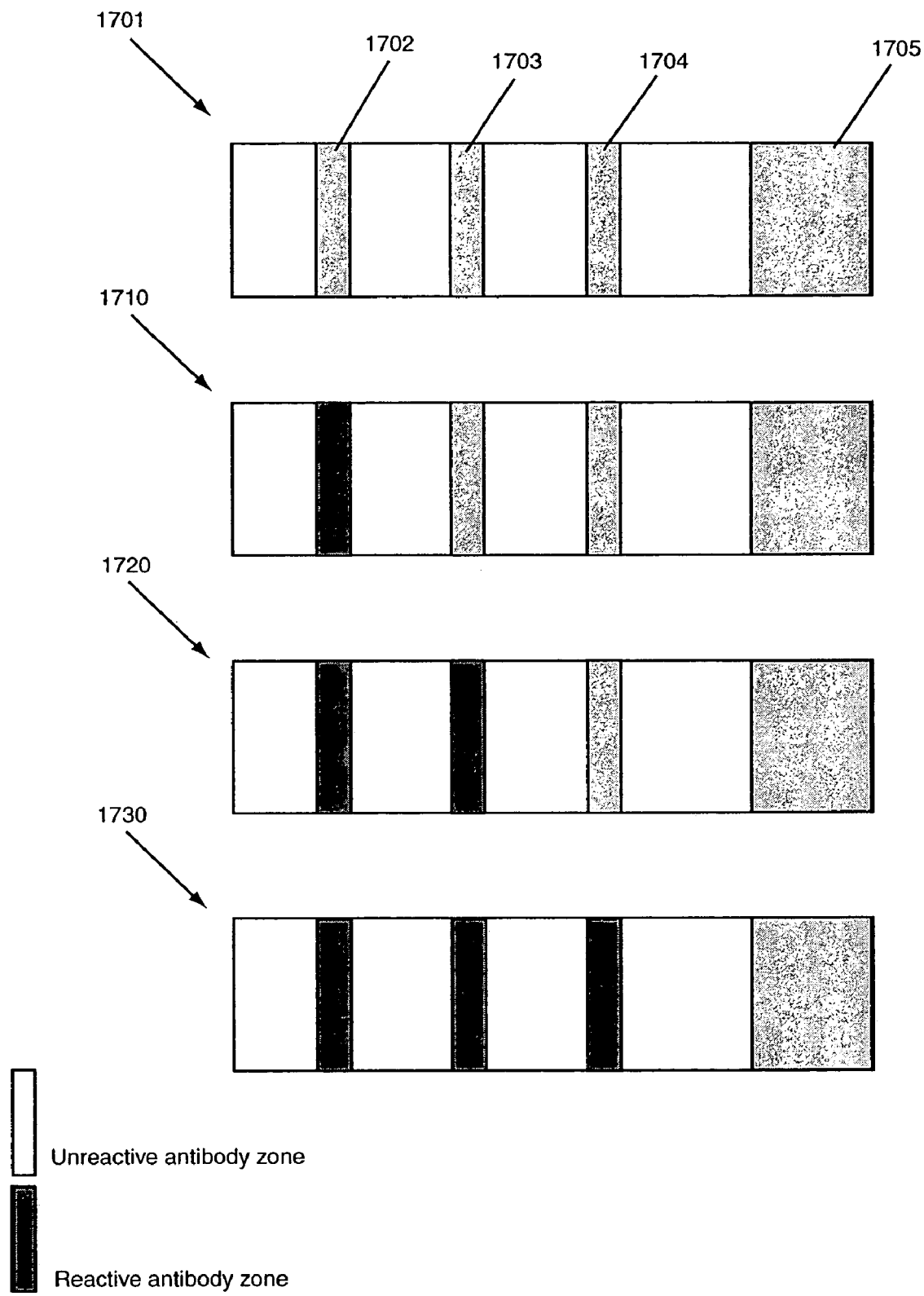
FIG. 17 shows a schematic of a lateral-flow or strip test for use in rapid detection of a flavivirus infection or rapid specific detection of a WNV infection according to the instant invention. See Detailed Description for further details.

In a preferred embodiment of the instant invention and referring to FIG. 17, the positive control zone (1702) of the membrane strip (1701) comprises anti-WNV E antigen antibodies, which can be monoclonal or polyclonal. A detection reagent, comprising a substantially pure antigen, such as WNV E glycoprotein, WNV NS5, or DENV NS5, each having an authentic conformation, are coupled to microparticles and applied to the reagent application pad (1705), along with a biological specimen, and a buffer. The microparticles can be colored polystyrene beads, fluorescently-labeled polystyrene beads, or metal particles, or any appropriate type known to one of skill in the art. In the case where the coupled antigen is WNV E glycoprotein, the coupled antigen is reactive with IgG and/or IgM antibodies against WNV and strongly cross-reactive with IgG and/or IgM antibodies against a flavivirus, especially, JEV, SLEV, or DENV, that may be present in the biological sample. In the case where the coupled antigen is WNV NS5 or DENV NS5, the coupled antigen is specifically reactive with IgG and/or IgM antibodies against WNV or DENV, respectively, but not cross-reactive with IgG and/or IgM antibodies against another flavivirus that may be present in the biological sample. Further, DENV NS5 is specific for antibodies against the same DENV strain from which it is isolated and not cross-reactive with antibodies to other DENV strains. For example, DENV-1 NS5 is specific for antibodies against DENV-1, but not cross-reactive with antibodies against DENV-2, -3, or -4. It will be appreciated that the DENV NS5 antigens thus can be used to discriminate the four different known DENV strains.

The detection reagent (further bound to IgG and/or IgM antibodies, if present in the biological sample) migrate up through the membrane strip by capillary action and successively come into contact with different antibody-containing zones. For example, the detection reagent first comes into contact with zone 1704, which can be coated with anti-IgM antibodies (such as, goat anti-human IgM antibodies). The detection reagent will bind to zone 1704 through the binding interaction between the zone 1704 anti-IgM antibodies and IgM antibodies of the detection reagent, if present. The detection reagent will also come into contact with zone 1703, which can be coated with anti-IgG antibodies (such as goat anti-human IgG antibodies). The detection reagent will bind to zone 1703 through the binding interaction between the zone 1703 anti-IgG antibodies and IgG antibodies of the detection reagent, if present. Further, the detection reagent will come into contact with and bind to zone 1702, a control zone coated with antibodies specific for the antigen of the detection reagent. The results of the flow immunoassay can be determined visually since the microparticles are held at zones 1702, 1703 and 1704 through antibody-antibody or antibody-antigen interactions.

One of ordinary skill in the art will appreciate that the instant invention encompasses any suitable configuration of the membrane strip test (immunochromatographic test). For example, the antigen of interest, such as a flavivirus antigen (e.g. WNV NS5, WNV E, or DENV NS5), can be coupled either to the microparticle or directly to the membrane strip. If the antigen of interest is coupled to the microparticle, detection of any anti-antigen antibodies present in a biological sample can be conducted by coupling a secondary antibody, such as anti-human IgG or IgM antibodies, to a specific location or zone on the membrane strip. In this case, as the antigen-coated microparticles are allowed first to interact with a biological sample containing anti-antigen antibodies such that the anti-antigen antibodies bind to the antigens of the coated microparticles. Next, the microparticles migrate through the membrane strip. The microparticles will be captured at the zones of the strip containing the secondary antibodies vis-à-vis binding interactions between the secondary antibody (e.g., anti-human IgG or IgM antibody) and the anti-antigen antibody bound from the sample bound to the antigen-coupled microparticle. The captured microparticles can be directly visualized by inspection thereby confirming either the presence or absence of anti-antigen antibodies in the biological sample. One of ordinary skill in the art will also appreciate that the antigens of interest can also be adsorbed or dried onto the surface of the membrane strip. In this case, the secondary antibodies would be coupled to the microparticles.

In various embodiments described herein, the flavivirus antigens of the instant invention, especially WNV E glycoprotein, WNV NS5, and DENV NS5, are covalently coupled to a microparticle. Microparticles can include, but are not limited to, polystyrene microparticles, colored or fluorescently labeled polystryene microparticles, latex and colored latex microparticles, paramagnetic microparticles, metal particles, such as gold, glass microparticles, and plastic microparticles. One of ordinary skill in the art will understand that "microparticles" one in the same as "microspheres" or "uniform latex particles." The inventor has further discovered that the antigens of the instant invention, especially WNV E glycoprotein, WNV NS5 and DENV NS5, are highly stable when coupled to microparticles, especially polystyrene microparticles. The data of FIG. 9 and a plot of 1I/T90 (time to 90% potency of reagent) against 1/T (Kelvin) gives an estimated T90 of three months. Further, the inventor has discovered that in practice, the stability of the antigen-coupled microparticles is greater than three months.

In various embodiments of the instant invention, WNV E glycoprotein-coupled or NS5-coupled microspheres are used in a microsphere immunoassay to detect antibodies against a flavivirus, especially WNV, JEV, SLEV, or DENV, in a biological sample. The WNV E glycoprotein is substantially pure and of native conformation, which allows for strong cross-reactivity of the WNV E glycoprotein among flaviviruses, especially WNV, JEV, SLEV, and DENV. Any kind of microsphere immunoassay known in the art is within the scope of the present invention, such as, but not limited to, agglutination assays, slide tests, lateral flow tests (previously described), or fluorescence-based assays, such as flow cytometric analyses and Luminex-based immunoassays (Austin, Tex.). A discussion of different immunoassays known in the art may be found in L. B. Bangs, Manual for The Latex Course, Bangs Laboratories, Inc., Carmel, Ind. (1996).

One of ordinary skill in the art will understand that microsphere-based immunoassays can be both qualitative and quanitative and are usually based upon a very specific interaction of antigen (Ag) with antibody (Ab). Sub-micron sized polystyrene microspheres are used as a solid support. The microspheres act to magnify or amplify the Ag-Ab reaction which takes place when they are mixed with a sample containing the opposite reactant.

The Luminex microsphere immunoassay allows the performance of multiplex analysis to detect antibodies against multiple antigens in a single tube. The antigens of the instant invention, especially the WNV E glycoprotein, WNV NS5, and DENV NS5 described above, can be covalently linked to microsphere beads containing different fluorochromes. During the assay readout, the first laser excites the intrinsic fluorochrome in the antigen-bearing microspheres, allowing identification of each bead in the assay mixture. The second laser excites the fluorochrome tag of the reporter molecule, measuring the level of antibodies that bind to the specific antigen. The multiplex assay should allow simultaneous primary and confirmatory diagnosis of a flavivirus infection, especially WNV, DENV, and other flaviviruses such as JEV and SLEV. About 100 different types of fluorescent polystyrene microspheres are commercially available (Luminex, Austin, Tex.). In principle, one can perform a multiplex analysis of up to 100 analytes. In practice, most multiplex immunoassays have included up to 20 analytes measured at one time. This technology should be useful for simultaneous detection of multiple pathogens in clinical laboratories.

Upon virus infection, the immune system first develops conformational epitopes. Antibodies against linear epitopes are produced later, as virus particles are broken down and presented in the context of the T cell receptors and major histocompatibility complex molecules on the surfaces of infected cells. Therefore, epitope mapping of various parts of structural and NS proteins is a good strategy by which to identify virus-type specific peptides. Synthetic peptides representative of linear, virus-type specific epitopes may be used as antigens for specific diagnosis of the particular virus. It should be borne in mind that the use of synthetic peptides as antigens may result in high background in immunoassays, depending upon the length of the peptide and the ionic strength of assay buffers. However, in combination with antigens that have native conformation (e.g., recombinant NS5), such virus-type specific peptide could add another layer of specificity to the current serological diagnosis.

Agglutination tests are portable, rapid, efficient, and useful under the most primitive conditions, e.g., when no laboratory equipment is available, such as a flow cytometer or a Luminex machine (Austin, Tex.). Diagnosis can occur quickly and simply (2 minutes from sample preparation). Diagnosis and treatment can commence promptly, before the patient is transferred or discharged. Agglutination tests can include liquid reagents made with plain, white microspheres. Tests can be run on either reusable glass slides or on disposable plastic or coated paper cards. These tests often require to operator to constantly mix the sample for several minutes to achieve agglutination, which is visually detectable following the formation of particulate clumps.

Slide tests, such as Roche's OnTrak™ (F. Hoffmann-La Roche Ltd, Basel, Switzerland) device, are more recent refinements of agglutination tests. In the slide test, the sample and reagent with coated microspheres are mixed and guided into a "track" or capillary. As the reactants move down the track by capillary action, they mix. Agglutination is detected with transmitted light one the sample travels towards the end of the slide. The test is mainly operator-independent, and therefore is more amendable to automation. The microspheres used can also be dyed or fluorescent to provide different contrasting colors to improve detection.

One of ordinary skill in the art will understand that slide tests and/or lateral flow immunoassays are synonymous with immunochromatographic tests. More discussion on immunochromatographic tests may be found in: L. Kittigul and K. Suankeow. Eur. J. Clin. Microbiol. Infect. Dis. 21:224-226 (2002); Tsuda, S., et al. Plant Disease 76, 466-469 (1992); Brown, W. E. I., Safford, S. E. & Clemens, J. M. Solid-Phase Analytical Device and Method for Using Same, U.S. Pat. No. 5,160,701, Nov. 3, 1992; Cole, F. X., MacDonnell, P. C. & Cicia, N. J., Porous Strip Form Assay Device Method, U.S. Pat. No. 5,141,850, Aug. 25, 1992; Fan, E., et al. Immunochromatographic Assay and Method of Using Same, WO 91/12336, Aug. 22, 1991; imrich, M. R., Zeis, J. K., Miller, S. P. & Pronovost, A. D. Lateral flow medical diagnostic assay device U.S. Pat. No. 5,415,994, May 16, 1995; and May, K., Prior, M. E. & Richards, I. Immunoassays and Devices Therefore, International Patent Number: WO 88/08534, Nov. 3, 1988.

Agglutination can be quantitated using instruments such as spectrophotometers and nephelomters to measure transmitted, absorbed, or scattered light, as a result of protein precipitation of the agglutination process.

With Luminex-based immunoassay technology, molecular reactions take place on the surface of microscopic beads called microspheres. For each reaction, thousands of molecules are attached to the surface of internally color-coded microspheres. The assigned color-code identifies the reaction throughout the test.

The magnitude of the biomolecular reaction is measured using a second molecule called a reporter. The reporter molecule signals the extent of the reaction by attaching to the molecules on the microspheres. Because the reporter's signal is also a color, there are two sources of color, the color-code inside the microsphere and the reporter color on the surface of the microsphere.

To perform a test, the color-coded microspheres, reporter molecules, and sample are combined. This mixture is then injected into an instrument that uses microfluidics to align the microspheres in single file where lasers illuminate the colors inside and on the surface of each microsphere. Next, advanced optics capture the color signals. Finally, digital signal processing translates the signals into real-time, quantitative data for each reaction. Further descriptions of Luminex-based immunoassays may be found in U.S. Pat. Nos. 6,449,562, 6,411,904, 6,268,222, 6,139,800, 5,981,180 and 5,736,330.

It will be recognized by one of ordinary skill in the art that the methods set forth in the present application are not limited to the use of WNV E glycoprotein, WNV NS5, or DENV NS5, to detect antibodies to flaviviruses specific to WNV or DENV. In contrast, the development of the microsphere immunoassay according to the present invention can be expanded to achieve other efficiencies in serologic testing for infectious diseases and/or autoimmune diseases where symptoms and geographic location of vectors and reservoirs are held in common, or when a need exists to test sera for exposure to multiples agents in a time-effective manner.

It will also be appreciated to one of ordinary skill in the art that the detection methods of the instant invention can be carried out using any known assay format readily available, such as, for example, an ELISA. ELISA methods are well known in the art. Example 26 sets forth further description on the application of ELISA with the antigens and methods of the present invention.

A better understanding of the present invention and of its many advantages will be had from the following examples which further describe the present invention and given by way of illustration. The examples that follow are not to be construed as limiting the scope of the invention in any manner. In light of the present disclosure, numerous embodiments within the scope of the claims will be apparent to those of ordinary skill in the art.

EXAMPLES

The following Materials and Methods Were Used in the Examples that Follow.

Reagents

Recombinant West Nile envelope glycoprotein antigen, provided by $L^2$ Diagnostics, New Haven, Conn., was expressed in a eukaryotic cell expression system and purified by column chromatography. N-Hydroxysuccinimide (Sulfo-NHS) and 1-ethyl-3-(3-dimethylamino-propyl) carbodiimide-HCL (EDC) were obtained from Pierce, Rockford, Ill. PBS with Tween 20, pH 7.4 (PBS-T); PBS with bovine serum albumin (BSA) (PBS-BSA), pH 7.4; PBS and Ultra Sodium Azide were from Sigma/Aldrich, St. Louis, Mo.

Goat F(ab')$_2$ anti-human immunoglobulins, IgG+IgA+IgM conjugated to red-phycoerythrin (R-PE); goat F(ab')$_2$ anti-human IgG R-PE conjugate; and goat F(ab')$_2$ anti-human IgM R-PE conjugate were from Bio-Source International, Camarillo, Calif.

Supplies and Equipment

A Luminex 100 flow analyzer was from Luminex Corporation, Austin, Tex. CL1/CL2 calibration microspheres, RP1 calibration microspheres, and multi-analyte microspheres with carboxylated surface were also obtained from Luminex Corporation. Multiscreen filter plates with 1.2 micron Durapore filters and a multiscreen vacuum manifold were from Millipore, Bedford, Mass. Slide-A-Lyzer mini-dialysis unit floats were from Pierce, Rockford, Ill. A Labquake Thermolyne tube rotator was from VWR, Bridgeport, N.J. Costar opaque black EIA/RIA plates with breakaway strips/wells, were from Corning Inc., Corning, N.Y. An ultrasonic cleaner (sonicator) was from Cole-Palmer, Vernon Hills, Ill.

Human Sera

Patient sera previously tested for WNV antibodies by the MAC ELISA and the IgG ELISA were coded, with all patient identifiers removed, and were provided from the serum bank at the Wadsworth Center, of the New York State Department of Health, or by the Arbovirus Laboratory of the Centers for Disease Control and Prevention of the United States Public Health Service (CDC), Ft. Collins, Colo. All sera were tested and evaluated under conditions approved by the Institutional Review Board of the New York State Department of Health.

Sera from Wadsworth Center archives were chosen to establish normal MIA ranges for positive and negative samples. Ten sera were selected on the basis of positive results in standard WN virus ELISA assays. WNV and St. Louis encephalitis virus (SLEV) PRN test results for paired acute and convalescent sera confirmed WNV as the infecting agent. Ten sera that were negative for WNV antibodies in IgM-capture and IgG ELISAs were selected as negative control sera. For assay covariance studies, the 10 WNV patient sera were combined into a positive control serum pool, and the 10 negative sera were combined into a negative control serum pool.

A coded panel of 19 sera provided by the CDC Arbovirus Diseases Branch included: three sera from confirmed WNV encephalitis patients; six sera from SLEV patients; and 3 sera from dengue fever virus (DENV) patients. For 10 of 12 sera from infected patients, the infectious agent was confirmed by virus PRN tests using WNV, SLEV, or DENV. Cross-neutralization data classified the sera as specific for WNV, DENV or SLEV infections. Seven negative control sera were from presumed healthy subjects lacking evidence of previous flavivirus infection. The CDC provided ELISA data for these sera when the samples were decoded.

A third serum panel was from eight individuals vaccinated with three doses of JE-VAX (Connaught Laboratories, Missisauga, ON, Canada). These sera were from the Wadsworth Center Arbovirus Laboratory. JE-VAX is a licensed, formalin-inactivated Japanese encephalitis virus (JEV) vaccine. The vaccinated individuals had a history of occupational exposure to flaviviruses and, in some cases, prior vaccination against a flavivirus. The sera, which included pre- and post-vaccination sera, were tested for neutralizing antibodies in JEV PRN assays.

Another serum panel represented serial specimens from a patient with WNV infection confirmed by PRN tests. Blood specimens were collected 2, 18, 72, 260, and 430 days post-disease onset, and, by coincidence, 3 days prior to virus exposure.

A fifth serum panel included human sera that previously tested positive in standard serological assays for antibodies to Epstein Barr virus (EBV), cytomegalovirus (CMV), herpes simplex virus (HSV), human immunodeficiency virus (HIV), *Treponema pallidum* (the syphilis spirochete), *Borrelia burgdorferi*, *Anaplasma phagocytophilum*, autoimmune nuclear antigens (antinuclear antibodies), or rheumatoid factor. These sera were from frozen sera archived at the Wadsworth Center. The syphilis patient sera were negative in WNV or SLEV PRN tests performed at the Arbovirus Laboratory of the Wadsworth Center. Sixteen normal human sera were purchased from United States Biological (Swampscott, Mass.). Twelve additional sera from healthy individuals were from the Wadsworth Center or $L^2$ Diagnostics (New Haven, Conn.).

The Wadsworth Center provided sera from 833 patients with suspected viral encephalitis. These sera were submitted to the New York State Department of Health between June and November of 2002. These sera had previously been tested for antibodies to WNV using the IgM-capture and IgG ELISAs.

IgG or IgM were selectively depleted from serum specimens with goat anti-human IgG or goat anti-human IgM, respectively. For IgG depletions, 5 µl of serum was mixed with 45 µl of goat anti-human IgG (GullSORB from Meridian Diagnostics, Cincinnati, Ohio). The mixtures were centrifuged at 14,000×g to remove antibody-bound IgG. According to the manufacturer, this is sufficient to deplete IgG at concentrations up to 15 mg/ml, the upper limit of normal human IgG concentration. Removal of detectable IgG antibodies to WN virus was confirmed by negative results in WNV IgG ELISAs and indirect immunofluorescence assays with SLEV antigen on arbovirus slides (Focus Technologies, Cypress, Calif.).

A similar pretreatment with anti-IgM antibody depleted serum samples of IgM. Ten µl of serum was mixed with 10 µl 2.5 mg/ml goat anti-human Mu chain (Jackson ImmunoResearch Laboratories, Inc., West Grove, Pa.) prior to addition of 20 µl PBS and centrifugation for 4 min at 14,000×g to remove antibody-bound IgM.

Human Sera for WNVNS5 Studies

Five panels of human sera were used in this study. (i) WNV patient sera were from serum archives at the Wadsworth Center, New York State Department of Health. These sera had previously been tested WNV-positive by the IgM capture and indirect IgG ELISA for antibodies reactive to noninfectious recombinant antigen (Davis et al., Martin et al., Johnson A. J., et al.). (ii) Acute and convalescent paired sera from DEN patients were provided by the National Microbiology Laboratory, Health Canada. The patients are Canadian residents who got infected with DEN during recent travels to various geographical regions. These sera had been tested by HI assays and PRNT against DEN, Powassan (POW), or SLE virus. (iii) Forty SLE patient sera were generously provided by the Centers for Disease Control and Prevention. These samples had been previously confirmed by PRNT against SLE and WNV. (iv) JE-vaccinated human sera were from laboratory employees who had received three doses of the formalin-inactivated JE vaccine. (v) A panel of human sera from the Diagnostic Immunology Laboratory of the Wadsworth Center were used to examine the specificity of the WNV assays, including human specimens that were reactive in serologic assays for Lyme disease (*Borrelia burgdorferi* infection), ehrlichiosis (*Anaplasma cytophilum* infection), syphilis (*Treponema pallidum* infection), human immunodeficiency virus (HIV), Epstein Barr Virus (EBV), cytomegalovirus (CMV), antinuclear antibodies (ANA), and rheumatoid factor. All samples were blind tested with patient identifiers removed, according to guidelines of the NIH and the Institutional Review Board of the New York State Department of Health.

Cross-species Plaque Reduction Neutralization Test (PRNT) and Hemagglutination Inhibition (HI) Assays.

Neutralizing antibodies were evaluated in PRNT with WNV, SLEV, or JEV virus as previously described by Lindsey H. S. et. al., which is incorporated herein in its entirety by reference. Standard HI tests for DENV, POWV, SLEV, and WNV were performed according to the method of Casals J. et. al., which is incorporated herein in its entirety by reference.

Microsphere Immunoassay (MIA)

Approximately 50 µg of recombinant NS3, NS5, or E protein was covalently linked to the carboxylated surface of $6.25 \times 10^6$ microspheres through a two-step carbodiimide linkage protocol as described by the manufacturer (Luminex Corporation, Austin, Tex.). A two-step suspension MIA was performed. A 96-well 1.2 µm-filter plate (Millipore, Bedford, Mass.) was blocked for 2 min with 100 µl of PBN buffer [phosphate buffered saline (pH 7.4) with 1% bovine serum albumin and 0.05% sodium azide], washed once with 150 µl of PBS-T buffer [phosphate buffered saline (pH 7.4) with 0.05% Tween-20], and then wetted with 20 µl of PBN buffer. Serum samples (50 µl, diluted 1:100 in PBN unless otherwise specified) and antigen-conjugated microspheres (2,500 in 50-µl PBN) were added to each well. The plate was incubated in the dark on a shaker at 37° C. for 30 min, and then washed three times with PBS-T using a vacuum manifold. Polyvalent goat anti-human immunoglobulins (IgG+ IgA+IgM, 50 µl of 1:250 dilution in PBN) conjugated with red-phycoerythrin (Bio-Source International, Camarillo, Calif.) were added. After incubation at 37° C. for 30 min, the plate was washed twice with PBS-T. Microspheres were resuspended in 125 µl of PBN per well, and 75 µl of suspension was transferred to an opaque black EIA/RIA 96-well plate (Costar, Corning, N.Y.). The microsphere fluorescence intensity was quantified using a Luminex 100 flow analyzer (Luminex Corporation). The MFI of 100 microspheres was recorded for each well. The mean of 20 normal sera plus 3 times SD was used as the cutoff value for each assay.

Human Cerebrospinal Fluid Specimens

Small volumes of spinal fluid (100-200 ul) were obtained from the frozen archives of the Encephalitis PCR laboratory and the Diagnostic Immunology Laboratory of the Wadsworth Center. These specimens had previously been tested for WNV by PCR and or the MAC ELISA. Patients with either a positive PCR result for WNV, or with a detectable IgM antibody to WNV also had follow-up plaque reduction neutralization testing against the likely flavivirus infections (WNV, SLE, DEN) on serum specimens. These specimens were tested with approval of the Institutional Review Board of the New York State Department of Health. All patient identifiers were removed from specimens prior to testing.

The microsphere immunoassay was performed on the spinal fluids under conditions previously described except that the fluids were tested at a 1:2 dilution by adding 25 microliters of spinal fluid to 25 microliters of PBS for the total polyvalent antibody result, or were tested by adding 25 microliters spinal fluid to 25 microliters of a 1/100 dilution of anti-IgG (Gull SORB) for the IgG depleted "IgM" result. This concentration of anti-human IgG is calculated to provide an optimal molar ratio to deplete IgG in the spinal fluid, based on the assumption that the IgG concentration in serum is 1000 fold greater than in spinal fluid (Burke et al, JCM 1982).

Configuration of the rE-MI to Detect IgM in Spinal Fluids.

For ease of technical performance and for quality control. We maintained, as much as possible, the similar assay configuration for the spinal fluids as used for the analysis of serum. The number of r-WNV-E coated beads added to spinal fluid in the wells was maintained at 2500 beads in a volume of 50 ul. Our chosen conjugate dilution was maintained at 1/250 of R-PE anti human immunoglobulins. A panel of 11 spinal fluids from patients confirmed to have flavivirual encephalitis was tested with the rE-MI. Data from the polyvalent assay and from the "IgM" (IgG depleted) assay are given in FIG. 15. Note that the P/N values for IgM assay were higher than the P/N values for the polyvalent assay in specimens from patients deemed to be "WNV Current or Recent" The patients determined to be WNV at undetermined time" had the lowest "IgM" P/N values. For the spinal fluids from "Dengue at Undetermined Time" patients, the IgM P/N values were less than the polyvalent P/N values.

IgM-capture and Indirect IgG ELISAs.

Sera provided by the CDC Arbovirus Diseases Branch were tested by the CDC for antibodies to WNV, SLEV, and/or DENV in IgM-capture and indirect IgG ELISAs in accordance with A. J. Johnson et al. (2000) and R. Mariella (2002), which are both incorporated herein in their entirety by reference. The ELISA antigens included: a WNV noninfectious recombinant antigen (NRA) preparation of recombinant E, prM and M proteins (B. S. Davis et al.); a sucrose acetone extract of SLE virus-infected suckling mouse brain; or acetone-extracted DENV from supernatants of infected C6/36 mosquito cell cultures. Control wells were coated with mock antigen prepared in a similar manner from uninfected cells or tissue.

The New York State Department of Health tested sera and CSF for antibodies to WNV using the WNV NRA and control mock antigen provided by CDC in the IgM-capture and indirect IgG ELISAs.

A specimen was considered positive if, at a P/N ratio$\geq 3.0$, a two-fold greater immunoreactivity was observed for viral antigen relative to control antigen. ELISA results were considered uninterpretable due to nonspecific binding if the latter criterion was not met.

Statistical Analysis.

Microsoft Excel software was used for statistical analysis. Data from different groups were compared with two-tailed Student's t tests. Relationships between paired variables were evaluated with Pearson r correlation. Two way contingency table analysis using distributed JavaStat software provided the kappa statistic, sensitivity, specificity and predictive values.

Example 1

Isolation of WNV in Connecticut

Several WNV isolates were obtained from mosquitoes and birds in Connecticut. Mosquitoes were captured in dry ice-baited Centers for Disease Control miniature light traps. One mosquito trap was placed at each location per night; the numbers of traps per site ranged from 1 to 6. Mosquitoes were transported alive to the laboratory where they were identified and grouped (pooled) according to species, collecting site, and date. The number of mosquitoes per pool ranged from 1 to 50. The total number of mosquitoes by species that were collected in 14 towns in Fairfield County, Conn., and tested for virus from 6 September through 14 Oct. 1999: *Aedes vexans*, 1688; *Ae. cinereus*, 172; *Ae. trivittatus*, 131; *Ae. taeniorhynchus*, 123; *Ae. sollicitans*, 109; *Ae. cantator*, 63; *Ae. triseriatus*, 28; *Ae. japonicus*, 19; *Ae. canadensis*, 1; *Anopheles punctipennis*, 82; *An. quadrimaculatus*, 4; *An. walkeri*, 2; *Coquillettidia perturbans*, 15; *Culex pipiens*, 744; *Cx. restuans*, 27; *Cx. erraticus*, 4; *Cx. territans*, 1; *Culiseta melanura*, 76; *Cs. morsitans*, 1; *Psorophoraferox*, 4; and *Uranotaenia sapphirina*, 104. Mosquitoes were stored at −80° C. until tested for virus. Additionally, we obtained isolated WNV from mosquitoes collected in New York City.

Most dead birds were collected by state or town personnel in Connecticut and sent to the Pathobiology Department at the University of Connecticut, Storrs, where they were examined for postmortem and nutritional condition, gross lesions, and microscopic evidence indicative of encephalitis. Brain tissue from birds with presumed encephalitis was frozen at −70° C. and then sent to the Connecticut Agricultural Experiment Station, New Haven, for virus testing. Connecticut towns from which dead crows were collected and virus isolated from brain tissues (number of isolates in parentheses): Bridgeport (1), Darien (1), Fairfield (4), Greenwich (3), Hamden (1), Madison (1), Milford (1), New Canaan (1), New Haven (3), North Haven (1), Norwalk (1), Redding (1), Stamford (5), Stratford (1), Weston (1), Westport (1), and Woodbridge (1).

For viral isolation from mosquitoes, frozen pools were thawed, triturated in tissue grinders or mortars with pestles in 1 to 1.5 ml of phosphate-buffered saline ("PBS") containing 0.5% gelatin, 30% rabbit serum, antibiotic, and antimycotic. After centrifugation for 10 min at 520×g, 100 µl samples of each pool of mosquitoes were inoculated onto a monolayer of Vero cells grown in a 25-cm$^2$ flask at 37° C. in 5% $CO_2$. Cells were examined microscopically for cytopathologic effect for up to 7 days after inoculation.

For viral isolation from bird brain tissue samples, a 10% suspension of each sampled brain tissue was prepared in 1.5 ml of PBS by triturating with a mortar and pestle as described above for mosquito samples except that Alundum® was added to facilitate homogenization of tissue. Two to seven tissue samples from each brain were tested for virus as follows. Suspensions were centrifuged at 520×g for 10 min. The supernatant of each sample was then passed through a 0.22-µm filter before inoculation of a 100-µl sample onto a monolayer of Vero cells. Cells were grown in a 25-cm$^2$ flask at 37° C. in 5% $CO_2$ and examined for cytopathologic effect for up to 7 days after inoculation.

Viral isolates were tested in an ELISA against reference antibodies to six viruses, in three families, isolated from mosquitoes in North America. The antibodies were prepared in mice and provided by the World Health Organization Center for Arbovirus Research and Reference, Yale Arbovirus Research Unit, Department of Epidemiology and Public Health, Yale University School of Medicine. The antibodies were to Eastern Equine Encephalomyelitis and Highlands J, Cache Valley, LaCrosse, Jamestown Canyon, and St. Louis Encephalitis viruses.

Example 2

PCR Amplification of DNA Encoding the WNV Envelope Glycoprotein

The Connecticut WNV isolate 2741 (GenBank™ Accession No. AF206518), as described Example 1, was grown in Vero cells which were subsequently scraped from the bottom of the flask and centrifuged at 4500×g for 10 min. The supernatants were discarded and RNA was extracted from the pellet using the RNeasy® mini protocol (Qiagen), eluting the column twice with 40 µl of ribonuclease-free water. Two microliters of each eluate was combined in a 50-µl reverse transcription-polymerase chain reaction (RT-PCR) with the SuperScript® one step RT-PCR system (Life Technologies), following the manufacturer's protocol.

PCR primers, WN-233F (5'-GACTGAAGAGGGCAAT-GTTGAGC-3'; SEQ ID: 16) and WN-189R (5'-GCAATAACTGCGGACYTCTGC-3'; SEQ ID: 17) were designed to specifically amplify envelope glycoprotein sequences from WNV based on an alignment of six flavivirus isolates listed in GenBank™ (accession numbers: M16614 (St. Louis encephalitis virus); M73710 (Japanese encephalitis virus); D00246 (Kunjin virus); M12294 (West Nile virus); AF130362 (West Nile virus strain R097-50); AF130363 (West Nile virus strain 96-1030)).

The resultant PCR products were purified with the QIAquick PCR Purification Kit® (Qiagen) following the manufacturer's protocol. The amplified DNA and sequenced by the Sanger method at the Keck Biotechnology Center at Yale University, New Haven, Conn. The sequence was confirmed to corresponded to the envelope glycoprotein encoding sequence by alignment with the envelope glycoprotein encoding sequence from other flavivirus isolates using the ClustalX 1.64B program (J. D. Thompson, et al., *Nucleic Acids Res*, 22, 4673 (1994)). We further purified the resulting DNA fragments by electrophoresis on a 1% agarose gel, excised the DNA band, and isolated the DNA using the QIAquick Gel Extraction Kit® (Qiagen) following the manufacturer's protocol.

Example 3

Expression and Purification of Recombinant WNV Envelope Glycoprotein

The DNA of Example 2 was expressed in *E. coli* using the pBAD/TOPO™ ThioFusion Expression System® (Invitrogen). This system is designed for highly efficient, five minute, one step cloning of PCR amplified DNA into the pBAD/TOPO™ ThioFusion expression vector. Fusion protein expression is inducible with arabinose. Fusion proteins were expressed with thioredoxin (12 kDa) fused to the N-terminus, and a C-terminal polyhistidine tag. The polyhistidine tag enables the fusion proteins to be rapidly purified by nickel affinity column chromatography. An enterokinase cleavage site in the fusion proteins can be used to remove the N-terminal thioredoxin leader.

The pBAD/TOPO ThioFusion Expression System® expression system was used to express and purify WNV envelope glycoprotein encoded by the DNA of Example 2 following the manufacturer's protocol. Specifically, the PCR product obtained as described above was added to a reaction containing the pBAD/Thio-TOPO™ vector (1 µl) and sterile water to a final volume of 5 µl. The reaction mix was incubated for five minutes at room temperature.

Figure 4:
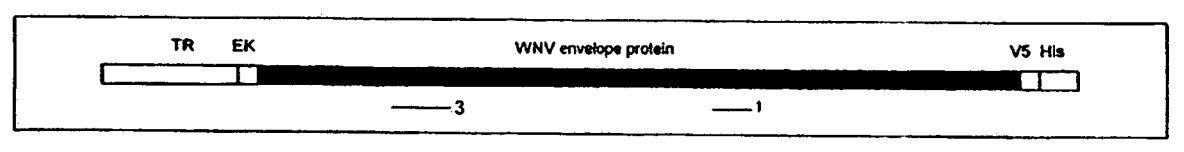

One Shot™ E. coli cells (Invitrogen) were transformed with the TOPO™ cloning reaction products by mixing the TOPO™ cloning reaction with competent cells, incubating the mixture on ice for 30 minutes and then heat shocking the cells for 30 seconds at 42° C. 250 µl of room temperature SOC medium was added to the cells followed by incubation at 37° C. for 30 minutes. 50 µl of the transformation mixture was spread on a pre-warmed LB plate containing 50 µg/ml ampicillin and incubated overnight at 37° C. A clone was identified and the DNA was isolated by standard methods. DNA sequence analysis of cloned DNA was used to confirm that the thioredoxin-envelope glycoprotein fusion protein (TR-env; FIG. 4) coding sequence was correct.

To analyze expression of the recombinant TR-env protein, E. coli containing the pBAD-TR-env expression vector was grown in cultures at 37° C. with vigorous shaking to an $OD_{600}$ ~0.5. Prior to protein expression, an aliquot was removed at the zero point and centrifuged at maximum speed. The supernatant was removed and the pellet was stored on ice. Protein expression was induced with arabinose at a final concentration of 0.02% followed by growth for an additional 4 hours. An aliquot of the arabinose-induced sample was centrifuged at maximum speed and the sample was placed on ice following removal of the supernatant. The uninduced and arabinose-induced cell pellets were resuspended in sample buffer, the samples were boiled for 5 minutes, analyzed by denaturing polyacrylamide (SDS-PAGE) gel and stained with Coomassie blue. The 71 kDa TR-env protein was the major protein found in the E. coli cells after arabinose induction.

The induced E. coli cells were lysed by sonication, centrifuged, and the TR-env protein was purified from the soluble supernatant with ThioBond™ phenylarsinine oxide resin (Invitrogen) following the manufacturer's protocol. The TR-env protein was bound to this affinity resin in a batch mode and then eluted with increasing concentrations of beta-mercaptoethanol. The fractions were run on a denaturing polyacrylamide (SDS-PAGE) gel and stained with Coomassie blue. The procedure yielded highly purified recombinant TR-env fusion protein (FIG. 5).

In immunoblots, the TR-env protein was recognized by both anti-thioredoxin antibody (Invitrogen) and human sera from two individuals seropositive for antibodies to WNV. The purified TR-env fusion protein, thus, contained an epitope recognized by antibodies induced by a natural WNV infection.

Thioredoxin expressed from the pBAD/TOPO™ ThioFusion expression vector was used as a negative control protein. The 16 kDa thioredoxin protein was expressed in E. coli and purified using ProBond™ metal-chelating affinity resin as described for the TR-env protein. Purified thioredoxin was recognized in immunoblots only by anti-thioredoxin antibody (Invitrogen) and not by human sera from two individuals seropositive for antibodies to WNV.

As an alternative method to express and purify the WNV envelope glycoprotein, a PCR product encoding the WNV E glycoprotein was engineered as a fusion protein with maltose binding protein (MBP). Nucleotides 1-1218 of the WNV E glycoprotein were amplified by PCR using the following primers which contain EcoRI and PstI restriction sites to facilitate subcloning: 5'GAATTCTTCAACTGC-CTTG GAATGAGC-3' (SEQ ID NO: 18) and 5'CTGCAGT-TATTTGCCAATGCTGCTT CC-3' (SEQ ID NO: 19). The resulting PCR product was digested with EcoRI and PstI and the resulting fragment was cloned into the pMAL™-c2X vector (New England Biolabs, Beverly, Mass.), creating a recombination fusion to the E. coli malE gene which encodes the maltose-binding protein (MBP).

E. coli DH5α transformed with the resulting plasmid was grown to a concentration of $2 \times 10^8$ cells/ml followed by the addition of isopropyl-D-thiogalactopyranoside (IPTG) to a final concentration of 0.3 mM. Following incubation of the culture for 2 hours at 37° C., the cells were harvested by centrifugation at 4,000×g for 20 minutes. The cells were lysed by freezing overnight at −20° C. and sonicating the cells for 10 minutes. The expression of a soluble 82 kDa MBP-env fusion protein in E. coli was confirmed by SDS-PAGE analysis and Coomassie blue staining. The MBP-env fusion protein was purified using a maltose-affinity column according to the manufacturer's instructions. 3 mg of of MBP-env protein was obtained from 250 ml of cell culture. MBP was purified as a control according to the same protocol.

The MBP-env fusion protein was used to analyze sera for the presence of antibodies to the WNV E glycoprotein. 2 µg of MBP-env fusion protein or MBP (control) protein was boiled in SDS-PAGE sample buffer (BioRad) containing 2% β-mercaptoethanol, and run on a 10% SDS-PAGE gel. The glycoproteins were transferred to nitrocellulose membrane using a semi-dry electrotransfer apparatus (Fisher Scientific).

The nitrocellulose membrane was probed with sera from 5 patients with confirmed WNV infection and sera from uninfected individuals. The membrane was incubated with the sera (1:100 dilution) for 1 hour, then washed 3 times with Tris-buffered saline with Tween 20 (TBST) and alkaline phosphatase-conjugated goat anti-human IgG (1:1,000 dilution; Sigma). The blots were developed with nitroblue tetrazolium and 5-bromo-4-chloro-3-indolyl phosphate (Kirkegaard & Perry Laboratories).

The MBP-env fusion protein detected IgG antibodies to the E glycoprotein in western blots with sera from 5 humans with confirmed WNV infection, but not in the control human sera. In essentially identical experiments, the MBP-env fusion protein also detects IgM antibodies to the E glycoprotein in western blots with sera from 5 humans with confirmed WNV infection, and IgG and IgM antibodies with sera from 10 horses with confirmed WNV infection, but not in control human or horse sera.

Example 4

Coupling of Recombinant WNV-E Antigen to Polystyrene Microspheres

A two-step carbodiimide process, recommended by Luminex Corporation, Austin Tex., was used to link 50 micrograms of purified recombinant WNV envelope glycoprotein antigen (WNV-E) to the surface of 6.25×106 microspheres. Activation was initiated with 50 microliters of 50 mg/ml Sulfo-NHS followed by 50 microliters of 50 mg/ml EDC and a 20 minute incubation at room temperature. Coupling of the recombinant antigen took place for 2 hours, in the dark, on a rotator at room temperature. Microspheres were washed by centrifugation, twice, in 1.0 ml PBS Azide blocking buffer, (PBN) composed of PBS, 1 BSA, 0.02% $NaN_3$.

Example 5

Stability of WNV-E-Coated Microspheres

Figure 9:
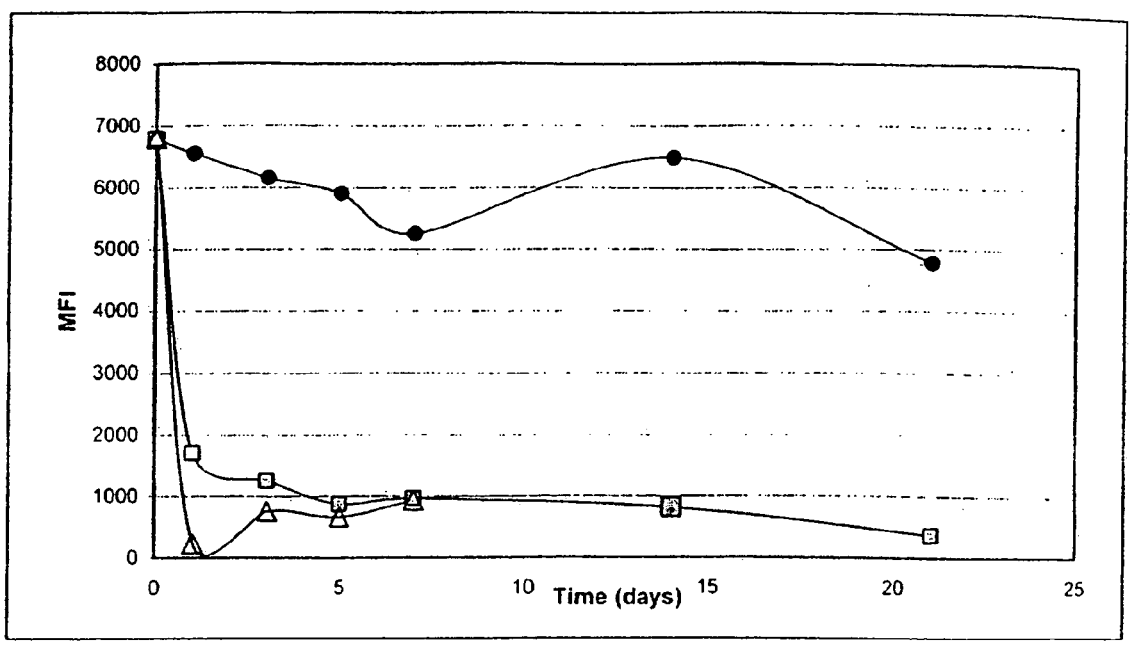
FIG. 9 shows the results of a stability analysis of the WNV E glycoprotein coated microspheres over time at the temperatures of 25° C., 37° C. and 50° C. The plot shows the Maximum Fluorescence Intensity (MFI) versus time at each given temperature. Antigen was shown to be stable on beads when stored at 4° C. for over four months. Curves in the plots of FIG. 9 are likely due to voltage fluctuation affecting the energy output of the lasers.

Microspheres coupled to recombinant WN E glycoprotein were held at 4° C., 25° C., 37° C. and 50° C. and tested at 1, 3, 5, and 7 days during the first week, then weekly thereafter for 3 weeks. A plot of the MFI versus time at 25°, 37°, and 50° C. is shown in FIG. 9. Thermal stability, as expressed by T90 (time to 90% potency of reagents), of this key reagent was 0.1 days at 50° C., 0.1 days at 37° C., and 1.5 days at 25° C. A straight line is obtained when the T90 is plotted (as ordinate) on a semi log scale against the 1/T Kelvin (abscissa). This is a recommended calculation for accelerated thermal stability or shelf-life studies. Interpolation to the desired storage temperature, 4° C., gives an estimated T90 of three months. Performance of this key reagent, the WNV-E coated microspheres, to within 10% of maximal reactivity is a realistic expectation for a robust clinical laboratory assay.

Example 6

WNV-E Microsphere Immunoassay to Detectantibodies to West Nile Virus

A two-step suspension microsphere immunofluorescence assay was performed. Multiscreen 96-well filter plates with 1.2 μm Durapore filters (Millipore, Bedford, Mass.) and a Multiscreen vacuum manifold (Millipore) facilitated microsphere washing. Briefly, filter plate wells were blocked for 2 min with 100 μl PBN buffer, washed once with 150 μl PBS-T buffer (phosphate-buffered saline, pH 7.4, with 0.05% Tween 20 from Sigma Aldrich), and then wetted with 20 μl PBN. Diluted serum samples (50 μl, diluted 1:100 in PBN unless otherwise noted) were added to test wells. IgG-depleted sera were diluted 10-fold during depletion, and were diluted an additional 10-fold in PBN for analysis in the rWNV-E MIA with polyvalent secondary antibody conjugate. IgM-depleted sera were similarly diluted in PBN to a final serum dilution of 1:100. Antigen-conjugated microspheres (2,500 in 50 μl PBN) were added to each well. The filter plates were incubated in darkness on a plate shaker for 30 min at 37° C., and then washed three times with PBS-T using the vacuum manifold. Diluted fluorochrome-labeled secondary antibody (50 μl of a 1:250 dilution in PBN) was added to each well. Unless otherwise noted, the secondary antibody was polyvalent goat F $(ab')_2$ anti-human immunoglobulins (IgG+IgA+IgM) conjugated to red-phycoerythrin (R-PE) from Bio-Source International (Camarillo, Calif.). Alternative secondary antibodies were goat $F(ab')_2$ anti-human IgG R-PE conjugate and goat $F(ab')_2$ anti-human IgM R-PE conjugate (Bio-Source International). After incubation for 30 min at 37° C. in darkness with shaking, filter plates were washed twice with PBS-T using the vacuum manifold. Microspheres were then resuspended in 125 μl PBN per well. Seventy five microliter aliquots were transferred to opaque black EIA/RIA 96-well plates with breakaway strips (Costar, Corning, N.Y.), and evaluated for microsphere fluorescence intensity using a Luminex 100 instrument (Luminex Corp.). This instrument is a dual laser flow analyzer. The first laser excites the flourochrome mixture intrinsic to the microspheres, enabling the bead identity to be determined as the bead passes single file through the laser path in the flow cell. The second laser excites the extrinisic flourochrome (red-phycoerythrin) that is covalently attached to the reporter antibodies (goat-anti human immunoglobulins). The dual lasers allow the operator to mix beads with different antigens together in a well of a filter plate, thus enabling multiplex analysis of different antibody specificities at one time.

The instrument was calibrated with CL1/CL2 and RP1 calibration microspheres from Luminex Corp. according to the manufacturer's directions. The median fluorescence intensity (MFI) of fluorochrome-conjugated secondary antibody bound to individual microspheres was derived from flow analysis of 100 microspheres per well. Results for each assay were expressed both as MFI and as a patient/negative (P/N) MFI ratio, i.e., the MFI for the patient's specimen divided by the MFI obtained from a pool of 10 negative control sera. The negative control sera contained no detectable antibodies to WN virus in IgM-capture and IgG ELISAs. Serum MIA P/N values ≧4.0 were considered positive for antibodies to WN virus E protein.

The rWNV-E MIA was performed on CSF as described for serum specimens, except that the CSF was tested at a 1:2 dilution, prepared by addition of 30 μl CSF to 30 μl PBS. IgG-depleted CSFs, diluted 1:2 during the IgG removal procedure, were assayed without further dilution. CSF results were reported as MFI values. CSF with MFI values >426 were considered positive for antibodies to WN virus E protein.

Example 7

Determination of the Normal Range of Detection of the WNV-E Microsphere Immunoassay Ten sera from cases of West Nile viral encephalitis, confirmed by plaque reduction neutralization tests with paired serum sets, and ten sera that were negative in both MAC ELISA and IgG ELISA WNV antibody tests were examined to establish normal ranges of detection of the WNV-E microsphere assay using both positive and negative WNV samples.

For each serum specimen, a Median Fluorescence Intensity (MFI) value was established by measuring immunoreactivity with the WNV-E antigen on 100 individual microspheres. The mean MFI value of microspheres for the ten negative sera was 247, with a standard deviation of 74. The mean MFI of ten positive sera was 7625 with a range from 2763 to 17188, corresponding to range of P/N ratios of 11.1 (2763/247) to 69.6 (17188/247).

Example 8

Covariance Analysis

Ten sera from West Nile encephalitis patients, in which infection with WNV was positively confirmed using MAC ELISA, IgG ELISA and plaque reduction nuetralization (PRN), were pooled ("ten positive sera"). A similar pool was made using ten human sera tested negative for WNV human subjects ("ten negative sera").

To determine the imprecision of the WNV-E microsphere immunoassay, ten aliquots of each pool were prepared and tested separately. Imprecision between measurements in the same assay (intra-assay measurements) of the aliquots of the positive pool yielded a covariance of 7%. Imprecision between measurements of the negative serum pool provided a covariance of 11%.

Further, the pools of ten positive and negative sera were analyzed over the course of several days to determine the imprecision between sets of measurements (inter-assay imprecision). The pool of positive sera provided an inter-assay covariance of 17%, whereas the pool of negative sera provided an inter-assay covariance of 32%. Results for 70 sera independently analyzed by two individuals showed that inter-operator correlation of measurements of 0.995 with a slope of 1.125. Overall, the data demonstrating that there is relatively low imprecision in carrying out the WNV-E microsphere immunoassay.

Example 9

Determination of the Specificity of the WNV-E Microsphere Immunoassay

Sera from patients with various viral infections, bacterial infections, or autoimmune diseases were tested in the rWNV-E MIA. Twenty-four sera from presumed healthy subjects were also tested—four (17%) were borderline positive with P/N values <4.9. Only sera from patients with syphilis had a high frequency of false-positive results (FIG. 35). Sera in the first syphilis panel were all treponemal antibody positive. In the second syphilis serum panel, sera were rapid plasma reagin (RPR) negative and less cross-reactive. Cross-reactive antibodies in syphilis patient sera were also detected by the WN virus IgG ELISA (data not shown). However, the syphilitic sera did not contain virus-specific neutralizing antibodies detectable in WN virus or SLE PRN tests (data not shown). A BLAST (1) computer search of the *T. pallidum* genomic database (C. M. Fraser et al.) failed to reveal possible cross-reactive epitopes.

Example 10

Separate Detection of Anti-WNV-E Glycoprotein IgM or IgG Antibodies Following Immunodepletion of IgM or IgG from a Serum Specimen Separate detection of IgM or IgG antibodies against the WNV E glycoprotein in selected sera was carried out using an immunodepletion step of the sera prior to the microsphere immunoassay. First, selected sera were tested for anti-WNV-E glycoprotein antibodies using the WNV-E microsphere immunoassay along with the polyvalent reporter antibody, which detects IgG, IgA and IgM. Second, the same sera were retested for either anti-WNV-E glycoprotein IgG or IgM antibodies using an immunodepletion step prior to the WNV-E microsphere immunoassay. Treatment with goat anti-human IgG or goat anti-human IgM resulted in the depletion of either IgG or IgM, respectively, from the human sera.

To carry out the immunodepletion step for the removal of IgG, 5 microliters of human serum was treated with 45 microliters of goat anti-human IgG, (Gull SORB, from Meridian Diagnostics, Cincinnati, Ohio). According to the manufacturer, this protocol is sufficient to deplete IgG at concentrations up to 15 mg/ml, the upper limit of normal human IgG concentration. This 1:10 serum dilution was mixed and centrifuged at 13,000 rpm in an Eppendorf centrifuge with a rotor radius of 7.5 cm. The supernatant is used for making the further 1:100 sample solution for reanalysis in the microsphere-based immunoassay. Negative IgG ELISA, and negative IFA tests using slides from Focus Technologies demonstrated that the Gull SORB pretreatment efficiently removes detectable IgG antibodies to WNV. Any remaining fluorescence activity after IgG depletion would represent the relative amount of IgM antibodies that recognize WNV E glycoprotein. Further, given that IgM antibodies typically do not persist for long periods of time, but are the first antibodies to respond to an antigen, any fluorescence following IgG depletion would indicate a current or recent infection.

To carry out IgM immunodepletion, 10 microliters of serum was treated with 10 microliters of goat anti-human Mu chain (anti-human IgM), at a concentration of 2.5 mg/ml. Twenty microliters of PBS was added to the treated serum prior to centrifugation at 13,000 rpm in an Eppendorf centrifuge as above. The supernatant was used to make a further dilution to 1:100, which was then tested in the WNV-E microsphere immunoassay with the polyvalent conjugate. The remaining fluorescence activity after IgM depletion represented the relative amount of IgG antibodies that recognize WNV E glycoprotein.

IgA antibodies may also be present, but their role in detection of flavivirus infection is not well documented in the literature, nor frequently considered.

Example 11

Comparison between WNV-E Microsphere Immunoassay and Elisa Methods Following an Immunodepletion Step to Detectacute Cases of WNV It was desirable to detect the presence of IgM antibody to detect acute cases of WNV infection. The WNV-E microsphere immunoassay provided strong positive MFI values for many patients' first serum specimens, indicating that the polyvalent assay detected IgM as well as IgG antibodies to WNV.

Five sequential sera from a WNV encephalitis patient were treated with anti-human IgG (Gull SORB) at a concentration designed to deplete all IgG reactivity. These treated sera were then tested again in the polyvalent WNV-E immunoassay.

The five sequential sera were also treated with anti human Mu chain (anti IgM) at a concentration calculated to deplete all IgM reactivity and then reanalyzed with the polyvalent WNV-E immunoassay.

The anti-IgG and anti-IgM treated sera were also analyzed in a WNV-E immunoassay using an anti-IgM R-PE fluorescent conjugate to detect IgM antibodies. Results of this experiment are presented in FIG. 12, along with P/N values from the MAC ELISA and the IgG ELISA.

The results showed that the Gull SORB treatment (removal of IgG) increased the P/N correlation coefficient with IgM ELISA assay from 0.75 to 0.93. Anti-IgM treatment increased the P/N correlation coefficient with the IgG ELISA assay from 0.92 to 0.99, with approximately five-fold higher P/N ratios observed with the microsphere immunoassay. Note that by the traditional assays, the third serum at 18 days post onset had the maximal IgM reactivity and the fourth sample at 72 days post onset had the maximal IgG reactivity.

Conclusions from WNV-E microsphere immunoassays on the different sera are comparable. The fourth serum specimen had the peak antibody reactivity as measured by MFI. Removal of IgG allowed once again the identification of the third serum as having peak IgM reactivity both with the polyvalent conjugate and with the anti-IgM conjugate. Removal of IgM allowed identification of the fourth serum as having the most IgG.

Overall, the results showed that the WNV-E microsphere immunoassay, unlike the MAC and IgG ELISAs, provided an IgM (IgG depleted) P/N ratio that was greater than the P/N ratio of the IgG (IgM depleted) sample for the early bleeds. This relationship may be an indicator of an active or recent infection. The use of the anti-IgM R-PE conjugate on the anti-IgM treated sera demonstrated that the IgM was effectively depleted to a level in the negative range (P/N<4.0) according to our established assay conditions.

Example 12

Comparison of the WNV-E Microsphere Immunoassay to Standard Elisas by Retrospective Parallel Testing Archived sera at the New York State Department of Health provided an opportunity to parallel test a larger panel of sera submitted for suspected viral encephalitis. The objective of this study was to determine whether a cut-off P/N value of 4.0 would provide test results concordant with the MAC ELISA and IgG ELISA previously used to screen the sera for antibodies to WNV.

FIGS. 11A and 11B provide scatter plots with polyvalent WNV-E microsphere immunoassay P/N vs. IgG ELISA P/N and/or MAC-ELISA P/N with trendline.

Out of 107 total sera tested, 20 West Nile reactive sera, identified previously by the MAC ELISA and or the IgG ELISA, were also correctly identified by the WNV-E microsphere immunoassay. Seven sera of 107 tested were just above the cut-off on the WNV-E microsphere immunoassay, whereas they were non-reactive in both of the traditional ELISA assays. Since these seven sera were non-reactive in the ELISAs, no follow up sera were provided to allow us to definitively rule out infection. The mean of the MFI for the 20 positive sera by traditional assays was 7804 (range 1084-21038). The mean of the borderline/equivocal samples was 1333 (range 1084-2118). The mean of the 53 sera that tested negative was 349 (range 49-607).

Example 13

Detection of Antibodies to Japanese Encephalitis Vaccine Using the WNV-E Microsphere Immunoassay Retrospective testing of the serum bank of the Wadsworth Center for flavivirus-reactive antibodies, demonstrated that the WNV-E microsphere immunoassay could detect antibodies to three flaviviruses in the Japanese encephalitis serogroup.

Twenty four human sera were received from the Arbovirus Research Laboratory of the Wadsworth Center, with all identifiers as to identity of the recipients of the Japanese Encephalitis (JEV) vaccine status or time of vaccination. This blinded serum panel consisted of twelve post-vaccine specimens (collected in June, 2002) and eight pre-vaccine sera (collected in April, 2001) from eight of the twelve vaccine recipients (the pre-bleed sera of these employees was not found in the freezer archives.) A further four serum samples were from new employees who had not received the vaccine, and who lacked an exposure history to WNV from dead birds or mosquitoes. These sera were tested by the microsphere immunoassay employing the polyvalent R-PE anti-human immunoglobulins conjugate. After testing the blinded specimens, the pre-vaccine specimens were matched with the post-vaccine specimens, and plaque reduction neutralization titers for the post-vaccine sera were obtained.

Results on the polyvalent WNV-E microsphere immunoassay are given in FIGS. 13A and 13B. Note that where pre and post samples were available, 6 of 8 employees made a large increase in detectable antibodies.

Figure 14:
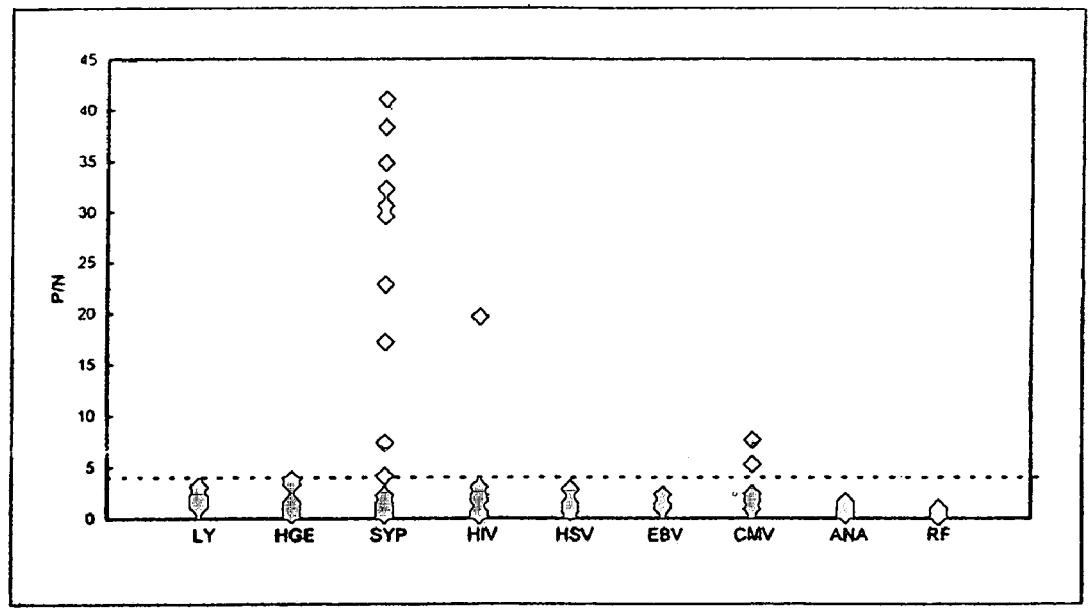
FIG. 14, according to Example 9, shows the results of testing different sera from patients with different viral infections, bacterial infections or autoimmune diseases by the WNV E glycoprotein microsphere immunoassay (A). The results demonstrate that the immunoassay performs well given that only sera from patients with syphilis had a high frequency of falsely positive test results with the microsphere immunoassay. Graphical representation of the data is shown in (B).

Since neutralizing protective antibodies are primarily IgG class, we treated all 24 sera with anti-IgM at a concentration calculated to provide an optimal proportion to deplete all IgM. We repeated the assay with the polyvalent red-phycoerythrin anti human immunoglobulin conjugate on the IgM-depleted sera. As expected, FIG. 14B demonstrates that the MFI were lower than in the untreated samples, yet clearly were positive in all but two vaccine recipients. The two vaccine recipients with negative post-vaccine MFI levels were the two employees who lacked a detectable neutralizing antibody response by plaque reduction neutralization testing.

The results demonstrated that the WNV-E microsphere immunoassay could detect antibodies to three flaviviruses in the Japanese encephalitis serogroup.

Example 14

Detection of WNV Antibody from Serum and Spinal Fluid Samples from Patients with Acute Viral Encephalitis Using WNV-E Microsphere Immunoassayas Compared to Results from MAC Elisa Seven pairs of serum along with same-day collected spinal fluid specimens from seven patients were tested using the recombinant WNV-E microsphere immunoassay using both the polyvalent antibody reagent and the "IgM" serum (anti-IgG treated serum). The seven patients were chosen on the basis of having been tested positive for WNV by either an IgM and/or an IgG ELISA using the reagents and protocol recommended by the CDC. The data are presented in FIG. 17.

The results showed that both patients with confirmed WNV infection by PRN testing, had high levels of detectable antibody in spinal fluid, as detected by the WNV-E microsphere immunoassay. Further, 5 patients who were shown to test negative for a WNV infection by MAC ELISA were shown to be strongly positive by the WNV-E assay.

The data from the paired serum and spinal fluid testing demonstrated the high sensitivity of the WNV-E assay since the P/N values of the WNV-E microsphere immunoassay are significantly greater than the P/N values of the MAC ELISA. The data further showed that WNV-E microsphere immunoassay is superior to the MAC ELISA since the WNV-E assay was able to detect a WNV infection in 5 patients who were shown not to have an infection by the MAC ELISA.

Example 15

Expression and Purification of NTPase/Helicase Domain of NS3 and NS5

WNV nonstructural proteins NS3 and NS5 were tested as targets to develop a novel serologic assay for WNV diagnosis. NS3 and NS5 are key enzymes in flavivirus RNA replication. NS3 functions as a serine protease (in the presence of cofactor NS2b), 5'-RNA triphosphatase, NTPase, and helicase; NS5 functions as a methyltransferase and RNA-dependent RNA polymerase (RdRp). Since the NS proteins are primarily involved in flavivirus replication, the immunogenic features of the NS proteins during WNV infection would be different from those of viral structural proteins. These unique features could be exploited to improve the current structural protein-based serologic assay.

The NTPase/helicase domain (amino acids 182 to 619) of NS3 (see FIG. 23B) and full-length NS5 (see FIG. 23C) of WNV were expressed and purified using an *E. coli* expression system as follows. The NTPase/helicase domain of NS3 (amino acids 182 to 619) and full-length NS5 were cloned into the pET-21a and pET-28a vectors, respectively, and expressed in *E. coli* BL21 cells upon induction with isopropyl-β-D-thiogalactopyranoside (IPTG) at 30° C. for 3 to 4 h. The recombinant NS5 and NS3 NTPase/helicase domain contained a His$_6$ tag (SEQ ID NO: 20) at the N-terminus and C-terminus, respectively, and were purified through a nickel column (Novagen, Madison, Wis.). The NTPase assay was performed as previously described (Cui, T. et al.). The RdRp activity of NS5 was assayed using a WNV subgenomic RNA transcript containing a large deletion from nucleotide 269 to 10408. The reactions were labeled with [α-$^{32}$P]UTP and analyzed on a 4% denaturing polyacrylamide gel followed by autoradiography (Ackermann, M. et al.).

Figure 23:
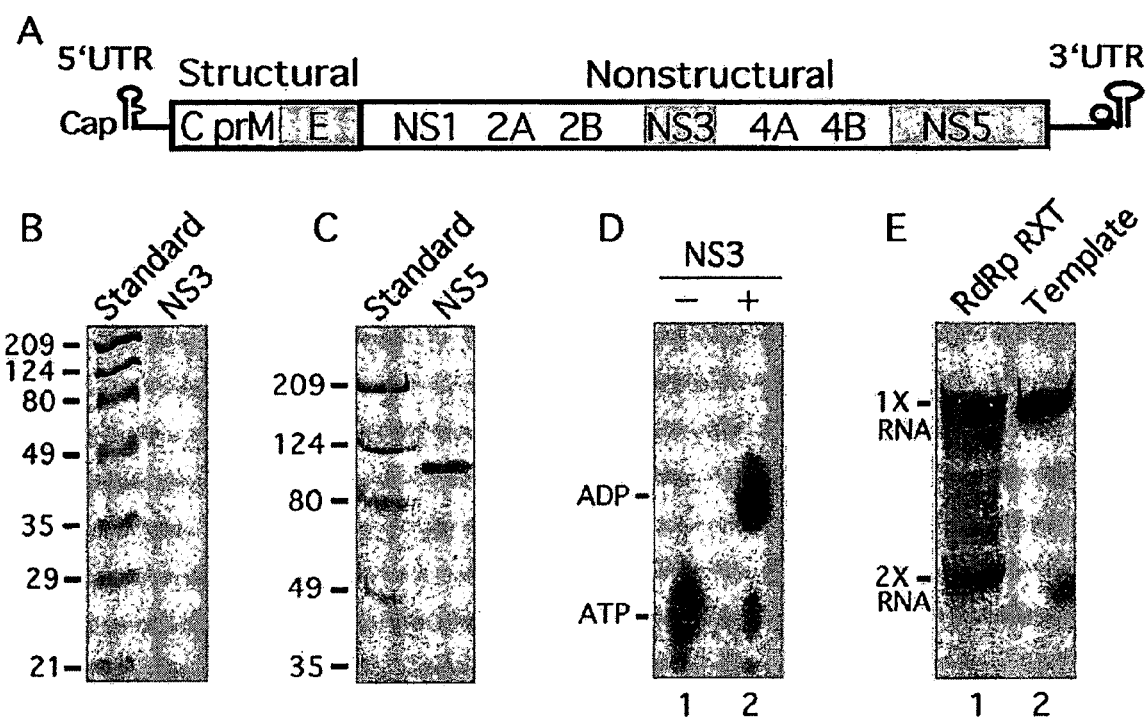
FIG. 23(A) shows WNV genome structure. Three recombinant proteins, E, NS3, and NS5 used, are shaded. (B and C) Purified NTPase/helicase domain of NS3 and full-length NS5 were analyzed on SDS-PAGE stained with Coomassie Blue. (D) ATPase activity of the recombinant NTPase/helicase domain of WNV NS3. In the presence of recombinant NS3, $[\alpha\text{-}^{32}P]$ATP was hydrolyzed to $[\alpha\text{-}^{32}P]$ADP and phosphate (lane 2). No ATP is hydrolyzed in the absence of NS3 (lane 1). (E) RdRp ("RNA-Dependent RNA Polymerase") activity of the recombinant NS5. The RdRp activity of NS5 was assayed using a WNV subgenomic RNA transcript (890-nt in length) containing a large deletion from nucleotide 269 to 10408. The reactions (RXT) were labeled with $[\alpha\text{-}^{32}P]$UTP, and the products of double-stranded RNA (a replicative 2× form) and single-stranded RNA (1× form) were analyzed on a denaturing polyacrylamide gel followed by autoradiography (lane 1). A $^{32}P$-labeled template RNA was loaded as a size control (lane 2).

The recombinant proteins were enzymatically active: the NS3 protein exhibited an NTPase activity in hydrolyzing ATP to ADP and phosphate (FIG. 23D); and the NS5 protein retained the RdRp activity, using WNV RNA as a temple to synthesize both double-stranded RNA (a replicative 2× form) and single-stranded RNA (1× form) (FIG. 23E). The enzymatic activities of WNV NS3 and NS5 are comparable to those of DNEV NS3 and NS5. The enzymatic activies indicate retention of native conformation by the recombinant NS3 and NS5.

Example 16

Microsphere Immunoassay (MIA) to Test NS5 in Serologic Assay

A microsphere immunoassay (MIA) was selected to establish the NS3- and NS5-based serologic assays to detect antibodies induced by WNV infection. Recombinant NS3 or NS5 was covalently linked to microsphere beads, and then reacted with patient serum followed by anti-human immunoglobulins with a fluorescent conjugate. The levels of reactive antibodies from the sera were quantified by a flow analyzer. Initially, 20 human sera from healthy individuals were used to establish cutoff levels for the assay. The mean median fluorescence intensity (MFI) for NS3 was 909 [standard deviation ("SD") 351], with an assay cut-off (X+3SD) of 1962; the mean MFI for NS5 was 1810 (SD 852), with an assay cut-off (X+3SD) of 4366. Analyses of five positive WNV sera, which had been previously confirmed by a subviral particle-based immunoassay (Davis, B. et al.) and PRNT, revealed that the NS5 MIA had an assay dynamic range of 32, from 100- to 3200-fold serum dilutions. The NS3-based MIA did not exhibit consistent signals above the background level with these sera (see below).

Example 17

NS5-Based MIA Reliably Detects WNV Infection and may Indicate Recent Infection

A total of 61 sera from WNV patients with clinical symptoms and confirmation by PRNT were tested using to NS5- and NS3-based MIA, along with the recombinant E protein-based MIA for comparison (S. J. Wong et al., J Clin Mircobiol., 2003, 41:2127-2223). The plot of MFI versus days post symptom onset (FIG. 24A) shows that the NS5-reactive signals appeared on day 6; the MFI of 35 of 38 (92%) sera collected from day 7 to day 77 were positive; and the MFI dropped to a negative level for two sera collected on day 259 and day 431. The reactive pattern derived from the NS5-based assay correlated well with that from the E-based assay, except that, in the latter assay, reactive signals appeared around day 2 to day 6, and the MFI remained positive throughout the later time points, including day 259 and day 431 (compare FIG. 24A with 24C). On the other hand, the NS3 MIA did not exhibit consistent signals above the background level, with less than half of the sera showing positive MFI (FIG. 24B); it therefore was not further analyzed. These results demonstrate that the NS5-based MIA is a sensitive assay for detection of human WNV infection.

Example 18

Persistance of Anti-E and Anti-NS5 Antibodies

Figure 24:
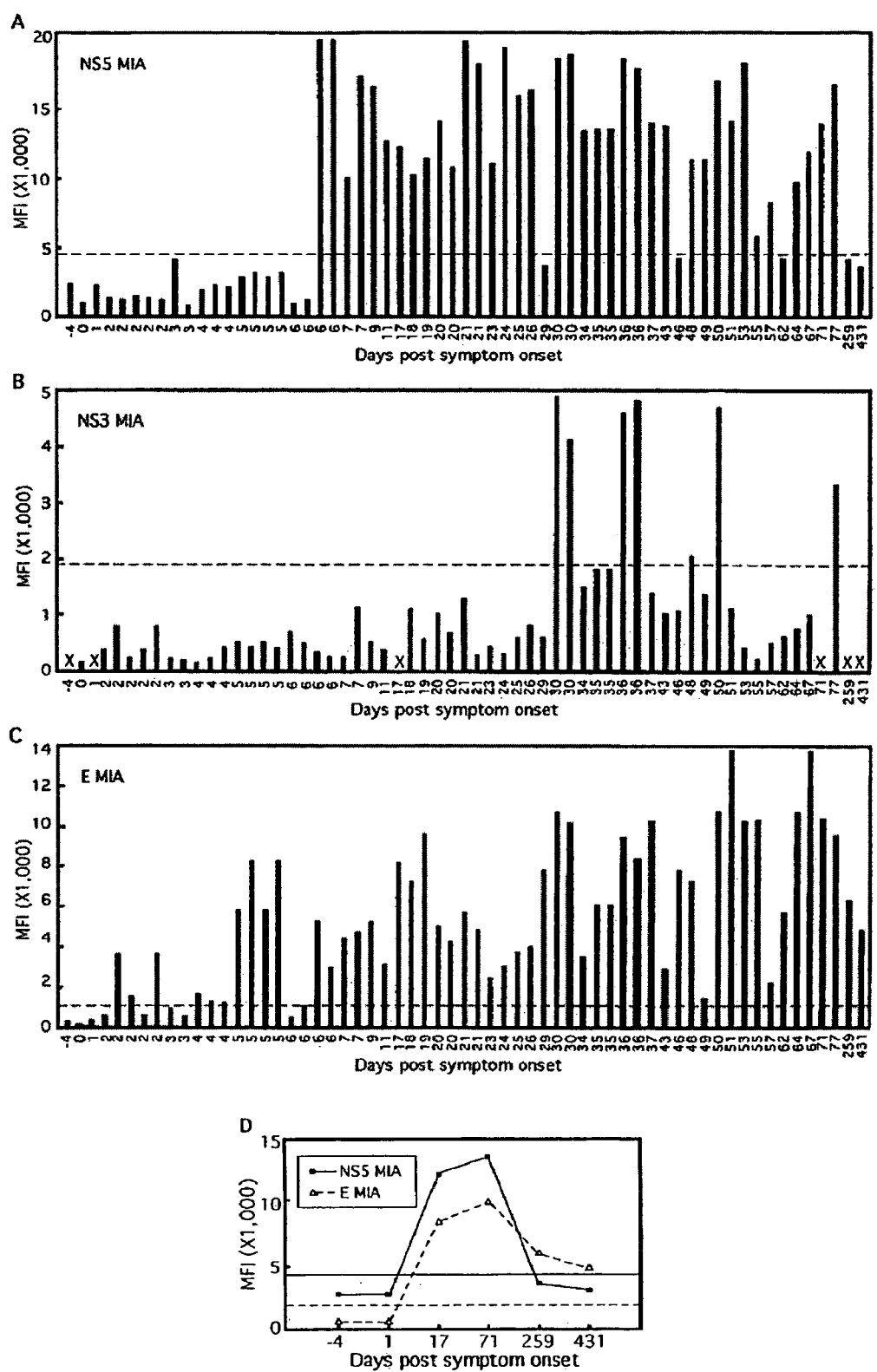
FIG. 24 shows the results of microphere immunoassays (MIA) using recombinant proteins of WNV NS5 (A), NS3 (B), and E (C). Median fluorescence intensity (MFI) of each WNV patient serum is plotted against days post-symptom onset. Dashed lines indicate assay cut-off levels. X in (B) indicates samples not tested. (D) A time course of reactivity to NS5 and E protein for sera collected from a patient infected with WNV. MFI from NS5- and E-based assays are indicated by solid and dashed lines, respectively. The cut-off values of the assays are correspondingly indicated.

To examine the persisitance of antibody against WNV E glycoprotein and NS5 antigen upon WNV infection, we examined a series of sera collected from a single patient at various time points post-infection (FIG. 24D). Positive MFI signals were detected on day 17 post symptom onset in both E and NS5 MIA. Signals from the E-based MIA remained positive for sera collected on days 71, 259, and 431 post-symptom onset (indicated by dashed lines in FIG. 24D). In contrast, signals from the NS5-based MIA were positive for sera collected on day 17 and 71 post-symptom onset, however, the MFI declined to a negative range on day 259 and 431 post-symptom onset (indicated by solid lines in FIG. 24D). These results suggest that a positive NS5-based MIF indicates current or recent infection.

The NS5 MIA can likely be used to indicate the timing of WNV infection. Time-course analysis of WNV patient sera showed that, after serum conversion at approximately day 6 post symptom onset, the anti-E antibody signal remained highly positive up to 431 days post symptom onset (FIGS. 24C and 24D), while antibodies against NS5 diminished to a negative level between 71 and 259 days post symptom onset (FIGS. 24A and 24D). More clinical samples at late time points post-infection are required to confirm this conclusion. Although not wishing to be bound by theory, since NS5 protein is only present during viral replication and associates with the replication complex located at the cytoplasmic side of the endoplasmic reticulum, NS5 may be more accessible to protein degradation, resulting in a shorter half-life in cells than the membrane-spanning E protein. It is also possible that antibodies generated in response to NS5 are of shorter duration than the anti-E antibodies.

Example 19

Specificity of NS5-Based MIA: Differention of WNV from other Nonflavivirus Infections or Diseases and from Flavivirus Vaccination The specificity of the NS5-based MIA was demonstrated by challenging 120 sera from patients with various infections, autoimmune conditions, JEV vaccination, YFV vaccination, or good health (FIG. 25). Only one patient with HIV infection showed an MFI (7,517) above the cut-off level of the NS5 MIA (4,366). It should be noted in particular that none of the sera from the JEV vaccine recipients reacted with the WNV NS5 antigen; only 1 of 19 (5%) YFV vaccine recipients exhibited a positive MFI singal. By contrast, all 10 (100%) JEV-vaccinated sera and 10 of the 19 (53%) YFV-vaccinated sera showed positive MFIs in the E-protein-based MIA. These results demonstrate that the NS5-based assay can be used to differentiate between WNV infection and vaccinations with either an inactivated (JEV) or a live attenuated (YFV) flavivirus. flavivirus

Example 20

Cross-Reactivity of WNV NS5 and E with DENV or SLEV Infections

The cross-reactivity of WNV NS5 and E with DENV infection was tested with 17 pairs of acute and convalescent sera from DENV-infected individuals (FIG. 26). The DENV patient sera reacted with WNV E protein. The MFI signal and the titer of the E MIA correlated well with the hemaglutination inhibition (HI) titer of the sera. Twenty-four of the 34 (71%) DENV sera tested positive in the E-based MIA; 8 samples with negative E MIA results were either HI negative or showed low HI titer. For the NS5-based MIA, only 3 of the 34 (9%) DENV sera were marginally positive (samples 3A, 4B, and 11A), with MFI values very close to the cut-off value. Next, we examined the potential cross-reactivity of WNV NS5 and E with SLEV patient sera. Among the 20 pairs of SLEV sera that had been previously confirmed by plaque reduction neutralization tests, only 2 (5%) sera were MFI positive (samples 3A and 3B) in the WNV NS5-based assay, while 11 of the 40 (27.5%) SLEV sera were positive in the E-based assay (FIG. 27). These results suggest that, compared with the E protein-based MIA, the NS5-based MIA exhibits substantially improved discrimination between DENV/SLEV and WNV infections.

Example 21

Three Advantages for NS5 Immunoassays as Compared to WNV E Immunoassays Flavivirus Flavivirus To improve the specificity of the diagnosis of a flavivirus infection using the WNV E glycoprotein, the RNA replication NS proteins were tested as an alternative to the WNV E glycoprotein for serologic diagnosis of WNV infection. The active NTPase/helicase domain of NS3 and full-length NS5 were expressed and purified. The NS5 protein-although not the NS3 NTPase/helicase domain-reacted consistently with WNV patient sera. Contrary to the WNV E glycoprotein, the NS5 when used in the immunoassays (MIA) of the present invention can provide the following three advantages.

First, unlike the WNV E-based MIA, the NS5-based MIA reliably discriminates between WNV infection and DENV (FIG. 27) or SLEV infections (FIG. 26) only 3 of the 34 DENV sera and 2 of the 40 SLEV sera showed weak NS5 MFI signals. On the other hand, WNV E protein cross-reacts with both DENV (26 out of the 34) and SLEV (11 out of 40) patient sera. These results appear to be consistent with a previous report suggesting that NS antigens can be viral type specific, whereas structural antigens can be cross-reactive among flaviviruses (Qureshi, A. A. et al.). However, the ordinary skilled person in the art would certainly appreciate that one could not reasonably know or predict the specificity of the WNV NS5 to anti-WNV sera, indeed as shown by the present inventors, without providing proof thereof by way of appropriate and necessary experimentation.flavivirus There are likely at least two reasons why the NS5-based immunoassay shows greater specificity for WNV detection than WNV E-based immunoassays. First, notwithstanding that the amino acid sequence homology of NS5 between WNV and DENV (75%) or SLEV (47% %) could be as high as that of E protein between WNV and DENV (62%) or SLEV (78% %), epitopes (either structure or sequence) presented by WNV E could be more conserved among the flaviviruses than those in the NS5, resulting in greater cross-reactivity in the WNV E-based assay. Alternatively, the specificity of the WNV NS5-based assay could have been a consequence of a failure an NS5 immune response during DENV and SLEV infections. This is unlikely because partially purified NS proteins of DENV, SLEV, or WNV were demonstrated to be reactive with only homologous sera, but not with heterologous sera, indicating the production of antibodies against the NS proteins during infections (Qureshi, A. A. et al.). Nevertheless, the specificity of the NS5-based assay may eliminate the need for plaque reduction neutralization tests, and therefore the requirement of Level 3 Biocontainment, to discriminate among infecting flaviviruses. Quick and accurate differentiation between WNV and DENV/SLEV infections will be important in diagnosing specimens where WNV co-circulates with DEN and/or SLEV viruses.

Second, the NS5 MIA differentiates between vaccination with inactivated flavivirus and natural WNV infection. None of the JE-vaccinated sera reacted with the WNV NS5. This feature was expected, because only replicative viruses produce NS proteins, while inactivated JE vaccines could not replicate and produce NS proteins. Distinguishing between vaccination and natural viral infection is important for WNV diagnosis in geographic regions where inactivated JE vaccination is performed, or in vaccinated military personnel or travelers. For the same reason, the NS5 MIA will be useful for testing whether horses previously vaccinated with inactivated WNV (Davis, B. et. al., Monath, T.) have encountered a new round of WNV infection.

Third, the NS5 MIA could potentially be used to indicate the timing of WNV infection. Time-course analysis of WNV patient sera showed that, after serum conversion at approximately day 6 post symptom onset, the anti-E antibody signal remained highly positive up to 431 days post symptom onset (FIGS. 24C and 24D), while antibodies against NS5 diminished to a negative level between 71 and 259 days post symptom onset (FIGS. 24A and 24D).

Overall, the unique features of the NS5-based immunoassay will be very useful for both clinical and veterinary diagnosis of WNV infection. The MIA assay format used in this study is highly sensitive (flow-cytometry based), has a rapid turnaround time (3 to 4 h for testing 96 specimens), and is cost-effective (approximately 50 tests per microgram of recombinant protein). More importantly, the MIA format allows the performance of multiplex assays to detect antibodies against E and NS5 proteins in a single tube, allowing simultaneous primary and confirmatory diagnosis.

Example 22

Animal Studies Show that Antibody Levels to NS Protein Decline over Timewhile Antibodies to Structural Proteins Increase over Time Animal model studies of WNV infection have added proof of the concept that antibody levels to nonstructural proteins decline while antibodies to structural proteins are increasing. In an experimental mouse model of infection where sequentially timed serum samples were drawn at 5, 10 and 28 days post infection, total antibodies to the WNV E, a structural protein, were still increasing at day 28 whereas the total of antibodies to the NS5 protein was decreasing. In a similar manner, IgM antibodies to WNV E were still increasing in the day 28 sample, whereas the IgM antibodies to NS5 were lower at 28 days than in the day 10 sample. Thus, NS5 appears to be a useful antigen to screen for WNV infections at an early and/or acute stage.

Example 23

Avian Response to Flavivirus Infection is Strain Specific

An evaluation of West Nile antibodies in wild birds of various orders and species, has demonstrated that some birds made much higher antibody responses to NS5 than to WNV E protein. For surveillance activities, a bird that has antibodies to NS5 must have been infected in the recent past, where as a bird that only has antibodies to WNV E only has evidence of infection in the remote past. Wild birds (house finches and morning doves) with SLEV infection made low to moderate antibody responses to WNV E, whereas they made no response to WNV NS5. This indicates that the avian response to flavivirus infections is strain specific, as we have have demonstrated in humans. Antibodies to WNV NS5 indicate recent infection with West Nile virus, whereas antibodies to WNV envelope protein indicate infection at some time with one of many flaviviruses.

Example 24

High Antibody Response to NS5 in Naturally Infected Horses

An evaluation of West Nile antibodies in naturally infected horses demonstrated high antibody responses to NS5, often greater than to Envelope protein. Antibodies generated by the Ft. Dodge inactivated West Nile vaccines were only to the Envelope protein. Horses with no infection and no vaccination were negative to Envelope and to NS5. Therefore, a high antibody level to NS5 in a vaccinated horse means active, recent infection. The duration of protective antibodies from the vaccine is short, and antibodies drop off within two months of the last dose of vaccine.

Example 25

High Levels of NS5 Antibodies Even in the Absence of High IgM to WNV may Indicate Recent WNV Infection A serosurvey of 871 solid organ transplant recipients has identified about 85 persons with antibodies to Envelope protein. Only 5 of these persons have IgM to WNV E protein, indicating current WNV infection. Ten of the 85 persons have high levels of antibodies to NS5. Studies are currently underway to demonstrate that these patients have evidence of recent WNV infection despite the lack of IgM to WNV.

Example 26

Enzyme-Linked Immunosorbent Assay (Elisa) Using WNV NS50R E Antigens

The NS5 protein can be used to detect human antibodies specific for NS5 from blood. More in particular, the NS5 protein can be used in connection with an ELISA to detect NS5-specific antibodies. Positive detection of NS5-specific antibodies would indicate a more recent WNV infection since the antibodies to NS5 show limited persistence in the blood; thus anti-NS5 antibodies are more likely to be present at higher titers early during infection (see Example 18). The WNV E glycoprotein, oweing to the fact that it shows consistent, reliable, and predictable cross-reactivity against antibodies to other flavivirus, in particular JEV, SLEV, and DENV, can be used in an ELISA to detect a flavivirus infection.

Although any known ELISA format is contemplated by the present invention, one standard ELISA assay format assay, the “three layer sandwich”, can be used. In this format, NS5 or WNV antigen are passively adsorbed to polycarbonate microtiter plates. The remaining reactive sites on the plate are then blocked with a solution of serum protein, serum albumin, non-fat dry milk, gelatin, or detergent (e.g. Tween, Triton X-100, SDS). The antigen coated plates are then incubated with a dilution of a patient’s serum. If the patient was infected with WNV, anti-WNV E or anti-WNV NS5 antibodies bind to the WNV E or NS5, respectively, on the plate. Following several washes, the plate is incubated with goat-anti-human antibody conjugated to an enzyme such as alkaline phosphatase or horse radish peroxidase. Following several washes, the plate is developed with a chromogen (substrate for the enzyme). The color development is read on a microtiter plate spectrophotometer. The deepness of the color is proportional to the amount of human antibody to NS5 in the sample applied to the plate.

Another ELISA format contemplated by the instant invention is the IgM antibody capture ELISA. In this assay, Goat anti-human IgM is used to coat the microtiter plates. After blocking reagents are added, such as solutions of serum protein, serum albumin, non-fat dry milk, gelatin, or detergent (e.g. Tween, Triton X-100, SDS), a dilution of human serum is added to the wells in the plate. The goat-anti human IgM captures the patient’s IgM. Subsequently, WNV E or NS5 antigen would be added to the wells. After an incubation period, the unbound antigen is washed away. Next, biotinylated monoclonal antibody to WNV NS5 or E is added to wells. Following an incubation period, the unbound monoclonal antibody is washed away. Streptavidin linked to a detector enzyme is then added to the wells of the plates. Following washing steps, the unbound Streptavidin conjugate is washed away. The assay is developed with a chromogen and read on a microtiter plate spectrophotometer. The amount of color developed is proportional to the amount of IgM the patient had to West Nile NS5.

The WNV NS5-based and E-based ELISAs can be run separately or in parallel. It will be appreciated that a positive result in the E-based assay is indicative of a flavivirus infection, including for example detection of WNV, SLEV, DENV, or JEV. It will be further appreciated by one of ordinary skill in the art that the teachings of the present invention demonstrate by experiment that substantially purified WNV E glycoportein antigen having a substantially authentic conformation is reliably, consistently, predictably, and strongly cross-reactive to antibodies against any of WNV, JEV, SLEV, and DENV, and is therefore useful to broadly assay or test for flavivirus infection. A positive result based on the NS5 ELISA indicates with specificity a WNV infection, in particular a recent infection.

It is again to be appreciated by one of ordinary skill in the art that any ELISA format currently used to detect WNV antibodies in serum or spinal fluid or other biological samples, can easily be adapted to detect antibodies to the NS5 or E antigens therein. The information obtained with the NS5 assays is more useful for identifying recent WNV, since the antibody response to NS5 is of shorter duration that the antibody response to the E glycoprotein. Further, information obtained with the E glycoprotein is more useful for identifying a general flavivirus infection, in particular, a recent or non-recent infection or flavivirus vaccination with WNV, JEV, SLEV, or DENV.

Example 27

Microsphere Immunofluorescence Assay Parameters

Figure 31:
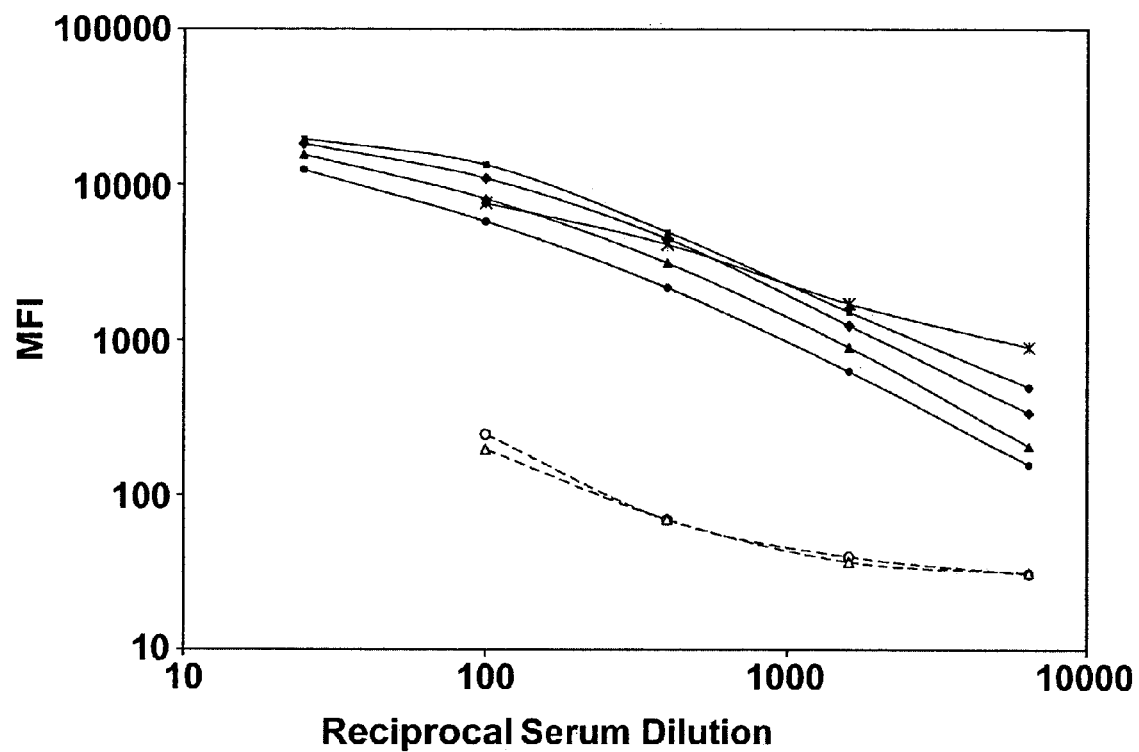
FIG. 31 shows rWNV-E MIA analysis of serially diluted serum specimens. Sera from patients with West Nile infection (closed symbols), and negative control human sera (open symbols) were serially diluted and evaluated in the rWNV-E MIA using polyvalent detector antibody. Results are reported as median fluorescent intensity per 100 microspheres (MFI).

Recombinant WN virus envelope protein (rWNV-E) conjugated to fluorescent microspheres provided the basis for a novel immunoassay to detect antibodies induced by flavivirus infection. The MIA quantitatively measures anti-E protein antibodies binding over a broad range of antibody concentrations (FIG. 31). A standardized, 2.5 h MIA procedure was developed to detect antibodies to WN virus E protein in $\leq 30$ μl of human serum or CSF, diluted 1:100 and 1:2 respectively. Performance of the suspension assay at 37° C. with continual shaking enhanced assay kinetics. Antigen-conjugated microspheres exhibited long-term stability when stored at 4° C. Conjugated microspheres were held at 4° C., 25° C., 37° C., or 50° C. Reactivities of the rWNV-E microspheres with a positive control serum were tested at several intervals during a 35-day storage period. Thermal stability of this key assay component (expressed as time to 90% potency), was observed to be<one day at 37° C. and 50° C., 3.1 days at 25° C., and >35 days at 4° C. The immunoreactivity of antigen-conjugated microspheres is stable for >4 months when used in serial MIAs (data not shown).

MIA ranges for positive and negative control sera were established by evaluation of 20 human sera. Ten negative control sera had no detectable virus-specific antibodies in WN virus IgM-capture and IgG ELISAs. The mean microsphere MFI for these sera was 247±74, establishing MFI$\geq$988 (P/N$\geq$4.0) as a cutoff for a positive result. The 10 sera from WN viral encephalitis patients all tested positive for antibodies to WN virus E protein. The mean MFI for the patient sera was 7,626±4,312 (P<0.001; range 2,763 to 17,188) corresponding to a mean P/N ratio of 30.8±17.4 (range 11.2 to 69.4). MIA results from repeated experiments were compared to determine inter-operator reproducibility. For intra-assay imprecision studies, 10 aliquots of a WN virus encephalitis patient serum pool and 10 aliquots of a negative control serum pool were tested separately in the rWNV-E MIA. Intra-assay imprecision of the positive pool provided a coefficient of variation (CV) of 7%. Intra-assay imprecision of the negative serum pool provided a CV of 11%. These same negative and positive serum pools were analyzed on several days for estimates of inter-assay imprecision. The inter-assay CVs for the positive serum and negative serum pools were 17% and 32%, respectively. MIA results for 91 positive and negative sera independently analyzed by two individuals demonstrated inter-operator assay reproducibility (kappa=0.85; P/N $r^2$=0.99; slope=1.12).

Example 28

Anti-E Protein-Based Microsphere Immunoassay (MIA) Detects Antibodies to Related Flaviviruses Testing of a coded serum panel revealed that the rWNV-E MIA detects human antibodies elicited by SLEV and DENV (FIG. 34). The serum panel, provided by CDC Arbovirus Diseases Branch, included sera from patients infected with WNV, SLEV or DENV. Ten of 19 sera in the panel were positive in the rWNV-E MIA (mean P/N 25.75±20.26; range, 4.28 to 55.23) using P/N>4.0 as a MIA positive cut-off value. Decoding of the serum panel revealed that the rWNV-E MIA detected 10 of 12 sera from flavivirus-infected individuals (kappa=0.79). All six sera from WNV encephalitis or DENV fever patients (FIG. 34) were positive. The MIA also identified four sera from patients infected with SLEV (FIG. 34). Two sera from patients infected with SLEV were negative in the rWNV-E MIA. These two sera were obtained within one day after disease onset, when significant anti-SLEV antibody titers may not be present. The MIA produced no false positive results with seven sera negative for neutralizing flavivirus antibodies in PRN assays (FIG. 34). One negative control specimen consistently tested false positive in IgM-capture ELISAs. Comparison of WNV ELISA results for negative control sera and sera containing anti-WNV antibodies (FIG. 34) indicated inter-laboratory agreement for IgG ELISA (kappa=1.00; P/N $r^2$=0.98) and IgM-capture ELISA (kappa=0.80; P/N $r^2$=0.94) results.

The rWNV-E MIA detects antibodies elicited by JE-VAX™, the licensed JE virus vaccine. Sera from eight individuals with occupational exposure to flaviviruses were collected before and after vaccination with JE-VAX™. Mean polyvalent rWNV-E MIA values were 4.2±4.5 for pre-vaccination sera, and 13.3±12.7 for post-vaccination sera (P<0.05). The vaccination induced JEV neutralizing antibodies in six vaccinees that were detectable in JEV PRN tests.

Example 29

Figure 32:
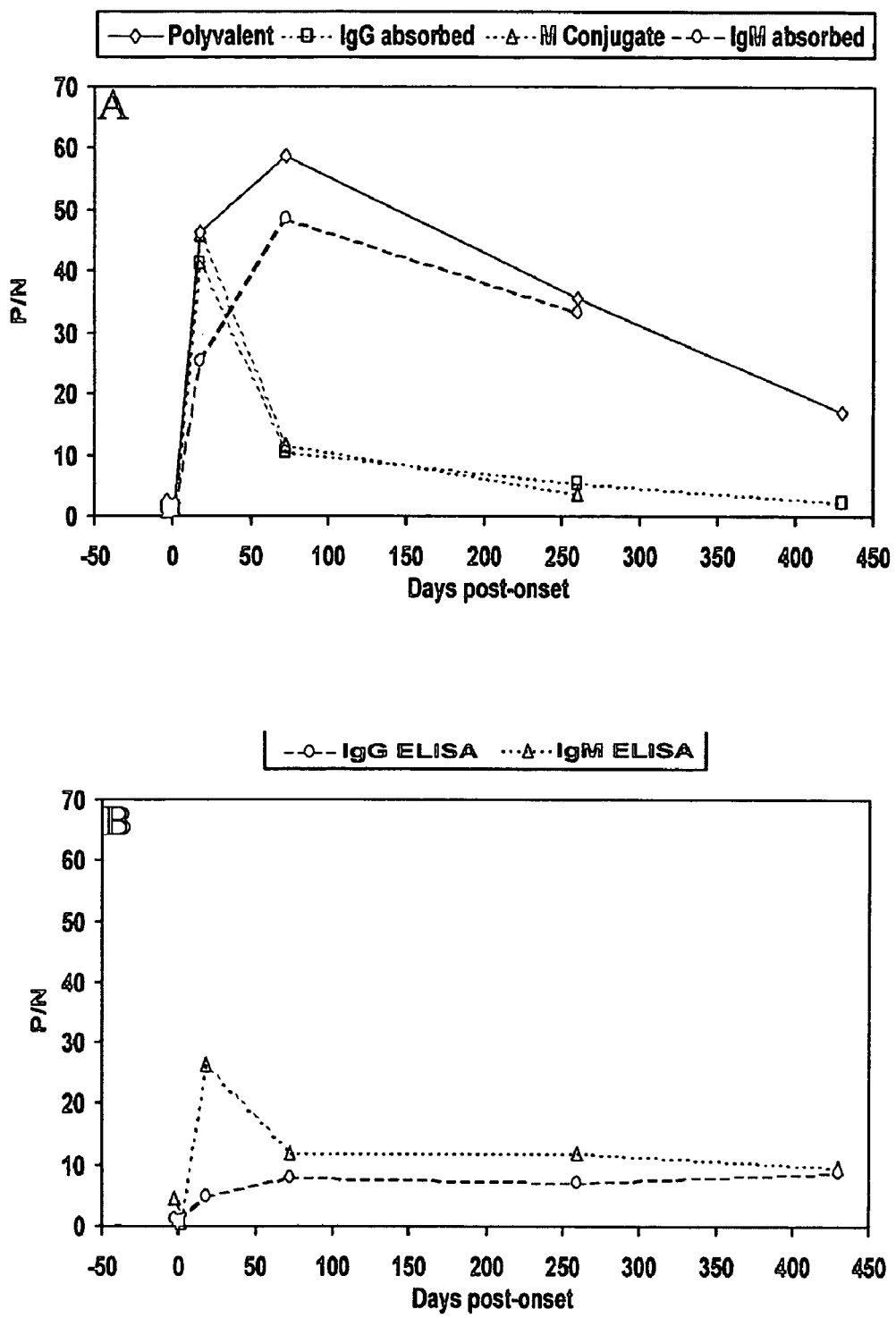
FIG. 32 shows rWNV-E MIA and ELISA analysis of anti-WN virus antibodies in sequential serum specimens from a patient infected with WN virus. A. Unadsorbed sera were evaluated in the rWNV-E MIA using polyvalent detector antibody (polyvalent). Sera adsorbed with anti-IgG (IgG adsorbed) or anti-IgM (IgM adsorbed) were evaluated in the rWNV-E MIA using polyvalent detector antibody. The IgM adsorbed sera were also analyzed in the rWNV-E MIA with anti-IgM detector antibody (M conjugate). B. The results with the MAC-ELISA and indirect IgG ELISA are compared on sequential sera.

Microsphere Immunoassay (MIA) Assessment of the Humoral Response to WNV Infection Several WN virus antibody detection methods were compared using serial serum samples from a patient with WN virus infection (FIG. 32). The polyvalent MIA, which detects both IgM and IgG (Panel A) and the ELISAs (Panel B) were first used to evaluate the specimens. The MIA procedure was then modified to measure IgM antibodies to WN virus E protein. Sera were depleted of IgG with goat anti-human IgG, and analyzed with polyvalent R-PE-conjugated detector antibody or with IgM-specific conjugate. These two detection systems yielded equivalent P/N results (FIG. 32, PanelA; $r^2$=0.998; slope=1.14) that correlated with P/N values obtained with the IgM-capture ELISA ($r^2$=0.85). Each method detected maximal IgM reactivity in the serum specimen obtained 18 days post disease-onset.

IgG antibodies to WN virus E protein in the serial serum samples were also evaluated by MIA (FIG. 32, Panel A). Removal of IgM with anti-human IgG enhanced the correlation between the MIA and IgG ELISA P/N values ($r^2$=0.45 and 0.98 before after IgM depletion, respectively). The MIA detected maximal IgG reactivity 72 days after disease onset whereas the IgG ELISA P/N value was highest at 430 days post onset. In convalescent specimens obtained at days 72 and 260 post-disease onset, anti-IgG treatment depleted >80% of rWNV-E MIA reactivity. Anti-IgG treatment of the day 18 specimen depleted only 11% of the MIA reactivity. These data indicate that this patient's IgM response to WN virus infection predominated only during acute infection.

Example 30 rWNV-E MIA Analysis of Sera from Patients with Suspected Viral Encephalitis

Figure 33:
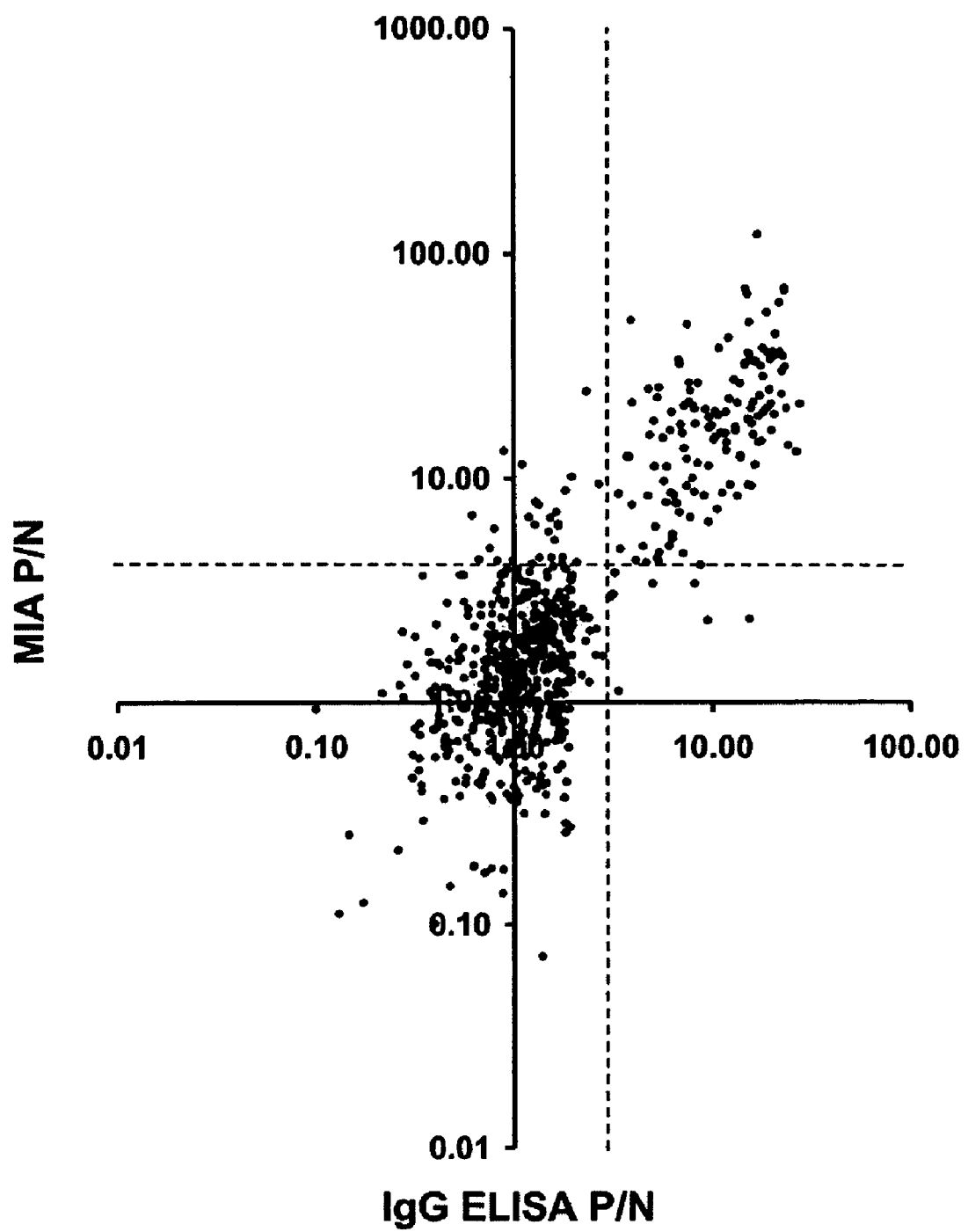
FIG. 33 shows a retrospective parallel WNV-E MIA and WN virus IgG ELISA analysis of sera from patients with suspected viral encephalitis. Dashed lines indicate P/N cut-off values for a positive result. n=702; $r^2$=0.60; slope=1.68.

New York State Department of Health serum archives provided an opportunity to evaluate 833 sera from patients with suspected viral encephalitis in the rWNV-E MIA. With P/N>4.0 used as a positive cutoff, 188 (23%) sera were positive in the MIA (mean P/N 18.3±15.8; range 4.07 to 122). A polyvalent (IgM+IgG) MIA result was obtained for each of the 833 sera. In contrast, IgG ELISA results for 131 (16%) sera were reported as "uninterpretable" due to high non-specific background in negative control ELISA assays. (A. J. Johnson et al., D. A. Martin et al.). One hundred fifty-one (18%) of the 833 sera were positive in the IgG ELISA (mean P/N 11.51±5.96; range 3.08 to 27.4). The MIA had high sensitivity (0.94) and specificity (0.95) for sera with anti-WN virus IgG antibodies detected by the IgG ELISA (positive predictive value=0.829; negative predictive value=0.98, Positive and negative test results for the two assays were concordant (kappa=0.85). FIG. 33 compares MIA and IgG ELISA P/N results for sera with interpretable IgG ELISA results.

IgM capture ELISA data were available for 806 of the 833 sera from patients with suspected viral encephalitis. Ninety-six (12%) sera were positive in this assay (mean P/N 12.49±4.13; range 7.18 to 25.9). Seven hundred (87%) sera were negative. Ten sera (1%) provided nonspecific results. The polyvalent MIA detected 80 (83%) of the 96 sera that were positive in the IgM-capture ELISA. Sera positive in the standard polyvalent MIA (n=172) were re-assayed after depletion of IgG to measure IgM antibodies to WN virus E protein. 80 (46%) sera were positive after removing IgG (mean P/N 19.5±29.9; range 4.00 to 178). The IgG-depleted MIA sensitivity (0.61) and specificity (0.64) for sera positive in the IgM-capture ELISA (kappa=0.25) suggested that capturing IgM antibodies may enhance anti-WN virus IgM assay sensitivity. However, twenty-three (36%) of the 64 discordant samples were positive in the IgG-depleted MIA, positive in the IgG ELISA, but negative in the IgM-capture ELISA. These samples apparently have IgM antibodies to WN virus E protein not detected by the IgM-capture ELISA. Forty-three (5%) of the 833 sera from patients with suspected flavivirus infection tested positive (mean P/N 7.28±5.74; range 4.07 to 39.5) in the polyvalent rWNV-E MIA, but were negative or uninterpretable in IgM-capture and IgG ELISAs. These sera were initially identified as non-reactive or non-specific in the ELISAs, and no diagnostic or clinical follow up was performed that could rule out WN virus infection. The combined data indicate that the rWNV-E MIA has ≧95% specificity in detecting flavivirus antibodies in sera from patients with suspected viral encephalitis.

Example 31

WNV E-Based Microsphere Immunoassay (MIA) Detectsanti-Flavivirus Antibodies in Cerebral Spinal Fluid (CFS)

Thirty-five CSF were evaluated in the rWNV-E MIA after depletion of IgG from the specimens. Twenty negative control CSF (mean MFI 69±119; range 5 to 540) were evaluated, establishing MFI >426 (3 standard deviations above the mean) as a cutoff for a positive CSF result. The MIA was then used to evaluate CSF from 15 encephalitis patients with flavivirus infection confirmed by serum PRN tests (FIG. 36). Twelve specimens (80%) were positive in the MIA before and after depletion of IgG, including eight CSF from patients infected with WNV, two CSF from patients infected with dengue virus, and two CSF from patients infected with an unidentified flavivirus. For most of these CSFs, depletion of IgG minimally reduced MFI values (FIG. 36), indicating that the anti-E protein antibodies were predominately IgM. MIA-negative CSF 9 and 10 were from patients with WN virus-specific serum antibodies. PRN tests of acute and convalescent sera indicated that these two patients did not have active flavivirus infection.

Paired CSF and serum obtained on the same day were available for Patients 1-6. These patients had WN virus infection confirmed by serum ELISA and PRN tests. All six CSF were positive in MIAs (FIG. 36). In contrast, only one of these CSF, from Patient 2, was positive in IgM-capture ELISAs (data not shown).

Example 32

WNV NS5-Based Immunoassay Determines Whether Previously-Vaccinated Horse has Sustained New Exposure to WNV Using the WNV NS5-based immunoassay, in particular the microsphere immunoassay (MIA), a determination can be made as to whether the horse has been exposed and infected with WNV. Compared with live attenuated virus vaccine, the duration of protective antibody in response to "killed" WNV vaccination is relatively short. Thus, there exists an ongoing risk that the horse could be infected with WNV upon exposure or reexposure thereto. In other words, since protective immunity wanes quickly, veterinarians may be increasingly challenged to diagnose neurological illness that could be due to WNV infection in previously WNV-vaccinated horses. Such diagnosis will be problematic for structural protein-based assays, such as the WNV E-glycoprotein assay, due to the presence of preexisting antibodies to the structural protein as a result of the immune response to the vaccination.

A two-step suspension microsphere immunofluorescence assay will be performed. Multiscreen 96-well filter plates with 1.2 μm Durapore filters (Millipore, Bedford, Mass.) and a Multiscreen vacuum manifold (Millipore) facilitated microsphere washing. Briefly, filter plate wells will be blocked for 2 min with PBN buffer. Diluted serum samples (for example, 50 μl, diluted 1:100 in PBN) will be added to test wells. IgG-depleted sera will be diluted 10-fold during depletion, and will diluted an additional 10-fold in PBN for analysis in the rWNV-NS5 MIA with polyvalent secondary antibody conjugate. NS5-antigen-conjugated microspheres (2,500 in 50 μl PBN) will be added to each well and incubated. Diluted fluorochrome-labeled secondary antibody (50 μl of a 1:250 dilution in PBN) will be added to each well. As an example, the secondary antibody can be polyvalent goat F (ab')$_2$ anti-horse immunoglobulins (IgG+IgA+IgM) conjugated to red-phycoerythrin (R-PE) obtained from a commercial or veterinary source. After incubation, microspheres will be resuspended in 125 μl PBN per well. Seventy-five microliter aliquots will be transferred to opaque black EIA/RIA 96-well plates with breakaway strips (Costar, Corning, N.Y.), and will be evaluated for microsphere fluorescence intensity using a Luminex 100 instrument (Luminex Corp.). This instrument is a dual laser flow analyzer. The first laser excites the flourochrome mixture intrinsic to the microspheres, enabling the bead identity to be determined as the bead passes single file through the laser path in the flow cell. The second laser excites the extrinisic flourochrome (red-phycoerythrin) that is covalently attached to the reporter antibodies (goat-anti horse immunoglobulins). The dual lasers allows the operator to mix beads with different antigens together in a well of a filter plate, thus enabling multiplex analysis of different antibody specificities at one time.

The instrument will be calibrated with CL1/CL2 and RP1 calibration microspheres from Luminex Corp. according to the manufacturer's directions. The median fluorescence intensity (MFI) of fluorochrome-conjugated secondary antibody bound to individual microspheres will be derived from flow analysis of 100 microspheres per well. Results for each assay will be expressed both as MFI and as a horse/negative (P/N) MFI ratio, i.e., the MFI for the horse's specimen divided by the MFI obtained from a pool of 10 negative control sera. The negative control sera will contain no detectable antibodies to WN virus in IgM-capture and IgG ELISAs.

Positive detection of anti-NS5 antibodies will indicate recent exposure of the horse to WNV or an ongoing WNV infection. Killed WNV vaccine is not expected to generate any immune response to NS5 proteins since the WNV vaccine is not expected to replicate. Non-replicating viruses do not produce new NS5 protein. Thus, the NS5-based microsphere immunoassay will be useful for discriminating between horses that have been vaccinated previously with killed WNV vaccine and those that have been previously been vaccinated and were exposed and infected with WNV.

We claim:

1. A method for the rapid detection of an anti-WNV antibody comprising the steps of:
   (a) contacting a biological sample with a microsphere suspension, each microsphere covalently attached via its carboxylated surface to a substantially pure WNV NS5 protein having a native conformation or nondenatured structure whereby each NS5 protein is specifically reactive to antibodies against WNV,
   (b) incubating the microsphere suspension under conditions sufficient to promote the binding of an anti-WNV antibody to the NS5 protein,
   (c) contacting the microsphere suspension with a detection reagent capable of detecting the anti-WNV antibody,
   (d) detecting the detection reagent,
   wherein detection of the detection reagent indicates the presence the anti-WNV antibody in the biological sample.

2. The method according to claim 1, wherein the biological sample is selected from the group consisting of bodily fluid, blood, serum, plasma, saliva, tears, feces, semen, mucous, tissue, tissue homogenate, cellular extract, and spinal fluid.

3. The method according to claim 2, wherein the biological sample is 10-20 microliters.

4. The method according to claim 1, wherein the step of incubating the microsphere suspension is performed under conditions sufficient to enhance reaction kinetics, wherein the conditions comprise incubating at 37° C., for about 30 minutes while keeping the microsphere suspension in motion.

5. The method according to claim 1, wherein the detection reagent comprises a antibody coupled to a fluorescent tag.

6. The method according to claim 1, wherein the detection reagent comprises a antibody coupled to an enzyme.

7. The method according to claim 6, wherein the enzyme is selected from the group consisting of an oxidase, luciferase, peptidase, protease, glycosidase and phosphatase.

8. The method according to claims 5, wherein step (d) comprises the step of immunofluorescence detection of said fluorescent tag of said antibody of said detection reagent.

9. A method for detecting a WNV infection in a biological specimen comprising the steps of:
   (a) obtaining a suspension of microspheres each covalently attached via its carboxylated surface to a substantially pure WNV NS5 protein having a native conformation or non-denatured structure wherein the WNV NS5 protein is specifically reactive with anti-WNV antibodies;
   (b) performing a microsphere immunoassay;
   (c) obtaining a result indicating either the presence or absence of an anti-WNV antibody;
wherein the presence of an anti-WNV antibody indicates a WNV infection.

10. The method according to claim 9, wherein the microsphere immunoassay is a Luminex-based test or flow cytometer-based test.

11. The method according to claim 9, wherein the microsphere immunoassay is a lateral flow test.

12. The method according to claim 9, wherein the microsphere immunoassay is an agglutination test.

13. The method according to claim 9, wherein the microsphere immunoassay is a strip test.

14. The method according to claim 9, wherein the microsphere immunoassay is automated.

15. A method for the transfer of information comprising the steps of:
   (a) carrying out the method of any of claims 1 or 9 to obtain a result;
   (b) providing the result to a third party.

16. A method for rapid detection of a WNV infection in an animal susceptible of infection by said WNV, comprising the steps of:
   (a) contacting a biological sample of said animal comprising anti-WNV antibodies with a microsphere suspension, each microsphere covalently attached via its carboxylated surface to a substantially pure WNV NS5 protein having a native conformation or non-denatured structure whereby each WNV NS5 protein is reactive to said anti-WNV antibodies,
   (b) incubating the microsphere suspension under conditions sufficient to promote the binding of said anti-WNV antibodies to the WNV NS5 protein,
   (c) contacting the microsphere suspension with a detection reagent capable of detecting the anti-WNV antibody,
   (d) detecting the detection reagent,
wherein detection of the detection reagent indicates the presence of said anti-WNV antibody in said biological sample.

17. A method for immunochromatographically testing for a WNV infection in an animal susceptible to said infection, comprising the steps of:
   (a) contacting a biological sample comprising anti-WNV antibodies with a suspension of WNV NS5-coated microspheres, wherein each microsphere is covalently attached via its carboxylated surface to a substantially pure WNV NS5 protein to form a reaction mixture under conditions sufficient to promote binding of the anti-WNV antibodies to the WNV NS5-coated microspheres,
   (b) placing the reaction mixture at the proximal end of the membrane strip having a proximal end, a distal end, and a plurality of zones each comprising secondary antibodies coupled thereto,
   (c) incubating the membrane strip under sufficient conditions to promote the movement of the reaction mixture towards the distal end, said conditions being also sufficient to promote the binding of the microparticles to said secondary antibodies coupled to the membrane strip vis-à-vis interactions between said secondary antibodies and the anti-WNV antibodies,
   (d) washing from the membrane strip any unbound microparticles, and
   (e) detecting bound microparticles, wherein bound microparticles indicates a WNV infection in said animal.

18. The method for the rapid detection of an anti-WNV antibody according to claim 1, wherein the method is performed as a microsphere immunoassay, an agglutination assay, a slide test, a lateral flow test, an immunochromatographic assay, a fluorescence-based assay, a flow cytometric-based assay, or a Luminex-based assay.

19. The method for the rapid detection of an anti-WNV antibody according to claim 18, wherein the method is performed in less than about 3 hours.

20. The method for the rapid detection of an anti-WNV antibody according to claim 1, wherein the biological sample is from an animal, a human, a bird, a wild bird, a horse, a mouse, a cat, or a dog.

21. The method for the rapid detection of an anti-WNV antibody according to claim 1, wherein the WNV NS5 protein is SEQ ID NO. 8 or is encoded by nucleic acid positions 7,633-10,377 of SEQ ID NO. 1.

22. The method for the rapid detection of an anti-WNV antibody according to claim 1, wherein the WNV NS5 protein is an immunogenic fragment thereof.

23. The method for detecting a WNV infection according to claim 9, wherein the method is performed as a microsphere immunoassay, an agglutination assay, a slide test, a lateral flow test, an immunochromatographic assay, a fluorescence-based assay, a flow cytometric-based assay, or a Luminex-based assay.

24. The method for detecting a WNV infection according to claim 23, wherein the method is performed in less than about 3 hours.

25. The method for detecting a WNV infection according to claim 9, wherein the biological sample is selected from the group consisting of bodily fluid, blood, serum, plasma, saliva, tears, feces, semen, mucous, tissue, tissue homogenate, cellular extract, and spinal fluid.

26. The method for detecting a WNV infection according to claim 9, wherein the biological sample is from an animal, a human, a bird, a wild bird, a horse, a mouse, a cat, or a dog.

27. The method for detecting a WNV infection according to claim 9, wherein the WNV NS5 protein is SEQ ID NO. 8 or is encoded by nucleic acid positions 7,633-10,377 of SEQ ID NO. 1.

28. The method for detecting a WNV infection according to claim 9, wherein the WNV NS5 protein is an immunogenic fragment thereof.

29. The method for the rapid detection of WNV infection according to claim 16, wherein the method is performed as a microsphere immunoassay, an agglutination assay, a slide test, a lateral flow test, an immunochromatographic assay, a fluorescence-based assay, a flow cytometric-based assay, or a Luminex-based assay.

30. The method for the rapid detection of a WNV infection according to claim 16, wherein the method is performed in less than about 3 hours.

31. The method for the rapid detection of a WNV infection according to claim 16, wherein the biological sample is selected from the group consisting of bodily fluid, blood, serum, plasma, saliva, tears, feces, semen, mucous, tissue, tissue homogenate, cellular extract, and spinal fluid.

32. The method for the rapid detection of a WNV infection according to claim 16, wherein the biological sample is from an animal, a human, a bird, a wild bird, a horse, a mouse, a cat, or a dog.

33. The method for the rapid detection of a WNV infection according to claim 16, wherein the WNV NS5 protein is SEQ ID NO. 8 or is encoded by nucleic acid positions 7,633-10,377 of SEQ ID NO. 1.

34. The method for the rapid detection of WNV infection according to claim 16, wherein the WNV NS5 protein is a fusion protein.

35. The method for the rapid detection of a WNV infection according to claim 16, wherein the WNV NS5 protein is an immunogenic fragment thereof.

36. The method for the rapid detection of a WNV infection according to claim 34, wherein said fusion protein comprises a maltose binding protein or thioredoxin and WNV NS5.

37. The method for immunochromatographically testing for a WNV infection according to claim 17, wherein the WNV NS5 protein is SEQ ID NO. 8 or is encoded by nucleic acid positions 7,633-10,377 of SEQ ID NO. 1.

38. The method for immunochromatographically testing for a WNV infection according to claim 17, wherein the method is performed in less than about 3 hours.

* * * * *

UNITED STATES PATENT AND TRADEMARK OFFICE
CERTIFICATE OF CORRECTION

| | | |
|---|---|---|
| PATENT NO. | : 7,351,547 B2 | Page 1 of 1 |
| APPLICATION NO. | : 10/699550 | |
| DATED | : April 1, 2008 | |
| INVENTOR(S) | : Susan J. Wong et al. | |

It is certified that error appears in the above-identified patent and that said Letters Patent is hereby corrected as shown below:

IN THE SPECIFICATION

Column 1, line 28, please insert the following:

--STATEMENT REGARDING FEDERALLY SPONSORED RESEARCH OR DEVELOPMENT

This invention was made with government support under US50/CCU212415 awarded by the CDC. The government has certain rights in the invention.--

Signed and Sealed this
Twenty-fourth Day of April, 2012

David J. Kappos
*Director of the United States Patent and Trademark Office*